United States Patent
Rennie et al.

(10) Patent No.: US 10,633,338 B2
(45) Date of Patent: Apr. 28, 2020

(54) BINDING FUNCTION 3 (BF3) SITE COMPOUNDS AS THERAPEUTICS AND METHODS FOR THEIR USE

(71) Applicants: THE UNIVERSITY OF BRITISH COLUMBIA, Vancouver (CA); SIMON FRASER UNIVERSITY, Burnaby (CA)

(72) Inventors: Paul Rennie, Richmond (CA); Artem Tcherkassov, Vancouver (CA); Robert N. Young, Burnaby (CA); Christophe M. Andre, Laissac (FR)

(73) Assignees: THE UNIVERSITY OF BRITISH COLUMBIA, Vancouver (CA); SIMON FRASER UNIVERSITY, Vancouver (CA)

( * ) Notice: Subject to any disclaimer, the term of this patent is extended or adjusted under 35 U.S.C. 154(b) by 0 days.

(21) Appl. No.: 16/426,406

(22) Filed: May 30, 2019

(65) Prior Publication Data
US 2019/0300480 A1    Oct. 3, 2019

Related U.S. Application Data

(62) Division of application No. 15/302,363, filed as application No. PCT/CA2015/000239 on Apr. 9, 2015, now Pat. No. 10,351,527.

(Continued)

(51) Int. Cl.
| | |
|---|---|
| C07D 209/14 | (2006.01) |
| C07D 235/30 | (2006.01) |
| C07D 231/56 | (2006.01) |
| C07D 277/82 | (2006.01) |
| C07D 417/10 | (2006.01) |
| C07D 401/10 | (2006.01) |
| C07D 401/06 | (2006.01) |
| C07D 405/12 | (2006.01) |
| C07D 405/14 | (2006.01) |

(Continued)

(52) U.S. Cl.
CPC .......... *C07D 209/14* (2013.01); *C07C 243/22* (2013.01); *C07D 209/08* (2013.01); *C07D 209/10* (2013.01); *C07D 209/30* (2013.01); *C07D 209/34* (2013.01); *C07D 209/42* (2013.01); *C07D 231/56* (2013.01); *C07D 235/18* (2013.01); *C07D 235/30* (2013.01); *C07D 277/82* (2013.01); *C07D 401/04* (2013.01); *C07D 401/06* (2013.01); *C07D 401/10* (2013.01); *C07D 403/04* (2013.01); *C07D 403/14* (2013.01); *C07D 405/12* (2013.01); *C07D 405/14* (2013.01); *C07D 413/04* (2013.01); *C07D 413/10* (2013.01); *C07D 417/04* (2013.01); *C07D 417/10* (2013.01); *C07D 417/14* (2013.01); *C07D 471/04* (2013.01)

(58) Field of Classification Search
CPC .................................................... C07D 209/14
USPC ..................................................... 514/235.2
See application file for complete search history.

(56) References Cited

U.S. PATENT DOCUMENTS

| | | |
|---|---|---|
| 3,417,096 A | 12/1968 | Juby |
| 6,172,084 B1 | 1/2001 | Cuny et al. |

(Continued)

FOREIGN PATENT DOCUMENTS

CN        101455661 A     6/2009

OTHER PUBLICATIONS

Bellina, F., et al., "Direct Palladium-Catalyzed C-3 Arylation of Free (NH)-Indoles with Aryl Bromides under Ligandless Conditions." The Journal of Organic Chemistry, 2008, 73(14): 5529-5535.

(Continued)

*Primary Examiner* — Nizal S Chandrakumar
(74) *Attorney, Agent, or Firm* — Brian C. Trinque; Lathrop GPM LLP

(57) ABSTRACT

This invention provides compound having a structure of Formulas:

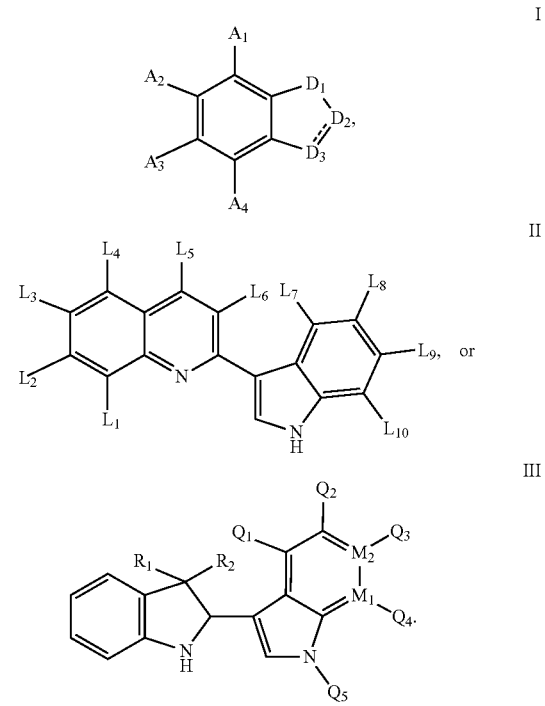

(Continued)

Uses of such compounds for treatment of various indications, including prostate cancer as well as methods of treatment involving such compounds are also provide.

16 Claims, No Drawings

Related U.S. Application Data

(60) Provisional application No. 61/977,445, filed on Apr. 9, 2014, provisional application No. 62/084,451, filed on Nov. 25, 2014.

(51) Int. Cl.

| | | |
|---|---|---|
| *C07D 413/04* | (2006.01) | |
| *C07D 413/10* | (2006.01) | |
| *C07D 417/04* | (2006.01) | |
| *C07C 243/22* | (2006.01) | |
| *C07D 209/08* | (2006.01) | |
| *C07D 209/10* | (2006.01) | |
| *C07D 209/30* | (2006.01) | |
| *C07D 209/34* | (2006.01) | |
| *C07D 209/42* | (2006.01) | |
| *C07D 471/04* | (2006.01) | |
| *C07D 417/14* | (2006.01) | |
| *C07D 403/14* | (2006.01) | |
| *C07D 403/04* | (2006.01) | |
| *C07D 401/04* | (2006.01) | |
| *C07D 235/18* | (2006.01) | |

(56) References Cited

U.S. PATENT DOCUMENTS

| | | |
|---|---|---|
| 6,376,670 B1 | 4/2002 | Cuny et al. |
| 6,897,231 B2 | 5/2005 | Bhagwat et al. |
| 6,982,274 B2 | 1/2006 | Oinuma et al. |

OTHER PUBLICATIONS

Bocchi, V., et al., "Reaction of 3,3-Dimethyl-3H-indole with Electron-Rich Arenes; Synthesis of 2-Aryl-(or-Heteroaryl)-3,3-dimethyl-2,3-dihydroindoles." Istituto di Chimica Organica dell'Università, 1977, (5): 343-345.

Brack, W., et al., "Effect-Directed Identification of Oxygen and Sulfur Heterocycles as Major Polycyclic Aromatic Cytochrome P4501A-Inducers in a Contaminated Sediment." Environ. Sci. Technol., 2003, 37(14):3062-3070.

Dekker, W.H., et al., "Structure-Activity Relationships of Some Antifungal Indoles." J. Agric. Food Chem, 1975, 23(4):785-791.

Juby, P.F., et al., "Preparation and Antiinflammatory Properties of Some 1-Substituted 3-(5-Tetrazolymethyl)indoles and Homologs." Journal of Medical Chemistry, 1969, 12(3): 396-401.

Junek, H., et al., "Beitrage zur Chemie der Enaminoketone, 14.Mitt. Zur Reaktion von 2-Amino-acetophenon mit Orthoestern." Vestn. Slov. Kern. Durs., 1986, Abstract.

Tavassoli, P., et al., "Rapid, non-destructive, cell-based screening assays for agents that modulate growth, death, and androgen receptor activation in prostate cancer cells." Wiley-Liss, Inc., 2007, 67: 416-426.

BINDING FUNCTION 3 (BF3) SITE COMPOUNDS AS THERAPEUTICS AND METHODS FOR THEIR USE

CROSS REFERENCE TO RELATED APPLICATIONS

This Application is a Divisional of U.S. application Ser. No. 15/302,363, filed Oct. 6, 2016, which is a National Stage Application of International Patent Application No. PCT/CA2015/000239, filed Apr. 9, 2015; which claims the benefit of U.S. Provisional Patent Application Ser. No. 61/977,445, filed Apr. 9, 2014 and U.S. Provisional Application No. 62/084,451, filed Nov. 25, 2014; all of which are incorporated herein by reference in their entireties.

TECHNICAL FIELD

This invention relates to therapeutics, their uses and methods for the treatment of various indications, including various cancers. In particular the invention relates to therapies and methods of treatment for cancers such as prostate cancer.

BACKGROUND

Androgens are known to mediate their effects through the androgen receptor (AR). Androgens play a role in a wide range of developmental and physiological responses, for example, male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Also, androgens are associated with the development of prostate carcinogenesis. Induction of prostatic carcinogenesis in rodent models has been associated with androgens (R. L. Noble, *Cancer Res* 37, 1929-1933 (1977); R. L. Noble, *Oncology* 34, 138-141 (1977)) and men receiving androgens in the form of anabolic steroids are reported to have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Furthermore, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (i.e. androgen ablation).

Prostate cancer is the second leading cause of male cancer-related death in Western countries (Damber, J. E. and Aus, G. Lancet (2008) 371:1710-1721). Numerous studies have shown that the androgen receptor (AR) is central not only to the development of prostate cancer, but also the progression of the disease to the castration resistance state (Taplin, M. E. et al. J. Clin. Oncol. (2003) 21:2673-8; and Tilley, W. D. et al. Cancer Res. (1994) 54:4096-4102). Thus, effective inhibition of human AR remains one of the most effective therapeutic approaches to the treatment of advanced, metastatic prostate cancer.

The AR possesses a modular organization characteristic of all nuclear receptors. It is comprised of an N-terminal domain, a central DNA binding domain, a short hinge region, and C-terminal domain that contains a hormone ligand binding pocket and the Activation Function-2 (AF2) site (Gao, W. Q. et al. Chem. Rev. (2005) 105:3352-3370). The latter represents a hydrophobic groove on the AR surface which is flanked with regions of positive and negative charges —"charge clamps" that are significant for binding AR activation factors (Zhou, X. E. et al. J. Biol. Chem. (2010) 285:9161-9171). Recent studies have identified a novel site on the AR called Binding Function 3 (BF3) that is involved into AR transcriptional activity.

It has been proposed a small molecule bound to the BF3 site could cause the AR protein to undergo an allosteric modification that prevents AR interactions with co-activators. Importantly, the BF3 site is located near, but distinct from, the ligand-binding site that is normally targeted by conventional anti-androgen drugs. Chemicals such as flufenamic acid (FLUF), thriiodothyronine (T3) and 3,3',5-triiodo thyroacetic acid (TRIAC), can bind to the BF3 cleft, inhibit AF2 interactions and interfere with AR activity (Estebanez-Perpina, E. et al. Proc Natl Acad Sci USA (2007) 104:16074-16079). While these compounds revealed the importance of the BF3 site, they have shown a low potency ($IC_{50}$>50 μM) and were found to bind non-specifically to the AR.

The activation of AR follows a well characterized pathway: in the cytoplasm, the receptor is associated with chaperone proteins that maintain agonist binding conformation of the AR (Georget, V. et al. *Biochemistry* (2002) 41:11824-11831). Upon binding of an androgen, the AR undergoes a series of conformational changes, disassociation from chaperones, dimerization and translocation into the nucleus (Fang, Y. F. et al. J. Biol. Chem. (1996) 271: 28697-28702; and Wong, C. I. et al. J. Biol. Chem. (1993) 268:19004-19012) where it further interacts with co-activator proteins at the AF2 site (Zhou, X. E. et al. J. Biol. Chem. (2010) 285:9161-9171). This event triggers the recruitment of RNA polymerase II and other factors to form a functional transcriptional complex with the AR.

Notably, the current anti-androgens such as bicalutamide, flutamide, nilutamide and MDV3100, all target this particular process. However, instead of affecting the AR-cofactor interaction directly, these anti-androgens act indirectly, by binding to the AR ligand binding site. Thus, by preventing androgens from binding they also prevent conformational changes of the receptor that are necessary for co-activator interactions. While treatment with these AR inhibitors can initially suppress the prostate cancer growth, long term hormone therapy becomes progressively less effective (Taplin, M. E. et al. J. Clin. Oncol. (2003) 21:2673-8; and Tilley, W. D. et al. Cancer Res. (1994) 54:4096-4102). Factors that make the AR less sensitive to conventional anti-androgens include resistance mutations at the ligand binding site that can even lead AR antagonists to act as agonists further contributing to cancer progression (Chen, Y. et al. Lancet Oncol. (2009) 10:981-991).

Androgens also play a role in female cancers. One example is ovarian cancer where elevated levels of androgens are associated with an increased risk of developing ovarian cancer (K. J. Helzlsouer, et al., *JAMA* 274, 1926-1930 (1995); R. J. Edmondson, et al, *Br J Cancer* 86, 879-885 (2002)). The AR has been detected in a majority of ovarian cancers (H. A. Risch, *J Natl Cancer Inst* 90, 1774-

1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

SUMMARY

This invention is based in part on the fortuitous discovery that compounds described herein modulate androgen receptor (AR) activity. Specifically, compounds identified herein, show inhibition of Androgen Receptor Binding Function-3 (BF3).

In accordance with a first aspect, there is provided a method of modulating AR activity, the method comprising administering a compound having the structure of Formula I:

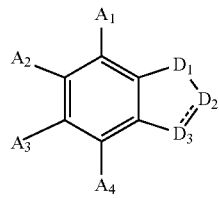

wherein,

⚡ is either a single or a double bond between $D_2$ and $D_3$;

$A_1$ may be H, $CH_3$, $CH_2CH_3$, OH, $CH_2OH$, $OCH_3$,

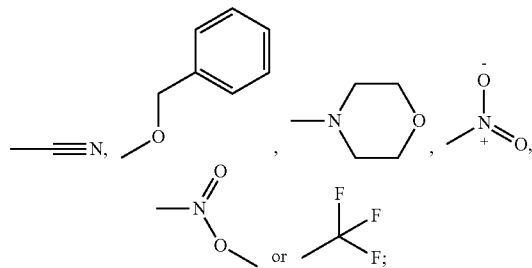

Alternatively $A_1$ may be F, Br or Cl, provided that $D_3$ is not

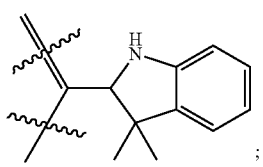 [SMILES: *C(=*)C1Nc2ccccc2C1(C)C]

$A_2$ may be H, Br, OH, Cl, F, I, $CH_3$, $NH_2$, $OCH_3$,

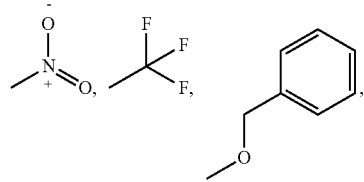

$A_3$ may be H, Br, $NH_2$, F, Cl, $OCH_3$, $CH_3$,

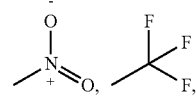

I, OH,

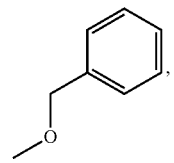

or =O;

$A_4$ may be H, Br, Cl, F, I, $CH_3$, $NH_2$, OH, $OCH_3$,

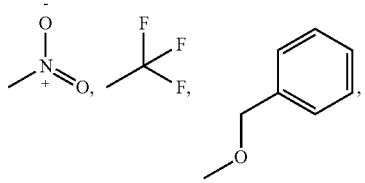

or =O;

$D_1$ is

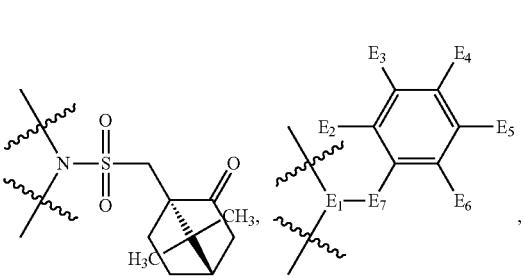

-continued

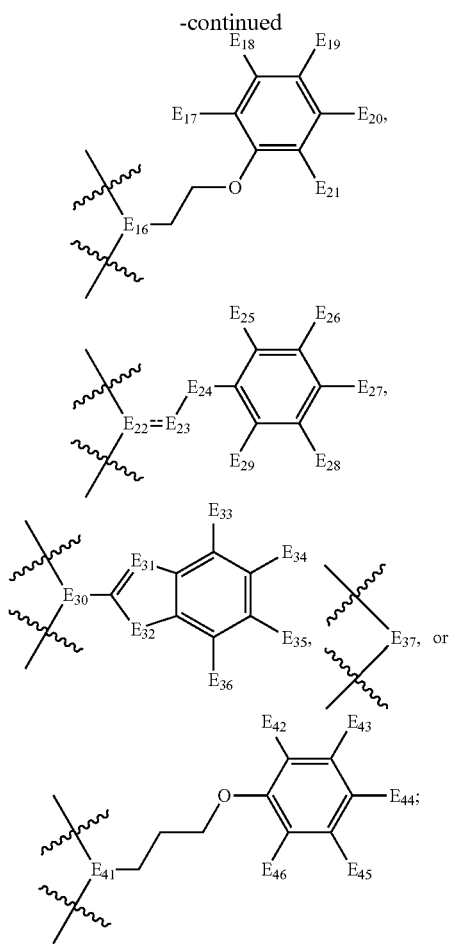

wherein $E_1$, $E_8$, $E_{14}$, $E_{16}$, $E_{22}$, $E_{30}$, and $E_{41}$, are each independently CH or N;

$E_2$, $E_3$, $E_4$, $E_5$, and $E_6$, are each independently H, OH,

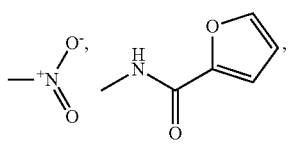

Br, Cl, F, I, or $E_7$ is $CH_2$, O, NH, or C=O;

$E_9$, $E_{10}$, $E_{11}$, $E_{12}$, and $E_{13}$, are each independently H,

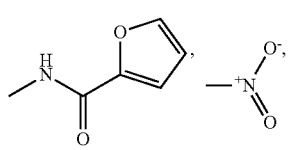

OH, Br, Cl, F, I, or $CH_3$;

$E_{15}$ is $CH_2$, O, NH, or C=O;

$E_{17}$, $E_{18}$, $E_{19}$, $E_{20}$, and $E_{21}$, are each independently H,

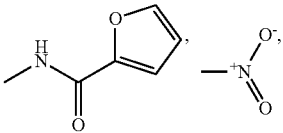

OH, Br, Cl, F, I, or $CH_3$;

$E_{23}$ is CH, $CH_2$, O, N, NH, or C=O;

where ⁀ is either a single or a double bond between $E_{22}$ and $E_{23}$;

$E_{24}$ is $CH_2$, O, NH, or C=O;

$E_{25}$, $E_{26}$, $E_{27}$, $E_{28}$, and $E_{29}$, are each independently H,

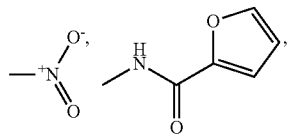

OH, Br, Cl, F, I, or $CH_3$;

$E_{31}$ is N, CH, CBr, CCl, CF, COH, C=O, or $CCH_3$;

$E_{32}$ is NH, $CH_2$, O, or S;

$E_{33}$, $E_{34}$, $E_{35}$, and $E_{36}$, are each independently H, OH,

Br, Cl, F, I, or $CH_3$;

$E_{37}$ is S, O, NH, $CH_2$, $NCH_3$,

C=O, N—N=O, N—$CH_2$—$CH_2$—OH, N—$CH_2$—C(O)—O—$CH_2$—$CH_3$,

N-$E_{38}$, CH-$E_{39}$, $\begin{matrix} E_{39} \\ E_{40} \end{matrix}$;

$E_{38}$ is $NH_2$, O—$CH_3$, O—$NH_2$, $CH_2$—N=O, $CH_2$—$CH_3$, N(H)OH, C(O)—O—$CH_2$—$CH_3$, C—O—$CH_3$, C(O)—O—$CH_3$, C(O)—O—$CH_2$—$CH_3$, C—O—$CH_2$—$CH_2$—$CH_3$, C(O)—$CH_2$—$CH_2$—$CH_3$, C(O)—O—$CH_2$—$CH_3$, or;

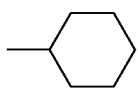

$E_{39}$ is $CH_3$, $CH_2—CH_3$, $CH_2$, $N=O$, $OH$, $OOH$, $NH_2$, $O—CH_3$, $O—NH_2$, $CH_2—N=O$, $CH_2—CH_3$, $N(H)OH$, $C(O)—O—CH_2—CH_3$, $C—O—CH_3$, $C(O)—O—CH_3$, $C(O)—O—CH_2—CH_2—CH_3$, $C—O—CH_2—CH_2—CH_3$, $C(O)—CH_2—CH_2—CH_3$, or $C(O)—O—CH_2—CH_3$;

$E_{40}$ is $CH_3$, $CH_2—CH_3$, $CH_2.N=O$, $OH$, $OOH$, $NH_2$, $O—CH_3$, $O—NH_2$, $CH_2—N=O$, $CH_2—CH_3$, $N(H)OH$, $C(O)—O—CH_2—CH_3$, $C—O—CH_3$, $C(O)—O—CH_3$, $C(O)—O—CH_2—CH_2—CH_3$, $C—O—CH_2—CH_2—CH_3$, $C(O)—CH_2—CH_2—CH_3$, or $C(O)—O—CH_2—CH_3$;

$E_{42}$, $E_{43}$, $E_{44}$, $E_{45}$, and $E_{46}$, are each independently H,

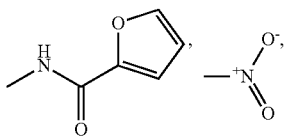

OH, Br, Cl, F, I, or $CH_3$;

$D_2$ is

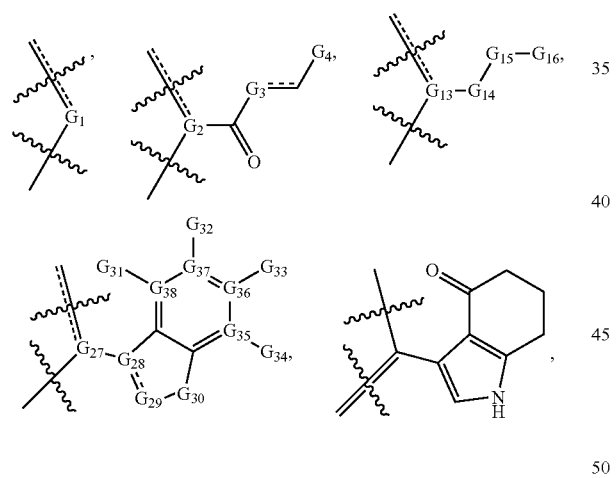

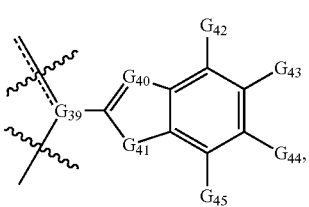

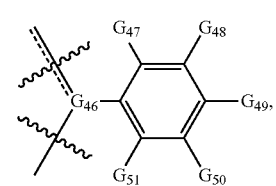

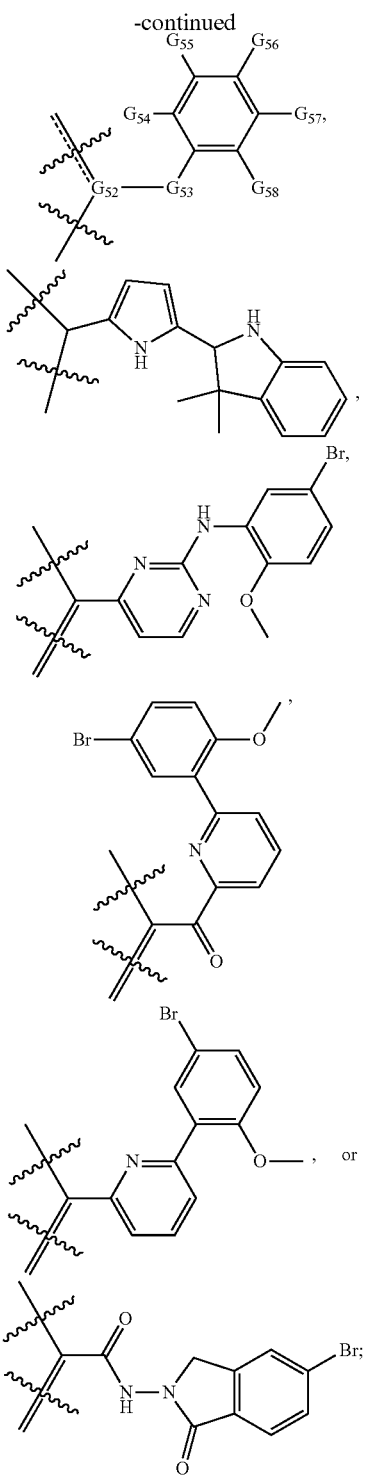

$G_1$ is CH, N, $CCH_3$, $CH_2$,

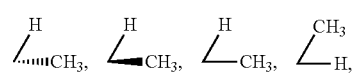

O, S, or NH;
$G_2$ is C, CH, or N;
$G_3$ is CH,

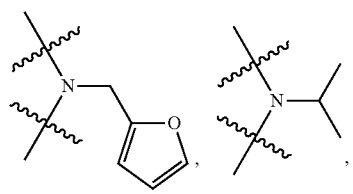, 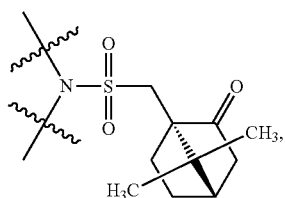,

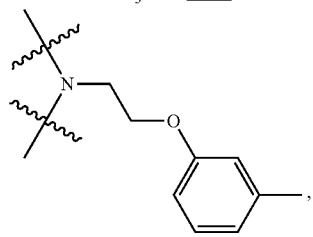

$CH_2$, or N;

$G_4$ is

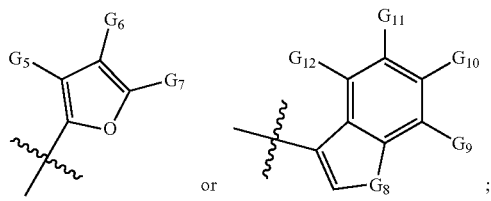

or NH;

$G_{31}$, $G_{32}$, and $G_{33}$, are each independently H, OH, $NH_2$, Br, Cl, F, I $G_5$, $G_6$, and $G_7$, are each independently H, OH, Br, Cl, F, I, or $CH_3$;

$G_8$ is NH, $CH_2$, O, or S;

$G_9$, $G_{10}$, $G_{11}$, and $G_{12}$, are each independently H, OH, Br, Cl, F, I, or $CH_3$;

$G_{13}$ is C, CH, or N;

$G_{14}$ is C=O, $CH_2$, or NH;

$G_{15}$ is C=O, $CH_2$, or NH;

$G_{16}$ is

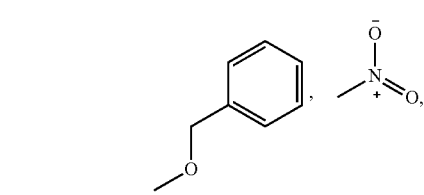

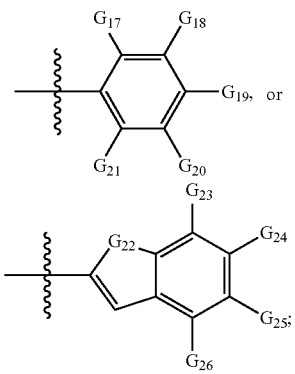

$OCH_3$,

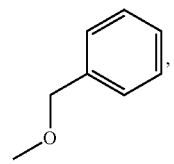

$CH_3$, $CH_2OH$, or absent when $G_{36}$, $G_{37}$, or $G_{38}$ is N;

$G_{34}$, is H, OH, $NH_2$, $G_{17}$, $G_{18}$, $G_{19}$, $G_{20}$, and $G_{21}$, are each independently H, OH, Br, Cl, F, I, or $CH_3$, provided that if $G_{17}$ is OH, then one or more of $G_{18}$, $G_{19}$, $G_{20}$, and $G_{21}$ are selected from OH, Br, Cl, F, I, or $CH_3$;

$G_{22}$ is NH, $CH_2$, O, or S;

$G_{23}$, $G_{24}$, $G_{25}$, and $G_{26}$, are each independently H, OH, Br, Cl, F, I, or $CH_3$;

$G_{27}$ is C, CH, $CCH_3$, $CC(O)OCH_2CH_3$, or N;

$G_{28}$ is C, CH, or N;

$G_{29}$ is CH, $CH_2$, C=O, $CCH_3$, or N;

where ⁓ is either a single or a double bond between $G_{28}$ and $G_{29}$;

$G_{30}$ is $CH_2$, N—N=O, $NCH_3$, $NCH_2CH_2OH$, CH—N=O, $CHCH_3$, $CHCH_2CH_2OH$, S, O, $OCH_3$, $CH_3$, $CH_2OH$, I or absent when $G_{35}$ is N;

$G_{35}$, $G_{36}$, $G_{37}$, and $G_{38}$, are each independently C or N;

$G_{39}$ is C, CH, or N;

$G_{40}$ is CH, or N;

$G_{41}$ is NH, S, O, or $CH_2$;

$G_{42}$, $G_{43}$, $G_{44}$, and $G_{45}$, are each independently H, OH, Br, Cl, F, I, or $CH_3$;

$G_{46}$ is C, CH, or N;

$G_{47}$, $G_{48}$, $G_{50}$, and $G_{51}$, are each independently H, OH, Br, Cl, F, I, or $CH_3$;

$G_{49}$ is OH, Br, Cl, F, I or $CH_3$;

$G_{52}$ is C, CH, or N;

$G_{53}$ is $CH_2$, NH, S, or O;

$G_{54}$, $G_{55}$, $G_{56}$, $G_{57}$, and $G_{58}$, are each independently H, OH, Br, Cl, F, I, or $CH_3$;

D₃ may be
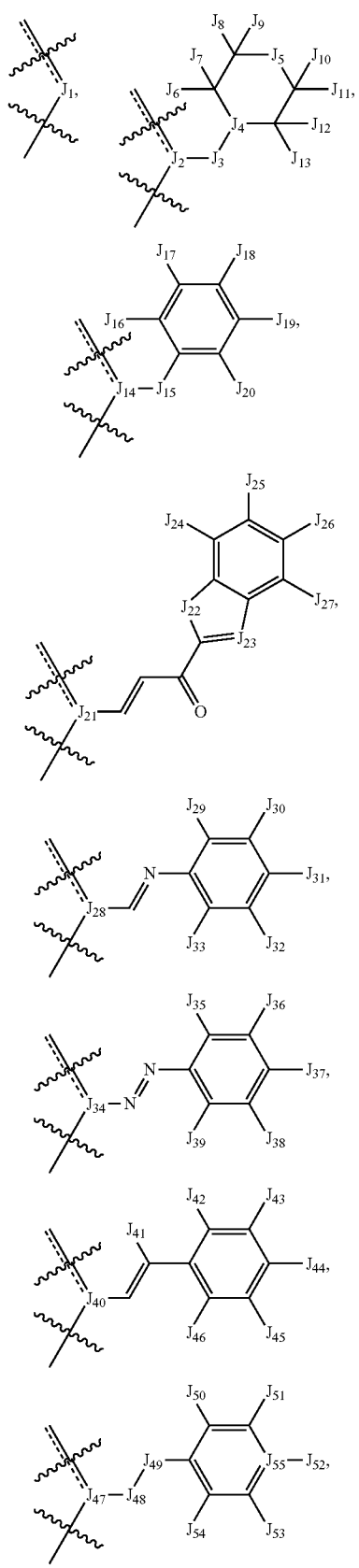
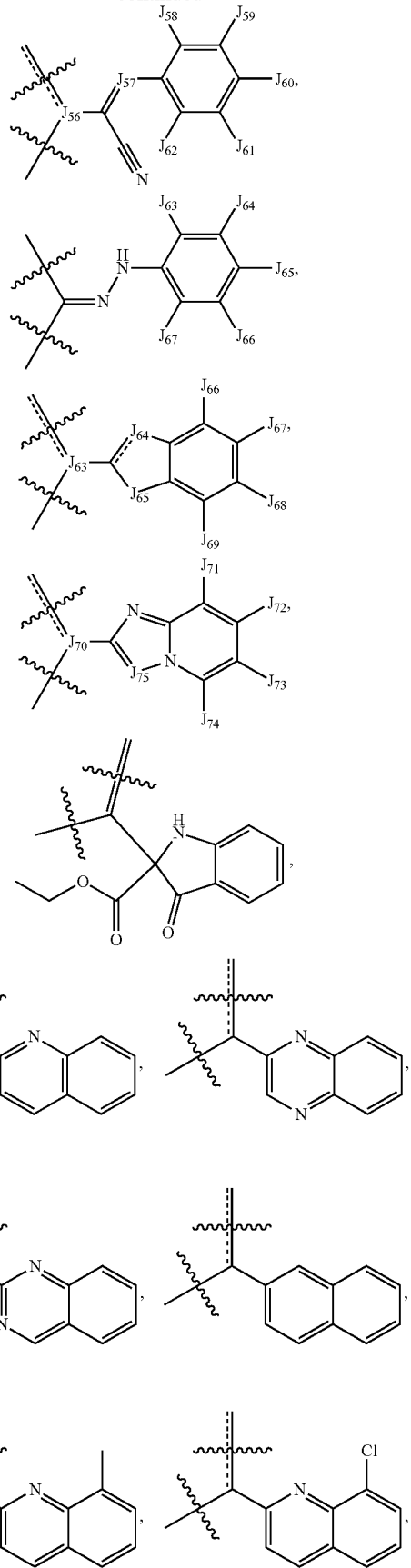

-continued
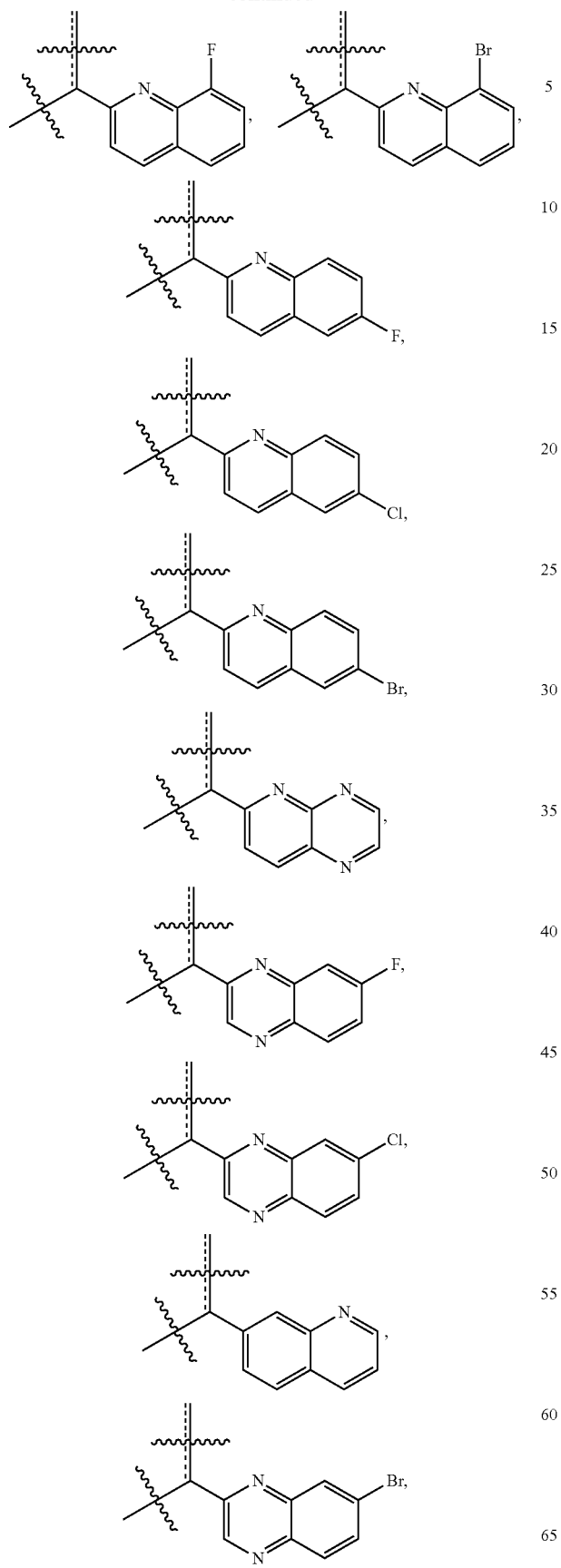
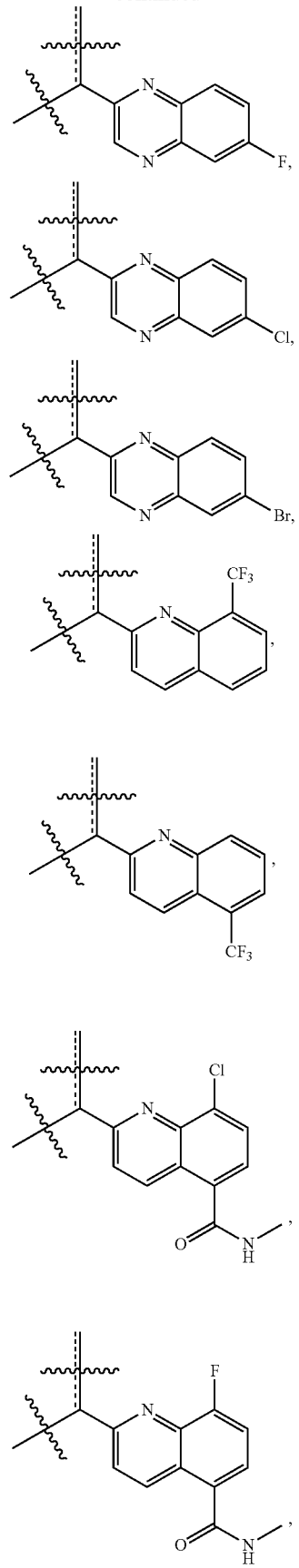

-continued
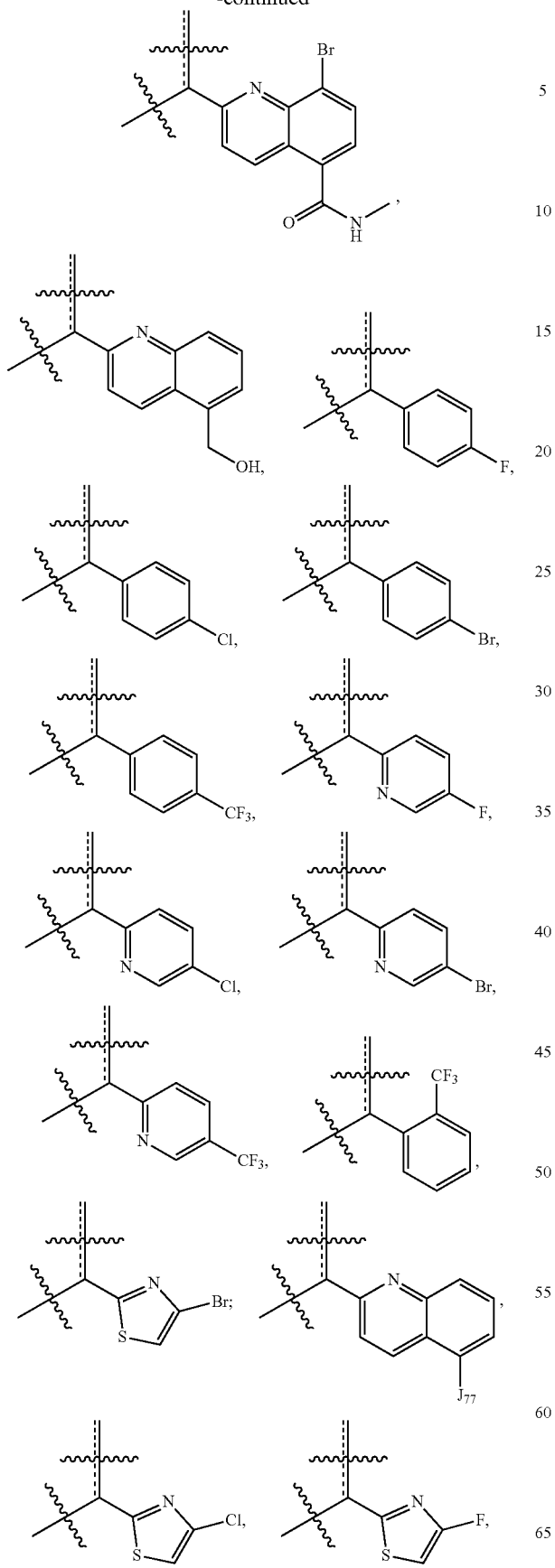
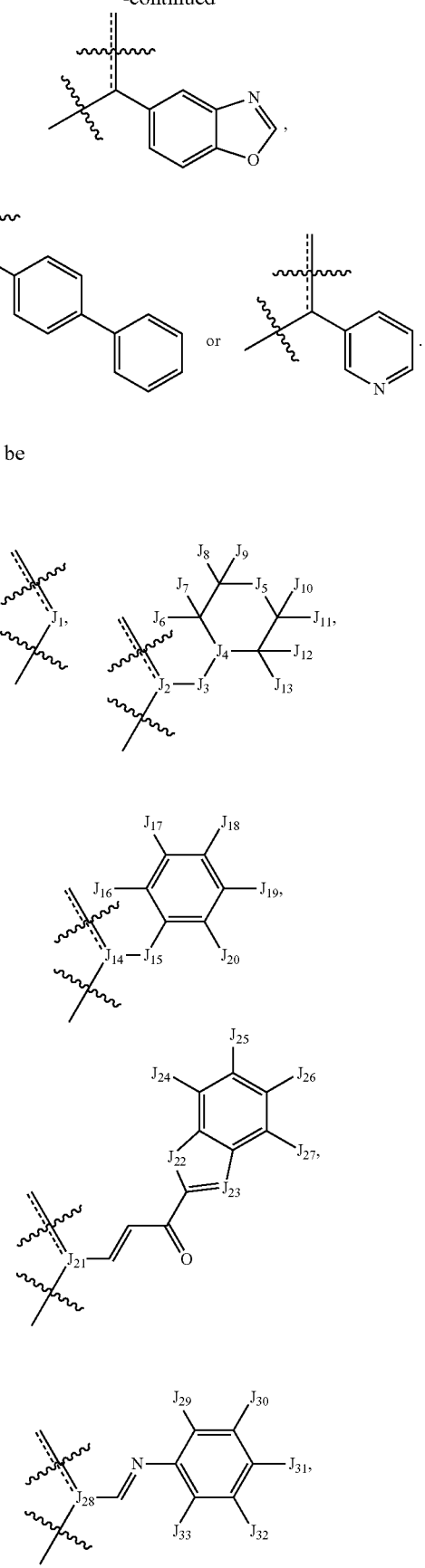
$D_3$ may be

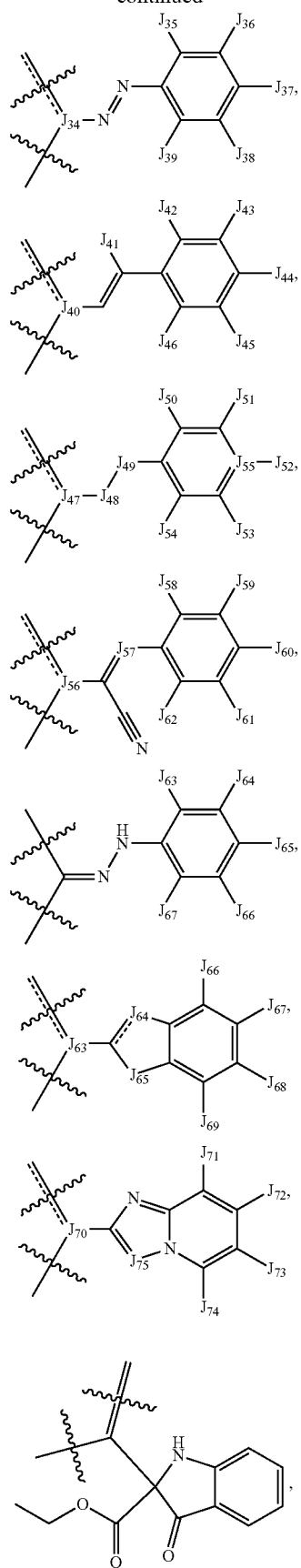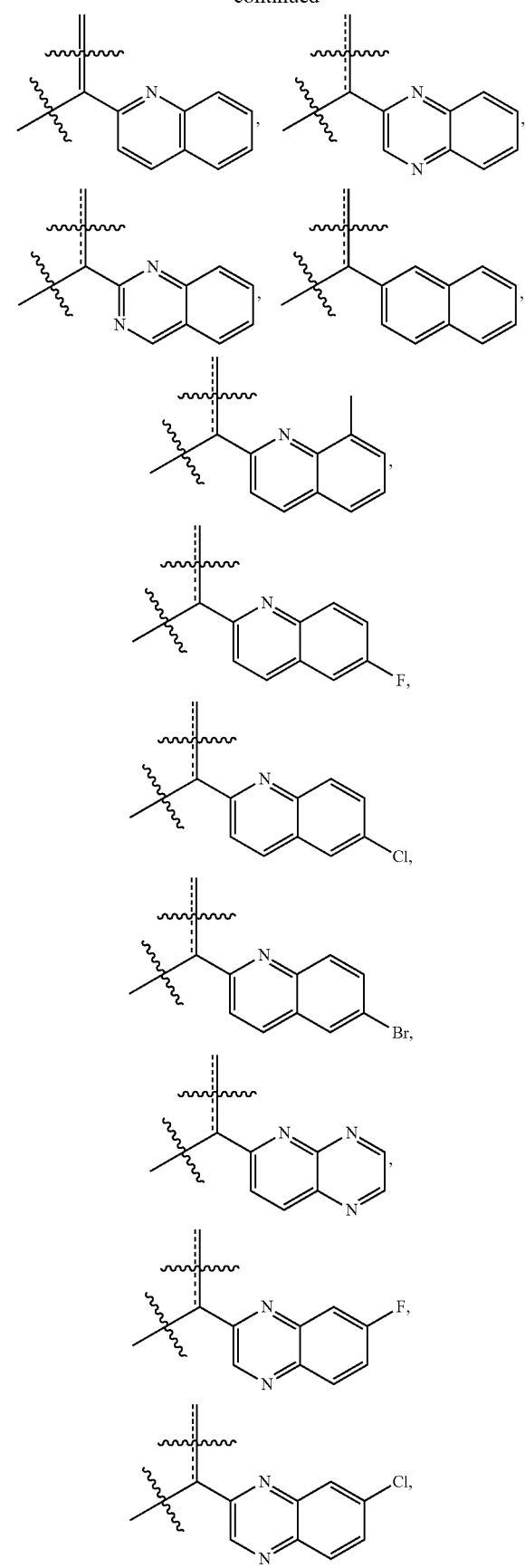

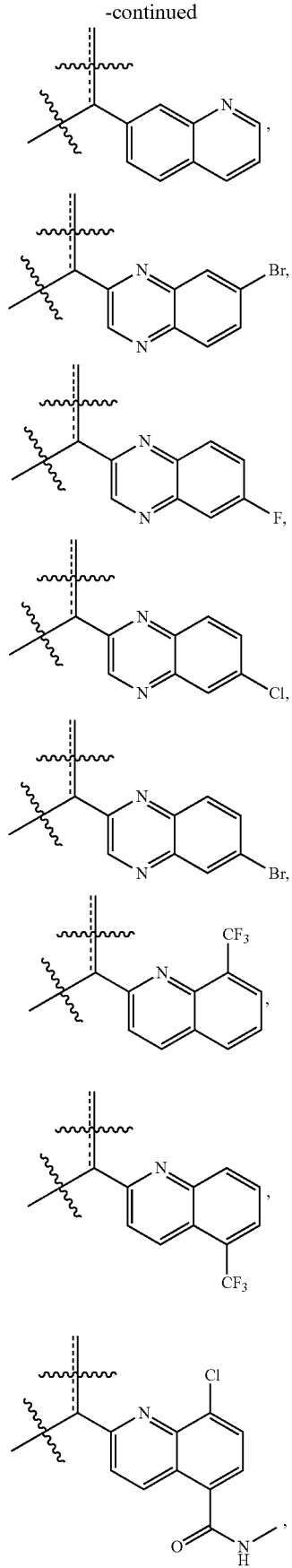
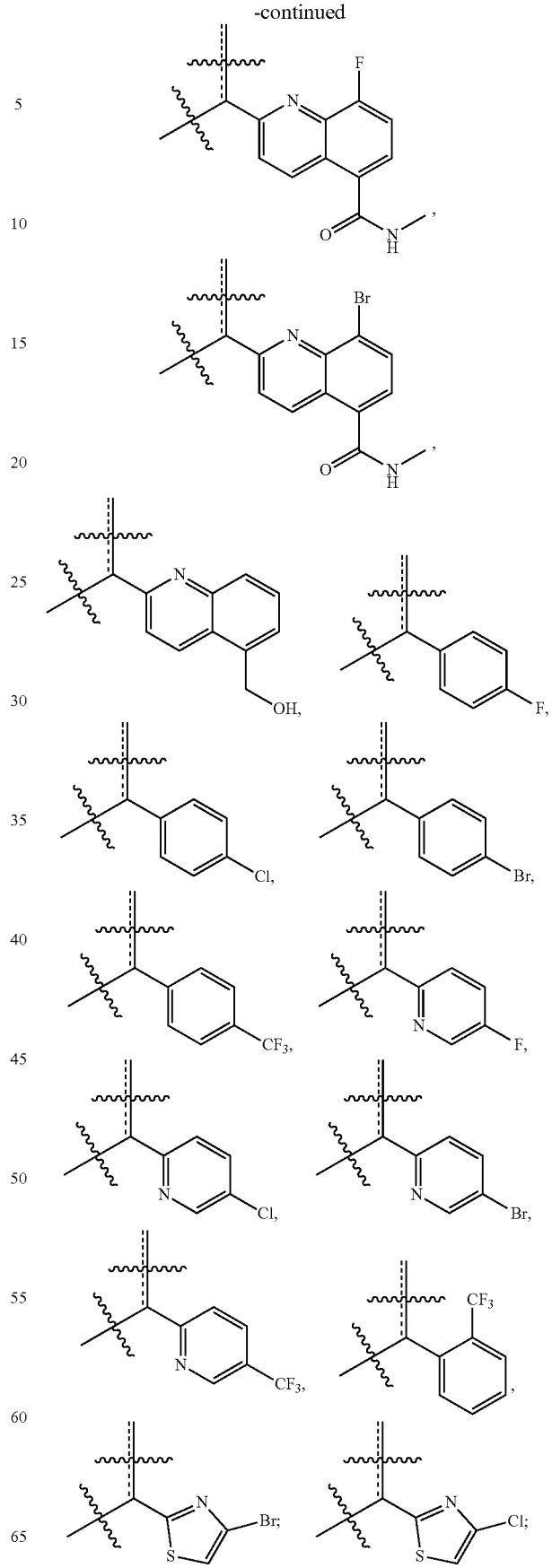

-continued

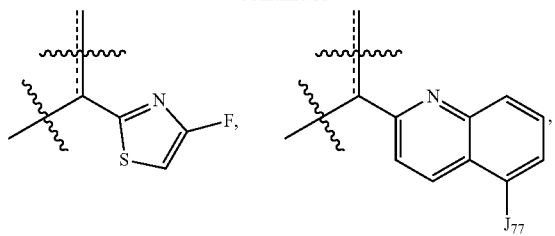

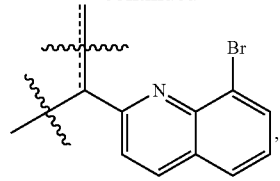

provided $A_1$ is $CH_3$, $A_2$ is F, $A_3$ is H and $A_4$ is H.
Alternatively, $D_3$ may be

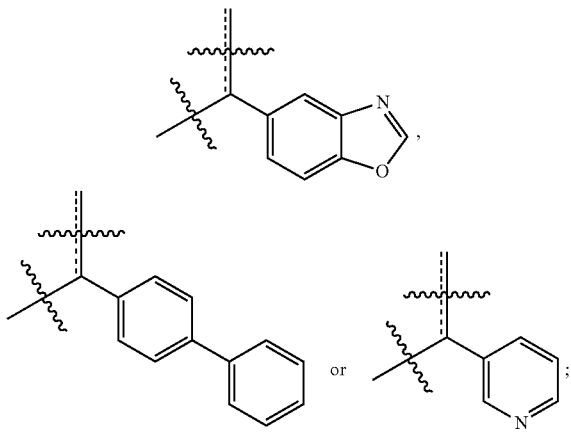

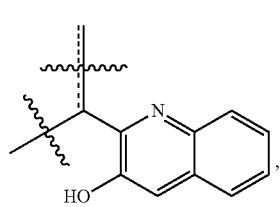

provided that at least one of $A_1$, $A_3$ or $A_4$ is F, Cl or Br and $A_2$ is H, $CH_3$, $NH_2$, OH or $OCH_3$.
Alternatively, $D_3$ may be Alternatively, $D_3$ may be

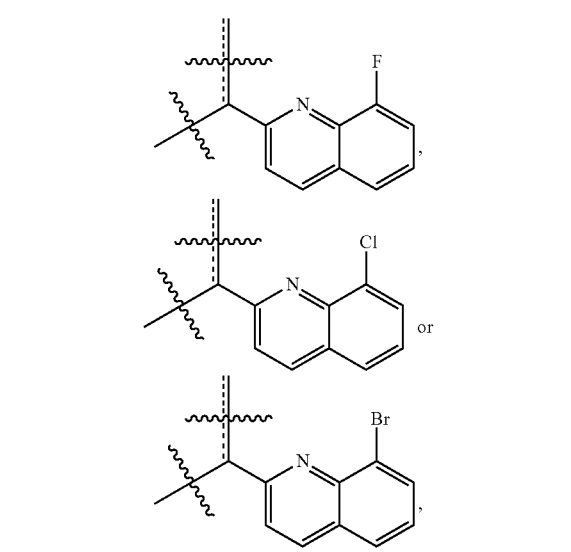

provided that $A_1$ is H, $CH_3$, F, Cl or Br and $A_2$ is H, $CH_3$, $NH_2$, OH or $OCH_3$, $A_3$ is H, F, Cl or Br and $A_4$ is H, F, Cl or Br.
Alternatively, $D_3$ may be,

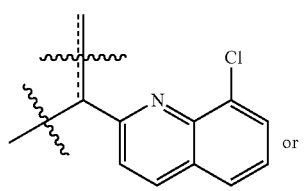

provided that at least one of $A_2$ or $A_3$ is F, Cl or Br.
Alternatively, $D_3$ may be

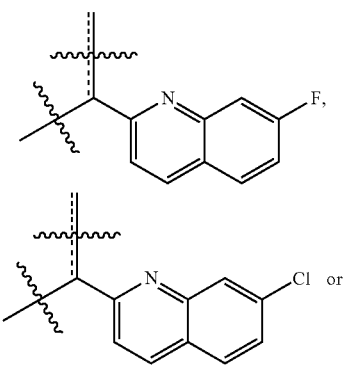

-continued

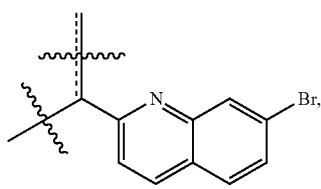

provided that A₄ is H.
Alternatively, D₃ may be

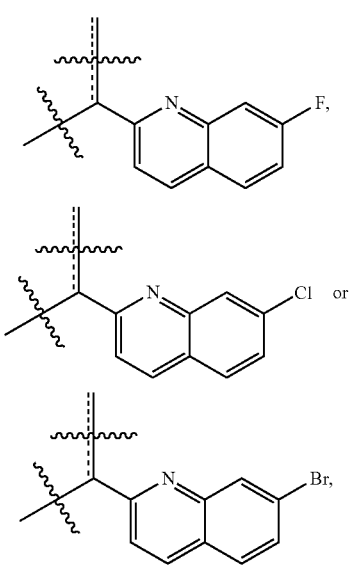

provided that A₁ is CH₃.
Alternatively, D₃ may be

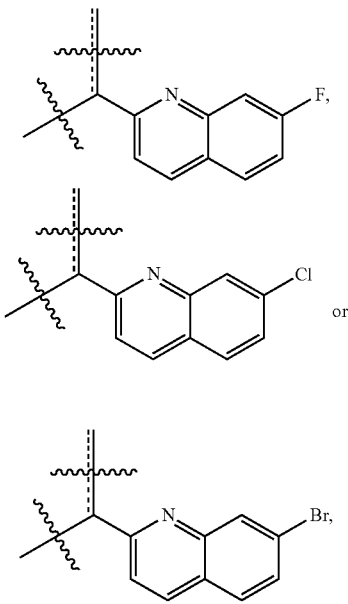

provided that at least one of A₁ or A₂ is F, Cl, Br or CH₃.

Alternatively, D₃ may be

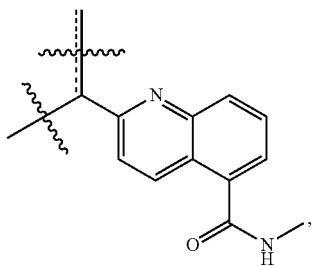

provided that if A₂ is F, Cl or Br then A₃ is F, Cl or Br.
Alternatively, D₃ may be

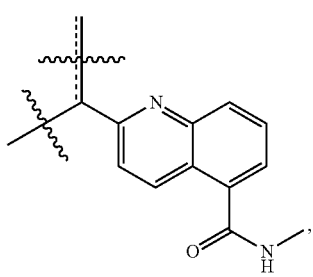

provided that if A₂ is F, Cl or Br then A₁ is H, OH, CH₂OH,

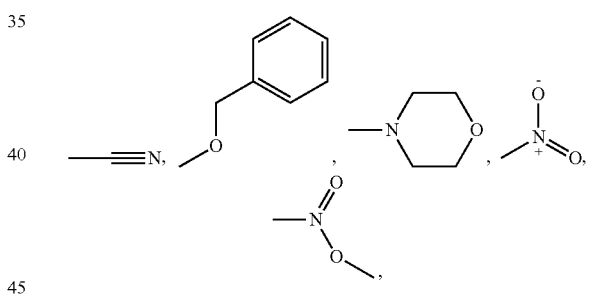

CF₃, F, Cl or Br, A₃ is H, Br, NH₂, F, Cl, OCH₃,

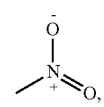

CF₃, I, OH,

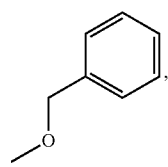

or =O and A₄ is H, Br, Cl, F, I, CH₃, NH₂, OH, OCH₃,

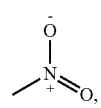

CF₃,

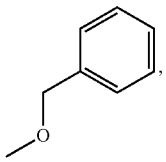

or =O.
Alternatively, D₃ may be

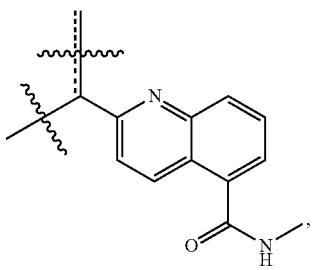

provided that if A₂ is F, Cl or Br then A₁ is not CH₃.
Alternatively, D₃ may be

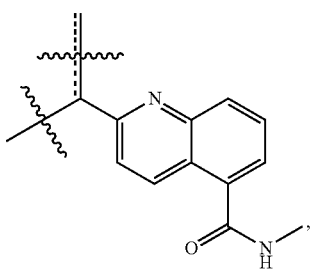

provided that if A₂ is F, Cl or Br then A₁ is not CH₃.
Alternatively, D₃ may be

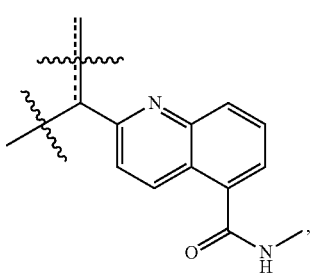

provided that if A₂ is F, Cl or Br then at least one or both of A₁ and A₃ are F, Cl or Br.

Alternatively, D₃ may be

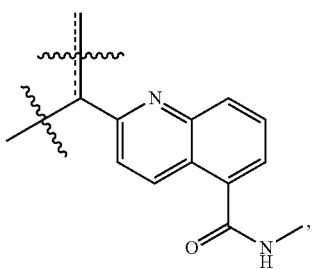

provided that if A₁ is CH₃ then A₂ is not F, Br or Cl.
Alternatively, D₃ may be

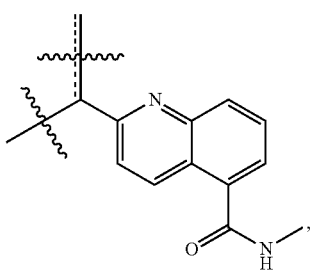

provided that if A₁ is CH₃ then A₂ is H.
Alternatively, D₃ may be

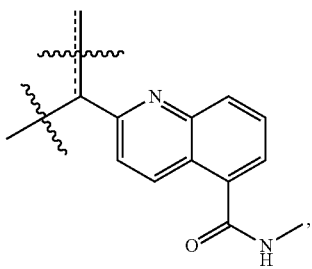

provided that A₁ is F, Br or Cl.
Alternatively, D₃ is

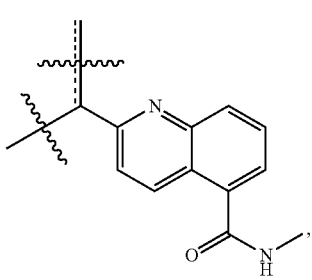

provided that A₁-A₄ are all H.

Alternatively, D₃ may be

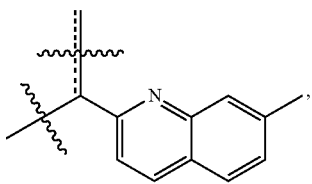

provided that if A₄ is CH₃, then A₁ is CH₂OH,

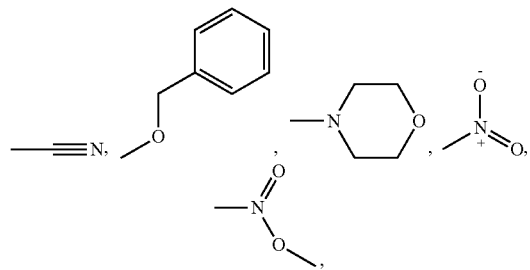

CF₃, F, Cl or Br, A₂ is Br, NH₂, F, Cl,

CF₃, I or

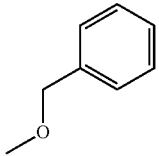

and A₃ is Br, Cl, F, I, CH₃, NH₂,

CF₃,

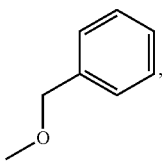

or ═O.

Alternatively, D₃ may be

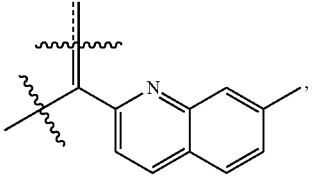

provided that A₄ is H, and A₁₋₄ are independently selected from Br, Cl, F, I, CH₃, NH₂,

CF₃,

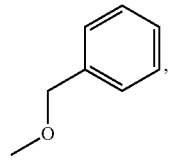

or ═O.

Alternatively, D₃ may be

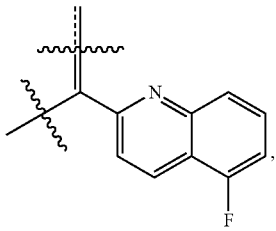

provided that A₂ is F and A₃ is F.

Alternatively, D₃ may be

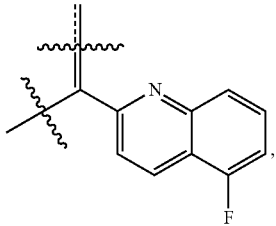

provided that A₂ is F, Cl or Br and A₃ is F, Cl or Br.

Alternatively, $D_3$ may be

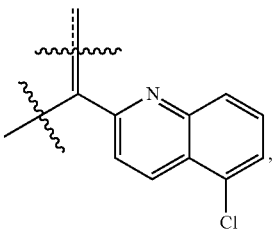, provided that $A_1$ is F, $A_3$ is F and $A_4$ is F.

Alternatively, $D_3$ may be

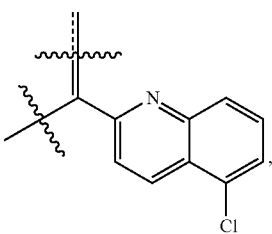, provided that $A_1$ is F, Cl or Br, $A_3$ is F, Cl or Br and $A_4$ is F, Cl or Br.

Alternatively, $D_3$ may be

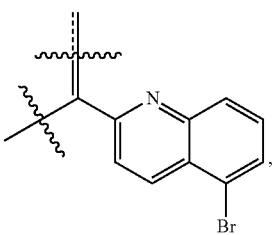, provided that $A_1$ is F, Cl or Br, $A_3$ is F, Cl or Br and $A_4$ is F, Cl or Br.

Alternatively, $D_3$ is

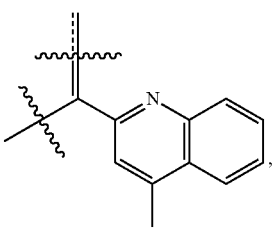, provided that $A_2$ is H, if $A_1$ is $CH_3$.

$J_1$ is CH, N, $CCH_3$, $CH_2$, $NCH_3$, $CN=O$, $C=O$,

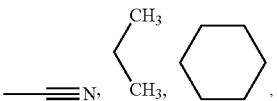

$N-CH_2-CH_2-CH_3$, $CH=O$, $N-N=O$,

$NCH_2C(O)OCH_2CH_3$, $N-CH_2-C(O)-O-CH_2-CH_3$, O, S, or NH.

$J_2$ is CH, C, or N.
$J_3$ is C=S, C=O, NH, or $CH_2$.
$J_4$ is CH or N;
$J_5$ is $CH_2$, NH, S or O;
$J_6$, $J_7$, $J_8$, $J_9$, $J_{10}$, $J_{11}$, $J_{12}$, and $J_{13}$ are each independently H, OH, Br, Cl, F, I, or $CH_3$;
$J_{14}$ is CH, C, or N;
$J_{15}$ is C=S, C=O, NH, or $CH_2$;
$J_{16}$, $J_{17}$, $J_{18}$, $J_{19}$, and $J_{20}$ are each independently H, OH, Br, Cl, F, I, or $CH_3$;
$J_{21}$ is CH, C, or N;
$J_{22}$ is $CH_2$, or NH;
$J_{23}$ is CH, or N;
$J_{24}$, $J_{25}$, $J_{26}$, and $J_{27}$ are each independently H, OH, Br, Cl, F, I, or $CH_3$;
$J_{28}$ is CH, C, or N;
$J_{31}$ is H, OH, Br, F, 1, $C(O)NH_2$, $OCH_3$, or $CH_3$;
$J_{29}$, $J_{30}$, $J_{32}$, and $J_{33}$ are each independently H, $OCH_3$, OH, Br, Cl, F, I, $C(O)NH_2$, $CF_3$, $NH_2$, or $CH_3$;
$J_{34}$ is CH, C, or N;
$J_{35}$, $J_{36}$, $J_{37}$, $J_{38}$, and $J_{39}$ are each independently H, $OCH_3$, OH, Br, Cl, F, I, $C(O)NH_2$, $CF_3$, $NH_2$, or $CH_3$;
$J_{40}$ is CH, C, or N;
$J_{41}$ is H, OH, Br, Cl, F, I, $NH_2$, or $CH_3$, or $J_{42}$, $J_{43}$, $J_{44}$, $J_{45}$, and $J_{46}$ are each independently H, OH, Br, Cl, F, I, $NH_2$, or $CH_3$;

$J_{47}$ is CH, C, or N;

$J_{48}$ is S, $CH_2$, C=O, O, or NH;

$J_{49}$ is $CH_2$, C=O, S, O, or NH;

$J_{55}$ is C, or N;

$J_{50}$, $J_{51}$, $J_{52}$, $J_{53}$, and $J_{54}$, are each independently H, OH, $NH_2$, Br, Cl, F, I,

[nitro group structure]

$OCH_3$, $CF_3$, $CH_3$ or is absent when $J_{50}$, $J_{51}$, $J_{52}$, $J_{53}$, or $J_{54}$ is N;

$J_{56}$ is CH, C, or N;

$J_{57}$ is N, or CH;

$J_{58}$, $J_{59}$, $J_{60}$, $J_{61}$, and $J_{62}$, are each independently H, OH, $NH_2$, Br, Cl, F, I,

[nitro group structure]

$OCH_3$, $CF_3$, or $CH_3$;

$J_{63}$, $J_{64}$, $J_{65}$, $J_{66}$, and $J_{67}$, are each independently H, OH, $NH_2$, Br, Cl, F, I,

[nitro group structure]

$OCH_3$, $CF_3$, or $CH_3$;

$J_{63}$ is CH, C, or N;

$J_{64}$ is CH, $CH_2$, NH, CN=O, C=O, O, $CCH_3$, $NCH_3$, $NC(O)OCH_3$,

[substituent group structures showing isopropyl, various methyl stereochemistry variants, cyclohexyl, and nitrobenzyl-N group]

or N;

$J_{65}$ is $CH_2$, NH, C=O, O, S, NN=O, $NCH_3$, NC(O)$OCH_3$,

[substituent group structures showing isopropyl, methyl stereochemistry variants, cyclohexyl, or nitrobenzyl-N group]

$J_{66}$, $J_{67}$, $J_{68}$, and $J_{69}$ may each independently be H, $OCH_3$, OH, Br, Cl, F, I, C(O)$NH_2$, $CF_3$,

[nitro group structure]

$NH_2$, or $CH_3$;

$J_{70}$ is CH, C, or N;

$J_{71}$, $J_{72}$, $J_{73}$, and $J_{74}$ may each independently be H, $OCH_3$, OH, Br, Cl, F, I, C(O)$NH_2$, $CF_3$,

[nitro group structure]

$NH_2$, or $CH_3$;

$J_{75}$ may be CH, or N;

$J_{77}$ is

[two thiazole structures] or ;

and provided that one or more of $D_1$-$D_3$ links to at least one ring in addition to the bicyclic structure of Formula I. For example, compounds 13720-13726, do not link to at least one ring in addition to the bicyclic structure of Formula I, whereas, for example, 13566 and 13742 do link to at least one ring in addition to the bicyclic structure of Formula I.

In accordance with a further aspect, there is provided a use of a compound having the structure of Formula I as described herein for modulating AR activity.

In accordance with a further aspect, there is provided a use of a compound having the structure of Formula I as described herein for the manufacture of a medicament for modulating AR activity.

33

$A_1$ may be H, $CH_3$, $CH_2CH_3$, OH, $CH_2OH$, $OCH_3$,

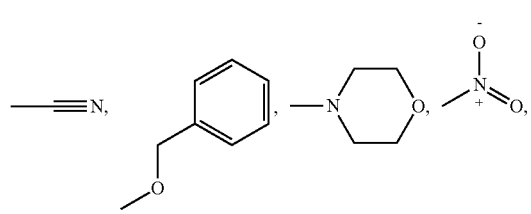

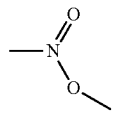

or $CF_3$.

Alternatively $A_1$ may be F, Br or Cl, provided that $D_3$ is not

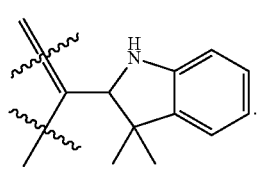 [SMILES: *C(=*)C1Nc2ccccc2C1(C)C]

$A_1$ may be H, $CH_3$, OH, $CH_2OH$, $OCH_3$,

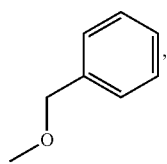

or $CF_3$. $A_1$ may be H, $CH_3$, OH, $CH_2OH$, $OCH_3$, or

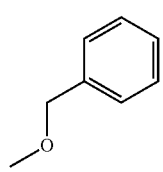

$A_1$ may be H, $CH_3$, OH, $CH_2OH$, or $OCH_3$. $A_1$ may be H, $CH_3$, OH, $CH_2OH$, or

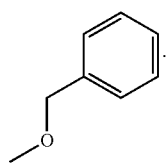

34

$A_2$ may be H, Br, OH, Cl, F, I, $CH_3$, $NH_2$, $OCH_3$,

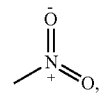

$CF_3$,

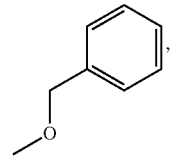

or =O. $A_2$ may be H, Br, OH, Cl, or

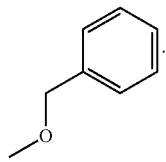

$A_2$ may be H, Br, OH, Cl, F, I, $CH_3$, $NH_2$, $OCH_3$ or =O. $A_2$ may be H, Br, OH, Cl, F, I, $CH_3$, $NH_2$ or $OCH_3$. $A_2$ may be H, Br, OH, or Cl. $A_2$ may be H, Br, OH, Cl, or F.

$A_3$ may be H, Br, $NH_2$, F, Cl, $OCH_3$, $CH_3$,

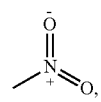

$CF_3$, I, OH,

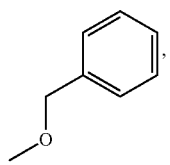

or =O. $A_3$ may be H, Br, $NH_2$, F, Cl, $OCH_3$, $CH_3$,

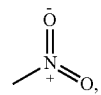

or $CF_3$. $A_3$ may be H, Br, $NH_2$, F, Cl, $OCH_3$, $CH_3$, OH or =O. $A_3$ may be H, Br, $NH_2$, F, Cl, $OCH_3$, $CH_3$,

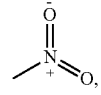

CF$_3$, or =O. A$_3$ may be H, Br, NH$_2$, F, Cl, OCH$_3$, CH$_3$,

CF$_3$, OH or =O. A$_3$ may be H, Br, NH$_2$, F, Cl, OCH$_3$, CH$_3$, OH or =O. A$_3$ may be H, Br, NH$_2$, F, Cl, OCH$_3$, or CH$_3$. A$_4$ may be H, Br, Cl, F, I, CH$_3$, NH$_2$, OH, OCH$_3$,

CF$_3$,

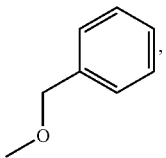

or =O. A$_4$ may be H, Br. A$_4$ may be H, Br, Cl, F, I, CH$_3$, NH$_2$, OH, OCH$_3$ or =O. A$_4$ may be H, Br, Cl, F, CH$_3$, NH$_2$, OH, OCH$_3$, or =O. A$_4$ may be H, Br, Cl, F, I, CH$_3$, NH$_2$, OH or OCH$_3$. A$_4$ may be H, Br, Cl, CH$_3$, NH$_2$, OH, OCH$_3$

CF$_3$,

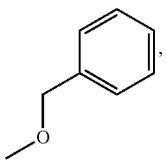

or =O.

D$_1$ may be

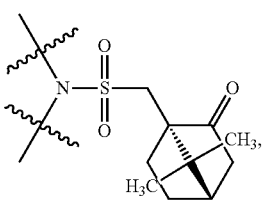

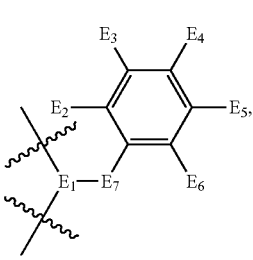

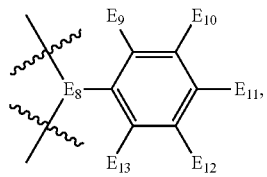

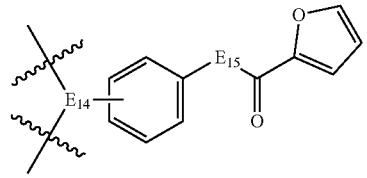

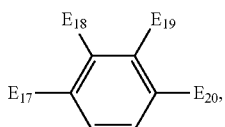

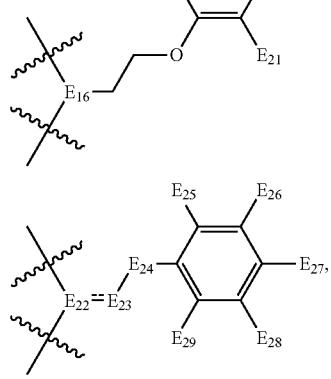

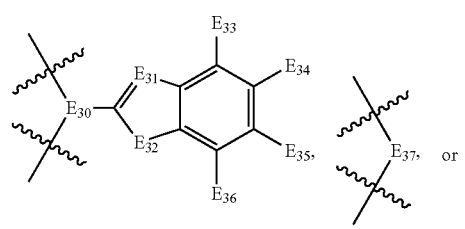

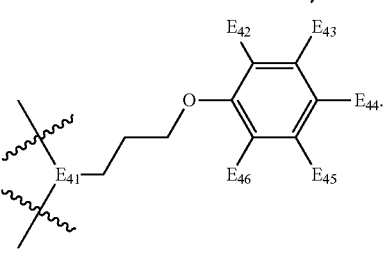

D$_1$ may each

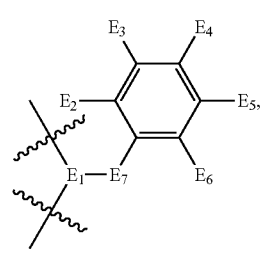

-continued

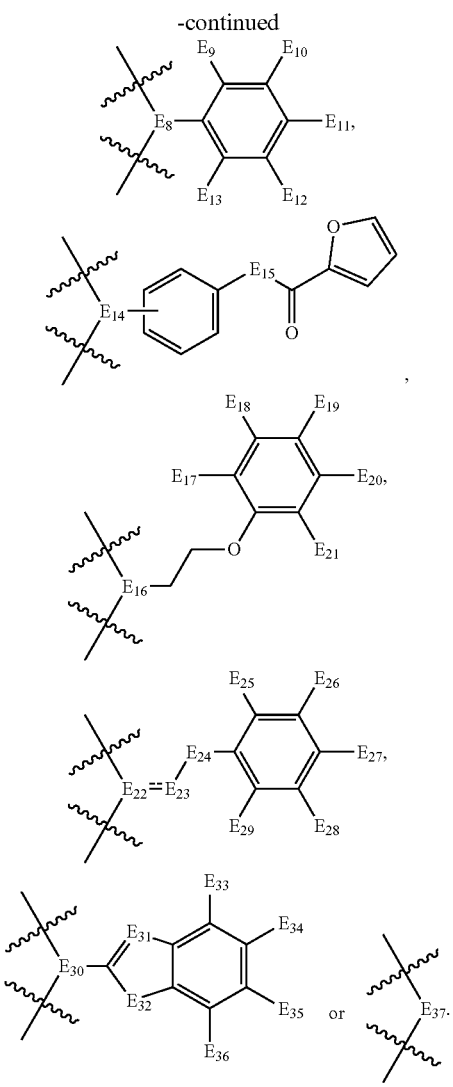

$E_1$, $E_8$, $E_{14}$, $E_{16}$, $E_{22}$, $E_{30}$, and $E_{41}$, may each independently be CH or N. $E_1$, $E_8$, $E_{14}$, $E_{16}$, $E_{22}$, $E_{30}$, and $E_{41}$, may be N. $E_1$, $E_8$, $E_{14}$, $E_{16}$, $E_{22}$, $E_{30}$, and $E_{41}$, may be CH.

$E_2$, $E_3$, $E_4$, $E_5$, and $E_6$, may each independently be H, OH,

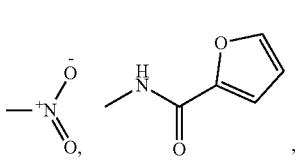

Br, Cl, F, I, or $CH_3$. $E_2$, $E_3$, $E_4$, $E_5$, and $E_6$, may each independently be H, OH, or

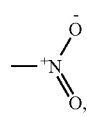

$E_2$, $E_3$, $E_4$, $E_5$, and $E_6$, may each independently be H or OH.

$E_7$ may be $CH_2$, O, NH, or C=O. $E_7$ may be $CH_2$. $E_7$ may be $CH_2$, O or C=O. $E_7$ may be $CH_2$ or O. $E_7$ may be $CH_2$, O, NH or C=O. $E_7$ may be $CH_2$, NH or C=O.

$E_9$, $E_{10}$, $E_{11}$, $E_{12}$, and $E_{13}$, may each independently be H,

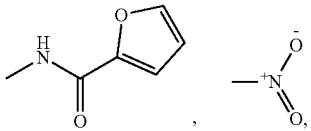

OH, Br, Cl, F, I or $CH_3$. $E_9$, $E_{10}$, $E_{11}$, $E_{12}$, and $E_{13}$, may each independently be H or

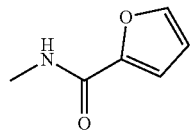

$E_9$, $E_{10}$, $E_{11}$, $E_{12}$, and $E_{13}$, may each independently be H, OH, Br, Cl, F, I or $CH_3$. $E_9$, $E_{10}$, $E_{11}$, $E_{12}$, and $E_{13}$, may each independently be H,

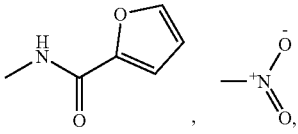

OH, Br, Cl, F, or $CH_3$. $E_9$, $E_{10}$, $E_{11}$, $E_{12}$, and $E_{13}$, may each independently be H, OH, or $CH_3$. $E_9$, $E_{10}$, $E_{11}$, $E_{12}$, and $E_{13}$, may each independently be H or $CH_3$.

$E_{15}$ may be $CH_2$, O, NH or C=O. $E_{15}$ may be NH. $E_{15}$ may be $CH_2$, O or NH. $E_{15}$ may be O, NH, or C=O. $E_{15}$ may be NH or C=O.

$E_{17}$, $E_{18}$, $E_{19}$, $E_{20}$, and $E_{21}$, may each independently be H, OH, Br, Cl, F, I, or $CH_3$. $E_{17}$, $E_{18}$, $E_{19}$, $E_{20}$, and $E_{21}$, may each independently be H, OH, Br, Cl, F, I or $CH_3$. $E_{17}$, $E_{18}$, $E_{19}$, $E_{20}$, and $E_{21}$, may each independently be H, Cl, or $CH_3$. $E_{17}$, $E_{18}$, $E_{19}$, $E_{20}$, and $E_{21}$, may each independently be H, OH, Br, Cl, F or $CH_3$.

$E_{23}$ may be CH, $CH_2$, O, N, NH, or C=O. $E_{23}$ may be N. $E_{23}$ may be O, N, NH, or C=O. $E_{23}$ may be CH, $CH_2$, O, N or NH. $E_{23}$ may be N or NH.

$E_{24}$ may be $CH_2$, O, NH, or C=O. $E_{24}$ may be NH. $E_{24}$ may be $CH_2$, NH, or C=O. $E_{24}$ may be O or NH. $E_{24}$ may be $CH_2$, O or NH. $E_{24}$ may be NH, or C=O. $E_{24}$ may be $CH_2$ or NH.

$E_{25}$, $E_{26}$, $E_{27}$, $E_{28}$, and $E_{29}$, may each independently be H,

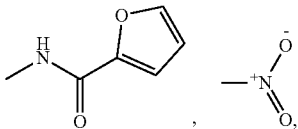

OH, Br, Cl, F, I, or $CH_3$. $E_{25}$, $E_{26}$, $E_{27}$, $E_{28}$, and $E_{29}$, may each independently be H, OH, Br, Cl, F, I or $CH_3$. $E_{25}$, $E_{26}$, $E_{27}$, $E_{28}$, and $E_{29}$, may each independently be H or Cl. $E_{25}$, $E_{26}$, $E_{27}$, $E_{28}$, and $E_{29}$, may each independently be H, OH, Br, Cl, F, or $CH_3$. $E_{25}$, $E_{26}$, $E_{27}$, $E_{28}$, and $E_{29}$, may each independently be H, OH, Cl or $CH_3$. $E_{25}$, $E_{26}$, $E_{27}$, $E_{28}$, and $E_{29}$, may each independently be H or $CH_3$. $E_{25}$, $E_{26}$, $E_{27}$, $E_{28}$, and $E_{29}$, may each independently be H, Br, Cl or $CH_3$.
$E_{31}$ may be N, CH, CBr, CCl, CF, COH, C=O, or $CCH_3$. $E_{31}$ may be N. $E_{31}$ may be N, CH, COH, C=O, or $CCH_3$. $E_{31}$ may be N, CH, CCl, COH, C=O, or $CCH_3$. $E_{31}$ may be N, CH, COH or $CCH_3$.
$E_{32}$ may be NH, $CH_2$, O, or S. $E_{32}$ may be NH or O. $E_{32}$ may be NH, $CH_2$ or O. $E_{32}$ may be NH. $E_{32}$ may be O. $E_{32}$ may be NH, O or S.
$E_{33}$, $E_{34}$, $E_{35}$, and $E_{36}$, may each independently be H, OH,

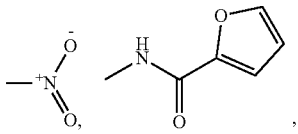

Br, Cl, F, I, or $CH_3$. $E_{33}$, $E_{34}$, $E_{35}$, and $E_{36}$, may each independently be H, OH, Br, Cl, F, I or $CH_3$. $E_{33}$, $E_{34}$, $E_{35}$, and $E_{36}$, may each independently be H, OH,

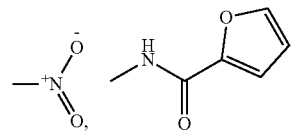

or $CH_3$. $E_{33}$, $E_{34}$, $E_{35}$, and $E_{36}$, may each independently be H, OH or $CH_3$.
$E_{37}$ may be S, O, NH, $CH_2$, $NCH_3$,

C=O, N—N=O, N—$CH_2$—$CH_2$—OH, N—$CH_2$—C(O)—O—$CH_2$—$CH_3$,

N-$E_{38}$, CH-$E_{39}$,

$E_{37}$ may be S, O, NH, $CH_2$, $NCH_3$,

C=O, N—N=O, N—$CH_2$—$CH_2$—OH, N—$CH_2$—C(O)—O—$CH_2$—$CH_3$ or

$E_{37}$ may be S, O, NH, $CH_2$, $NCH_3$,

C=O, N—N=O, N—$CH_2$—$CH_2$—OH, N—$CH_2$—C(O)—O—$CH_2$—$CH_3$,

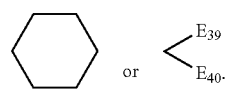

$E_{37}$ may be S, O, NH, $CH_2$, $NCH_3$,

C=O, N—N=O, N—$CH_2$—$CH_2$—OH, or N—$CH_2$—C(O)—O—$CH_2$—$CH_3$.
$E_{38}$ may be $NH_2$, O—$CH_3$, O—$NH_2$, $CH_2$—N=O, $CH_2$—$CH_3$, N(H)OH, C(O)—O—$CH_2$—$CH_3$, C—O—$CH_3$, C(O)—O—$CH_3$, C(O)—O—$CH_2$—$CH_2$—$CH_3$, C—O—$CH_2$—$CH_2$—$CH_3$, C(O)—$CH_2$—$CH_2$—$CH_3$, C(O)—O—$CH_2$—$CH_3$, or

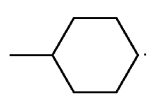

$E_{38}$ may be $NH_2$, O—$CH_3$ or O—$NH_2$. $E_{38}$ may be $NH_2$ or O—$CH_3$.
$E_{39}$ may be $CH_3$, $CH_2$—$CH_3$, $CH_2$.N=O, OH, OOH, $NH_2$, O—$CH_3$, O—$NH_2$, $CH_2$—N=O, $CH_2$—$CH_3$, N(H)OH, C(O)—O—$CH_2$—$CH_3$, C—O—$CH_3$, C(O)—O—$CH_3$, C(O)—O—$CH_2$—$CH_2$—$CH_3$, C—O—$CH_2$—$CH_2$—$CH_3$, C(O)—$CH_2$—$CH_2$—$CH_3$ or C(O)—O—$CH_2$—$CH_3$. $E_{39}$ may be $CH_3$, $CH_2$—$CH_3$, $CH_2$N=O, OH, OOH, $NH_2$, O—$CH_3$, O—$NH_2$, $CH_2$—N=O, or $CH_2$—$CH_3$. $E_{39}$ may be $CH_3$, $CH_2$—$CH_3$, OH, OOH, $NH_2$, O—$CH_3$, O—$NH_2$, C—O—$CH_3$ or C(O)—O—$CH_3$.
$E_{40}$ may be $CH_3$, $CH_2$—$CH_3$, $CH_2$.N=O, OH, OOH, $NH_2$, O—$CH_3$, O—$NH_2$, $CH_2$—N=O, $CH_2$—$CH_3$, N(H)OH, C(O)—O—$CH_2$—$CH_3$, C—O—$CH_3$, C(O)—O—$CH_3$, C(O)—O—$CH_2$—$CH_2$—$CH_3$, C—O—$CH_2$—$CH_2$—$CH_3$, C(O)—CH$_2$—CH$_2$—CH$_3$, or C(O)—O—CH$_2$—CH$_3$. E$_{40}$ may be CH$_3$, CH$_2$—CH$_3$, CH$_2$.N=O, OH, OOH, NH$_2$, O—CH$_3$ or O—NH$_2$.

E$_{42}$, E$_{43}$, E$_{44}$, E$_{45}$, and E$_{46}$, may each independently be H,

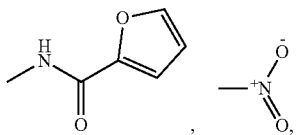

OH, Br, Cl, F, I or CH$_3$. E$_{42}$, E$_{43}$, E$_{44}$, E$_{45}$, and E$_{46}$, may each independently be H, OH, Cl, or CH$_3$. E$_{42}$, E$_{43}$, E$_{44}$, E$_{45}$, and E$_{46}$, may each independently be H or Cl. E$_{42}$, E$_{43}$, E$_{44}$, E$_{45}$, and E$_{46}$, may each independently be H, Cl, or CH$_3$. E$_{42}$, E$_{43}$, E$_{44}$, E$_{45}$, and E$_{46}$, may each independently be H, OH or Cl.

D$_2$ may be

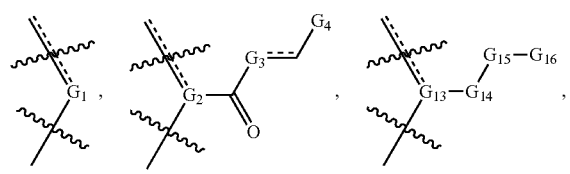

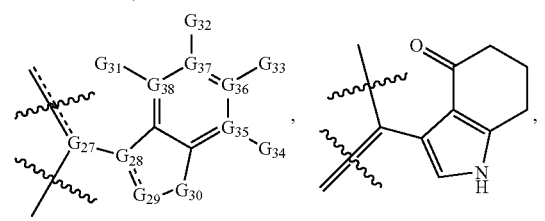

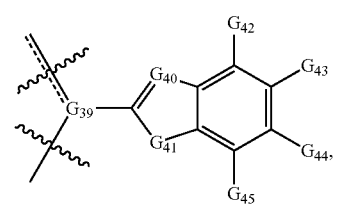

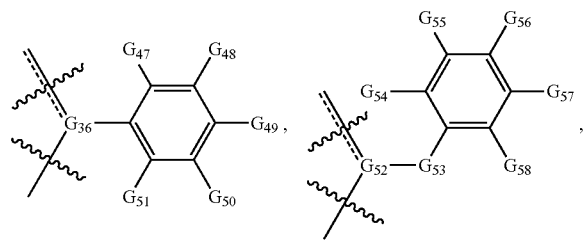

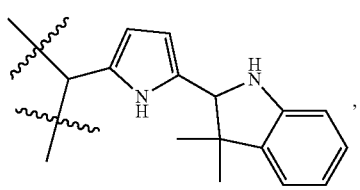

-continued

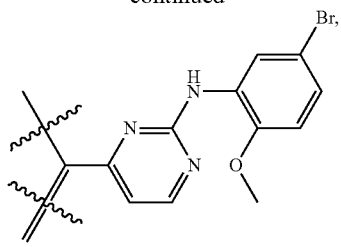

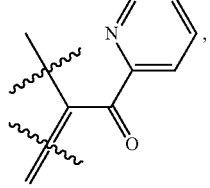

, or

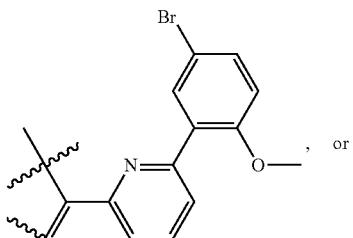

D$_2$ may be

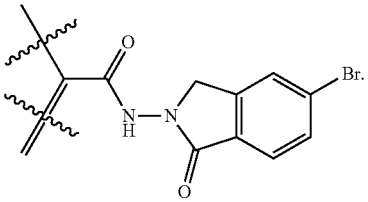

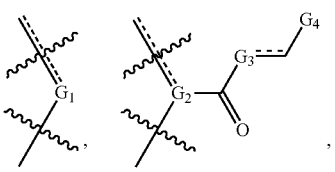

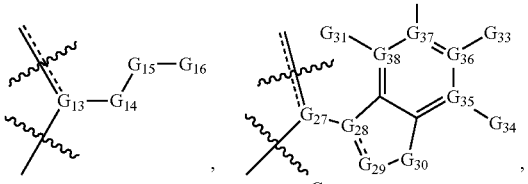

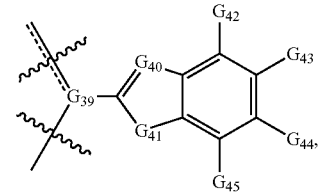

-continued

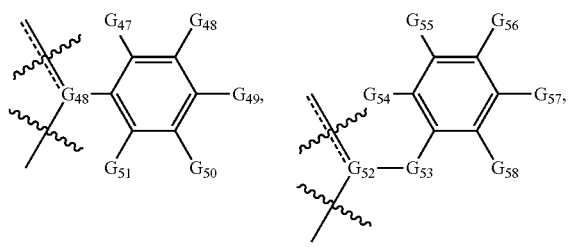

$D_2$ may be

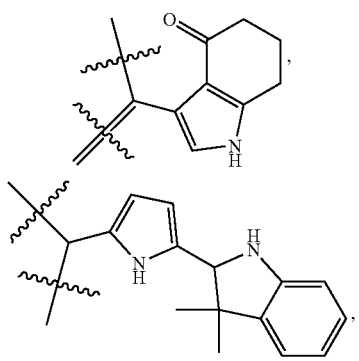

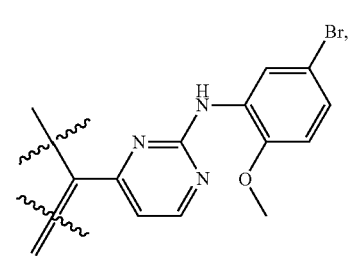

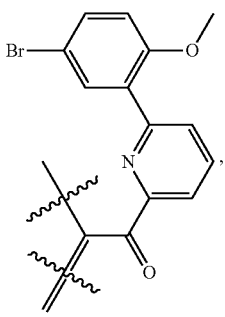

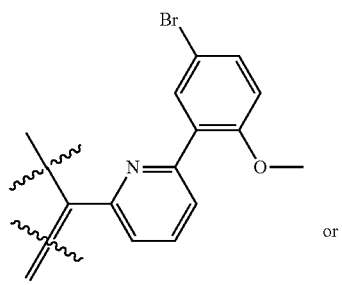

or

-continued

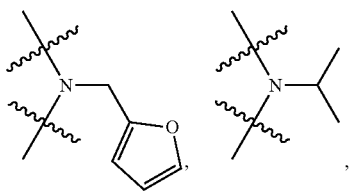

$G_1$ may be CH, N, CCH$_3$, CH$_2$,

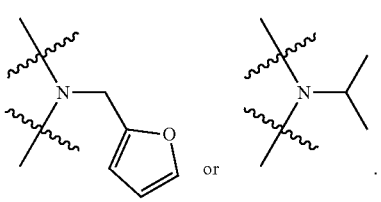

O, S, or NH. $G_1$ may be CH, N, CCH$_3$, CH$_2$, or

[structure: H/CH$_3$ wedge]

$G_1$ may be CH, N, CCH$_3$, CH$_2$,

[four stereochemistry structures]

$G_1$ may be CH, N, CCH$_3$, CH$_2$, O, S, or NH. $G_1$ may be CH, N, CCH$_3$ or CH$_2$.

$G_2$ may be C, CH, or N. $G_2$ may be C. $G_2$ may be C. $G_2$ may be C or CH. $G_2$ may be C or N.

$G_3$ may be CH,

CH$_2$, or N. $G_3$ may be CH, $G_3$ may be CH, CH$_2$ or N. $G_3$ may be CH.

$G_4$ may be

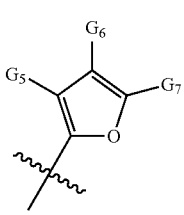 or 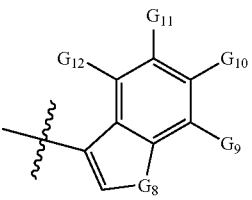.

$G_4$ may be

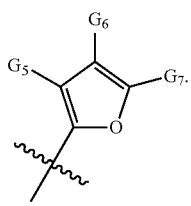

$G_4$ may be

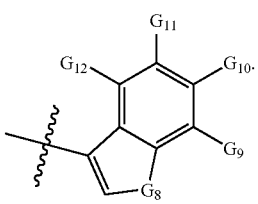

$G_5$, $G_6$, and $G_7$, may each independently be H, OH, Br, Cl, F, I, or $CH_3$. $G_5$, $G_6$, and $G_7$, may each independently be H or $CH_3$. $G_5$, $G_6$, and $G_7$, may each independently be H, OH, or $CH_3$. $G_5$, $G_6$, and $G_7$, may each independently be H, Br, Cl, F, or $CH_3$. $G_5$, $G_6$, and $G_7$, may each independently be H, OH, Br, $CH_3$.

$G_8$ may be NH, $CH_2$, O, or S. $G_8$ may be NH. $G_8$ may be NH, O, or S. $G_8$ may be NH, $CH_2$, or S. $G_8$ may be NH or S. $G_8$ may be NH or $CH_2$.

$G_9$, $G_{10}$, $G_{11}$, and $G_{12}$, may each independently be H, OH, Br, Cl, F, I or $CH_3$. $G_9$, $G_{10}$, $G_{11}$, and $G_{12}$, may each independently be H or Br. $G_9$, $G_{10}$, $G_{11}$, and $G_{12}$, may each independently be H, OH, Br, Cl or F. $G_9$, $G_{10}$, $G_{11}$, and $G_{12}$, may each independently be H, OH, Br, Cl, F or $CH_3$. $G_9$, $G_{10}$, $G_{11}$, and $G_{12}$, may each independently be H, OH or Br.

$G_{13}$ may be C, CH, or N. $G_{13}$ may be C or N. $G_{13}$ may be N. $G_{13}$ may be C.

$G_{14}$ may be C=O, $CH_2$, or NH. $G_{14}$ may be NH. $G_{14}$ may be $CH_2$. $G_{14}$ may be NH.

$G_{15}$ may be C=O, $CH_2$, or NH. $G_{15}$ may be C=O. $G_{15}$ may be $CH_2$. $G_{15}$ may be NH.

$G_{15}$ may be

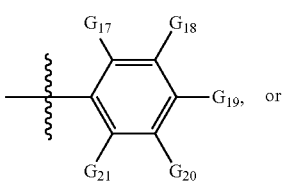 or $G_{15}$ may be

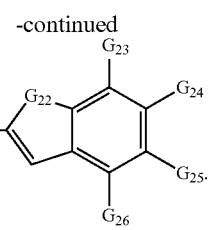

$G_{15}$ may be

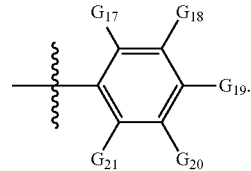

$G_{15}$ may be

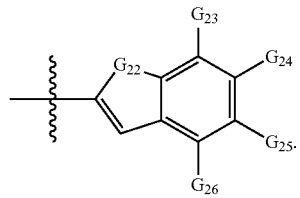

$G_{17}$, $G_{18}$, $G_{19}$, $G_{20}$, and $G_{21}$, are each independently H, OH, Br, Cl, F, I, or $CH_3$, provided that if $G_{17}$ is OH, then one or more of $G_{18}$, $G_{19}$, $G_{20}$, and $G_{21}$ are selected from OH, Br, Cl, F, I, or $CH_3$.

$G_{22}$ may be NH, $CH_2$, O, or S. $G_{22}$ may be NH. $G_{22}$ may be NH or S. $G_{22}$ may be NH, O or S. $G_{22}$ may be NH or $CH_2$. $G_{22}$ may be NH, O, or S. $G_{22}$ may be NH or O.

$G_{23}$, $G_{24}$, $G_{25}$, and $G_{26}$, may each independently be H, OH, Br, Cl, F, I or $CH_3$. $G_{23}$, $G_{24}$, $G_{25}$, and $G_{26}$, may each independently be H or Br. $G_{23}$, $G_{24}$, $G_{25}$, and $G_{26}$, may each independently be H, OH, Br, Cl, F, or $CH_3$. $G_{23}$, $G_{24}$, $G_{25}$, and $G_{26}$, may each independently be H, Br, Cl, F or I. $G_{23}$, $G_{24}$, $G_{25}$, and $G_{26}$, may each independently be H, OH, Br or $CH_3$.

$G_{27}$ may be C, CH, $CCH_3$, $CC(O)OCH_2CH_3$, or N. $G_{27}$ may be C, CH, $CCH_3$ or $CC(O)OCH_2CH_3$. $G_{27}$ may be C. $G_{27}$ may be CH. $G_{27}$ may be $CCH_3$. $G_{27}$ may be $CC(O)OCH_2CH_3$.

$G_{28}$ may be C, CH, or N. $G_{28}$ may be C or N. $G_{28}$ may be C. $G_{28}$ may be N.

$G_{29}$ may be CH, $CH_2$, C=O, $CCH_3$, or N. $G_{29}$ may be CH. $G_{29}$ may be $CH_2$. $G_{29}$ may be C=O, $CCH_3$.

$G_{30}$ may be $CH_2$, N—N=O, $NCH_3$, $NCH_2CH_2OH$, CH—N=O, $CHCH_3$, $CHCH_2CH_2OH$ S, O,

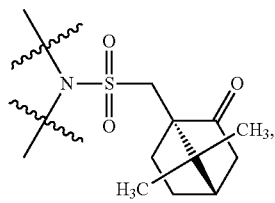

-continued

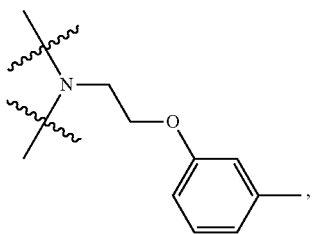

or NH. $G_{30}$ may be $CH_2$, N—N=O, $NCH_3$, $NCH_2CH_2OH$,

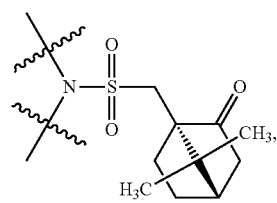

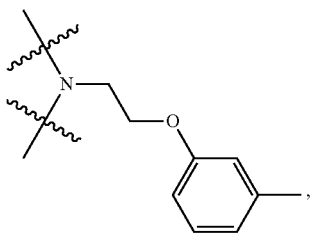

or NH. $G_{30}$ may be $CH_2$, N—N=O, $NCH_3$, $NCH_2CH_2OH$, CH—N=O, $CHCH_3$, $CHCH_2CH_2OH$, S, O, or NH. $G_{30}$ may be $CH_2$, N—N=O, $NCH_3$, $NCH_2CH_2OH$, or NH.

$G_{31}$, $G_{32}$, and $G_{33}$, may each independently be H, OH, $NH_2$, Br, Cl, F, I,

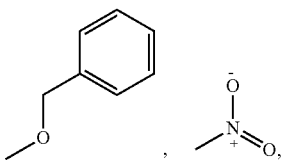

$OCH_3$, $CF_3$, $CH_3$, $CH_2OH$, or absent when $G_{36}$, $G_{37}$, or $G_{38}$ is N. $G_{31}$, $G_{32}$, and $G_{33}$, may each independently be H, OH, $NH_2$, Br, Cl, F, I

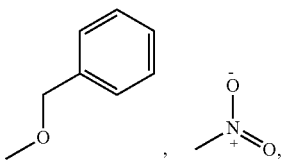

$OCH_3$, $CF_3$, $CH_3$, $CH_2OH$, or absent when $G_{36}$, $G_{37}$, or $G_{38}$ is N. $G_{31}$, $G_{32}$, and $G_{33}$, may each independently be H, OH, $NH_2$, Br, Cl, F, $OCH_3$, $CH_3$, $CH_2OH$, or absent when $G_{36}$, $G_{37}$, or $G_{38}$ is N.

$G_{34}$, may be H, OH, $NH_2$,

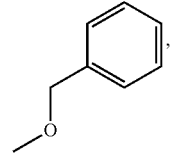

$OCH_3$, $CH_3$, $CH_2OH$, I or absent when $G_{35}$ is N. $G_{34}$, may be H, OH, $NH_2$,

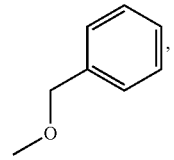

$OCH_3$, $CH_3$, $CH_2OH$, or absent when $G_{35}$ is N. $G_{34}$, may be H, OH, $NH_2$, $OCH_3$, $CH_3$, $CH_2OH$, or absent when $G_{35}$ is N.
$G_{35}$, $G_{36}$, $G_{37}$, and $G_{38}$, may each independently be C or N. $G_{35}$, $G_{36}$, $G_{37}$, and $G_{38}$, may each be N. $G_{35}$, $G_{36}$, $G_{37}$, and $G_{38}$, may each be C.
$G_{39}$ may be C, CH or N. $G_{39}$ may be C. $G_{39}$ may be C or CH. $G_{39}$ may be C or N.
$G_{40}$ may be CH, or N. $G_{40}$ may be N. $G_{40}$ may be CH.
$G_{41}$ may be NH, S, O, or $CH_2$. $G_{41}$ may be NH, S or O. $G_{41}$ may be NH. $G_{41}$ may be S.
$G_{42}$, $G_{43}$, $G_{44}$, and $G_{45}$, may each independently be H, OH, Br, Cl, F, I or $CH_3$. $G_{42}$, $G_{43}$, $G_{44}$, and $G_{45}$, may each independently be H or Br. $G_{42}$, $G_{43}$, $G_{44}$, and $G_{45}$, may each independently be H, OH, Br or $CH_3$.
$G_{46}$ may be C, CH, or N. $G_{46}$ may be C. $G_{46}$ may be C or N. $G_{46}$ may be CH or N.
$G_{47}$, $G_{48}$, $G_{50}$, and $G_{51}$, are each independently be H, OH, Br, Cl, F, I or $CH_3$. $G_{47}$, $G_{48}$, $G_{50}$, and $G_{51}$, are each independently be H or OH. $G_{47}$, $G_{48}$, $G_{50}$, and $G_{51}$, are each independently be H, OH or $CH_3$. $G_{47}$, $G_{48}$, $G_{50}$, and $G_{51}$, are each be H. $G_{47}$, $G_{48}$, $G_{50}$, and $G_{51}$, are each independently be OH. $G_{49}$ is OH, Br, Cl, F, I or $CH_3$. $G_{49}$ is Br, Cl, F or I. $G_{49}$ is OH or $CH_3$.
$G_{52}$ may be C, CH or N. $G_{52}$ may be C. $G_{52}$ may be C or N. $G_{52}$ may be C or CH.
$G_{53}$ may be $CH_2$, NH, S or O. $G_{53}$ may be NH. $G_{53}$ may be $CH_2$ or NH. $G_{53}$ may be NH or O. $G_{53}$ may be NH or S.
$G_{54}$, $G_{55}$, $G_{56}$, $G_{57}$, and $G_{58}$, may each independently be H, OH, Br, Cl, F, I or $CH_3$. $G_{54}$, $G_{55}$, $G_{56}$, $G_{57}$, and $G_{58}$, may each independently be H, Cl or F. $G_{54}$, $G_{55}$, $G_{56}$, $G_{57}$, and $G_{58}$, may each be H. $G_{54}$, $G_{55}$, $G_{56}$, $G_{57}$, and $G_{58}$, may each be Cl. $G_{54}$, $G_{55}$, $G_{56}$, $G_{57}$, and $G_{58}$, may each be F. $G_{54}$, $G_{55}$, $G_{56}$, $G_{57}$, and $G_{58}$, may each independently be H, Br, Cl, F or $CH_3$.

$D_3$ may be

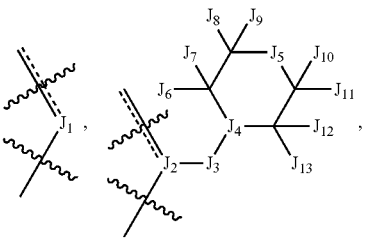

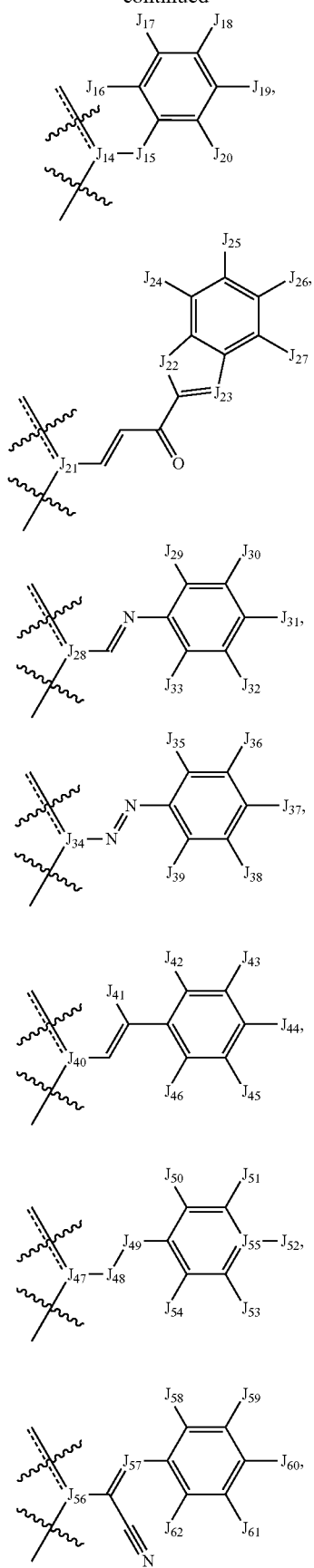
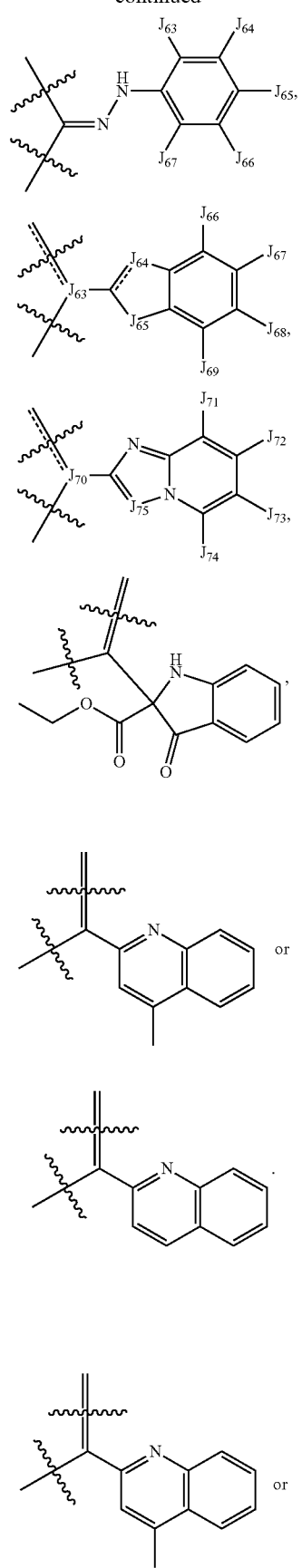
$D_3$ may be
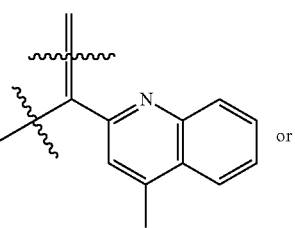

51
-continued
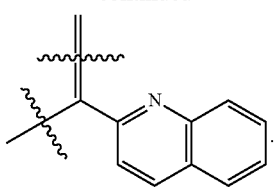
$D_3$ may be
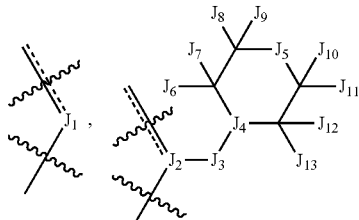
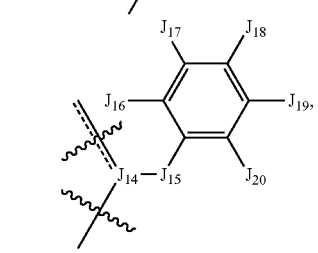
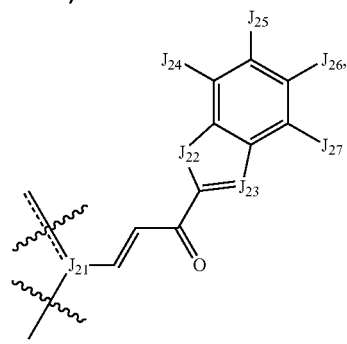
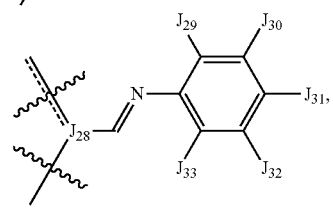
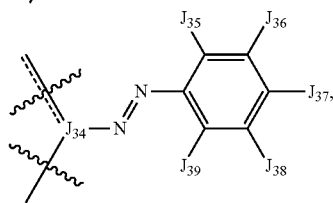
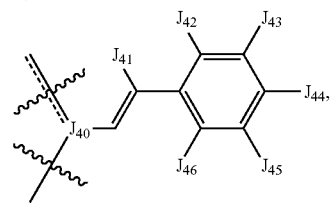
52
-continued
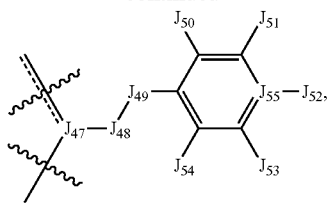
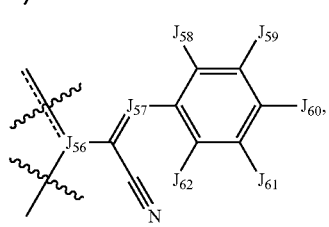
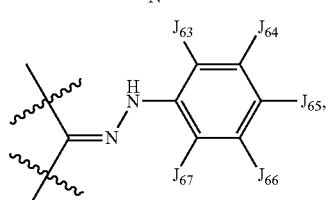
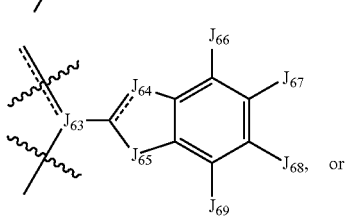
or
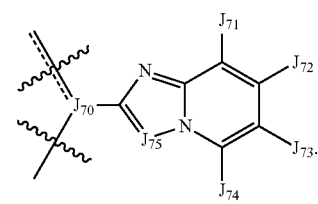
$J_1$ may be CH, N, CCH$_3$, CH$_2$, NCH$_3$, CN=O, C=O,
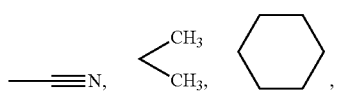
N, CH$_3$, O N—CH$_2$—CH$_2$—CH$_3$, CH=O, N—N=O,
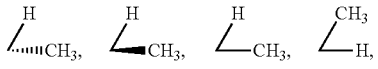
NCH$_2$C(O)OCH$_2$CH$_3$, N—CH$_2$—C(O)—O—CH$_2$—CH$_3$, O, S or NH. $J_1$ may be CH, N, CH$_2$, NCH$_3$, CN=O, C=O,
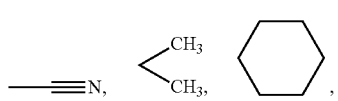
N, CH$_3$, O, or NH.

$J_1$ may be CH, N, CCH$_3$, CH$_2$, NCH$_3$, CN=O, C=O,

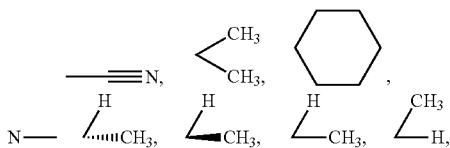

O, S or NH. $J_2$ may be CH, C, or N. $J_2$ may be CH. $J_2$ may be CH or C. $J_2$ may be CH, or N. $J_3$ may be C=S, C=O, NH, or CH$_2$. $J_3$ may be C=S. $J_3$ may be C=S or CH$_2$. $J_3$ may be C=S or C=O. $J_3$ may be C=S or NH. $J_4$ may be CH or N. $J_4$ may be N. $J_4$ may be CH. $J_5$ may be CH$_2$, NH, S or O. $J_5$ may be O. $J_5$ may be CH$_2$ or O. $J_5$ may be NH, S or O. $J_5$ may be S or O. $J_5$ may be NH or O. $J_6$, $J_7$, $J_8$, $J_9$, $J_{10}$, $J_{11}$, $J_{12}$, and $J_{13}$ may each independently be H, OH, Br, Cl, F, I or CH$_3$. $J_6$, $J_7$, $J_8$, $J_9$, $J_{10}$, $J_{11}$, $J_{12}$, and $J_{13}$ may each independently be H. $J_6$, $J_7$, $J_8$, $J_9$, $J_{10}$, $J_{11}$, $J_{12}$, and $J_{13}$ may each independently be H, OH, Br, Cl, F or CH$_3$. $J_{14}$ may be CH, C, or N. $J_{14}$ may be N. $J_{14}$ may be CH or N. $J_{14}$ may be C or N. $J_{15}$ may be C=S, C=O, NH or CH$_2$. $J_{15}$ may be CH$_2$. $J_{15}$ may be NH or CH$_2$. $J_{15}$ may be C=S or CH$_2$. $J_{15}$ may be C=O or CH$_2$.

$J_6$, $J_{17}$, $J_{18}$, $J_{19}$, and $J_{20}$ may each independently be H, OH, Br, Cl, F, I,

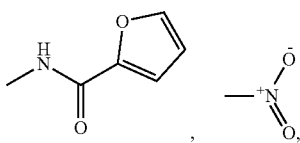

or CH$_3$. $J_{16}$, $J_{17}$, $J_{18}$, $J_{19}$, and $J_{20}$ may each independently be H or

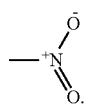

$J_{16}$, $J_{17}$, $J_{18}$, $J_{19}$, and $J_{20}$ may each independently be H, OH, Br, Cl, F,

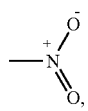

or CH$_3$. $J_{21}$ may be CH, C or N. $J_{21}$ may be CH. $J_{21}$ may be CH or N. $J_{21}$ may be CH or C. $J_{22}$ may be NH. $J_{22}$ may be CH$_2$. $J_{22}$ may be CH$_2$ or NH. $J_{23}$ may be CH or N. $J_{23}$ may be CH. $J_{23}$ may be N. $J_{24}$, $J_{25}$, $J_{26}$, and $J_{27}$ may each independently be H, OH, Br, Cl, F, I or CH$_3$. $J_{24}$, $J_{25}$, $J_{26}$, and $J_{27}$ may each independently be H. $J_{24}$, $J_{25}$, $J_{26}$, and $J_{27}$ may each independently be H, OH or CH$_3$. $J_{24}$, $J_{25}$, $J_{26}$, and $J_{27}$ may each independently be H, OH, Br, Cl or CH$_3$. $J_{28}$ may be CH, C or N. $J_{28}$ may be C. $J_{28}$ may be CH or C. $J_{28}$ may be C or N. $J_{31}$ may be H, OH, Br, F, I, C(O)NH$_2$, OCH$_3$ or CH$_3$. $J_{31}$ may be H, Br, OCH$_3$ or CH$_3$. $J_{31}$ may be H, OH, Br, Cl, F, I, C(O)NH$_2$, OCH$_3$ or CH$_3$. $J_{31}$ may be Cl. $J_{31}$ may be H. $J_{31}$ may be Br. $J_{31}$ may be OCH$_3$. $J_{31}$ may be CH$_3$. $J_{29}$, $J_{30}$, $J_{32}$, and $J_{33}$ may each independently be H, OCH$_3$, OH, Br, Cl, F, I, C(O)NH$_2$, CF$_3$,

NH$_2$, or CH$_3$. $J_{29}$, $J_{30}$, $J_{32}$, and $J_{33}$ may each independently be H, OH, Br, Cl, C(O)NH$_2$, CF$_3$ or CH$_3$. $J_{29}$, $J_{30}$, $J_{32}$, and $J_{33}$ may each independently be H, OCH$_3$, OH, Br, Cl, F, I, C(O)NH$_2$, NH$_2$, or CH$_3$. $J_{34}$ may be CH, C, or N. $J_{34}$ may be C. $J_{34}$ may be CH or C. $J_{34}$ may be C or N. $J_{35}$, $J_{36}$, $J_{37}$, $J_{38}$, and $J_{39}$ may each independently be H, OCH$_3$, OH, Br, Cl, F, I, C(O)NH$_2$, CF$_3$,

NH$_2$, or CH$_3$. $J_{35}$, $J_{36}$, $J_{37}$, $J_{38}$, and $J_{39}$ may each independently be H, Cl or CH$_3$. $J_{35}$, $J_{36}$, $J_{37}$, $J_{38}$, and $J_{39}$ may each independently be H, OCH$_3$, OH, Br, Cl, F, NH$_2$ or CH$_3$. $J_{35}$, $J_{36}$, $J_{37}$, $J_{38}$, and $J_{39}$ may each be H, Cl or CH$_3$. $J_{35}$, $J_{36}$, $J_{37}$, $J_{38}$, and $J_{39}$ may each independently be H. $J_{35}$, $J_{36}$, $J_{37}$, $J_{38}$, and $J_{39}$ may each independently be Cl. $J_{35}$, $J_{36}$, $J_{37}$, $J_{38}$, and $J_{39}$ may each independently be CH$_3$. $J_{35}$, $J_{36}$, $J_{37}$, $J_{38}$, and $J_{39}$ may each independently be CF$_3$. $J_{40}$ may be CH, C, or N. $J_{40}$ may be C. $J_{40}$ may be CH or C. $J_{40}$ may be C or N. $J_{41}$ may be H, OH, Br, Cl, F, I, NH$_2$, CH$_3$ or

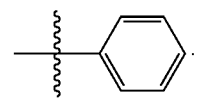 [SMILES: *c1ccccc1]

$J_{41}$ may be H. $J_{41}$ may be H, OH, Br, Cl, F, NH$_2$ or CH$_3$. $J_{42}$, $J_{43}$, $J_{44}$, $J_{45}$, and $J_{46}$ may each independently be H, OH, Br, Cl, F, I, NH$_2$ or CH$_3$. $J_{42}$, $J_{43}$, $J_{44}$, $J_{45}$, and $J_{46}$ may each independently be H. $J_{42}$, $J_{43}$, $J_{44}$, $J_{45}$, and $J_{46}$ may each independently be H, OH, NH$_2$, or CH$_3$. $J_{42}$, $J_{43}$, $J_{44}$, $J_{45}$, and $J_{46}$ may each independently be H, OH, Br, Cl, NH$_2$ or CH$_3$. $J_{47}$ may be CH, C or N. $J_{47}$ may be C. $J_{47}$ may be CH or N. $J_{47}$ may be CH or C. $J_{47}$ may be C or N. $J_{48}$ may be S, CH$_2$, C=O, O, or NH. $J_{48}$ may be S, CH$_2$ or NH. $J_{48}$ may be S. $J_{48}$ may be CH$_2$. $J_{48}$ may be NH. $J_{49}$ may be CH$_2$, C=O, S, O, or NH. $J_{49}$ may be CH$_2$ or C=O. $J_{49}$ may be S, O, or NH. $J_{49}$ may be CH$_2$, C=O or NH. $J_{49}$ may be CH$_2$, C=O or S. $J_{49}$ may be CH$_2$, C=O or O. $J_{55}$ may be C, or N. $J_{55}$ may be C. $J_{55}$ may be N. $J_{50}$, $J_{51}$, $J_{52}$, $J_{53}$, and $J_{54}$, may each independently be H, OH, NH$_2$, Br, Cl, F, I,

OCH$_3$, CF$_3$, CH$_3$ or may be absent when $J_{50}$, $J_{51}$, $J_{52}$, $J_{53}$, or $J_{54}$ is N. $J_{50}$, $J_{51}$, $J_{52}$, $J_{53}$, and $J_{54}$, may each independently be H, OH, Br, F, CH$_3$ or may be absent when J$_{50}$, J$_{51}$, J$_{52}$, J$_{53}$, or J$_{54}$ is N. J$_{50}$, J$_{51}$, J$_{52}$, J$_{53}$, and J$_{54}$, may each be H or may be absent when J$_{50}$, J$_{51}$, J$_{52}$, J$_{53}$, or J$_{54}$ is N. J$_{50}$, J$_{51}$, J$_{52}$, J$_{53}$, or J$_{54}$ is N. J$_{50}$, J$_{51}$, J$_{52}$, J$_{53}$, and J$_{54}$, may each be OH or may be absent when J$_{50}$, J$_{51}$, J$_{52}$, J$_{53}$, or J$_{54}$ is N. J$_{50}$, J$_{51}$, J$_{52}$, J$_{53}$, and J$_{54}$, may each be Br or may be absent when J$_{50}$, J$_{51}$, J$_{52}$, J$_{53}$, or J$_{54}$ is N. J$_{50}$, J$_{51}$, J$_{52}$, J$_{53}$, and J$_{54}$, may each be F or may be absent when J$_{50}$, J$_{51}$, J$_{52}$, J$_{53}$, or J$_{54}$ is N. J$_{50}$, J$_{51}$, J$_{52}$, J$_{53}$, and J$_{54}$, may each be CH$_3$ or may be absent when J$_{50}$, J$_{51}$, J$_{52}$, J$_{53}$, or J$_{54}$ is N. J$_{56}$ may be CH, C or N. J$_{56}$ may be C. J$_{56}$ may be CH or C. J$_{56}$ may be C or N. J$_{57}$ may be N or CH. J$_{57}$ may be CH. J$_{57}$ may be N. J$_{58}$, J$_{59}$, J$_{60}$, J$_{61}$, and J$_{62}$, may each independently be H, OH, NH$_2$, Br, Cl, F, I,

OCH$_3$, CF$_3$, or CH$_3$. J$_{58}$, J$_{59}$, J$_{60}$, J$_{61}$, and J$_{62}$, may each independently be H, F or CF$_3$, J$_{58}$, J$_{59}$, J$_{60}$, J$_{61}$, and J$_{62}$, may each independently be H, OH, NH$_2$, Br, Cl, F, I, OCH$_3$ or CH$_3$. J$_{63}$, J$_{64}$, J$_{65}$, J$_{66}$, and J$_{67}$, may each independently be H, OH, NH$_2$, Br, Cl, F, I,

OCH$_3$, CF$_3$, or CH$_3$. J$_{63}$, J$_{64}$, J$_{65}$, J$_{66}$, and J$_{67}$, may each independently be H, F or CF$_3$, J$_{63}$, J$_{64}$, J$_{65}$, J$_{66}$, and J$_{67}$, may each independently be H, OH, NH$_2$, Br, Cl, F, OCH$_3$ or CH$_3$. J$_{63}$ may be CH, C, or N. J$_{63}$ may be C or N. J$_{63}$ may be C. J$_{63}$ may be N. J$_{64}$ may be CH, CH$_2$, NH, CN=O, C=O, O, NCH$_3$, NC(O)OCH$_3$,

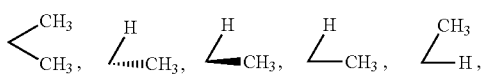

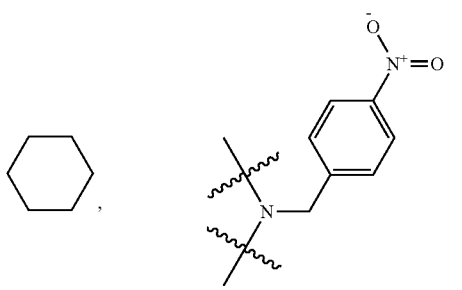

or N. J$_{64}$ may be CH, CH$_2$, NH, CN=O, C=O, O, CCH$_3$, NCH$_3$, NC(O)OCH$_3$, CH$_3$,

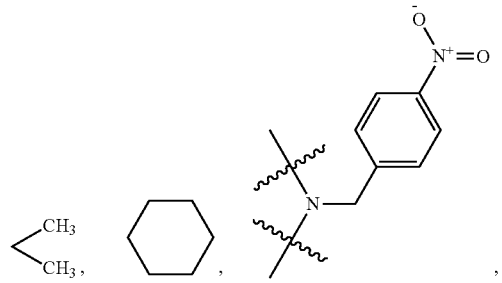

or N. J$_{64}$ may be CH, CH$_2$, NH, CN=O, C=O, O, NCH$_3$, NC(O)OCH$_3$,

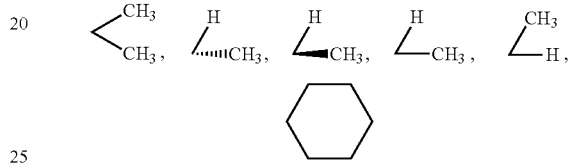

or N. J$_{65}$ may be CH$_2$, NH, C=O, O, S, NN=O, NCH$_3$, NC(O)OCH$_3$,

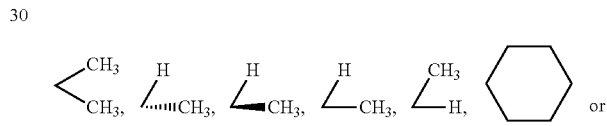

J$_{65}$ may be CH$_2$, NH, C=O, O, NN=O, NCH$_3$, NC(O)OCH$_3$,

J$_{66}$, J$_{67}$, J$_{68}$, and J$_{69}$ may each independently be H, OCH$_3$, OH, Br, Cl, F, I, C(O)NH$_2$, CF$_3$,

$NH_2$, or $CH_3$. $J_{66}$, $J_{67}$, $J_{68}$, and $J_{69}$ may each independently be H, $OCH_3$, Br or $CF_3$. $J_{66}$, $J_{67}$, $J_{68}$, and $J_{69}$ may each independently be H, $OCH_3$, OH, Br, Cl, F, $C(O)NH_2$, $NH_2$ or $CH_3$. $J_{70}$ may be C. $J_{70}$ may be CH or C. $J_{70}$ may be C or N. $J_{70}$ may be CH, C, or N. $J_{71}$, $J_{72}$, $J_{73}$, and $J_{74}$ may each independently be H, $OCH_3$, OH, Br, Cl, F, I, $C(O)NH_2$, $CF_3$,

$NH_2$, or $CH_3$. $J_{71}$, $J_{72}$, $J_{73}$, and $J_{74}$ may each independently be H, Br, $CF_3$, or $CH_3$. $J_{71}$, $J_{72}$, $J_{73}$, and $J_{74}$ may be H. $J_{71}$, $J_{72}$, $J_{73}$, and $J_{74}$ may be Br. $J_{71}$, $J_{72}$, $J_{73}$, and $J_{74}$ may be $CF_3$. $J_{71}$, $J_{72}$, $J_{73}$, and $J_{74}$ may be $CH_3$. $J_{75}$ may be CH, or N. $J_{75}$ may be CH. $J_{77}$ may be

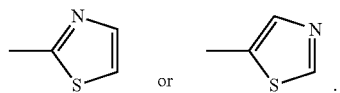

$J_{77}$ may be

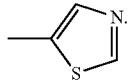

One or more of $D_1$-$D_3$ links to at least one ring in addition to the bicyclic structure of Formula I.

In accordance with a further aspect of the invention, there is provided a compound having the structure of Formula I as described herein, but provided that the compound is not one of the compounds in TABLE 1.

TABLE 1

Known AR $BF_3$ Interactors.

| Internal Number | External Identifier | STRUCTURE |
|---|---|---|
| 13312 | ZINC 00298052 | 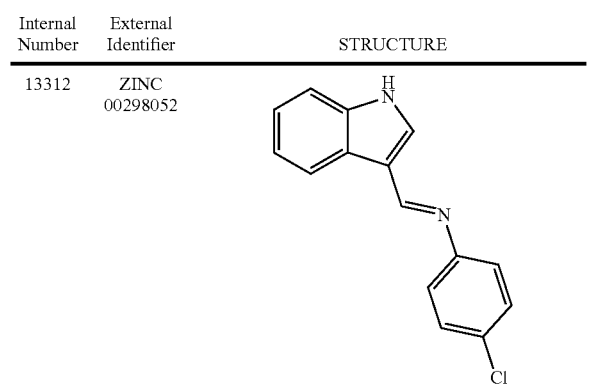 |

TABLE 1-continued

Known AR $BF_3$ Interactors.

| Internal Number | External Identifier | STRUCTURE |
|---|---|---|
| 13309 | ZINC 01234071 | 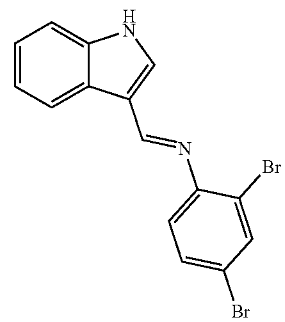 [SMILES: Brc1ccc(/N=C/c2c[nH]c3ccccc23)c(Br)c1] |
| 13310 | ZINC 00297221 | 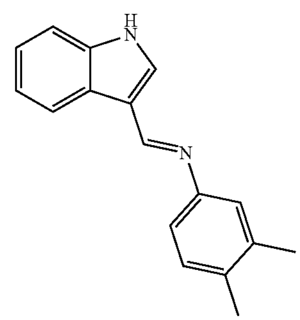 [SMILES: Cc1ccc(/N=C/c2c[nH]c3ccccc23)cc1C] |
| 13232 | ZINC 02992016 | 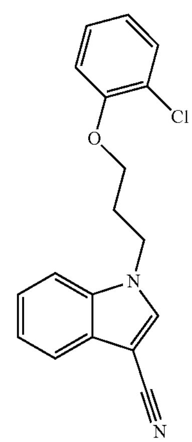 [SMILES: N#Cc1cn(CCCOc2ccccc2Cl)c2ccccc12] |
| 13050 | ZINC 03365783 | 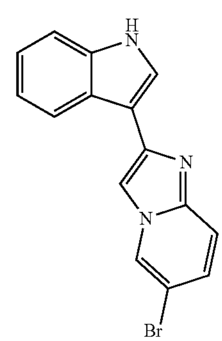 [SMILES: Brc1ccc2nc(-c3c[nH]c4ccccc34)cn2c1] |

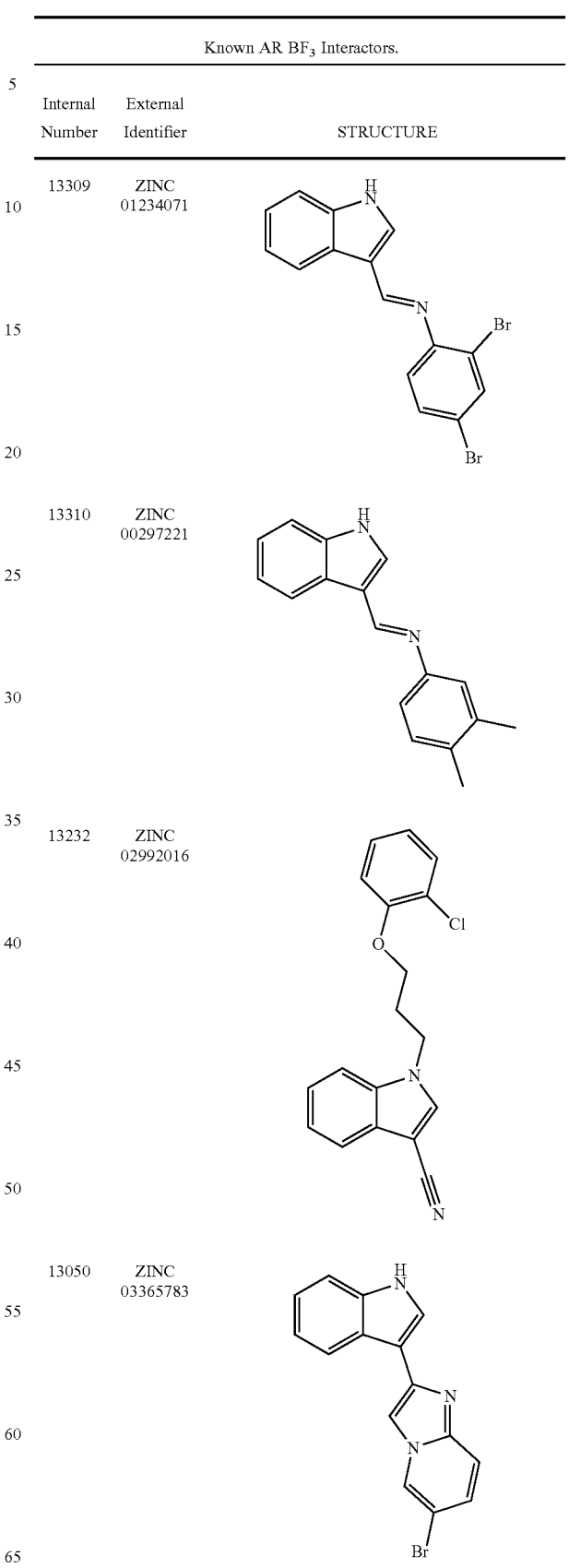

TABLE 1-continued
Known AR BF₃ Interactors.
| Internal Number | External Identifier | STRUCTURE |
|---|---|---|
| 13300 | ZINC 00270867 | 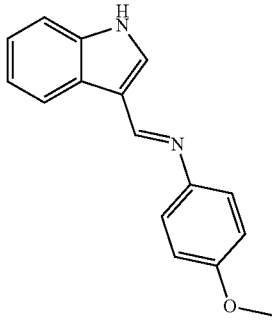 [SMILES: COc1ccc(/N=C/c2c[nH]c3ccccc23)cc1] |
| 13299 | ZINC 00499454 | 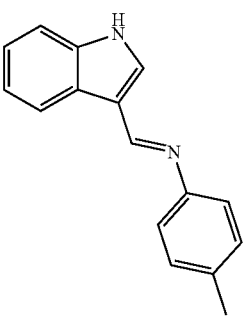 [SMILES: Cc1ccc(/N=C/c2c[nH]c3ccccc23)cc1] |
| 13304 | ZINC 00270887 | 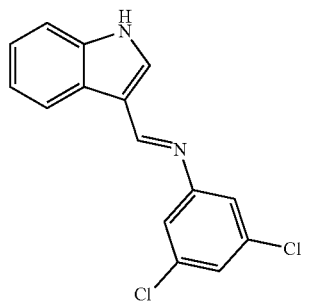 [SMILES: Clc1cc(Cl)cc(/N=C/c2c[nH]c3ccccc23)c1] |
| 13258 | ZINC 18191564 | 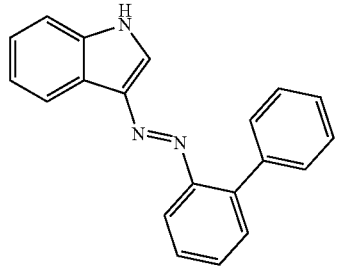 [SMILES: c1ccc(-c2ccccc2/N=N/c2c[nH]c3ccccc23)cc1] |
| 9125 | ZINC 30469682 | 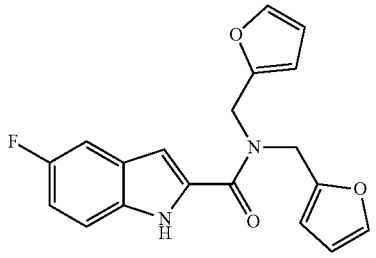 [SMILES: O=C(c1cc2cc(F)ccc2[nH]1)N(Cc1ccco1)Cc1ccco1] |
| 13186 | ZINC 00513042 | 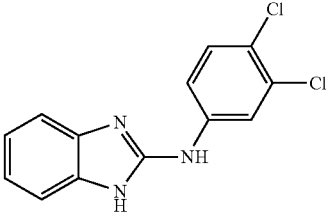 [SMILES: Clc1ccc(Nc2nc3ccccc3[nH]2)cc1Cl] |
| 13224 | ZINC 04106386 | 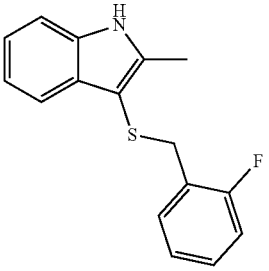 [SMILES: Cc1[nH]c2ccccc2c1SCc1ccccc1F] |
| 13250 | ZINC 03149578 | 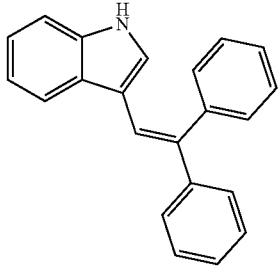 [SMILES: C(=C(c1ccccc1)c1ccccc1)c1c[nH]c2ccccc12] |
| 13303 | ZINC 00270884 | 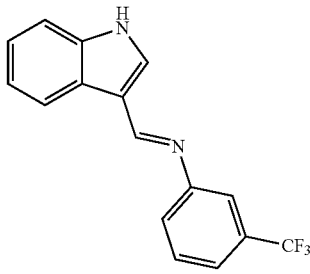 [SMILES: FC(F)(F)c1cccc(/N=C/c2c[nH]c3ccccc23)c1] |
| 13257 | ZINC 12345945 | 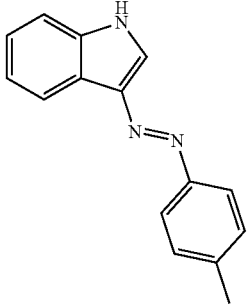 |

TABLE 1-continued
Known AR BF$_3$ Interactors.
| Internal Number | External Identifier | STRUCTURE |
|---|---|---|
| 13243 | ZINC 00253227 | 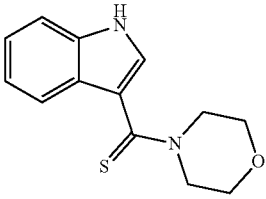 [SMILES: S=C(c1c[nH]c2ccccc12)N1CCOCC1] |
| 13424 | ZINC 12346351 | 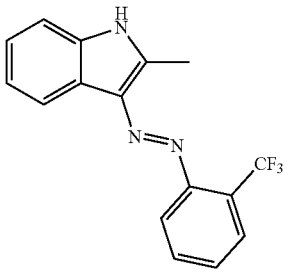 [SMILES: Cc1[nH]c2ccccc2c1/N=N/c1ccccc1C(F)(F)F] |
| 6054 | ZINC 08718421 | 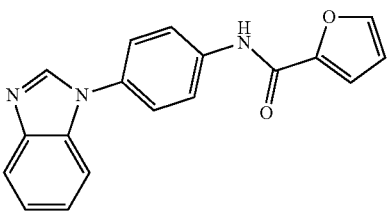 [SMILES: O=C(Nc1ccc(-n2cnc3ccccc32)cc1)c1ccco1] |
| 13029 | ZINC 00210926 | 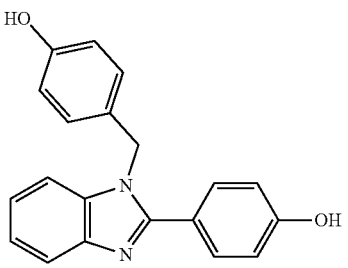 [SMILES: Oc1ccc(Cn2c(-c3ccc(O)cc3)nc3ccccc32)cc1] |
| 9128 | ZINC 47424036 | 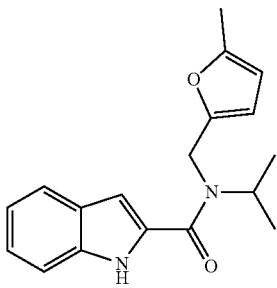 [SMILES: Cc1ccc(CN(C(=O)c2cc3ccccc3[nH]2)C(C)C)o1] |
| 13216 | ZINC 06025409 | 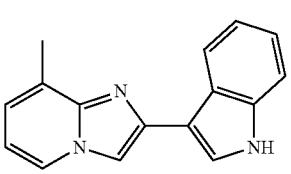 [SMILES: Cc1cccn2cc(-c3c[nH]c4ccccc34)nc12] |
| 13260 | ZINC 49491101 | 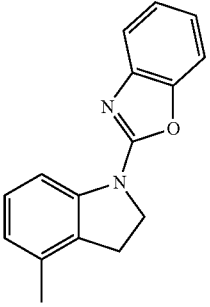 [SMILES: Cc1cccc2c1CCN2c1nc2ccccc2o1] |
| 13416 | ZINC 01869964 | 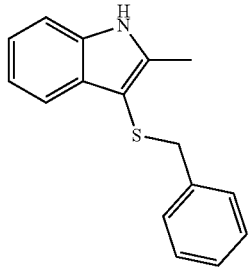 [SMILES: Cc1[nH]c2ccccc2c1SCc1ccccc1] |
| 13411 | ZINC 04106386 | 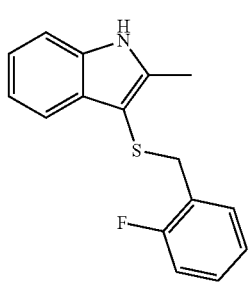 [SMILES: Cc1[nH]c2ccccc2c1SCc1ccccc1F] |
| 13214 | ZINC 26472877 | 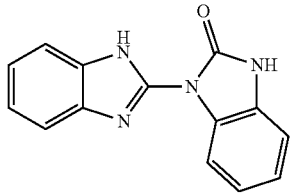 [SMILES: O=c1[nH]c2ccccc2n1-c1nc2ccccc2[nH]1] |
| 13235 | ZINC 01037115 | 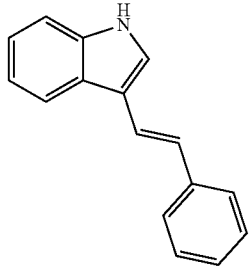 [SMILES: C(=C\c1c[nH]c2ccccc12)/c1ccccc1] |

TABLE 1-continued

Known AR BF₃ Interactors.

| Internal Number | External Identifier | STRUCTURE |
|---|---|---|
| 13127 | ZINC 00392643 | 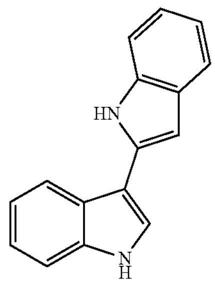 [SMILES: c1ccc2[nH]c(-c3c[nH]c4ccccc34)cc2c1] |
| 13261 | ZINC 48546225 | 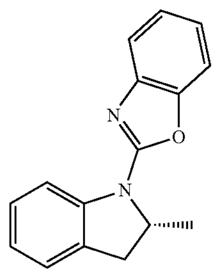 [SMILES: C[C@@H]1Cc2ccccc2N1c1nc2ccccc2o1] |
| 13215 | ZINC 05504717 | 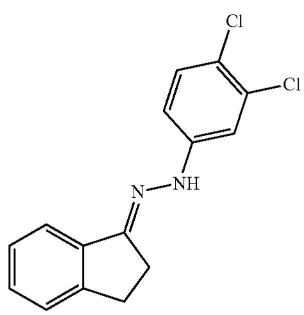 [SMILES: Clc1ccc(N/N=C2\CCc3ccccc32)cc1Cl] |
| 13167 | NSC 105329 | 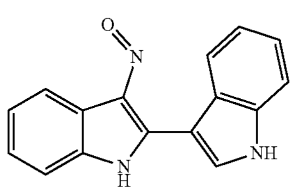 [SMILES: O=Nc1c(-c2c[nH]c3ccccc23)[nH]c2ccccc12] |
| 13206 | ZINC 04962047 | 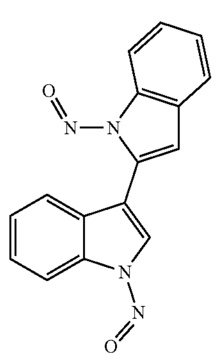 [SMILES: O=Nn1cc(-c2cc3ccccc3n2N=O)c2ccccc21] |
| 13145 | ZINC 34603778 | |
| 13245 | ZINC 00555700 | |
| 13036 | ZINC 14961821 | |
| 13166 | ZINC 01723993 | |
| 13164-B | ZINC 02046058 | |

TABLE 1-continued
Known AR BF₃ Interactors.
| Internal Number | External Identifier | STRUCTURE |
|---|---|---|
| 13254 | ZINC 18191551 | 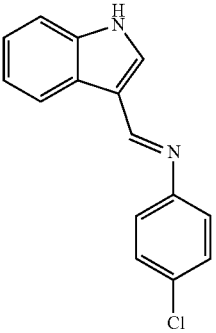 [SMILES: Clc1ccc(/N=C/c2c[nH]c3ccccc23)cc1] |
| 13410 | ZINC 04106383 | 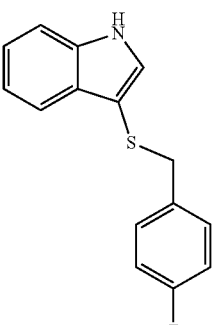 |
| 13423 | ZINC 18191568 | 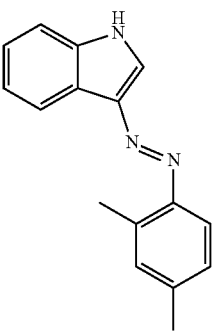 [SMILES: Cc1ccc(/N=N/c2c[nH]c3ccccc23)c(C)c1] |
| 13222 | ZINC 02718340 | 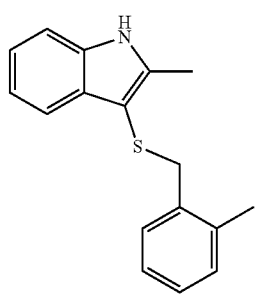 [SMILES: Cc1ccccc1CSc1c(C)[nH]c2ccccc12] |
| 13247 | ZINC 48090221 | 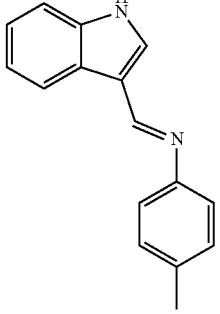 |
| 13412 | ZINC 02718340 | 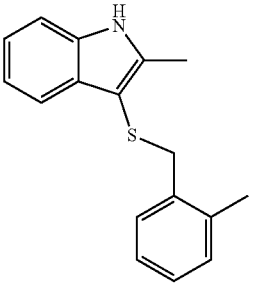 [SMILES: Cc1ccccc1CSc1c(C)[nH]c2ccccc12] |
| 13434 | ZINC 00069102 | 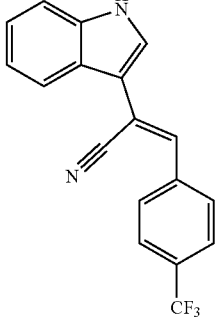 |
| 13164-A | ZINC 02046058 | 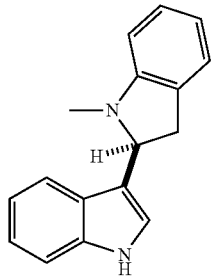 |
| 13220 | ZINC 48544111 | 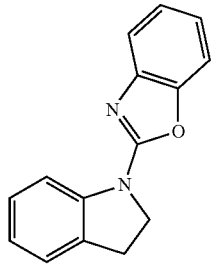 [SMILES: c1ccc2c(c1)CCN2c1nc2ccccc2o1] |

TABLE 1-continued

Known AR BF₃ Interactors.

| Internal Number | External Identifier | STRUCTURE |
|---|---|---|
| 13225 | ZINC 18191568 | (structure) |
| 13436 | ZINC 00068959 | (structure) |
| 13255 | ZINC 18191553 | (structure) |
| 13163-A | ZINC 02043019 | (structure) |
| 13163-B | ZINC 02043019 | (structure) |
| 13256 | ZINC 05848672 | (structure) |
| 13427 | ZINC 00588219 | (structure) |
| 13259 | ZINC 18191559 | (structure) |
| 13226 | ZINC 18191571 | (structure) |
| 13562 | Known see U.S. Pat. No. 6,207,679 | (structure) |
| 13566 | Known see U.S. Pat. No. 6,207,679 | (structure) |

The compound may be selected from one or more of the active synthetic derivatives set out in TABLE 2.

TABLE 2

List of Active Synthetic AR BF₃ Interactor Derivatives

| Internal Number | STRUCTURE |
|---|---|
| 9040 | |
| 9034 | |
| 13551 | |
| 13550 | |
| 9026 | |
| 13544 | |
| 13561 | 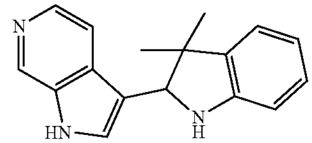 [SMILES: CC1(C)c2ccccc2NC1c1c[nH]c2cnccc12] |
| 9028 | 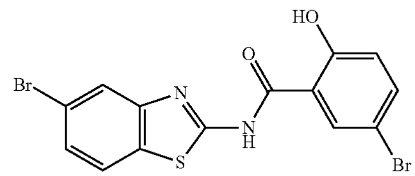 [SMILES: O=C(Nc1nc2cc(Br)ccc2s1)c1cc(Br)ccc1O] |
| 9027 | 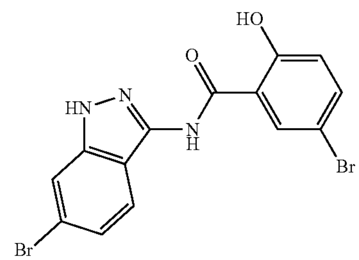 [SMILES: O=C(Nc1n[nH]c2cc(Br)ccc12)c1cc(Br)ccc1O] |
| 13538 | 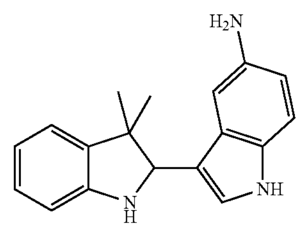 [SMILES: CC1(C)c2ccccc2NC1c1c[nH]c2ccc(N)cc12] |
| 13559 | 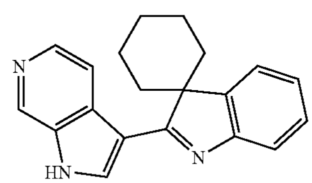 [SMILES: c1ccc2c(c1)N=C(c1c[nH]c3cnccc13)C21CCCCC1] |
| 13512 | 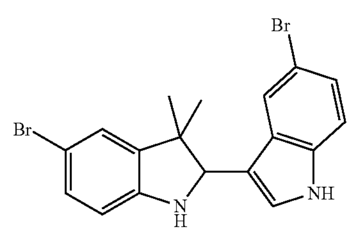 [SMILES: CC1(C)c2cc(Br)ccc2NC1c1c[nH]c2ccc(Br)cc12] |
| 13542 | 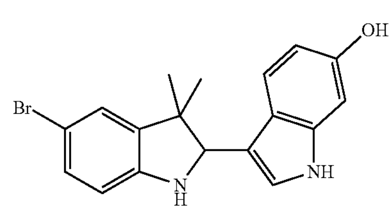 [SMILES: CC1(C)c2cc(Br)ccc2NC1c1c[nH]c2cc(O)ccc12] |

TABLE 2-continued

List of Active Synthetic AR BF₃ Interactor Derivatives

| Internal Number | STRUCTURE |
|---|---|
| 13524 | |
| 13508 | |
| 13530 | |
| 13503 | |
| 13502 | |
| 9037 | 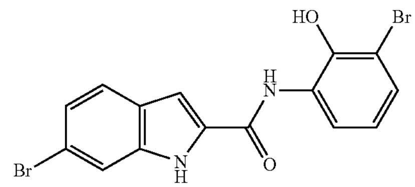 [SMILES: O=C(Nc1cccc(Br)c1O)c1cc2ccc(Br)cc2[nH]1] |
| 13543 | 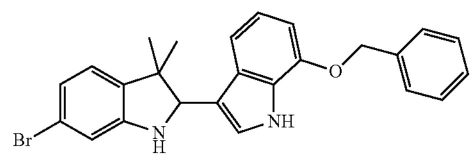 [SMILES: CC1(C)c2ccc(Br)cc2NC1c1c[nH]c2c(OCc3ccccc3)cccc12] |
| 13516 | 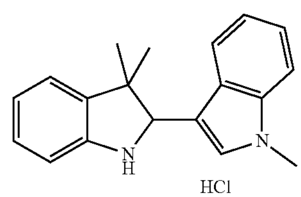 [SMILES: Cn1cc(C2Nc3ccccc3C2(C)C)c2ccccc21 ; Cl] |
| 13505 | 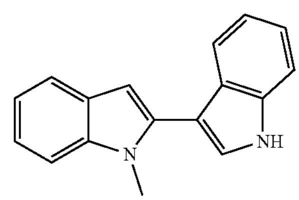 [SMILES: Cn1c(-c2c[nH]c3ccccc23)cc2ccccc21] |
| 13522 | 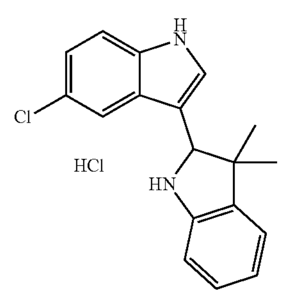 [SMILES: CC1(C)c2ccccc2NC1c1c[nH]c2ccc(Cl)cc12 ; Cl] |
| 13548 | 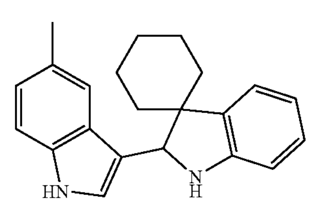 [SMILES: Cc1ccc2[nH]cc(C3Nc4ccccc4C34CCCCC4)c2c1] |

TABLE 2-continued

List of Active Synthetic AR BF₃ Interactor Derivatives

| Internal Number | STRUCTURE |
|---|---|
| 13525 | 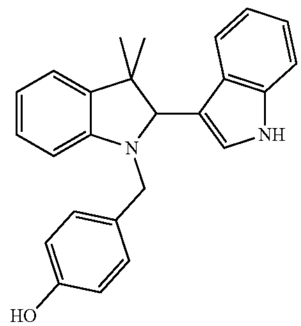 [SMILES: CC1(C)c2ccccc2N(Cc2ccc(O)cc2)C1c1c[nH]c2ccccc12] |
| 13532 | 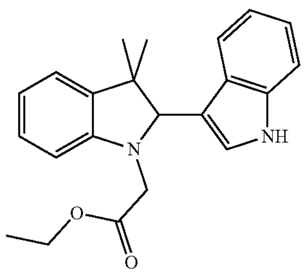 [SMILES: CCOC(=O)CN1c2ccccc2C(C)(C)C1c1c[nH]c2ccccc12] |
| 13511 | 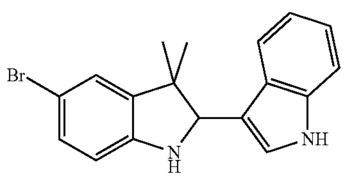 [SMILES: CC1(C)c2cc(Br)ccc2NC1c1c[nH]c2ccccc12] |
| 9043 | 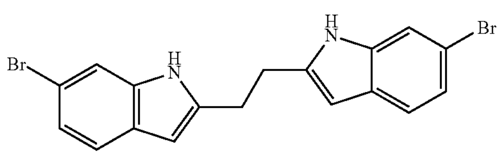 [SMILES: Brc1ccc2cc(CCc3cc4ccc(Br)cc4[nH]3)[nH]c2c1] |
| 13509 | 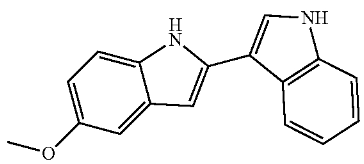 [SMILES: COc1ccc2[nH]c(-c3c[nH]c4ccccc34)cc2c1] |
| 13510 | 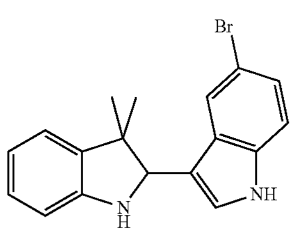 [SMILES: CC1(C)c2ccccc2NC1c1c[nH]c2ccc(Br)cc12] |
| 13540 | 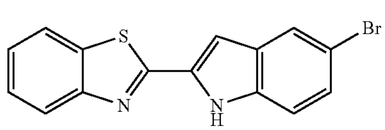 [SMILES: Brc1ccc2[nH]c(-c3nc4ccccc4s3)cc2c1] |
| 13560 | |
| 13536 | |
| 13556 | |
| 13504 | |
| 13549 | |
| 13558 | |
| 13535 | |

TABLE 2-continued

List of Active Synthetic AR BF$_3$ Interactor Derivatives

| Internal Number | STRUCTURE |
|---|---|
| 13500 | |
| 13552 | |
| 13534 | |
| 13537 | |
| 13554 | |
| 13541 | |
| 13521 | |
| 13506 | 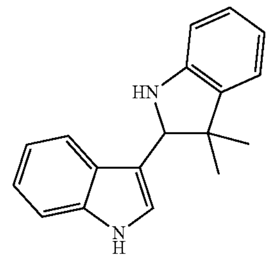 [SMILES: CC1(C)c2ccccc2NC1c1c[nH]c2ccccc12] |
| 13567 | 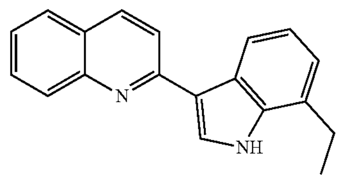 [SMILES: CCc1cccc2c(-c3ccc4ccccc4n3)c[nH]c12] |
| 13568 | 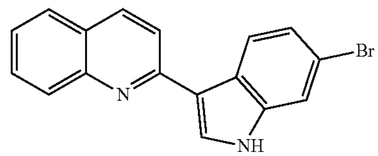 [SMILES: Brc1ccc2c(-c3ccc4ccccc4n3)c[nH]c2c1] |
| 13570 | 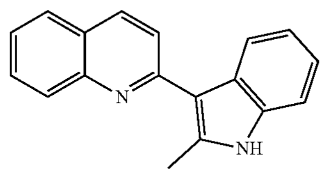 [SMILES: Cc1[nH]c2ccccc2c1-c1ccc2ccccc2n1] |
| 13569 | 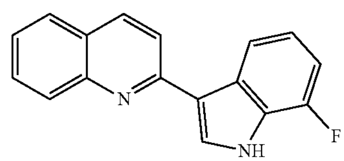 [SMILES: Fc1cccc2c(-c3ccc4ccccc4n3)c[nH]c12] |
| 13571 | 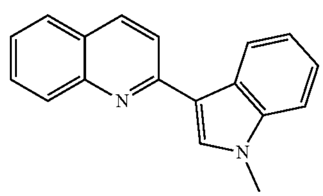 [SMILES: Cn1cc(-c2ccc3ccccc3n2)c2ccccc21] |
| 13573 | 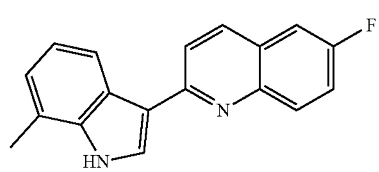 [SMILES: Cc1cccc2c(-c3ccc4cc(F)ccc4n3)c[nH]c12] |
| 13574 | 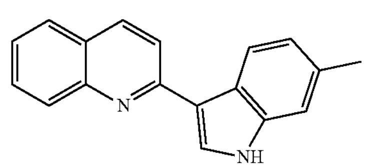 [SMILES: Cc1ccc2c(-c3ccc4ccccc4n3)c[nH]c2c1] |

TABLE 2-continued

List of Active Synthetic AR BF₃ Interactor Derivatives

| Internal Number | STRUCTURE |
|---|---|
| 13576 | quinoline-indole with 6-F on indole, NH |
| 13577 | quinoline-indole with methyl on indole, NH |
| 13579 | indazole-quinoline (HN-N) |
| 13580 | quinoline-indole with 6-CF₃ on indole, NH |
| 13582 | quinoline-indole with 7-Br on indole, NH |
| 13585 | quinoxaline-indole with 7-methyl on indole, HN |
| 13587 | quinazoline-indole, HN |
| 13589 | quinoline-indole with 6-OBn (OCH₂Ph) on indole, NH |
| 13591 | naphthalene-indole with 7-methyl on indole, NH |
| 13592 | quinoline-indole with 4,7-dimethyl on indole, NH |
| 13593 | 8-Cl-quinoline-indole with 7-methyl on indole, NH |
| 13594 | 4-methyl-quinoline-indole with 7-methyl on indole, NH |
| 13595 | 8-methyl-quinoline-indole with 7-methyl on indole, NH |
| 13597 | quinoline (5-CONHMe)-indole with 7-methyl on indole, NH |
| 13600 | quinoline-indole with 4,7-dimethyl on indole, NH |
| 13601 | quinoline-indole with 4-F, 7-methyl on indole, NH |
| 13602 | 5-CF₃-quinoline-indole with 7-methyl on indole, NH |

TABLE 2-continued

List of Active Synthetic AR BF$_3$ Interactor Derivatives

| Internal Number | STRUCTURE |
|---|---|
| 13603 | 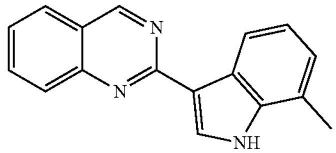 [SMILES: Cc1cccc2c(-c3ncc4ccccc4n3)c[nH]c12] |
| 13606 | 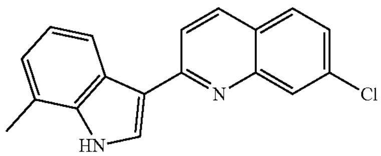 [SMILES: Cc1cccc2c(-c3ccc4ccc(Cl)cc4n3)c[nH]c12] |
| 13607 | 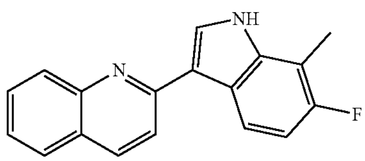 [SMILES: Cc1c(F)ccc2c(-c3ccc4ccccc4n3)c[nH]c12] |
| 13610 | 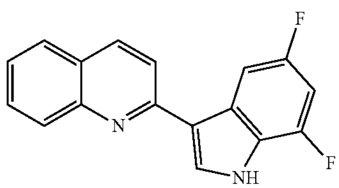 |
| 13611 | 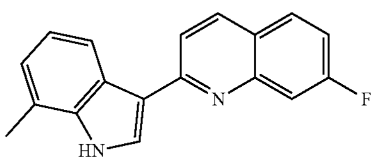 [SMILES: Cc1cccc2c(-c3ccc4ccc(F)cc4n3)c[nH]c12] |
| 13612 | 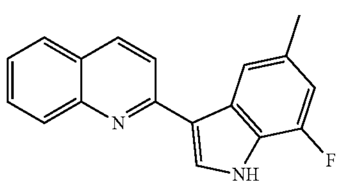 [SMILES: Cc1cc(F)c2[nH]cc(-c3ccc4ccccc4n3)c2c1] |
| 13613 | 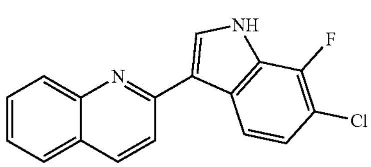 [SMILES: Fc1c(Cl)ccc2c(-c3ccc4ccccc4n3)c[nH]c12] |
| 13614 | 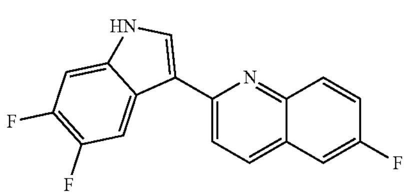 [SMILES: Fc1ccc2nc(-c3c[nH]c4cc(F)c(F)cc34)ccc2c1] |
| 13618 | |
| 13619 | |
| 13621 | HCl |
| 13622 | HCl |
| 13624 | |
| 13625 | |
| 13626 | |
| 13627 | |

TABLE 2-continued
List of Active Synthetic AR BF$_3$ Interactor Derivatives
| Internal Number | STRUCTURE |
|---|---|
| 13628 | 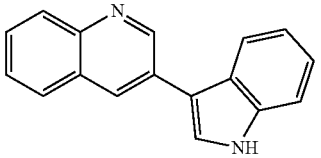 [SMILES: c1ccc2ncc(-c3c[nH]c4ccccc34)cc2c1] |
| 13629 |  |
| 13630 | 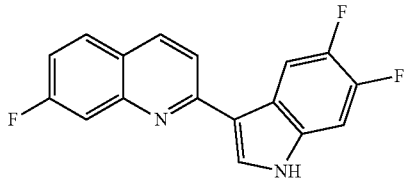 [SMILES: Fc1ccc2ccc(-c3c[nH]c4cc(F)c(F)cc34)nc2c1] |
| 13633 | 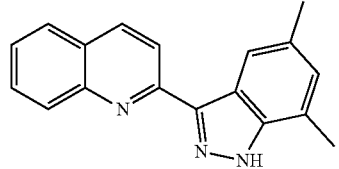 [SMILES: Cc1cc(C)c2[nH]nc(-c3ccc4ccccc4n3)c2c1] |
| 13634 | 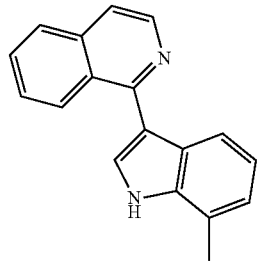 [SMILES: Cc1cccc2c(-c3nccc4ccccc34)c[nH]c12] |
| 13639 | 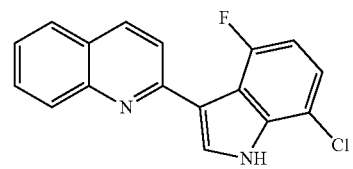 [SMILES: Fc1ccc(Cl)c2[nH]cc(-c3ccc4ccccc4n3)c12] |
| 13640 | 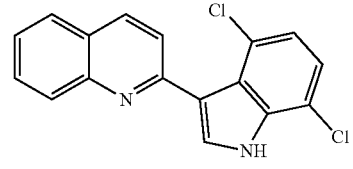 [SMILES: Clc1ccc(Cl)c2c(-c3ccc4ccccc4n3)c[nH]c12] |
| 13641 | 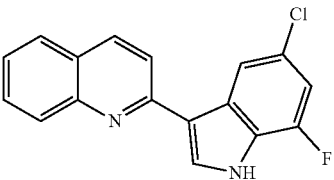 [SMILES: Fc1cc(Cl)cc2c(-c3ccc4ccccc4n3)c[nH]c12] |
| 13642 | 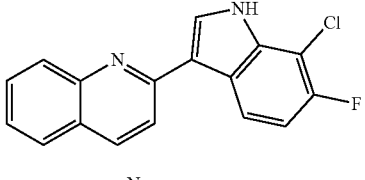 |
| 13643 | 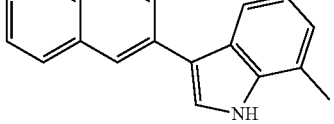 |
| 13644 | 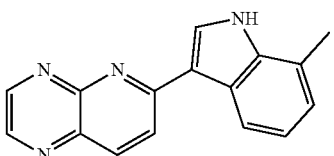 |
| 13645 | 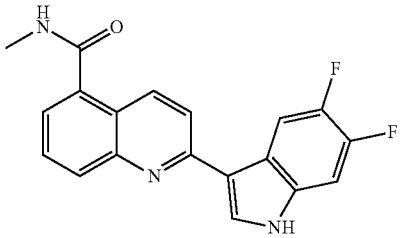 |
| 13646 | 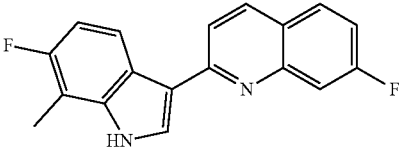 [SMILES: Cc1c(F)ccc2c(-c3ccc4ccc(F)cc4n3)c[nH]c12] |
| 13650 | 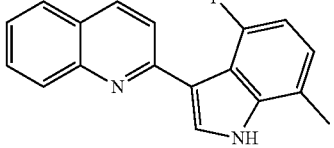 |
| 13651 | 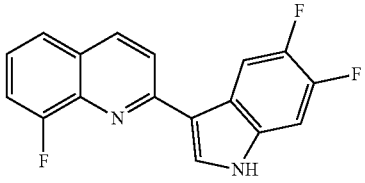 [SMILES: Fc1cc2[nH]cc(-c3ccc4cccc(F)c4n3)c2cc1F] |

TABLE 2-continued

List of Active Synthetic AR BF3 Interactor Derivatives

| Internal Number | STRUCTURE |
|---|---|
| 13652 | *(structure)* |
| 13653 | *(structure)* |
| 13654 | *(structure)* |
| 13655 | *(structure)* |
| 13656 | *(structure)* |
| 13658 | *(structure)* |
| 13660 | *(structure)* |
| 13665 | *(structure)* |
| 13674 | *(structure)* |
| 13677 | *(structure)* |
| 13680 | *(structure)* |
| 13681 | *(structure)* |
| 13682 | *(structure)* |
| 13683 | *(structure)* |
| 13684 | *(structure)* |
| 13688 | *(structure)* |

TABLE 2-continued
List of Active Synthetic AR BF₃ Interactor Derivatives
| Internal Number | STRUCTURE |
|---|---|
| 13691 | 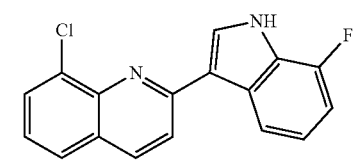 |
| 13692 | 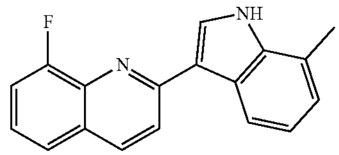 [SMILES: Cc1cccc2c(-c3ccc4cccc(F)c4n3)c[nH]c12] |
| 13693 | 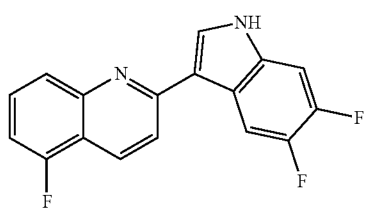 [SMILES: Fc1cc2[nH]cc(-c3ccc4c(F)cccc4n3)c2cc1F] |
| 13694 | 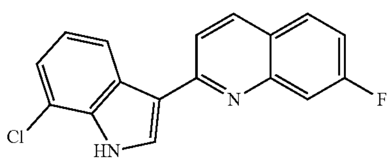 [SMILES: Fc1ccc2ccc(-c3c[nH]c4c(Cl)cccc34)nc2c1] |
| 13695 | 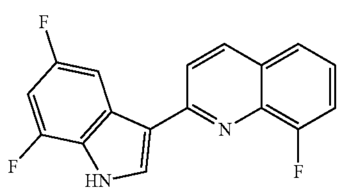 [SMILES: Fc1cc(F)c2[nH]cc(-c3ccc4cccc(F)c4n3)c2c1] |
| 13696 | 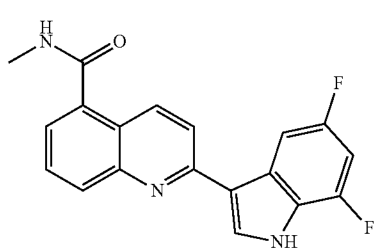 [SMILES: CNC(=O)c1cccc2nc(-c3c[nH]c4c(F)cc(F)cc34)ccc12] |
| 13697 | 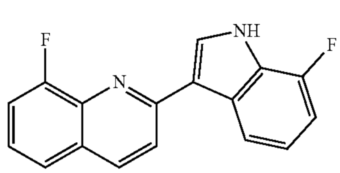 [SMILES: Fc1cccc2ccc(-c3c[nH]c4c(F)cccc34)nc12] |
| 13698 | 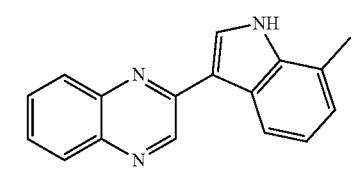 |
| 13699 | 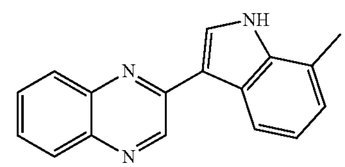 [SMILES: Cc1cccc2c(-c3cnc4ccccc4n3)c[nH]c12] |
| 13702 | 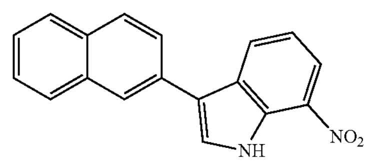 [SMILES: O=[N+]([O-])c1cccc2c(-c3ccc4ccccc4c3)c[nH]c12] |
| 13704 | 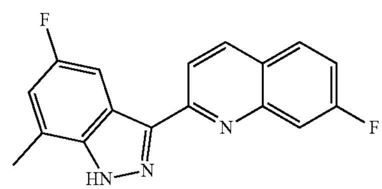 |
| 13708 | 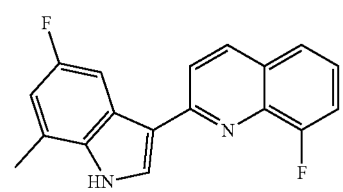 [SMILES: Cc1cc(F)cc2c(-c3ccc4cccc(F)c4n3)c[nH]c12] |
| 13710 | 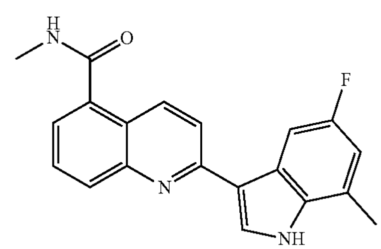 |
| 13713 | 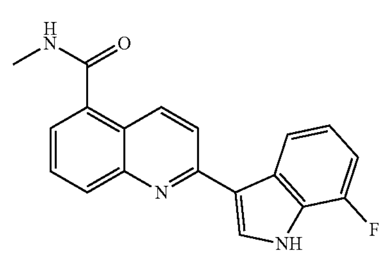 [SMILES: CNC(=O)c1cccc2nc(-c3c[nH]c4c(F)cccc34)ccc12] |

TABLE 2-continued

List of Active Synthetic AR BF₃ Interactor Derivatives

| Internal Number | STRUCTURE |
|---|---|
| 13717 | |
| 13718 | |
| 13719 | |
| 13730 | |
| 13731 | |
| 13732 | |
| 13733 | |
| 13736 | 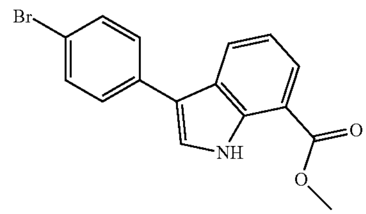 [SMILES: COC(=O)c1cccc2c(-c3ccc(Br)cc3)c[nH]c12] |
| 13738 | 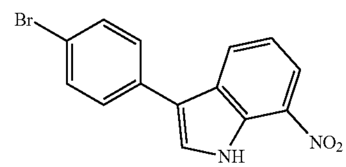 [SMILES: O=[N+]([O-])c1cccc2c(-c3ccc(Br)cc3)c[nH]c12] |
| 13741 | 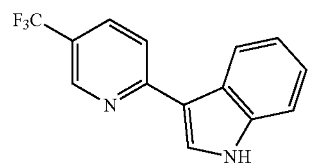 [SMILES: FC(F)(F)c1ccc(-c2c[nH]c3ccccc23)nc1] |
| 13742 | 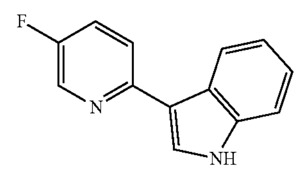 [SMILES: Fc1ccc(-c2c[nH]c3ccccc23)nc1] |
| 13743 | 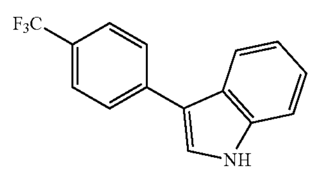 [SMILES: FC(F)(F)c1ccc(-c2c[nH]c3ccccc23)cc1] |
| 13744 | 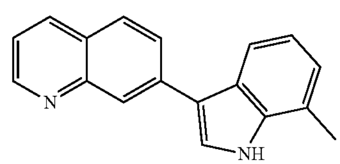 [SMILES: Cc1cccc2c(-c3ccc4cccnc4c3)c[nH]c12] |
| 13745 | 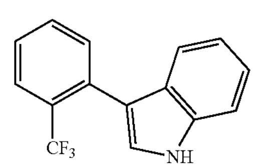 [SMILES: FC(F)(F)c1ccccc1-c1c[nH]c2ccccc12] |
| 13749 | 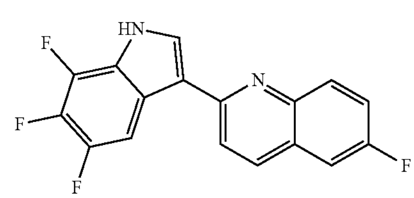 [SMILES: Fc1ccc2nc(-c3c[nH]c4c(F)c(F)c(F)cc34)ccc2c1] |

TABLE 2-continued

List of Active Synthetic AR BF₃ Interactor Derivatives

| Internal Number | STRUCTURE |
|---|---|
| 13752 | (structure) |
| 13753 | (structure) |
| 13754 | (structure) |
| 13755 | (structure) |
| 13759 | (structure) |
| 13760 | (structure) |
| 13761 | (structure) |
| 13762 | (structure) |
| 13764 | (structure) |
| 13766 | (structure) |
| 13770 | (structure) |
| 13771 | (structure) |
| 13772 | (structure) |
| 13773 | (structure) |

TABLE 2-continued

List of Active Synthetic AR BF₃ Interactor Derivatives

| Internal Number | STRUCTURE |
|---|---|
| 13774 | 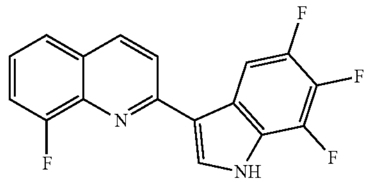 [SMILES: Fc1cc2c(-c3ccc4cccc(F)c4n3)c[nH]c2c(F)c1F] |
| 13775 | 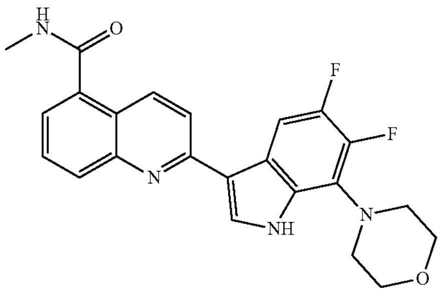 [SMILES: CNC(=O)c1cccc2nc(-c3c[nH]c4c(N5CCOCC5)c(F)c(F)cc34)ccc12] |
| 13776 | 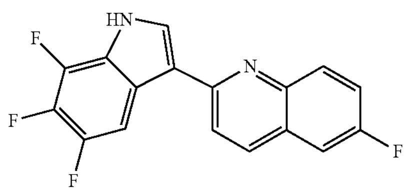 [SMILES: Fc1ccc2nc(-c3c[nH]c4c(F)c(F)c(F)cc34)ccc2c1] |
| 13782 | 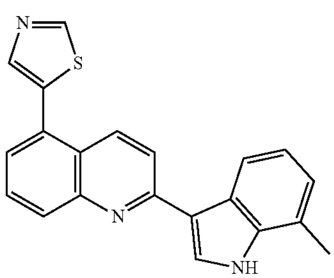 [SMILES: Cc1cccc2c(-c3ccc4c(-c5cncs5)cccc4n3)c[nH]c12] |
| 13785 | 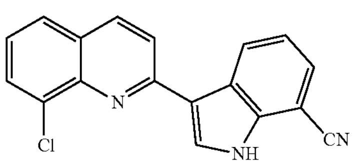 [SMILES: N#Cc1cccc2c(-c3ccc4cccc(Cl)c4n3)c[nH]c12] |
| 13786 | 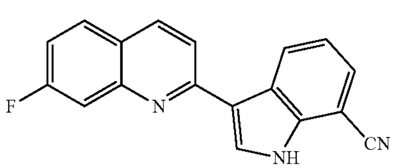 [SMILES: N#Cc1cccc2c(-c3ccc4ccc(F)cc4n3)c[nH]c12] |
| 13787 | 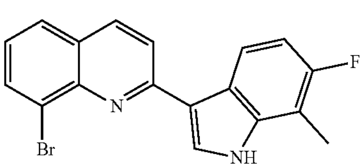 [SMILES: Cc1c(F)ccc2c(-c3ccc4cccc(Br)c4n3)c[nH]c12] |

Alternatively, the compound may be selected from one or more of the following:

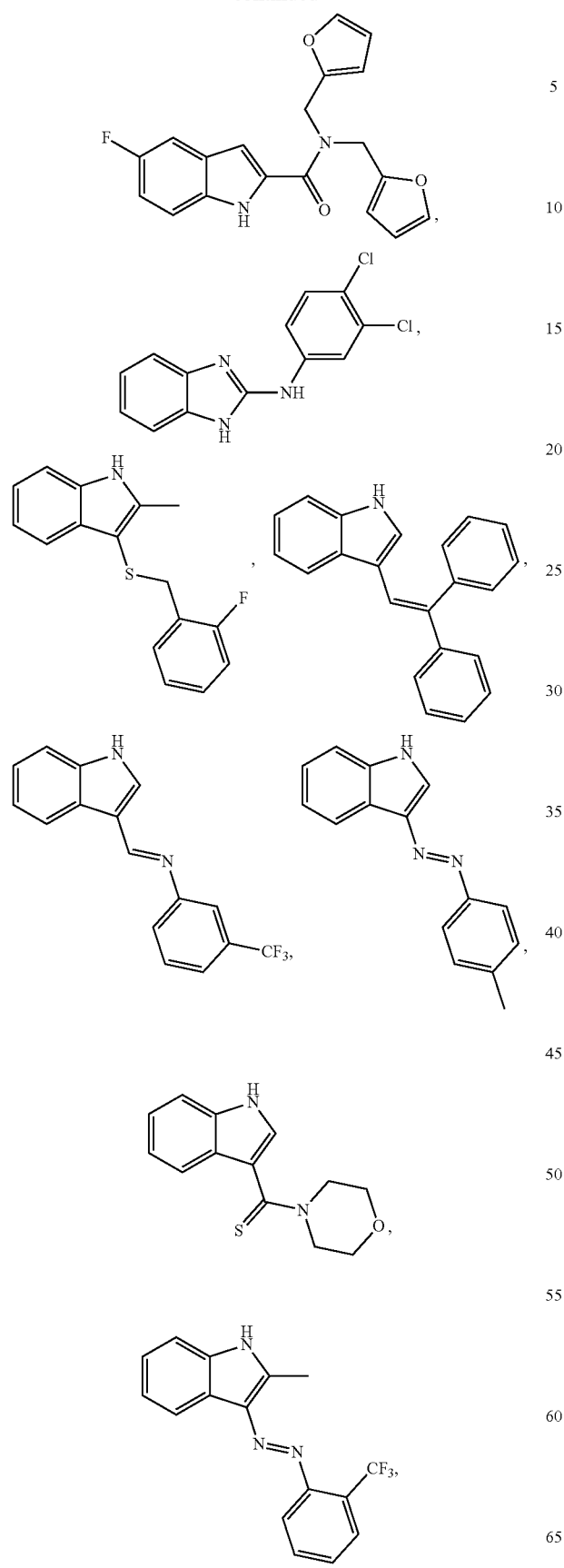
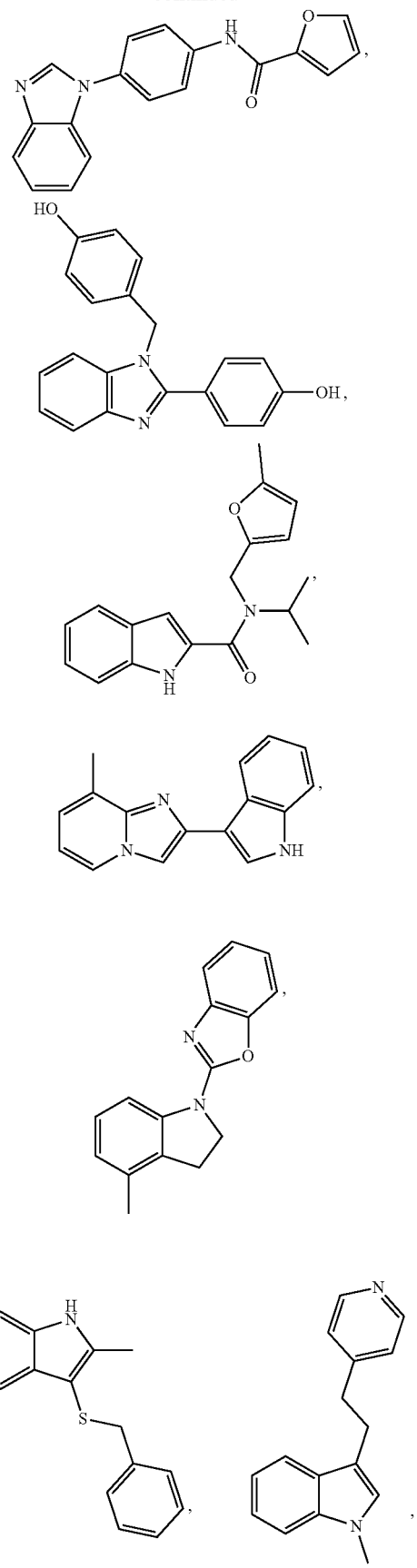

-continued
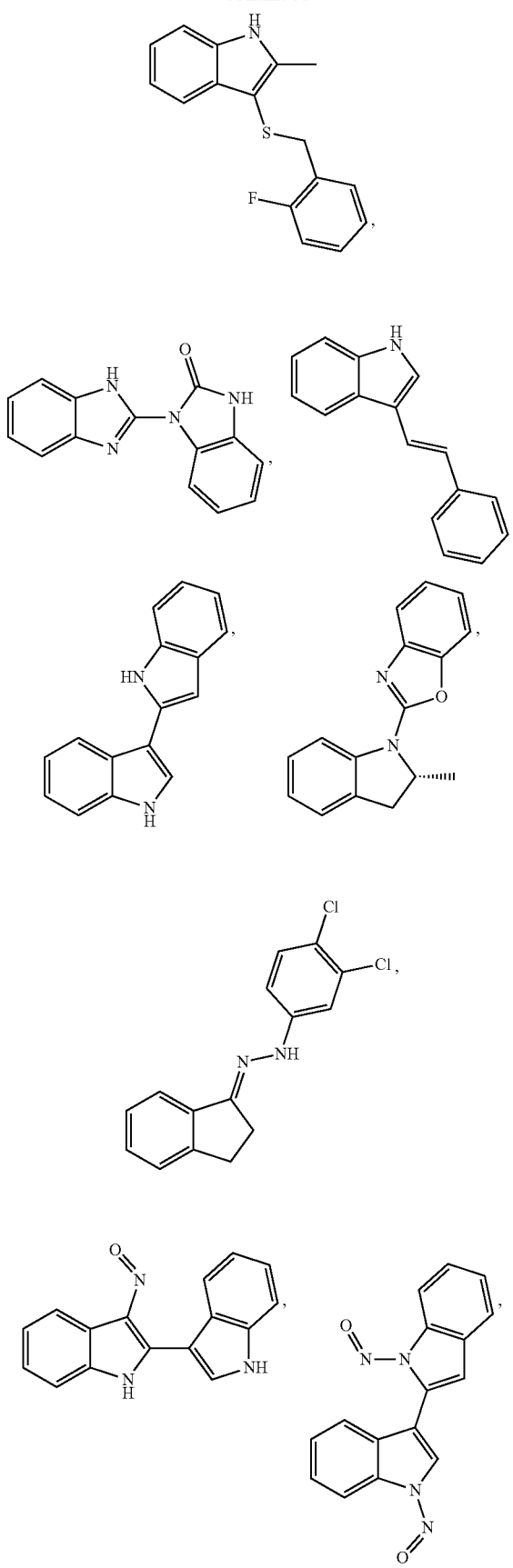
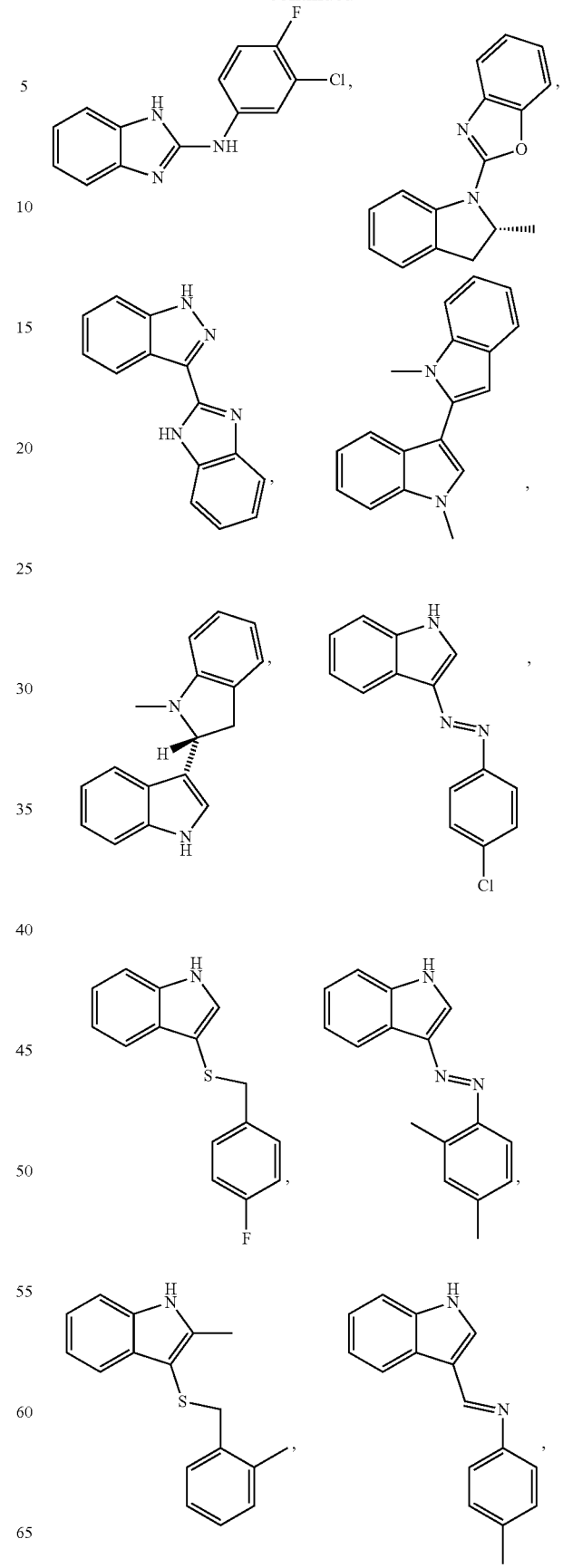

-continued
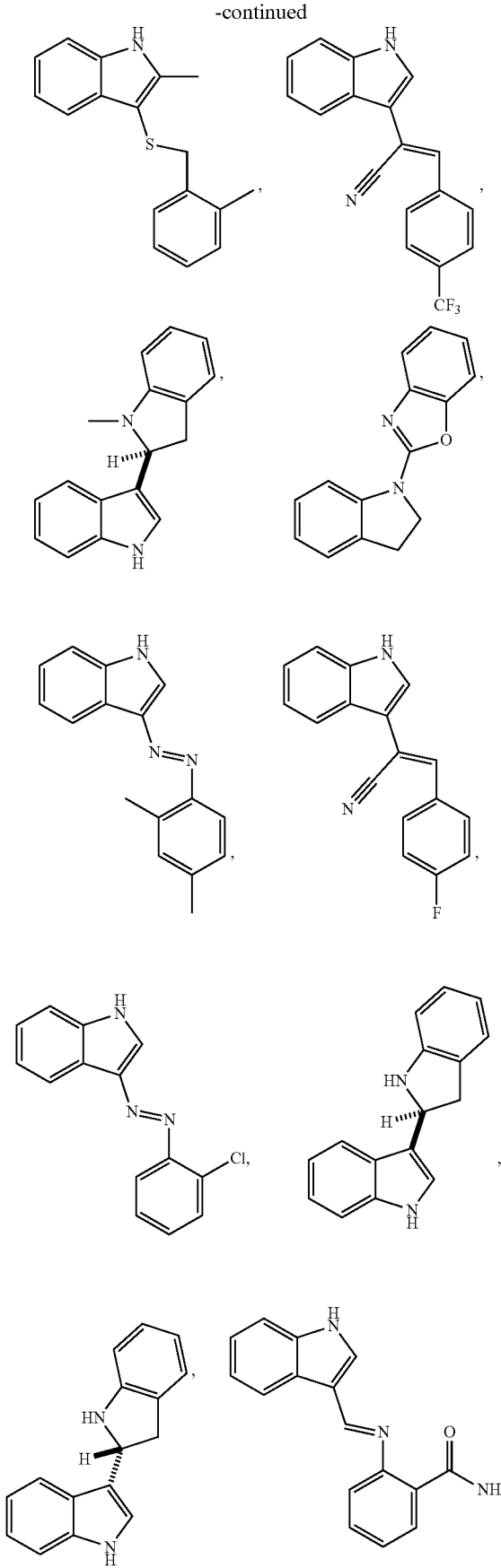
-continued
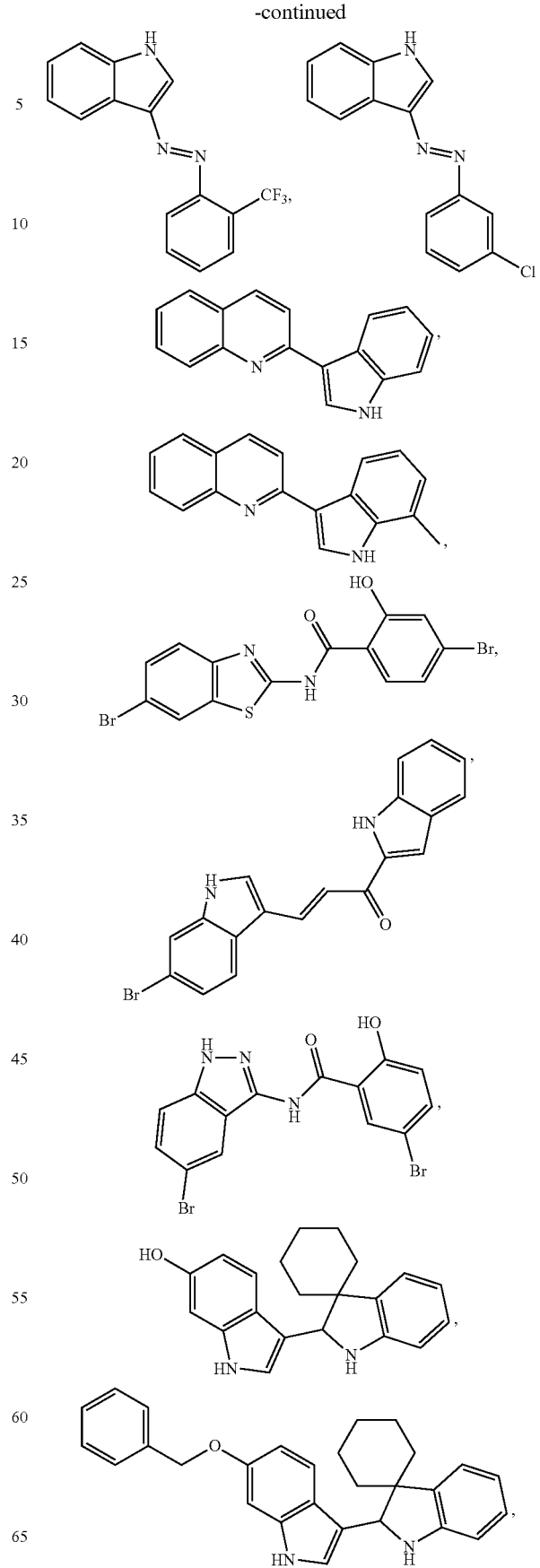

99
-continued
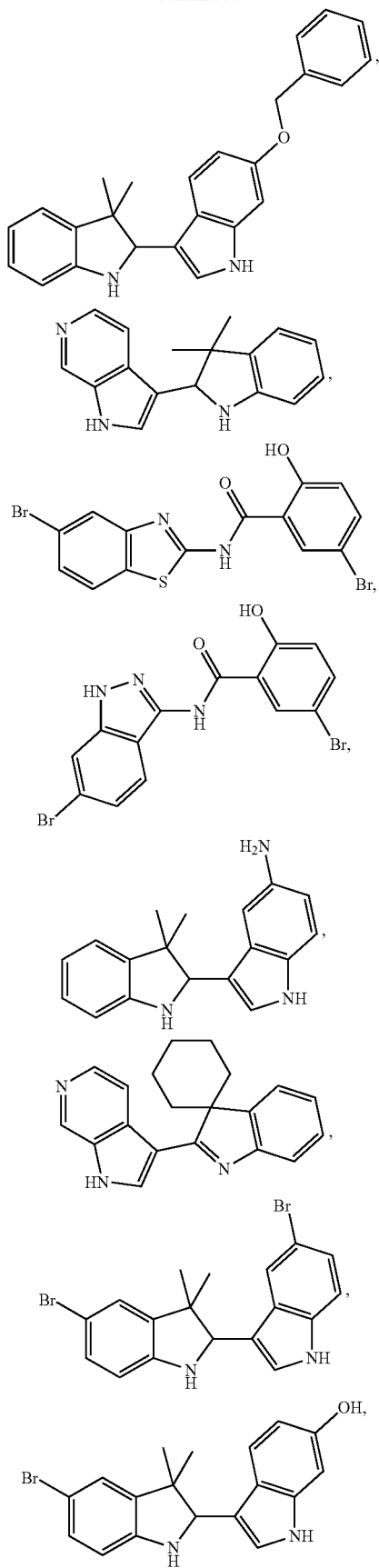
100
-continued
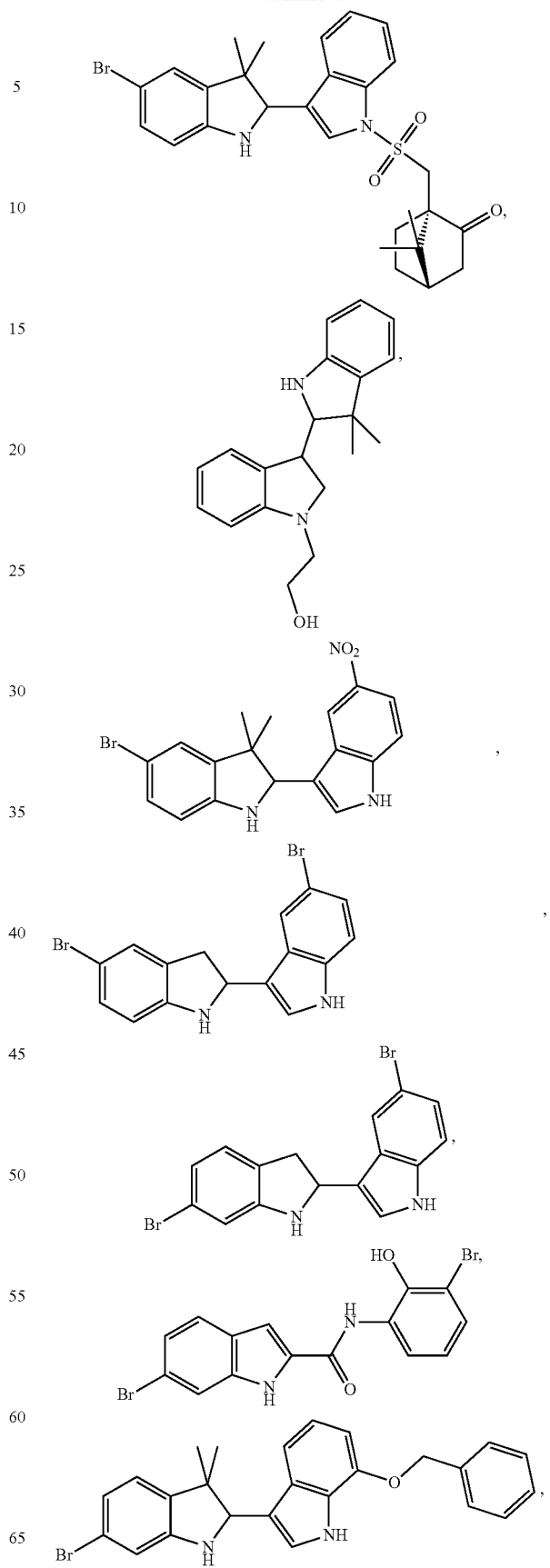

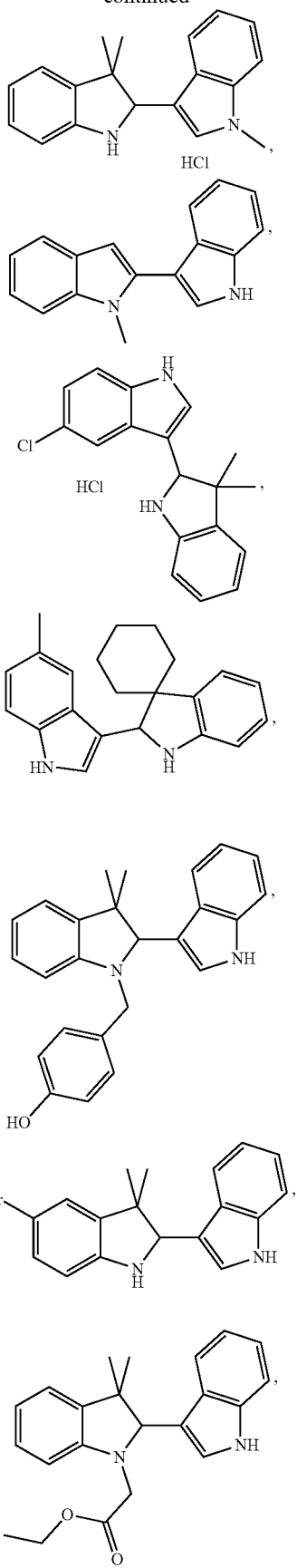
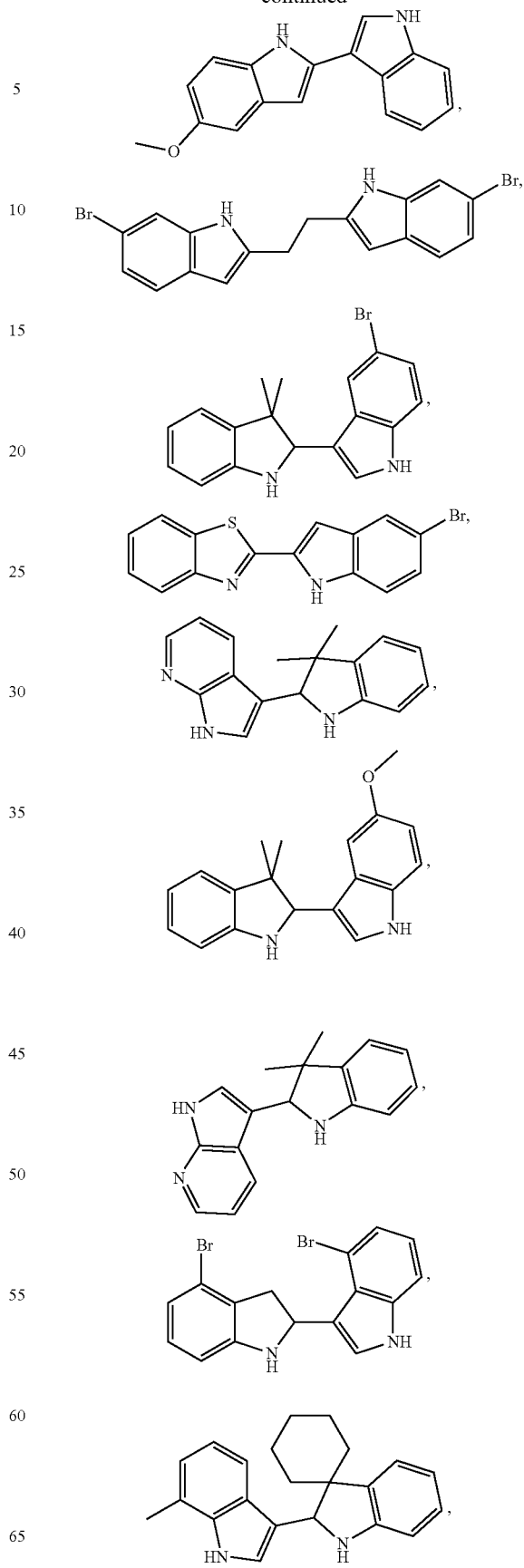

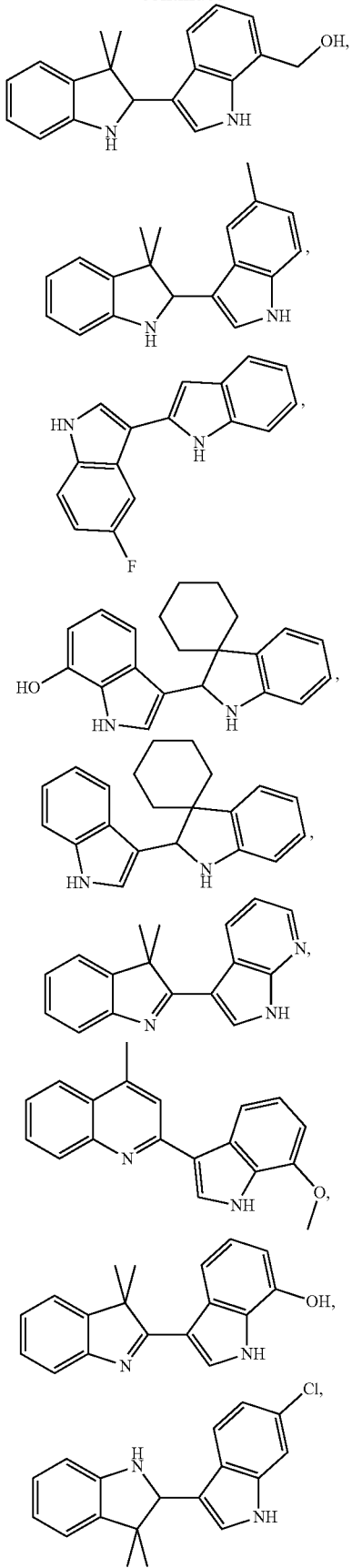
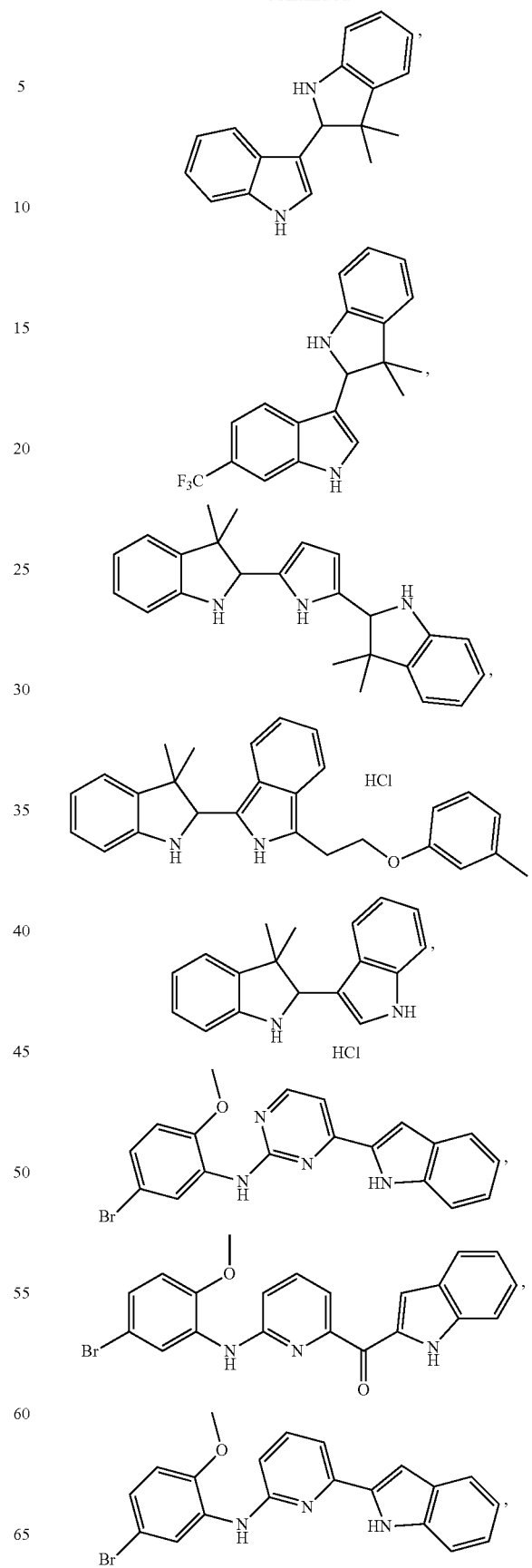

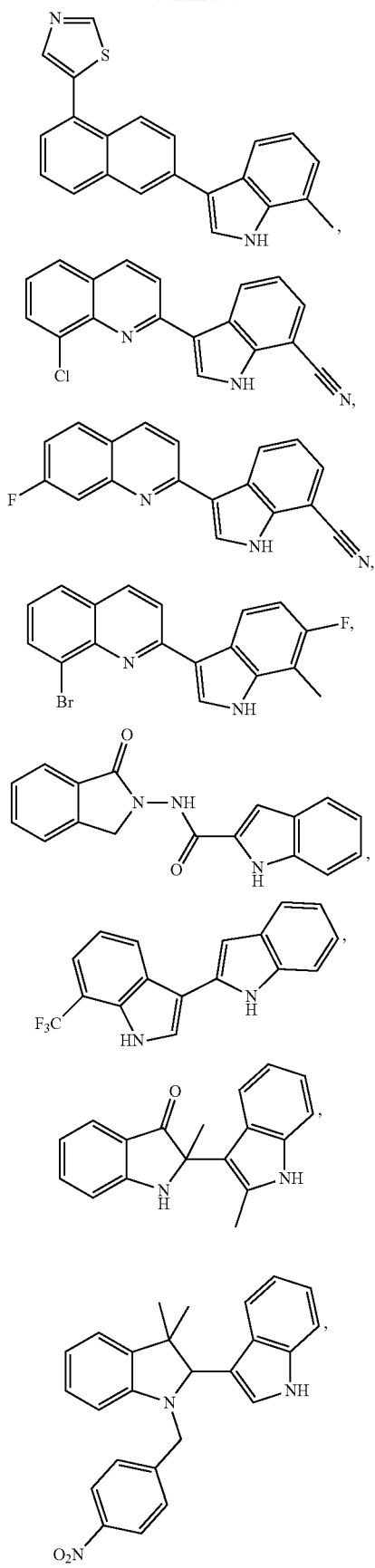
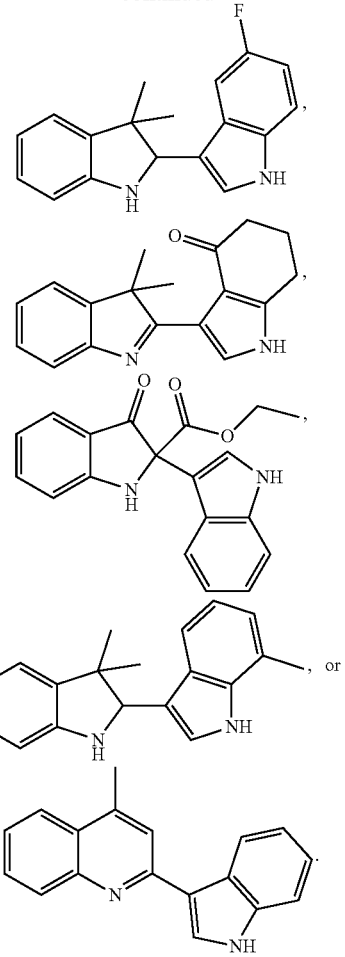
The compound may have the structure of Formula II:
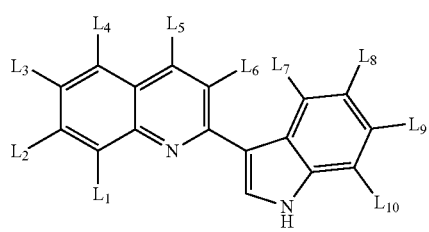
wherein,
L$_1$ may be H, Cl, F, Br, OH, CF$_3$, NH$_2$, OCH$_3$, or CH$_3$;
L$_2$ may be H, Cl, F, Br, OH, NH$_2$, OCH$_3$, or CH$_3$;
L$_3$ may be H, Cl, F, Br, OH, NH$_2$, OCH$_3$, or CH$_3$;
L$_4$ may be H, Cl, F, Br, OH, NH$_2$, C(O)NHCH$_3$, CH$_2$OH, OCH$_3$, CF$_3$, CH$_3$,
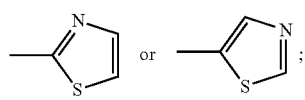
L$_5$ may be H, OH, NH$_2$, OCH$_3$, CH$_2$CH$_3$, or CH$_3$;
L$_6$ may be H, OH, NH$_2$, OCH$_3$, CH$_2$CH$_3$, or CH$_3$;

L₇ may be H, F, Cl or Br;
L₈ may be H, Cl, F, Br, OH, NH₂, OCH₃, or CH₃;
L₉ may be H, Cl, F, Br, OH, NH₂, OCH₃, or CH₃; and
L₁₀ may be H, Cl, F, Br, OH, NH₂, I, CN, CH₂CH₃, CF₃, OCH₃,
or CH₃,
provided that the compound is not one of the following:
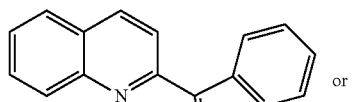
or
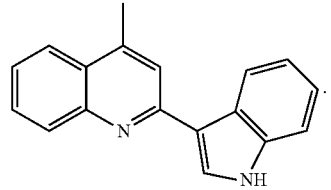
The compound may be:
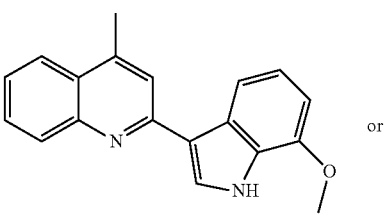
or
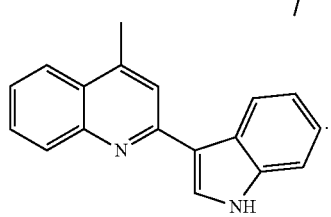
The compound may be:
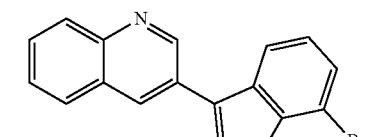
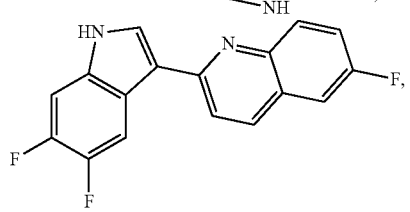
-continued
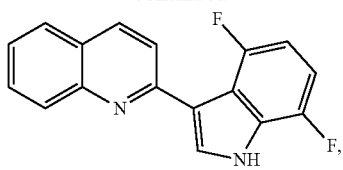
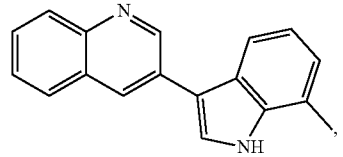
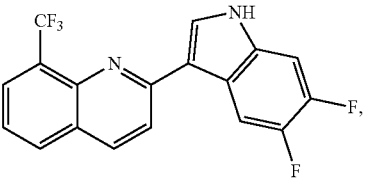
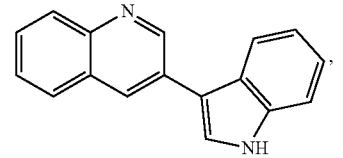
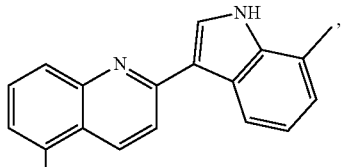
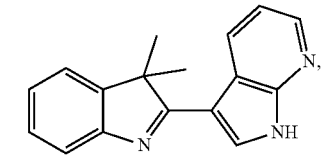
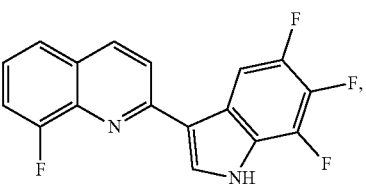
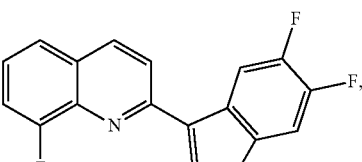
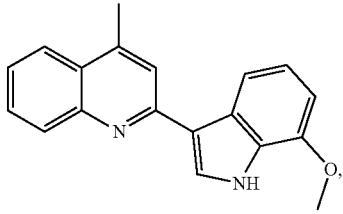

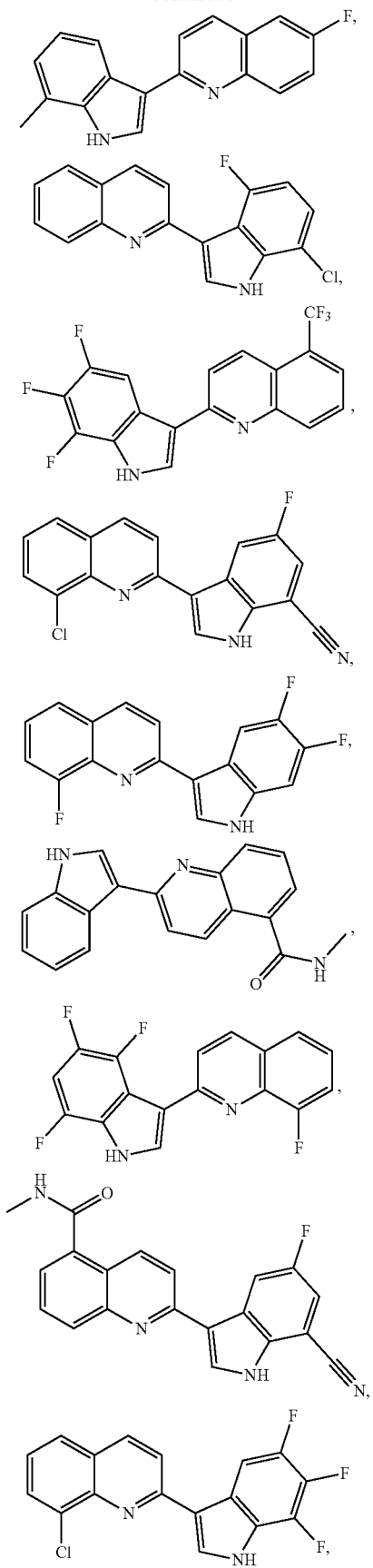
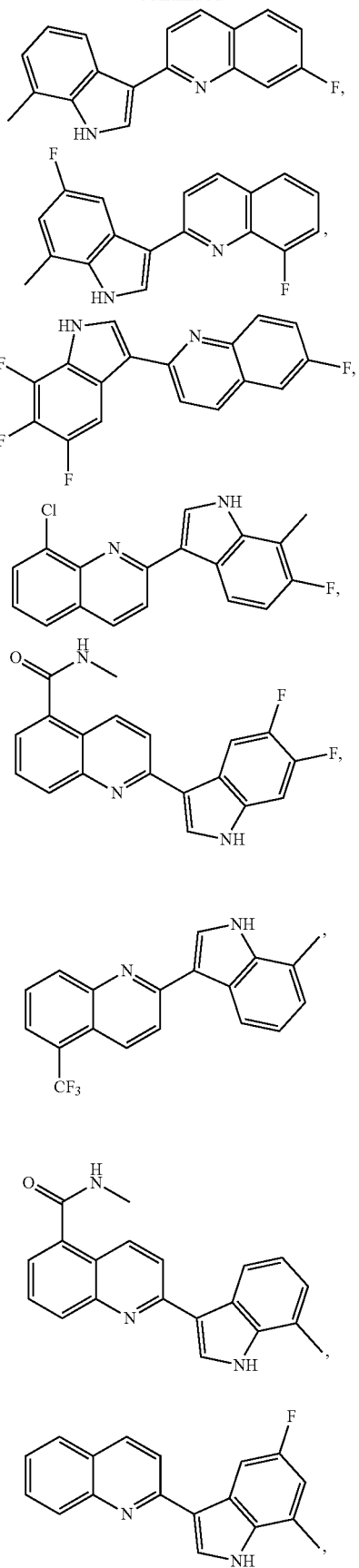

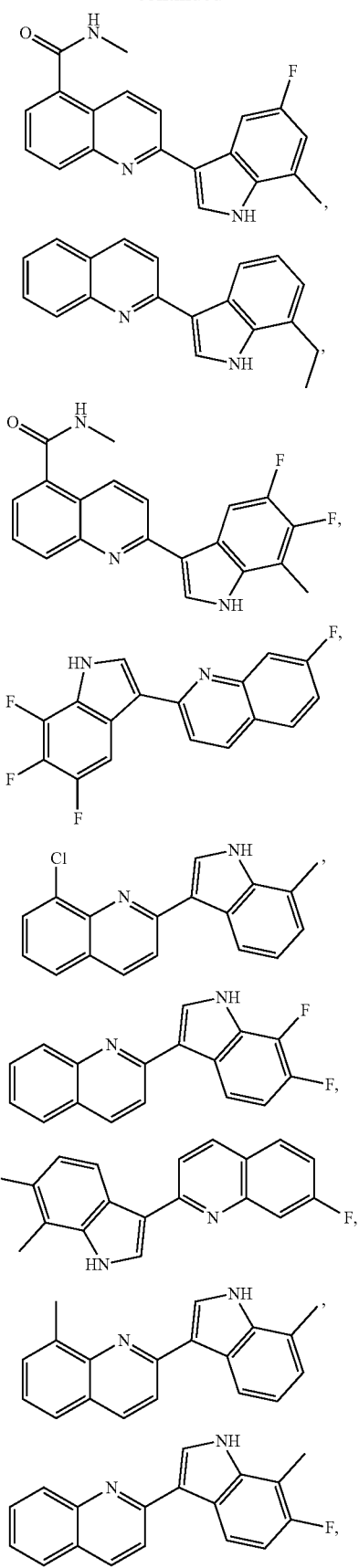
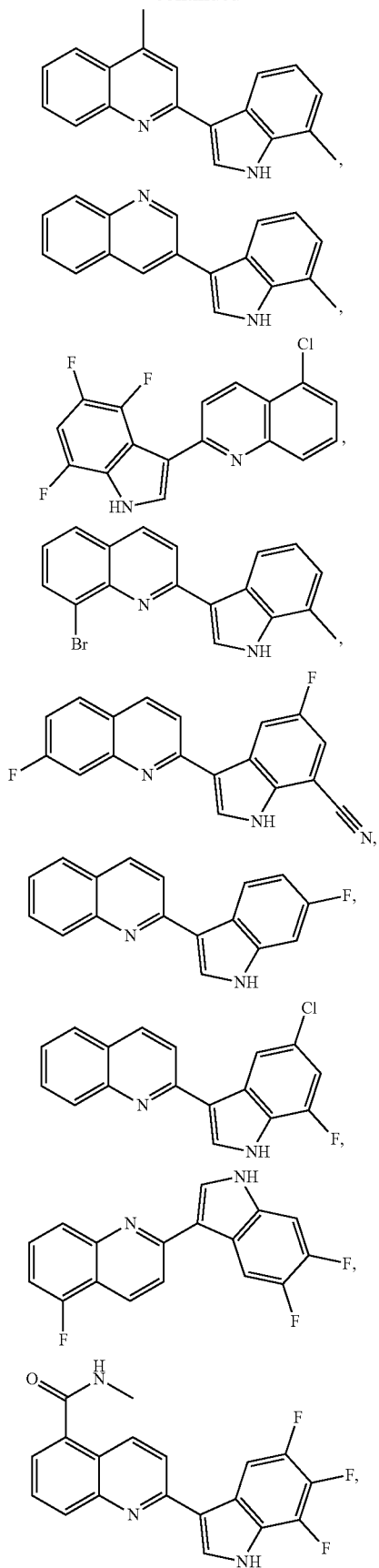

-continued
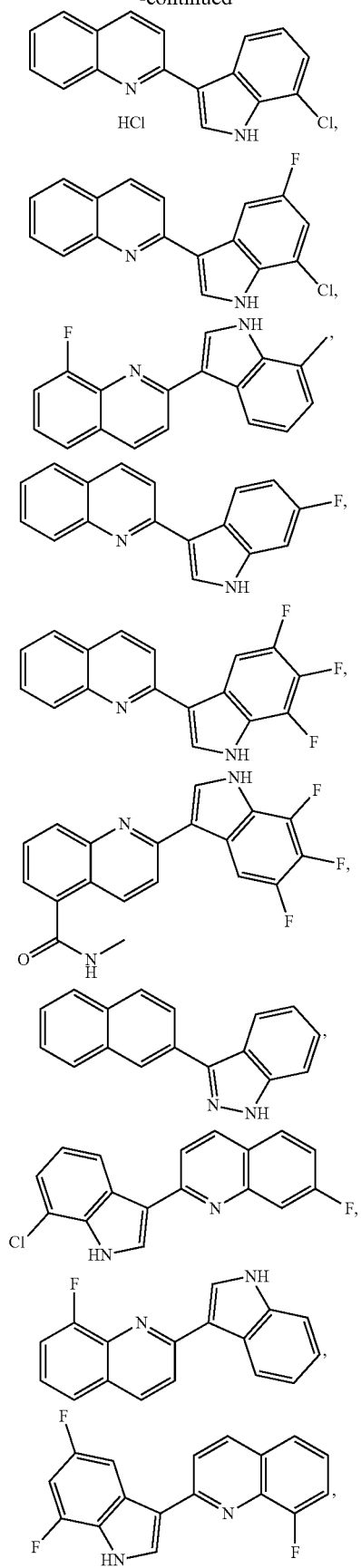
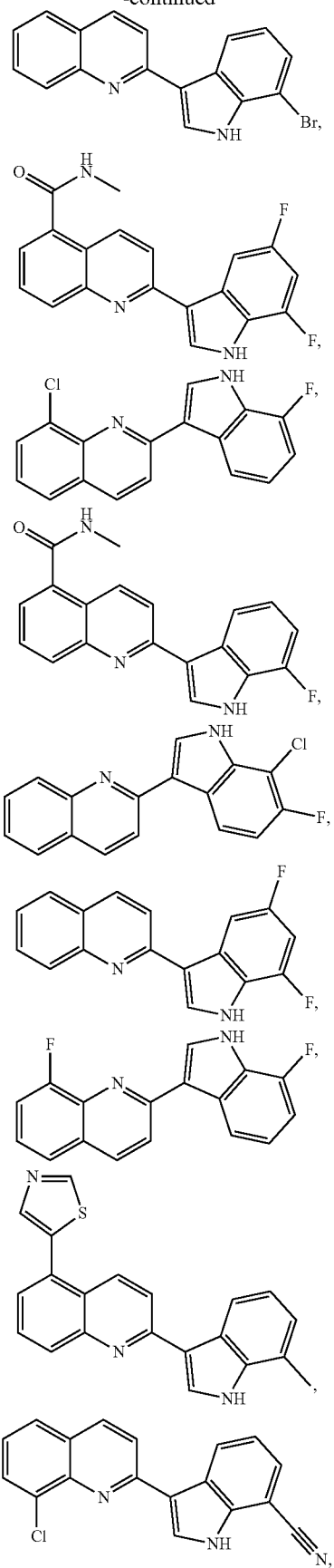

-continued

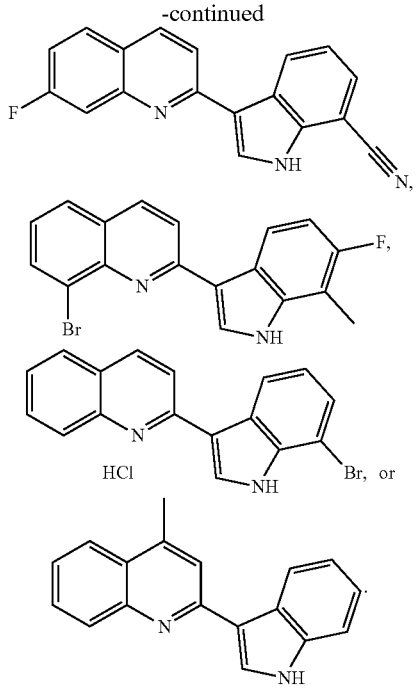

The compound may have the structure of Formula III:

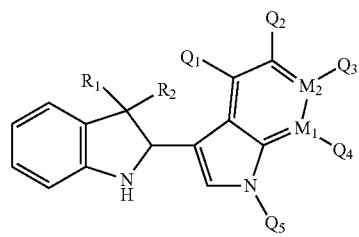

wherein,
R₁ is CH₃, OH, OCH₃, CH₂CH₃, or OCH₂CH₃;
R₂ is CH₃, OH, OCH₃, CH₂CH₃, or OCH₂CH₃;
or R₁ and R₂ form

;

M₁ is C or N;
M₂ is C or N;
Q₁ is H;
Q₂ is NH₂, Br, Cl, H, OCH₃, CH₂OH, OCH₂-Ph,

OH, F, I, C(O)NH₂,

NH₂, or CH₃;
Q₃ is NH₂, Br, Cl, H, OCH₃, CH₂OH, OCH₂-Ph,

OH, F, I, C(O)NH₂,

NH₂, or CH₃;
Q₄ is NH₂, Br, Cl, H, OCH₃, CH₂OH, OCH₂-Ph,

OH, F, I, C(O)NH₂,

NH₂, or CH₃; and
Q₅ is H, CH₃, CH₂CH₂OH,

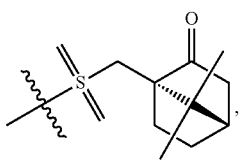 [SMILES: *S(=C)(=C)C[C@]12CC[C@@H](CC1=O)C2(C)C]

OH, F, Br, Cl, I, or

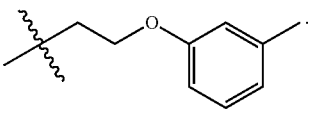 [SMILES: *CCOc1cccc(C)c1]

The compound may be selected from one or more of the following:

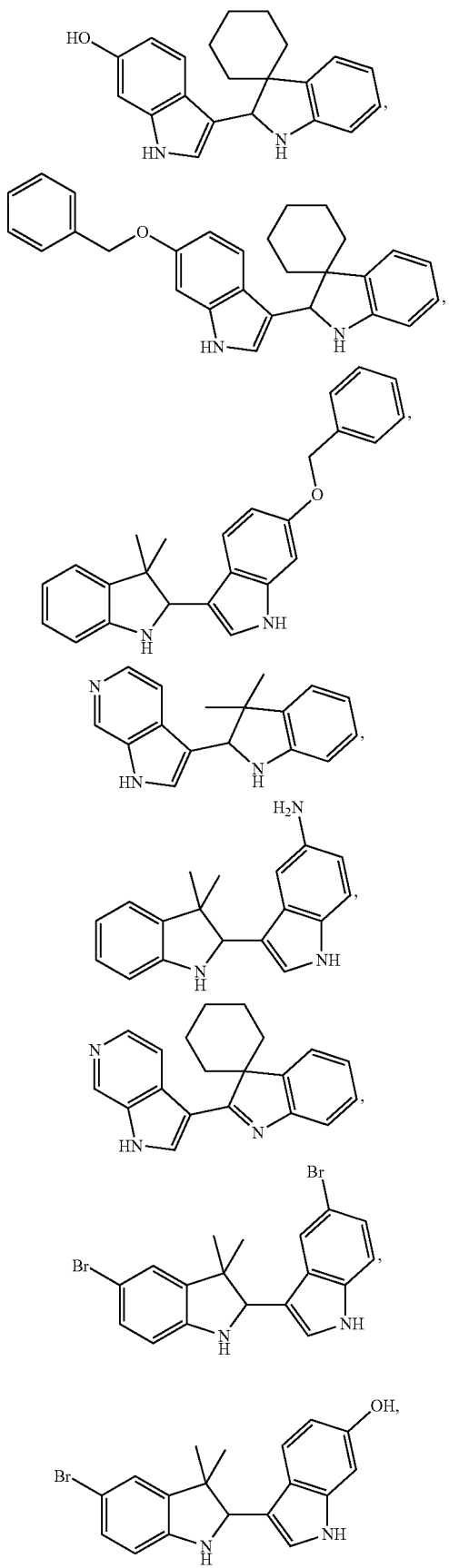
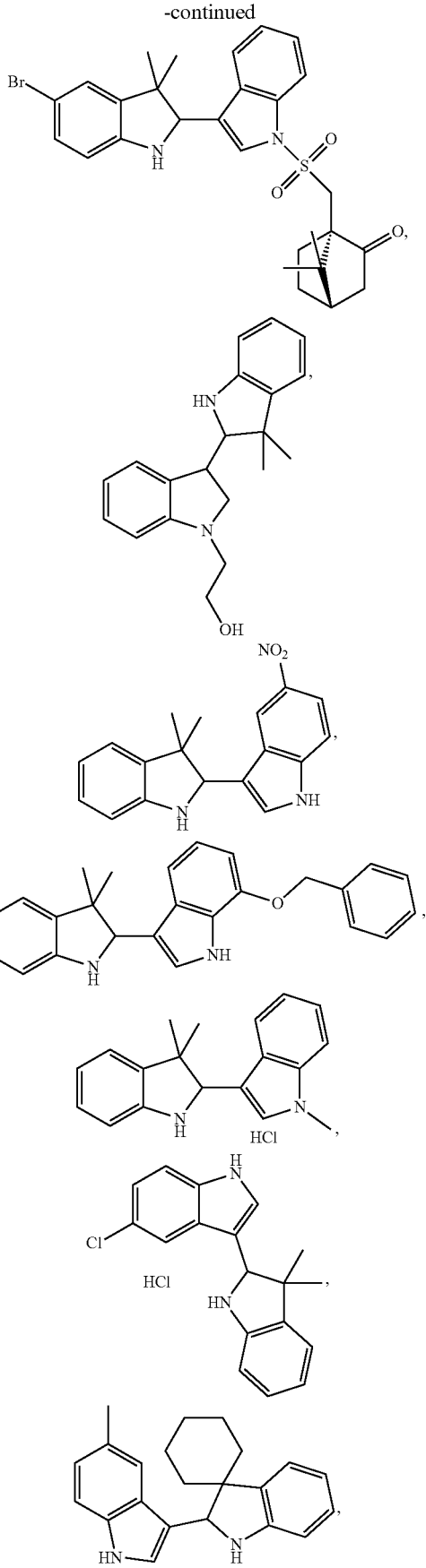

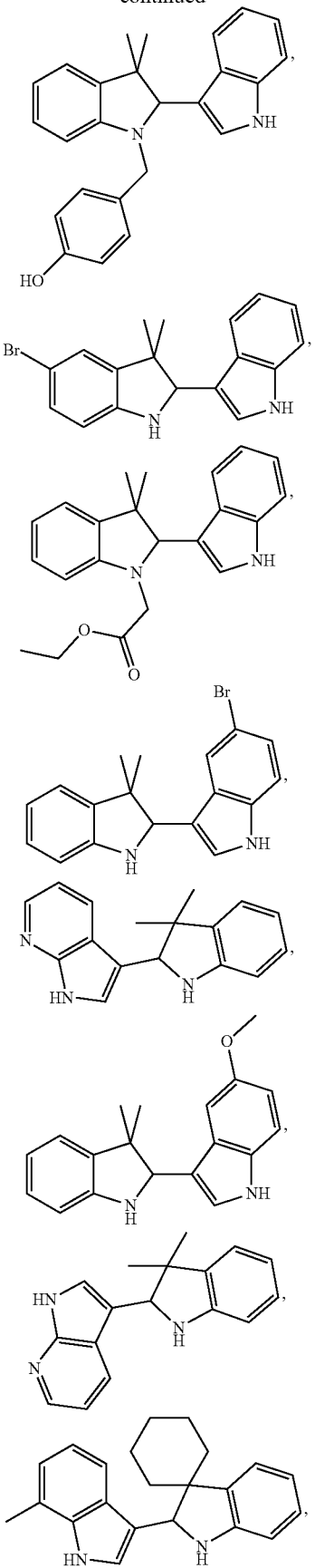
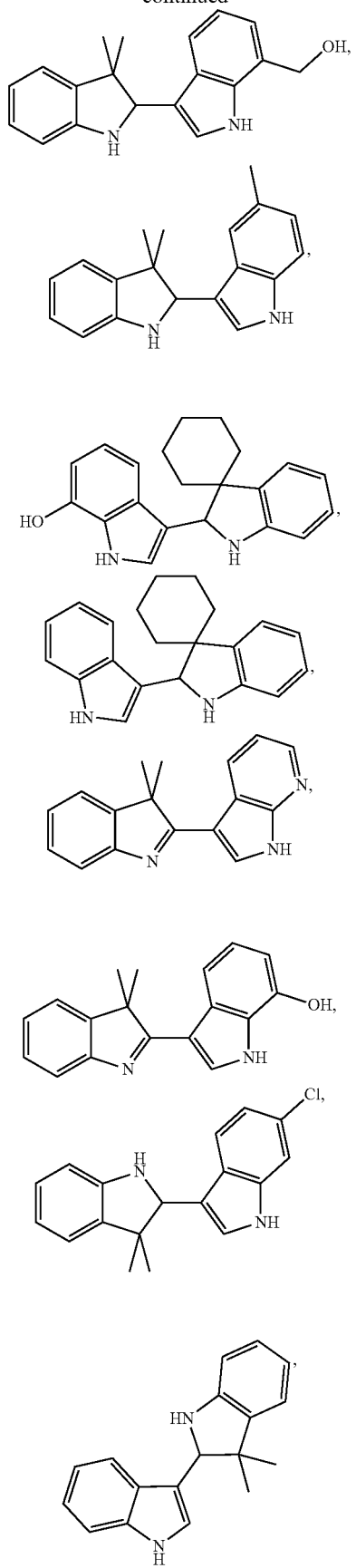

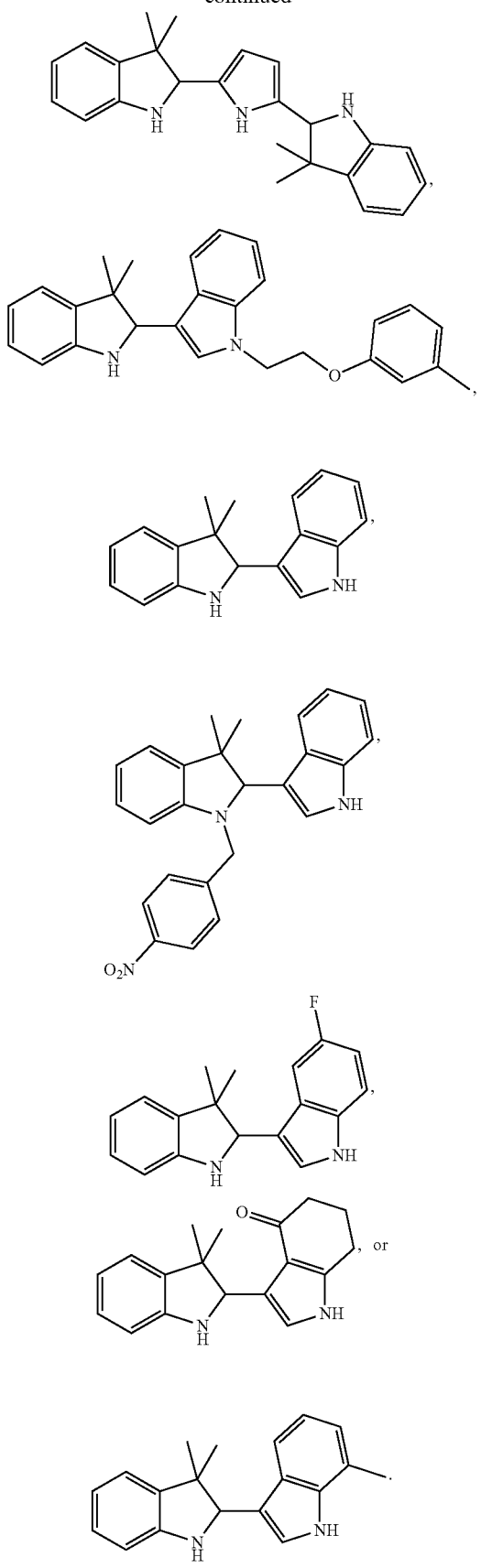
The compound may be
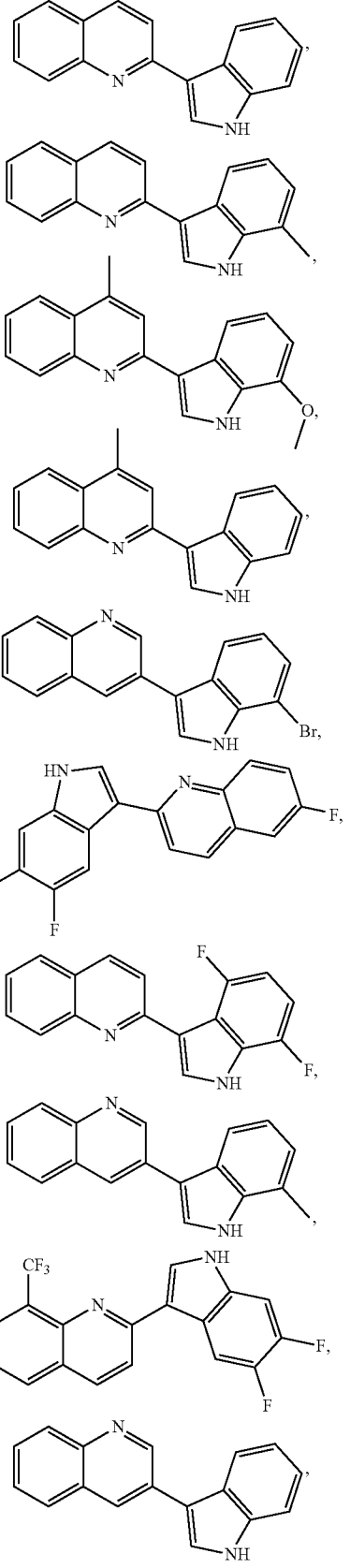

123
-continued
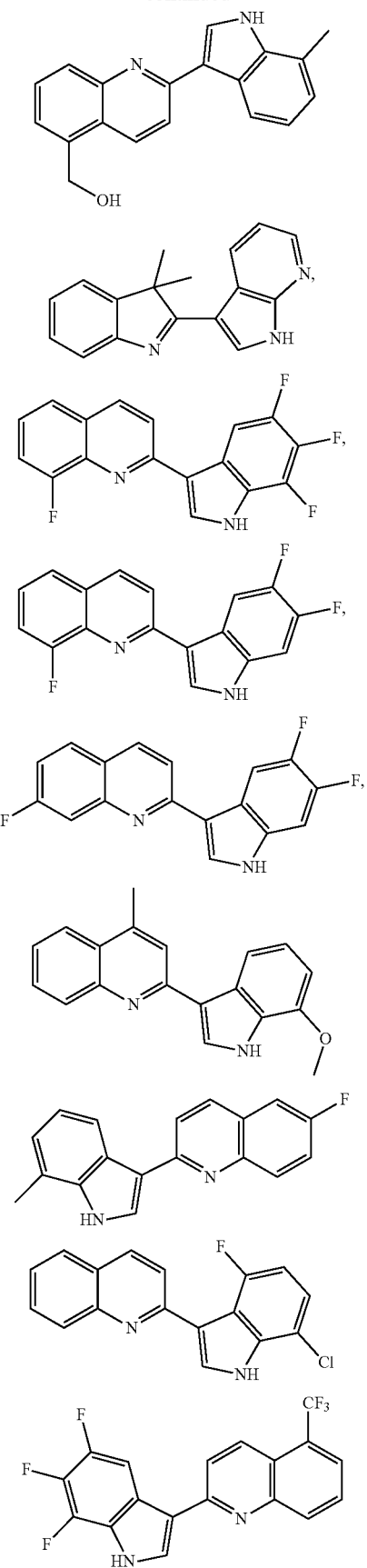
124
-continued
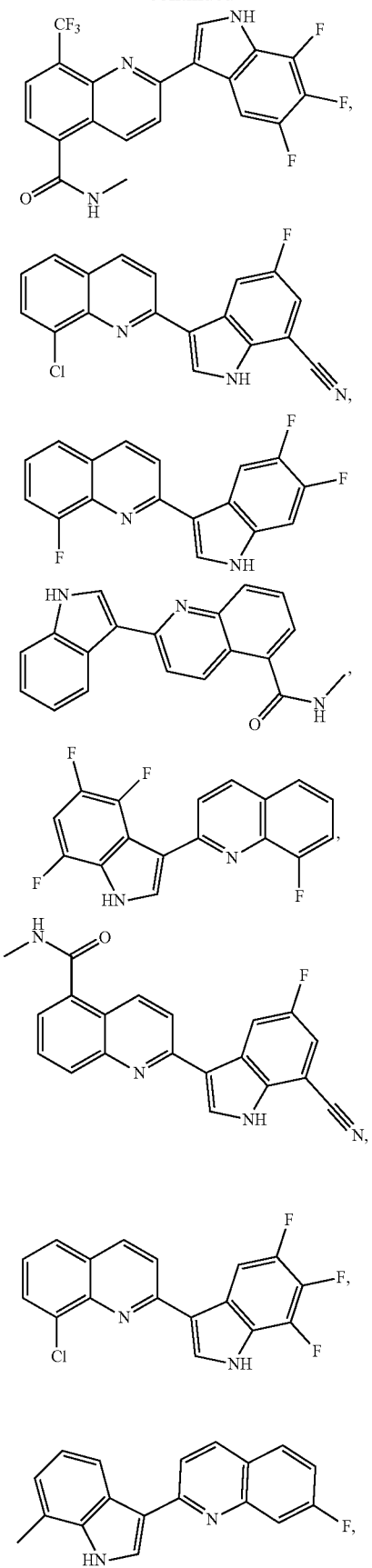

-continued
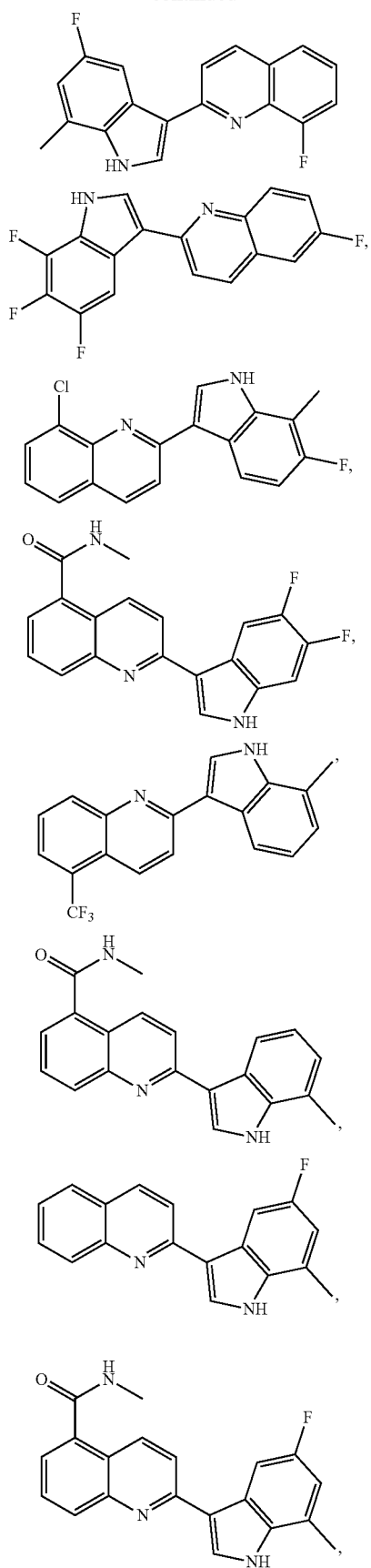
-continued
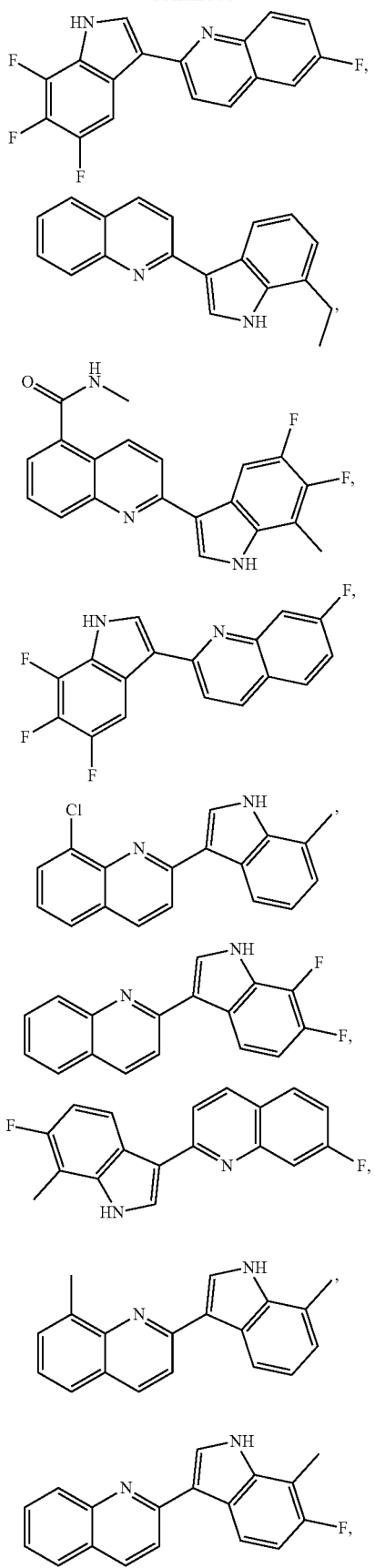

-continued
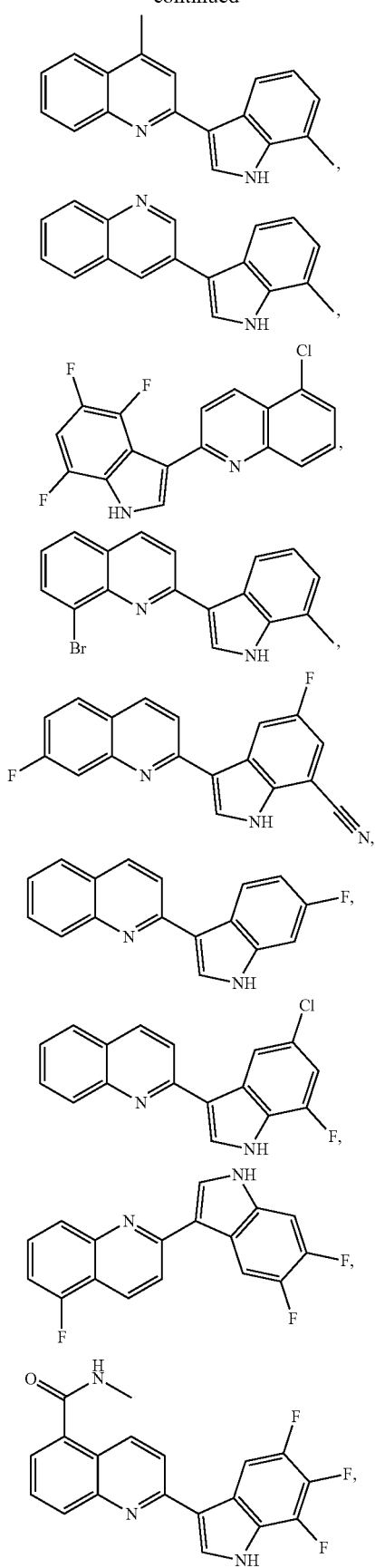
-continued
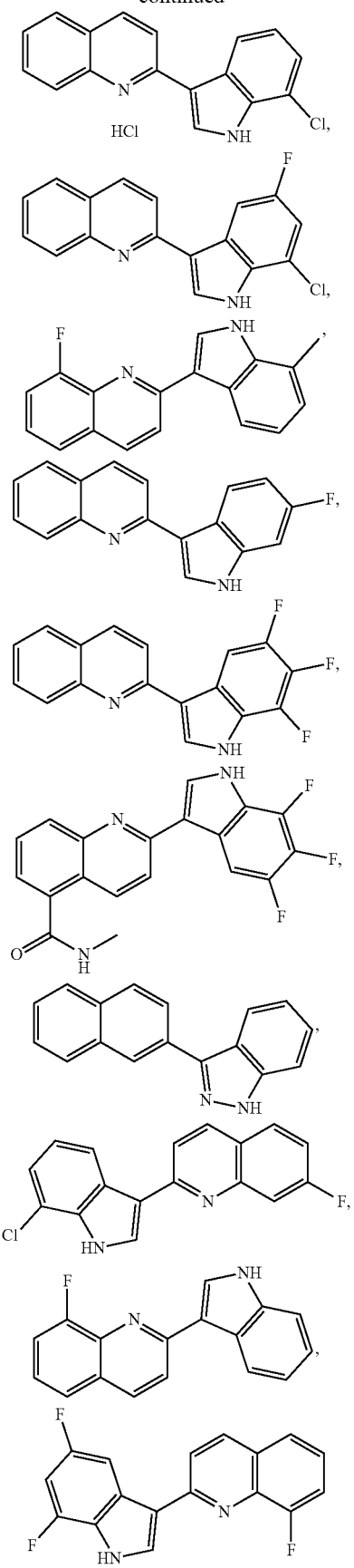

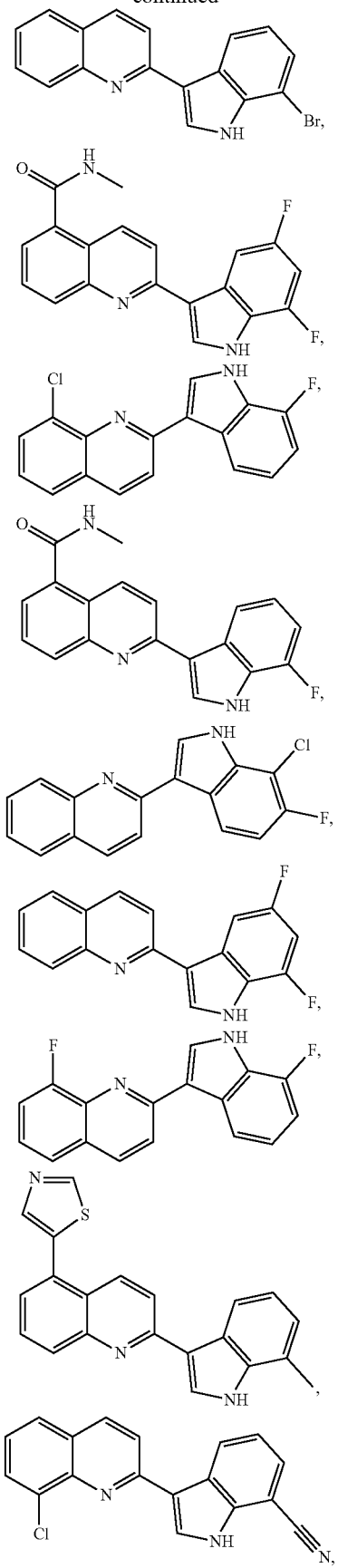

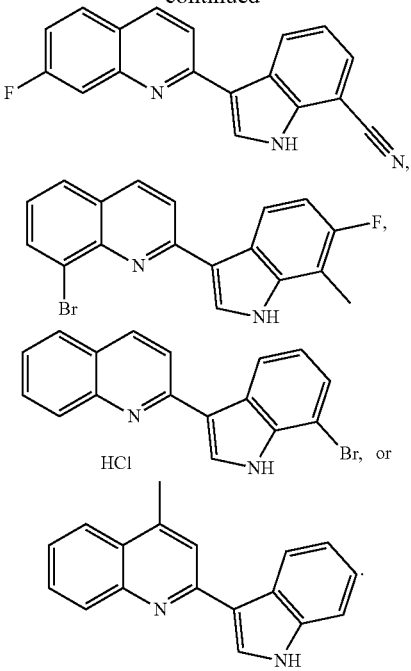

The compound may be for use in the treatment of at least one indication selected from the group including: prostate cancer, breast cancer, ovarian cancer, endometrial cancer, hair loss, acne, hirsutism, ovarian cysts, polycystic ovary disease, precocious puberty, and age-related macular degeneration.

The modulating AR activity is for the treatment of at least one indication selected from the group including: prostate cancer, breast cancer, ovarian cancer, endometrial cancer, hair loss, acne, hirsutism, ovarian cysts, polycystic ovary disease, precocious puberty, and age-related macular degeneration.

The modulating AR activity may be for the treatment of prostate cancer. The mammalian cell may be a human cell. The cell may be a prostate cell. The cell may be a prostate cancer cell.

The compound may be for use in the treatment of at least one indication selected from the group consisting of: cancer, hair loss, acne, hirsutism, ovarian cysts, polycystic ovary disease, precocious puberty, and age related macular degeneration. The cancer may be AR-mediated cancer. The cancer may be selected from the group including of: prostate cancer, breast cancer, ovarian cancer, endometrial cancer and bladder cancer. The cancer may be Taxene resistant triple negative breast cancer.

In accordance with a further aspect, there is provided a pharmaceutical composition for modulating AR activity, the composition including a compound described herein, and a pharmaceutically acceptable carrier.

In accordance with a further aspect, there is provided a method of modulating AR activity, the method including (a) administering a compound described herein or a pharmaceutical composition described herein to a subject in need thereof.

In accordance with a further aspect, there is provided a method for modulating AR activity, the method including administering to a mammalian cell a compound or pharmaceutically acceptable salt thereof as described herein.

In accordance with a further aspect, there is provided a use of a compound described herein, for modulating AR activity.

In accordance with a further aspect, there is provided a use of a compound described herein, for the manufacture of a medicament for modulating AR activity.

In accordance with a further aspect, there is provided a pharmaceutical composition including a compound or pharmaceutically acceptable salt thereof described herein and a pharmaceutically acceptable excipient.

In accordance with a further aspect, there is provided a commercial package including (a) a compound described herein; and (b) instructions for the use thereof for modulating AR activity.

In accordance with a further aspect, there is provided a commercial package including (a) a pharmaceutical composition comprising a compound described herein and a pharmaceutically acceptable carrier; and (b) instructions for the use thereof for modulating AR activity.

DETAILED DESCRIPTION

The BF3 site is an attractive target for direct inhibition of the AR co-activation. In silico computational drug discovery methods were used to conduct a virtual screen of ~4 million purchasable lead-like compounds from the ZINC database (Irwin, J. et al. Abstracts of Papers Am. Chem. Soc. (2005) 230:U1009) to identify potential BF3 binders. The in silico methods included large-scale docking, in-site rescoring and consensus voting procedures.

It will be understood by a person of skill that COOH and $NR_2$ may include the corresponding ions, for example carboxylate ions and ammonium ions, respectively.

Alternatively, where the ions are shown, a person of skill in the art will appreciate that the counter ion may also be present.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds of Formula I or Formula II above may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments compounds of Formula I or Formula II may be used in the preparation of a medicament or a composition for systemic treatment of an indication described herein. In some embodiments, methods of systemically treating any of the indications described herein are also provided.

Compounds as described herein may be in the free form or in the form of a salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU).

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines using PC3 cells as a negative control that do not express AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age-related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age-related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age-related macular degeneration are known to those of ordinary skill in the art.

Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK).

Some compounds and compositions as described herein may interfere with a mechanism specific to ligand-dependent activation (e.g., accessibility of the ligand binding domain (LBD) to androgen) or to ligand-independent activation of the AR.

Various alternative embodiments and examples of the invention are described herein. These embodiments and examples are illustrative and should not be construed as limiting the scope of the invention.

Materials and Methods

In Silico Screening

Ten million commercially available compounds from the ZINC12.0 structural libraries (Irwin, J. J. and Shoichet, B. K. ZINC—a free database of commercially available compounds for virtual screening. J Chem Inf Model 2005, 45, 177-182) were imported into a molecular database using Molecular Operating Environment (MOE) version 2007.09 (MOE, Chemical Computing Group, Inc., 2008, www.chemcomp.com). These structures were energy minimized using an MMFF94x force field, exported in SD format and rigidly docked into the BF3 site of the protein structures 4HLW with Glide software (Friesner, R. A. et al. Glide: a new approach for rapid, accurate docking and scoring. 1. Method and assessment of docking accuracy. J Med Chem. 2004, 25, 739-49). About 2 million molecules that had a GlideScore<−5.0 were then re-docked into the same BF3 binding cavity using the electronic high-throughput screening (eHiTS) docking module (Zsoldos, Z. et al. eHiTS: a new fast, exhaustive flexible ligand docking system. J Mol Graph Model 2007, 26, 198-212). From this, 500,000 structures with eHiTS docking scores<−3.0 threshold were identified. They were scored by the LigX™ module of the MOE to account for the receptor/ligand flexibility. The pKi binding affinity was scored after energy minimization to select the ligands that showed the best binding characteristics defined mainly by the energy of hydrogen bonds and hydrophobic interactions. The virtual hits were scored using Molecular Mechanics, the Generalized Born model and Solvent Accessibility (MM-GB/SA) method with OPLS 2005 and GB/SA in MacroModel™ to calculate the free energies of the optimal chemical poses (Maestro, Schrödinger, LLC, New York, N.Y., 2008. www.schrodinger.com). The root mean square deviation (RMSD) was calculated between the Glide poses and the eHiTS poses to evaluate the docking consistency and thus to establish the most probable binding pose for a given ligand. Finally, very large and very small molecules were penalized based on a heavy atom count.

With this information, a cumulative scoring of five different predicted parameters (RMSD, heavy atoms count, LigX, Macromodel, pKi) was generated where each molecule receive a binary 1.0 score for every 'top 10% appearance'. The final cumulative vote (with the maximum possible value of 5) was then used to rank the training set entries. Based on the cumulative score 5000 compounds were selected and subjected to visual inspection. After this final selection step 200 compounds were selected out of which 150 chemical substances could be readily purchased in sufficient purity and quantity.

General Synthesis and Characterization of Compounds

Exemplary Scheme 1: Synthesis of Compound 13163

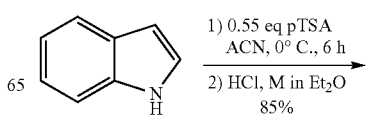

-continued

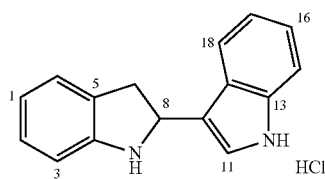

At 0° C., a solution of para-toluenesulfonic acid (13.4 g, 0.55 eq, 70.4 mmol) in acetonitrile (150 mL) was added drop-wise over 1 h to a solution of indole (15 g, 1.0 eq, 128.0 mmol) in acetonitrile (500 mL). The mixture was kept for additional 6 h at 0° C. The subsequent precipitate was filtered (at 0° C.) and washed with acetonitrile (three times). The precipitate was neutralized with saturated $NaHCO_3$ solution and extracted with AcOEt (3×100 mL). The organic extracts were combined, washed with brine, dried over $Na_2SO_4$; filtered and concentrated under reduced pressure. Any purification was needed and the crude was transformed in corresponding hydrochloride with HCl 2 M solution in ether and the precipitate salt was filtered to afford 14.8 g of the white solid (54.7 mmol, 85%).

Analysis

M.p.=169-170° C.

$t_R$ (HPLC)=3.01 min

MS (ESI+) m/z=235.12 [(M+H)$^+$]

HRMS (ESI+): calculated for $C_{16}H_{15}N_2$, m/z=235.1230; found, 235.1237; calculated for $C_{16}H_{14}N_2Na$, m/z=257.1049; found, 257.1058.

$^1$H NMR (400 MHz, DMSO-d$_6$): δ (ppm)=11.45 (s, 1H, $H_{12}$), 7.77 (d, J=8.0 Hz, 1H, His), 7.68 (d, J=2.6 Hz, 1H, $H_{11}$), 7.58-7.50 (m, 1H, $H_6$), 7.45 (d, J=8.4 Hz, 1H, $H_{15}$), 7.43-7.38 (m, 4H, $H_{12}$), 7.35-7.33 (m, 1H, $H_3$), 7.17 (ddd, J=8.2, 7.1, 1.1 Hz, 1H, $H_{16}$), 7.07 (ddd, J=8.0, 7.1, 1.0 Hz, 1H, $H_{17}$), 5.58 (t, J=8.7 Hz, 1H, $H_{18}$), 3.67 (d, J=8.7 Hz, 2H, $H_9$).

$^{13}$C NMR (101 MHz, DMSO-d$_6$): δ (ppm)=137.96 ($C_4$-arom.), 137.00 ($C_{13}$-arom.), 135.72 ($C_5$-arom.), 128.74 ($C_1$H-arom.), 128.50 ($C_2$H-arom.), 126.36 ($C_{14}$-arom.), 126.11 ($C_6$H-arom.), 125.72 ($C_{11}$H-arom.), 122.31 ($C_{16}$H-arom.), 119.69 ($C_{17}$H-arom.), 119.48 ($C_{18}$H-arom.), 119.38 ($C_3$H-arom.), 112.30 ($C_{15}$H-arom.), 110.24 ($C_{10}$-arom.), 56.55 ($C_8$H), 35.37 ($C_9H_2$).

General Synthesis Methods $^1$H and $^{13}$C NMR spectra (COSY, $^1$H/$^{13}$C 2D-correlations) were recorded with Bruker Avance III™ 400 MHz. Processing of the spectra was performed with MestRec™ software and data are reported as follows: chemical shifts (δ) in parts per million, coupling constants (J) in hertz (Hz). The high-resolution mass spectra were recorded in positive ion-mode with an ESI ion source on an Agilent™ Time-of-Flight LC/MS mass spectrometer. HPLC analyses and purity of >95% were performed by analytical reverse-phase HPLC with a Agilent™ instrument with variable detector using column Agilent Zorbax 4.6×5 mm, 5 um; flow: 2.0 mL·min$^{-1}$, $H_2O$ (0.1% FA)/$CH_3CN$ (0.1% FA), gradient 2→98% (6 min) and 98% (0.3 min). Melting points were determined with a Fischer-Jonhs.

Analytical Methods:

$^1$H and $^{13}$C NMR spectra (COSY, $^1$H/$^{13}$C 2D-correlations) were recorded with Bruker Avance III™ 400 MHz. Processing of the spectra was performed with MestRec™ software and data are reported as follows: chemical shifts (δ) in parts per million, coupling constants (J) in hertz (Hz). The high-resolution mass spectra were recorded in positive ion-mode with an ESI ion source on an Agilent™ Time-of-Flight LC/MS mass spectrometer. HPLC analyses and purity of >95% were performed by analytical reverse-phase HPLC with a Agilent™ instrument with variable detector using column Agilent Zorbax 4.6×5 mm, 5 um; flow: 2.0 mL·min$^{-1}$, $H_2O$ (0.1% FA)/$CH_3CN$ (0.1% FA), gradient 2→98% (6 min) and 98% (0.3 min).

Dimethyl- & Cyclohexyl-Hydroindole Moiety

General Procedure 1

Phenylhydrazine (1.0 eq) aldehyde (isobutyraldehyde or cyclohexanecarboxaldehyde) (1.0 eq) were diluted in AcOH (0.1 M). The mixture was heated at 65° C. for 2 h (until complete conversion). Reaction mixture containing imine intermediate was allowed to reach r.t. and indole (1.0 eq) was added to the mixture which was stirred additional 2 h at r.t. (until complete conversion). Acetic acid was removed under vacuo. Then, the residue was poured with $H_2O$ and neutralized at pH 7 with sat. $NaHCO_3$ solution. The aqueous layer was extracted with AcOEt (×3) and organic layers were combined, washed with brine, dried over $Na_2SO_4$ and evaporated under reduced pressure. Then, crude was purified by automated combi-flash to afford the good compound.

General Procedure 2

Benzyloxy compound (1.0 eq) was dissolved in mixture of MeOH (0.05 M) and the system was purged with vacuum/$N_2$ (×3). Then, Pd/C (20% w/w) was added to the mixture and purged again with vacuum/$H_2$ and put under $H_2$ atmosphere. The reaction was stirred overnight at r.t. under $H_2$ atmosphere. The reaction mixture was filtered on a plug of Celite which was washed with MeOH. The filtrate was concentrated under reduced pressure and the residue was purified by combi-flash to afford the good compound.

General Procedure 3

Imine compound (1.0 eq) was dissolved in AcOH (0.1 M) and the system was put under argon atmosphere. Then, $NaBH_3CN$ (1.1 eq) was added quickly. Then, the reaction was stirred at r.t. After overnight, the reaction mixture was concentrated and the crude was quenched with $H_2O$. Aqueous layer was neutralized with saturated $NaHCO_3$ solution until pH 7 and extracted with AcOEt (×2). The combined organic layers were washed with brine, dried over $Na_2SO_4$ and rotary evaporated. The crude was purified by automated combi-flash to afford the good compound.

General Procedure 4

From ester compound (1.0 eq) was diluted in mixture of MeOH/Acetone (1:3, 0.1 M). The mixture was stirred and a solution of LiOH (2.0 eq) in $H_2O$ (0.85 M) was added drop-wise over 5 min. Then, the mixture was stirred overnight at r.t. The reaction mixture was diluted in a mixture of $Et_2O$ and $H_2O$ and the aqueous phase was washed and then acidified with concentrated HCl solution until pH 3. The aqueous layer was extracted with $Et_2O$ (×2). The combined organic layers were washed with brine, dried over $Na_2SO_4$, filtered and concentrated under reduced pressure to give pure product.

General Procedure 5

A dried vessel was charged with LiAlH$_4$ (4.0 eq), enclosed with condenser and rubber cap and put under argon atmosphere. Then, carboxylic acid (1.0 eq) was dissolved in anhydrous THF (0.28 M) and was added in system which was stirred 2 h at 70° C. The excess of LiAlH$_4$ was destroyed by adding AcOEt drop-wise (exothermic reaction) and then by adding H$_2$O. Aqueous saturated NH$_4$Cl solution was added and the whole was extracted with AcOEt (×2). The combined organic layers were washed with H$_2$O and brine, dried over Na$_2$SO$_4$, filtered and concentrated under reduced pressure. The crude was purified by automated combi-flash to afford the good compound.

General Procedure 6

Phenylhydrazine (1.0 eq) and isobutyraldehyde (1.0 eq) were diluted in AcOH (0.1 M). The mixture was heated at 65° C. for 2 h (until complete conversion). Reaction mixture containing imine intermediate was allowed to reach r.t. Acetic acid was removed under vacuo. The residue was poured with H$_2$O and neutralized at pH 7 with sat. NaHCO$_3$ solution. The aqueous layer was extracted with AcOEt (×3) and organic layers were combined, washed with brine, dried over Na$_2$SO$_4$ and evaporated under reduced pressure. Then, residue corresponding to imine intermediate was diluted in ACN (0.5 M). Azaindole (0.9 eq) and ZnCl$_2$ (0.9 eq) were introduced in microwave vessel. The mixture was stirred and heated by microwave 3 h at 120° C. The resulting crystals (after overnight at r.t.) was filtered and washed with 1 N aqueous NaOH solution (50 mL) and extracted with AcOEt (×2). The organic layers were combined, washed with brine, dried over Na$_2$SO$_4$ and concentrated under reduced pressure to provide pure compound.

Dimethyl-Hydroindole Moiety 3-(3,3-dimethylindolin-2-yl)-5-methyl-1H-indole (Procedure 1)

| VPC Number | LabBook Code | ✓ IC$_{50}$ (eGFP) = 1.5 |
|---|---|---|
| 13 535 | CA 2-36 F9-15 (yield = 63%) | ✓ IC$_{50}$ (PSA) = 1.87 |

✓ t$_R$ (HPLC) = 4.07 min    ✓ MS (ESI+) m/z = 277.1719
[(M + H)$^+$]
✓ HRMS (ESI+): calculated for C$_{19}$H$_{21}$N$_2$O, m/z = 277.1699; found, 277.1708
✓ $^1$H NMR (400 MHz, DMSO-d$_6$): δ (ppm) = 10.83 (s, 1H, H$_{14}$), 7.33 (d, J = 0.6 Hz, 1H, H$_{20}$), 7.26 (d, J = 2.0 Hz, H$_{13}$), 7.25 (d, J = 8.0 Hz, 1H, H$_{17}$), 7.01 (d, J = 7.2 Hz, 1H, H$_6$), 6.97 (td, J = 7.6, 1.3 Hz, 1H, H$_2$), 6.88 (dd, J = 8.3, 1.5 Hz, 1H, H$_{18}$), 6.60 (td, J = 7.6, 1.2 Hz, 1H, H$_1$), 6.59 (d, J = 7.6 Hz, 1H, H$_3$), 5.82 (d, J = 2.4 Hz, 1H, H$_7$), 4.76 (d, J = 2.2 Hz, 1H, H$_8$), 2.33 (s, 3H, H$_{21}$), 1.39 (s, 3H, H$_{10}$), 0.74 (s, 3H, H$_{11}$).
✓ $^{13}$C NMR (101 MHz, DMSO-d$_6$): δ (ppm) = 150.99 (C$_4$-arom.), 138.68 (C$_5$-

(Brown Solid)

arom.), 135.33 (C$_{15}$-arom.), 127.54 (C$_{19}$-arom.), 127.29 (C$_2$H-arom.), 127.01 (C$_{16}$-arom.), 124.09 (C$_{13}$H-arom.), 122.80 (C$_{18}$H-arom.), 122.45 (C$_6$H-arom.), 119.77 (C$_{20}$H-arom.), 117.53 (C$_1$H-arom.), 113.64 (C$_{12}$-arom.), 111.60 (C$_{17}$H-arom.), 108.85 (C$_3$H-arom.), 68.17 (C$_8$H), 45.20 (C$_9$), 27.15 (C$_{10}$H$_3$), 25.01 (C$_{11}$H$_3$), 21.87 (C$_{21}$H$_3$).

3-(3,3-dimethylindolin-2-yl)-5-methoxy-1H-indole (Procedure 1)

| VPC Number | LabBook Code | ✓ IC$_{50}$ (eGFP) = 2.2 |
|---|---|---|
| 13 536 | CA 2-38 F10-19 (yield = 46%) | ✓ IC$_{50}$ (PSA) = 2.52 |

✓ t$_R$ (HPLC) = 3.82 min    ✓ MS (ESI+) m/z = 293.1668
[(M + H)$^+$]
✓ HRMS (ESI+): calculated for C$_{19}$H$_{21}$N$_2$O, m/z = 293.1648; found, 293.1654
✓ $^1$H NMR (400 MHz, DMSO-d$_6$): δ (ppm) = 10.79 (s, 1H, H$_{14}$), 7.27 (d, J = 2.5 Hz, 1H, H$_{13}$), 7.24 (d, J = 8.8 Hz, 1H, H$_{17}$), 7.02 (br d, J = 7.2 Hz, 1H, H$_6$), 6.97 (td, J = 7.6, 1.3 Hz, 1H, H$_2$), 6.88 (d, J = 2.4 Hz, 1H, H$_{20}$), 6.70 (dd, J = 8.8, 2.4 Hz, 1H, H$_{18}$), 6.61 (td, J = 7.6, 1.2 Hz, 1H, H$_1$), 6.59 (d, J = 7.6 Hz, 1H, H$_3$), 5.82 (d, J = 2.0 Hz, 1H, H$_7$), 4.73 (d, J = 1.9 Hz, 1H, H$_8$), 3.62 (s, 3H, H$_{22}$), 1.38 (s, 3H, H$_{10}$), 0.78 (s, 3H, H$_{11}$).
✓ $^{13}$C NMR (101 MHz, DMSO-d$_6$): δ (ppm) = 153.22 (C$_{19}$-arom.), 151.10 (C$_4$-arom.), 138.59 (C$_5$-arom.), 132.18 (C$_{15}$-arom.), 127.37 (C$_2$H-arom.), 127.36

(Yellow Solid)

(C$_{16}$-arom.), 124.83 (C$_{13}$H-arom.), 122.32 (C$_6$H-arom.), 117.51 (C$_1$H-arom.), 114.38 (C$_{12}$-arom.), 112.44 (C$_{17}$H-arom.), 111.21 (C$_{18}$-arom.), 108.72 (C$_3$H-arom.), 102.31 (C$_{20}$H-arom.), 68.27 (C$_8$H), 55.63 (C$_{22}$H$_3$), 45.21 (C$_9$), 27.73 (C$_{10}$H$_3$) 24.58 (C$_{11}$H$_3$).

3-(3,3-dimethylindolin-2-yl)-5-amine-1H-indole (Procedure 1)

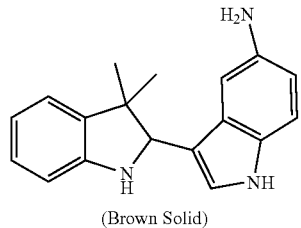 [SMILES: CC1(C)c2ccccc2NC1c1c[nH]c2ccc(N)cc12]
(Brown Solid)

| VPC Number | LabBook Code | |
|---|---|---|
| 13 538 | CA 2-47 F7-17 (yield = 45%) | ✓ $IC_{50}$ (eGFP) = 7.7<br>✓ $IC_{50}$ (PSA) = No Data |

✓ $t_R$ (HPLC) = 2.56 min ✓ MS (ESI+) m/z = 278.1668 [(M + H)+]
✓ HRMS (ESI+): calculated for $C_{18}H_{20}N_3$, m/z = 278.1652; found, 278.1657
✓ $^1$H NMR (400 MHz, DMSO-$d_6$): δ (ppm) = 10.53 (d, J = 1.6 Hz, 1H, $H_{14}$), 7.14 (d, J = 2.4 Hz, 1H, $H_{13}$), 7.08 (d, J = 8.4 Hz, 1H, $H_{17}$), 7.00 (dd, J = 7.2, 0.7 Hz, 1H, $H_6$) 6.95 (td, J = 7.6, 1.3 Hz, 1H, $H_2$), 6.86 (d, J = 2.0 Hz, 1H, $H_{20}$), 6.60 (td, J = 7.6, 0.8 Hz, 1H, $H_2$,) 6.57 (d, J = 7.6 Hz, 1H, $H_3$), 6.51 (dd, J = 8.5, 2.0 Hz, 1H, $H_{18}$), 5.78 (s, 1H, $H_7$), 4.86 (s 2H, $H_{21}$), 4.69 (s, 1H, $H_8$), 1.39 (s, 3H, $H_{10}$), 0.75 (s, 3H, $H_{11}$).
✓ $^{13}$C NMR (101 MHz, DMSO-$d_6$): δ (ppm) = 150.97 ($C_4$-arom.), 138.81 ($C_5$-arom.), 140.00 ($C_{19}$-arom.), 131.08 ($C_{15}$-arom.), 128.25 ($C_{16}$-arom.), 127.21 ($C_2$H-arom.), 123.86 ($C_{13}$H-arom.), 122.47 ($C_6$H-arom.), 117.47 ($C_1$H-arom.), 112.50 ($C_{12}$-arom.), 112.36 ($C_{18}$H-arom.), 111.97 ($C_{17}$-arom.), 108.86 ($C_3$H-arom.), 104.09 ($C_{20}$H-arom.), 68.29 ($C_8$H), 45.21 ($C_9$), 27.00 ($C_{10}H_3$), 25.15 ($C_{11}H_3$).

3-(3,3-dimethylindolin-2-yl)-6-(benzyloxy)-1H-indole (Procedure 1)

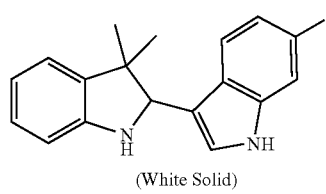
(White Solid)

| VPC Number | LabBook Code | |
|---|---|---|
| 13 544 | CA 2-54 Precipitate (yield = 53%) | ✓ $IC_{50}$ (eGFP) = 11.4<br>✓ $IC_{50}$ (PSA) = No Data |

✓ $t_R$ (HPLC) = 4.60 min ✓ MS (ESI+) m/z = 369.1981 [(M + H)+]
✓ HRMS (ESI+): calculated for $C_{25}H_{25}N_2O$, m/z = 369.1961; found, 369.1979
✓ $^1$H NMR (400 MHz, DMSO-$d_6$): δ (ppm) = 10.77 (s, 1H, $H_{14}$), 7.47 (d, J = 7.1 Hz, 2H, $H_{24, 28}$), 7.42-7.38 (m, 3H, $H_{20, 25, 27}$), 7.35-7.31 (m, 1H, $H_{26}$) 7.18 (d, J = 2.1 Hz, 1H, $H_{13}$), 6.99 (d, J = 6.8 Hz, 1H, $H_6$), 6.98-6.94 (m, 2H, $H_{2, 17}$), 6.69 (dd, J = 8.7, 2.3 Hz, 1H, $H_{19}$), 6.63-6.55 (m, 2H, $H_{1, 3}$,), 5.83 (d, J = 2.3 Hz, 1H, $H_7$), 5.11 (s, 2H, $H_{22}$), 4.73 (d, J = 2.2 Hz, 1H, $H_8$), 1.37 (s, 3H, $H_{10}$), 0.73 (s, 3H, $H_{11}$).
✓ $^{13}$C NMR (101 MHz, DMSO-$d_6$): δ (ppm) = 154.69 ($C_{18}$-arom.), 150.96 ($C_4$-arom.), 138.64 ($C_5$-arom.), 138.14 ($C_{23}$-arom.), 137.52 ($C_{15}$-arom.), 128.84 ($C_{25, 27}$H-arom.), 128.08 ($C_{26}$H-arom.), 127.96 ($C_{24, 28}$H-arom.), 127.32 ($C_2$H-arom.), 122.77 ($C_{13}$H-arom.), 122.41 ($C_6$H-arom.), 121.88 ($C_{16}$-arom.), 120.79 ($C_{20}$H-arom.), 117.54 ($C_1$H-arom.), 114.22 ($C_{12}$-arom.), 109.60 ($C_{19}$H-arom.), 108.83 ($C_3$H-arom.), 96.33 ($C_{17}$H-arom.), 69.92 ($C_{22}H_2$), 68.20 ($C_8$H, 45.15 ($C_9$), 27.16 ($C_{10}H_3$), 24.91 ($C_{11}H_3$).

3-(3,3-dimethylindolin-2-yl)-7-(benzyloxy)-1H-indole (Procedure 1)

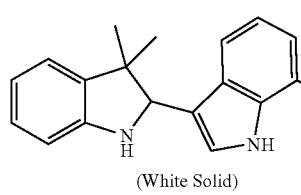
(White Solid)

| VPC Number | LabBook Code | |
|---|---|---|
| 13 543 | CA 2-55 F7-10 (yield = 61%) | ✓ $IC_{50}$ (eGFP) = 3.7<br>✓ $IC_{50}$ (PSA) = 3.19 |

✓ $t_R$ (HPLC) = 4.67 min ✓ MS (ESI+) m/z = 369.1976 [(M + H)+]
✓ HRMS (ESI+): calculated for $C_{25}H_{25}N_2O$, m/z = 369.1961; found, 369.1957
✓ $^1$H NMR (400 MHz, DMSO-$d_6$): δ (ppm) = 11.10 (d, J = 1.6 Hz, 1H, $H_{14}$), 7.58 (d, J = 7.8 Hz, 2H, $H_{24, 28}$), 7.46-7.39 (m, 2H, $H_{25, 27}$), 7.38-7.31 (m, 1H, $H_{26}$) 7.22 (d, J = 2.4 Hz, 1H, $H_{13}$), 7.15 (d, J = 8.0 Hz, 1H, $H_{20}$), 7.00 (d, J = 7.0 Hz, 1H, $H_6$), 6.96 (td, J = 7.6, 1.3 Hz, 1H, $H_2$), 6.85 (t, J = 7.8 Hz, 1H, $H_{19}$), 6.73 (d, J = 7.6 Hz, 1H, $H_{18}$, 6.62-6.56 (m, 2H, $H_{1, 3}$), 5.85 (d, J = 2.4 Hz, 1H, $H_7$), 5.26 (s, 2H, $H_{22}$), 4.77 (d, J = 2.2 Hz, 1H, $H_8$), 1.38 (s, 3H, $H_{10}$), 0.74 (s, 3H, $H_{11}$).
✓ $^{13}$C NMR (101 MHz, DMSO-$d_6$): δ (ppm) = 150.95 ($C_4$-arom.), 145.54 ($C_{17}$-arom.), 138.61 ($C_5$-arom.), 137.89 ($C_{23}$-arom.), 128.97 ($C_{16}$-arom.), 128.83 ($C_{25, 27}$H-arom.), 128.17 ($C_{26}$H-arom.), 128.01 ($C_{24, 28}$H-arom.), 127.32 ($C_2$H-arom.), 127.15 ($C_{15}$-arom.), 123.71 ($C_{13}$H-arom.), 122.43

($C_6$H-arom.), 119.23 ($C_{19}$H-arom.), 117.57 ($C_1$H-arom.), 114.81 ($C_{12}$-arom.), 113.19 ($C_{20}$H-arom.), 108.83 ($C_3$H-arom.), 103.08 ($C_{18}$H-arom.), 69.56 ($C_{22}$H$_2$), 68.03 ($C_8$H), 45.20 ($C_9$), 27.19 ($C_{10}$H$_3$), 24.89 ($C_{11}$H$_3$).

3-(3,3-dimethylindolin-2-yl)-6-hydroxy-1H-indole (Procedure 2)

| VPC Number | LabBook Code | | |
|---|---|---|---|
| 13 542 | CA 2-61 F3-8 (yield = 62%) | ✓ $IC_{50}$ (eGFP) = 5.7 | |
| | | ✓ $IC_{50}$ (PSA) = No Data | |

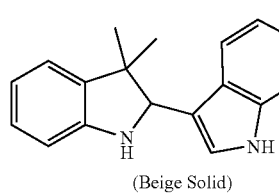
(Beige Solid)

✓ $t_R$ (HPLC) = 3.25 min      ✓ MS (ESI+) m/z = 279.1485 [(M + H)$^+$]
✓ HRMS (ESI+): calculated for $C_{18}H_{19}N_2O$, m/z = 279.1492; found, 279.1485
✓ $^1$H NMR (400 MHz, DMSO-d$_6$): δ (ppm) = 10.55 (s, 1H, H$_{14}$), 8.84 (s, 1H, H$_{21}$), 7.28 (d, J = 8.5 Hz, 1H, H$_{20}$), 7.08 (d, J = 2.0 Hz, 1H, H$_{13}$), 6.99 (d, J = 6.8 Hz, 1H, H$_6$), 6.95 (td, J = 7.6, 1.3 Hz, 1H, H$_2$), 6.71 (d, J = 2.0 Hz, 1H, H$_{17}$), 6.62-6.54 (m, 2H, H$_{1, 3}$), 6.47 (dd, J = 8.6, 2.2 Hz, 1H, H$_{19}$), 5.79 (d, J = 2.4 Hz, 1H, H$_7$) 4.70 (d, J = 2,1 Hz, 1H, H$_8$), 1.37 (s, 3H, H$_{10}$), 0.73 (s, 3H, H$_{11}$).
✓ $^{13}$C NMR (101 MHz, DMSO-d$_6$): δ (ppm) = 153.20 ($C_{18}$-arom.), 150.98 ($C_4$-arom.), 138.70 ($C_5$-arom.), 138.04 ($C_{15}$-arom.), 127.28 ($C_2$H-arom.), 122.40 ($C_6$H-arom.), 121.88 ($C_{13}$H-arom.), 120.84 ($C_{16}$-arom.), 120.50 ($C_{20}$H-arom.), 117.48 ($C_1$H-arom.), 114.08 ($C_{12}$-arom.), 109.39 ($C_{19}$H-arom.), 108.78 ($C_3$H-arom.), 96.92 ($C_{17}$H-arom.), 68.27 ($C_8$H), 45.10 ($C_9$), 27.17 ($C_{10}$H$_3$), 24.90 ($C_{11}$H$_3$).

3-(3,3-dimethylindolin-2-yl)-7-hydroxy-1H-indole (Procedure 2)

| VPC Number | LabBook Code | | |
|---|---|---|---|
| 13 541 | CA 2-62 F6-11 (yield = 37%) | ✓ $IC_{50}$ (eGFP) = 0.5 | |
| | | ✓ $IC_{50}$ (PSA) = 0.94 | |

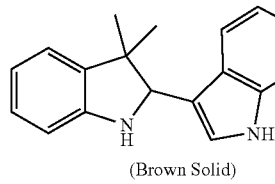
(Brown Solid)

✓ $t_R$ (HPLC) = 3.51 min      ✓ MS (ESI+) m/z = 279.1525 [(M + H)$^+$]
✓ HRMS (ESI+): calculated for $C_{18}H_{19}N_2O$, m/z = 279.1492; found, 279.1496
✓ $^1$H NMR (400 MHz, DMSO-d$_6$): δ (ppm) = 10.76 (s, 1H, H$_{14}$), 9.46 (s, 1H, H$_{21}$), 7.19 (d, J = 2.4 Hz, 1H, H$_{13}$), 7.02-6.98 (m, 2H, H$_{6, 20}$), 6.96 (td, J = 7.6, 1.3 Hz, 1H, H$_2$), 6.73 (t, J = 7.7 Hz, 1H, H$_{19}$), 6.62-6.55 (m, 2H, H$_{1, 3}$), 6.48 (dd, J = 7.5, 0.6 Hz, 1H, H$_{18}$), 5.82 (d, J = 2.4 Hz, 1H, H$_7$), 4.75 (d, J = 2.2 Hz, 1H, H$_8$), 1.38 (s, 3H, H$_{10}$), 0.74 (s, 3H, H$_{11}$).
✓ $^{13}$C NMR (101 MHz, DMSO-d$_6$): δ (ppm) = 150.98 ($C_4$-arom.), 143.94 ($C_{17}$-arom.), 138.67 ($C_5$-arom.), 129.24 ($C_{16}$-arom.), 127.29 ($C_2$H-arom.), 126.97 ($C_{13}$H-arom.), 123.40 ($C_{13}$H-arom.), 122.41 ($C_6$H-arom.), 119.42 ($C_{19}$H-arom.), 117.52 ($C_1$H-arom.), 114.60 ($C_{12}$-arom.), 111.24 ($C_{20}$H-arom.), 108.80 ($C_3$H-arom.), 105.55 ($C_{18}$H-arom.), 68.08 ($C_8$H), 45.16 ($C_9$), 27.17 ($C_{10}$H$_3$), 24.88 ($C_{11}$H$_3$).

3-(3,3-dimethylindolin-2-yl)-7-methyl-1H-indole (Procedure 1)

| VPC Number | LabBook Code | | |
|---|---|---|---|
| 13 546 | CA 2-67 F4-10 (yield = 62%) | ✓ $IC_{50}$ (eGFP) = No Data | |
| | | ✓ $IC_{50}$ (PSA) = No Data | |

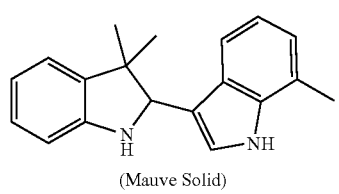 [SMILES: Cc1cccc2c(C3Nc4ccccc4C3(C)C)c[nH]c12]
(Mauve Solid)

✓ $t_R$ (HPLC) = 4.16 min      ✓ MS (ESI+) m/z = 277.1705 [(M + H)$^+$]
✓ HRMS (ESI+): calculated for $C_{19}H_{21}N_2$, m/z = 277.1699; found, 277.1707
✓ $^1$H NMR (400 MHz, DMSO-d$_6$): δ (ppm) = 10.94 (s, 1H, H$_{14}$), 7.39-7.35 (m, 1H, H$_{20}$), 7.31 (d, J = 2.4 Hz, 1H, H$_{13}$), 7.01 (d, J = 7.2 Hz, 1H, H$_6$), 6.97 (td, J = 7.6, 1.3 Hz, 1H, H$_2$), 6.87-6.83 (m, 2H, H$_{18, 19}$), 6.61 (td, J = 7.2, 0.8 Hz, 1H, H$_1$), 6.58 (d, J = 7.6 Hz, 1H, H$_3$), 5.84 (d, J = 2.4 Hz, 1H, H$_7$), 4.80 (d, J = 2.2 Hz, 1H, H$_8$), 2.46 (s, 3H, H$_{21}$), 1.39 (s, 3H, H$_{10}$), 0.74 (s, 3H, H$_{11}$).
✓ $^{13}$C NMR (101 MHz, DMSO-d$_6$): δ (ppm) = 150.97 ($C_4$-arom.), 138.68

(C$_5$-arom.), 136.42 (C$_{15}$-arom.), 127.32 (C$_2$H-arom.), 126.97 (C$_{16}$-arom.), 123.73 (C$_{13}$H-arom.), 122.42 (C$_6$H-arom.), 121.72 (C$_{19}$H-arom.), 120.90 (C$_{17}$-arom.), 118.96 (C$_{18}$H-arom.), 117.73 (C$_{20}$H-arom.), 117.57 (C$_1$H-arom.), 114.63 (C$_{12}$-arom.), 108.85 (C$_3$H-arom.), 68.11 (C$_8$H), 45.17 (C$_9$), 27.16 (C$_{10}$H$_3$), 24.95 (C$_{11}$H$_3$), 17.27 (C$_{21}$H$_3$).

3-(3,3-dimethylindolin-2-yl)-7-fluoro-1H-indole (Procedure 1)

| VPC Number | LabBook Code | ✓ IC$_{50}$ (eGFP) = No Data |
|---|---|---|
| 13 555 | CA 2-90 F4-7 (yield = 62%) | ✓ IC$_{50}$ (PSA) = No Data |

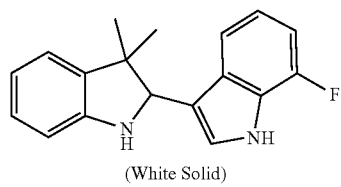 [SMILES: CC1(C)c2ccccc2NC1c1c[nH]c2c(F)cccc12]

(White Solid)

✓ $t_R$ (HPLC) = 4.12 min   ✓ MS (ESI+) m/z = 281.1456 [(M + H)$^+$]
✓ HRMS (ESI+): calculated for C$_{18}$H$_{18}$FN$_2$, m/z = 281.1449; found, 281.1454
✓ $^1$H NMR (400 MHz, DMSO-d$_6$): δ (ppm) = 11.49 (s, 1H, H$_{14}$), 7.41-7.34 (m, 2H, H$_{13, 20}$), 7.01 (d, J = 7.2 Hz, 1H, H$_6$), 6.97 (td, J = 7.6, 1.3 Hz, 1H, H$_2$), 6.94-6.86 (m, 2H, H$_{18, 19}$), 6.65-6.57 (m, 2H, H$_{1, 3}$), 5.91 (d, J = 2.5 Hz, 1H, H$_7$), 4.79 (d, J = 2.2 Hz, 1H, H$_8$), 1.38 (s, 3H, H$_{10}$), 0.74 (s, 3H, H$_{11}$).
✓ $^{13}$C NMR (101 MHz, DMSO-d$_6$): δ (ppm) = 150.85 (C$_4$-arom.), 148.48 (C$_{17}$-arom.), 138.51 (C$_5$-arom.), 131.28 (d, J = 5.9 Hz, C$_{16}$-arom.), 127.39 (C$_2$H-arom.), 125.19 (d, J = 0.6 Hz, C$_{13}$H-arom.), 124.70 (d, J = 13.1 Hz, C$_{15}$-arom.), 122.45 (C$_6$H-arom.), 119.05 (d, J = 6.3 Hz, C$_{19}$H-arom.), 117.70 (C$_1$H-arom.), 116.45 (d, J = 3.2 Hz, C$_{20}$H-arom.), 115.49 (d, J = 1.9 Hz, C$_{12}$-arom.), 108.91 (C$_3$H-arom.), 106.02 (d, J = 15.9 Hz, C$_{18}$H-arom.), 67.86 (C$_8$H), 45.25 (C$_9$), 27.12 (C$_{10}$H$_3$), 24.90 (C$_{11}$H$_3$).

3-(3,3-dimethylindolin-2-yl)-1H-pyrrolo[2,3-b]pyridine (Procedure 3)

| VPC Number | LabBook Code | IC$_{50}$ (eGFP) = 2.1 |
|---|---|---|
| 13 556 | CA 2-100 F3-7 (yield = 76%) | IC$_{50}$ (PSA) = 2.18 |

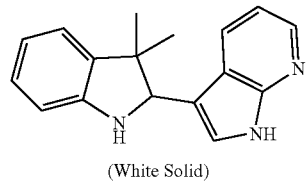

(White Solid)

$t_R$ (HPLC) = 3.52 min   MS (ESI+) m/z = 264.1501 [(M + H)$^+$]
HRMS (ESI+): calculated for C$_{17}$H$_{18}$N$_3$, m/z = 264.1495; found, 264.1500
$^1$H NMR (600 MHz, DMSO-d$_6$): δ (ppm) = 11.51 (s, 1H, H$_{14}$), 8.18 (dd, J = 4.6, 1.5 Hz, 1H, H$_{20}$), 7.86 (dd, J = 7.9, 1.1 Hz, 1H, H$_{18}$), 7.44 (d, J = 2.4 Hz, 1H, H$_{13}$), 7.02 (d, J = 7.2 Hz, 1H, H$_6$), 7.00-6.96 (m, 2H, H$_{2,19}$), 6.63 (td, J = 7.4, 0.9 Hz, 1H, H$_1$), 6.60 (d, J = 7.7 Hz, 1H, H$_3$), 5.92 (d, J = 2.3 Hz, 1H, H$_7$), 4.74 (d, J = 2.0 Hz, 1H, H$_8$), 1.38 (s, 3H, H$_{10}$), 0.74 (s, 3H, H$_{11}$).
$^{13}$C NMR (151 MHz, DMSO-d$_6$): δ (ppm) = 150.38 (C$_4$-arom.), 148.74 (C$_{15}$-arom.), 142.28 (C$_{20}$H-arom.), 137.95 (C$_5$-arom.), 127.99 (C$_{18}$H-arom.), 126.96 (C$_2$H-arom.), 123.93 (C$_{13}$H-arom.), 121.97 (C$_6$H-arom.), 118.98 (C$_{16}$-arom.), 117.26 (C$_1$H-arom.), 114.92 (C$_{19}$H-arom.), 112.80 (C$_{12}$-arom.), 108.47 (C$_3$H-arom.), 67.77 (C$_8$H), 44.77 (C$_9$), 26.62 (C$_{10}$H$_3$), 24.34 (C$_{11}$H$_3$).

3-(3,3-dimethylindolin-2-yl)-1H-indole-7-carboxylic acid (Procedure 4)

| VPC Number | LabBook Code | IC$_{50}$ (eGFP) = No Data |
|---|---|---|
| 13 557 | CA 2-104 Ap Tmt (yield = 82%) | IC$_{50}$ (PSA) = No Data |

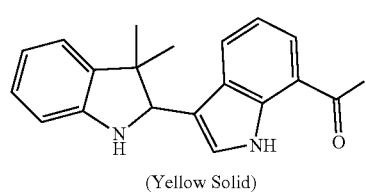

(Yellow Solid)

$t_R$ (HPLC) = 3.74 min   MS (ESI+) m/z = 307.1442 [(M + H)$^+$]
HRMS (ESI+): calculated for C$_{19}$H$_{19}$N$_2$O$_2$, m/z = 307.1441; found, 304.1442
$^1$H NMR (400 MHz, DMSO-d$_6$): δ (ppm) = 13.01 (br s, 1H, H$_{22}$), 10.98 (s, 1H, H$_{14}$), 7.87 (d, J = 7.8 Hz, 1H, H$_{20}$), 7.74 (d, J = 6.8 Hz, 1H, H$_{18}$), 7.35 (d, J = 2.3 Hz, 1H, H$_{13}$), 7.07 (t, J = 7.7 Hz, 1H, H$_{19}$), 7.02 (d, J = 7.2 Hz, 1H, H$_6$), 6.98 (td, J = 7.6, 1.1 Hz, 1H, H$_2$), 6.65-6.58 (m, 2H, H$_{1,3}$), 5.93 (br s, 1H, H$_7$), 4.83 (s, 1H, H$_8$), 1.39 (s, 3H, H$_{10}$), 0.73 (s, 3H, H$_{11}$).

$^{13}$C NMR (101 MHz, DMSO-d$_6$): δ (ppm) = 168.45 (C$_{21}$O), 150.89 (C$_4$-arom.), 138.46 (C$_5$-arom.), 135.63 (C$_{15}$-arom.), 128.93 (C$_{16}$-arom.), 127.41

($C_2$H-arom.), 125.68 ($C_{20}$H-arom.), 125.66 ($C_{13}$H-arom.), 124.20 ($C_{18}$H-arom.), 122.48 ($C_6$H-arom.), 118.42 ($C_{19}$H-arom.), 117.69 ($C_1$H-arom.), 114.65 ($C_{12}$-arom.), 113.89 ($C_{17}$-arom.), 108.90 ($C_3$H-arom.), 67.76 ($C_8$H), 45.25 ($C_9$), 27.08 ($C_{10}H_3$), 24.91 ($C_{11}H_3$).

---

(3-(3,3-dimethylindolin-2-yl)-1H-indole-7-yl)methanol
(Procedure 5)

| | | |
|---|---|---|
| VPC Number<br>13 558 | LabBook Code<br>CA 2-105 F6-11 (yield = 81%) | $IC_{50}$ (eGFP) = 1.6<br>$IC_{50}$ (PSA) = No Data |

(White Solid)

$t_R$ (HPLC) = 3.45 min

MS (ESI+) m/z = 293.1651 [(M + H)$^+$]

HRMS (ESI+): calculated for $C_{19}H_{21}N_2O$, m/z = 293.1648; found, 293.1651

$^1$H NMR (400 MHz, DMSO-d$_6$): δ (ppm) = 10.82 (s, 1H, H$_{14}$), 7.45 (d, J = 7.8 Hz, 1H, H$_{20}$), 7.29 (d, J = 2.4 Hz, 1H, H$_{13}$), 7.05 (d, J = 6.8 Hz, 1H, H$_{18}$), 7.01 (d, J = 7.2 Hz, 1H, H$_6$), 6.97 (td, J = 7.6, 1.3 Hz, 1H, H$_2$), 6.92 (dd, J = 7.8, 6.8 Hz, 1H), 6.61 (m, 2H, H$_{1,3}$), 5.84 (d, J = 2.4 Hz, 1H, H$_7$), 5.14 (t, J = 5.7 Hz, 1H, H$_{18}$), 4.81 (d, J = 2.1 Hz, 1H, H$_8$), 4.78 (d, J = 5.7 Hz, 2H, H$_{21}$), 1.39 (s, 3H, H$_{10}$), 0.74 (s, 3H, H$_{11}$).

$^{13}$C NMR (101 MHz, DMSO-d$_6$): δ (ppm) = 150.97 ($C_4$-arom.), 138.66 ($C_5$H-arom.), 134.66 ($C_{15}$-arom.), 127.36 ($C_2$H-arom.), 127.32 ($C_{16}$-arom.), 125.92 ($C_{17}$-arom.), 123.87 ($C_{13}$H-arom.), 122.43 ($C_6$H-arom.), 119.41 ($C_{18}$H-arom.), 118.92 ($C_{20}$H-arom.), 118.62 ($C_{19}$H-arom.), 117.57 ($C_1$H-arom.), 114.36 ($C_{12}$-arom.), 108.85 ($C_3$H-arom.), 68.06 ($C_8$H), 60.82 ($C_{21}H_2$), 45.19 ($C_9$), 27.15 ($C_{10}H_3$), 24.94 ($C_{11}H_3$).

---

(3-(3,3-dimethylindolin-2-yl)-1H-pyrrolo[2,3-c]pyridine
(Procedure 6)

| | | |
|---|---|---|
| VPC Number<br>13 561 | LabBook Code<br>CA 2-121 Ap Tmt (yield = 35%) | $IC_{50}$ (eGFP) = 10.7<br>$IC_{50}$ (PSA) = No Data |

(White Solid)

$t_R$ (HPLC) = 3.07 min

MS (ESI+) m/z = 264.1497 [(M + H)$^+$]

HRMS (ESI+): calculated for $C_{17}H_{18}N_3$, m/z = 264.1495; found, 264.1498

$^1$H NMR (400 MHz, DMSO-d$_6$): δ (ppm) = 11.52 (s, 1H, H$_9$), 8.73 (s, 1H, H$_3$), 8.03 (s, 1H, H$_5$), 7.59 (d, J = 1.7 Hz, 1H, H$_8$), 7.49 (d, J = 4.3 Hz, 1H, H$_6$), 7.04-6.95 (m, 2H, H$_{11,15}$), 6.66-6.58 (m, 2H, H$_{10,12}$), 5.94 (d, J = 1.9 Hz, 1H, H$_{16}$), 4.78 (d, J = 2.3 Hz, 1H, H$_{17}$), 1.38 (s, 3H, H$_{19}$), 0.72 (s, 3H, H$_{20}$).

$^{13}$C NMR (151 MHz, DMSO-d$_6$): δ (ppm) = 150.34 ($C_{13}$-arom.), 137.94 ($C_{14}$-arom.), 137.08 ($C_5$H-arom.), 134.44 ($C_3$H-arom.), 133.68 ($C_2$-arom.), 130.91 ($C_1$-arom.), 127.79 ($C_8$H-arom.), 126.96 ($C_{11}$H-arom.), 121.98 ($C_{15}$-arom.), 117.32 ($C_{10}$H-arom.), 114.54 ($C_6$H-arom.), 113.67 ($C_7$-arom.), 108.51 ($C_{12}$H-arom.), 67.25 ($C_{17}$H), 44.83 ($C_{18}$), 26.51 ($C_{19}H_3$), 24.33 ($C_{20}H_3$).

---

(3-(3,3-dimethylindolin-2-yl)-1H-pyrrolo[3,2-b]pyridine
(Procedure 6)

| | | |
|---|---|---|
| VPC Number<br>13 560 | LabBook Code<br>CA 2-123 Ap Tmt (yield = 72%) | $IC_{50}$ (eGFP) = 2.3<br>$IC_{50}$ (PSA) = No Data |

(Beige Solid)

$t_R$ (HPLC) = 3.05 min

MS (ESI+) m/z = 264.1502 [(M + H)$^+$]

HRMS (ESI+): calculated for $C_{17}H_{18}N_3$, m/z = 264.1495; found, 264.1502

$^1$H NMR (400 MHz, DMSO-d$_6$): δ (ppm) = 11.16 (s, 1H, H$_9$), 8.32 (dd, J = 4.6, 1.5 Hz, 1H, H$_5$), 7.75 (dd, J = 8.2, 1.5 Hz, 1H, H$_3$), 7.58 (d, J = 2.1 Hz, 1H, H$_8$), 7.09 (dd, J = 8.2, 4.6 Hz, 1H, H$_4$), 6.99 (d, J = 7.2 Hz, 1H, H$_{15}$), 6.96 (td, J = 7.6, 1.3 Hz, 1H, H$_{11}$), 6.63-6.57 (m, 2H, H$_{10,12}$), 5.86 (d, J = 2.7 Hz, 1H, H$_{16}$), 5.06 (dd, J = 2.8, 0.6 Hz, 1H, H$_{17}$), 1.51 (s, 3H, H$_{19}$), 0.72 (s, 3H, H$_{20}$).

$^{13}$C NMR (101 MHz, DMSO-d$_6$): δ (ppm) = 150.85 ($C_{13}$H-arom.), 145.29 ($C_1$-arom.), 142.28 ($C_5$H-arom.), 139.08 ($C_{14}$-arom.), 129.27 ($C_2$-arom.), 127.40 ($C_8$H-arom.), 127.23 ($C_{11}$H-arom.), 122.51 ($C_{15}$H-arom.), 118.77

($C_3$H-arom.), 117.72 ($C_{10}$H-arom.), 116.55 ($C_4$H-arom.), 115.09 ($C_7$-arom.), 108.96 ($C_{12}$H-arom.), 65.98 ($C_{17}$H), 45.02 ($C_{18}$), 27.20 ($C_{19}H_3$), 25.21 ($C_{20}H_3$).

Cyclohexyl-Hydroindole Moiety

3-(spiro[cyclohexane-1,3'-indolin]-2'-yl)-1H-indole (Procedure 1)

| VPC Number | LabBook Code | |
|---|---|---|
| 13 534 | CA 2-8 F18-23 (yield = 47%) | $IC_{50}$ (eGFP) = 0.8<br>$IC_{50}$ (PSA) = 1.25 |

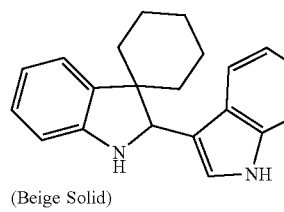
(Beige Solid)

$t_R$ (HPLC) = 4.39 min   MS (ESI+) m/z = 303.1775 [(M + H)$^+$]
HRMS (ESI+): calculated for $C_{21}H_{23}N_2$, m/z = 303.1856; found, 303.1852
$^1$H NMR (400 MHz, DMSO-d6): δ (ppm) = 10.92 (s, 1H, $H_{12}$), 7.32 (d, J = 8.0 Hz, 1H, $H_{18}$), 7.27 (d, J = 2.4 Hz, 1H, $H_{11}$), 7.17 (d, J = 7.1 Hz, 1H, $H_6$), 7.02-6.96 (m, 3H, $H_{2,15,17}$), 6.78 (td, J = 7.6, 0.8 Hz, 1H, $H_{16}$), 6.61 (td, J = 7.4, 1.0 Hz, 1H, $H_1$), 6.53 (d, J = 7.4 Hz, 1H, $H_3$), 5.71 (s, 1H, $H_7$), 4.83 (s, 1H, $H_8$), 1.82-1.14 (m, 2H, $H_{19,20,21,22,23}$).
$^{13}$C NMR (101 MHz, DMSO-d6): δ (ppm) = 151.59 ($C_4$-arom.), 137.65 ($C_5$-arom.), 137.07 ($C_{13}$-arom.), 127.58 ($C_2$H-arom.), 126.78 ($C_{14}$-arom.), 124.83 ($C_{11}$H-arom.), 123.58 ($C_6$H-arom.), 121.08 ($C_{17}$H-arom.), 120.68 ($C_{15}$H-arom.), 118.75 ($C_{16}$H-arom.), 117.00 ($C_1$H-arom.), 115.58 ($C_{10}$-arom.), 111.86 ($C_{18}$H-arom.), 108.32 ($C_3$H-arom.), 65.96 ($C_8$H), 48.29 (C9), 37.43 ($C_{19}H_2$), 31.94 ($C_{23}H_2$), 25.99 ($C_{21}H_2$), 22.96 ($C_{20}H_2$), 22.81 ($C_{22}H_2$).

3-(spiro[cyclohexane-1,3'-indolin]-2'-yl)-5-methyl-1H-indole (Procedure 1)

| VPC Number | LabBook Code | |
|---|---|---|
| 13 548 | CA 2-72 F12-18 (yield = 69%) | IC50 (eGFP) = 3.2<br>IC50 (PSA) = 4.24 |

(Beige Solid)

tR (HPLC) = 4.57 min   (MS (ESI+) m/z = 317.1950 [(M + H)$^+$]
HRMS (ESI+): calculated for $C_{22}H_{25}N_2$, m/z = 317.2012; found, 317.2008
$^1$H NMR (400 MHz, DMSO-$d_6$): δ (ppm) = 10.78 (d, J = 1.4 Hz, 1H, $H_9$), 7.22-7.19 (m, 2H, , $H_{3,8}$), 7.17 (d, J = 7.6 Hz, 1H, $H_{15}$), 7.00 (td, J = 7.6, 1.2 Hz, 1H, $H_{11}$), 6.82 (dd, J = 8.3, 1.5 Hz, 1H, $H_4$), 6.75 (br s, 1H, $H_6$), 6.62 (td, J = 7.4, 1.0 Hz, 1H, $H_{10}$), 6.53 (d, J = 7.6 Hz, 1H, $H_{12}$), 5.65 (s, 1H, $H_{16}$), 4.78 (s, 1H, $H_{17}$), 2.18 (s, 3H, $H_{24}$), 1.80-1.16 (m, 10H, $H_{19,20,21,22,23}$).
13C NMR (101 MHz, DMSO-$d_6$): δ (ppm) = 151.69 ($C_{13}$-arom.), 137.72 ($C_{14}$-arom.), 135.43 ($C_2$-arom.), 127.45 ($C_{11}$H-arom.), 127.03 ($C_5$-arom.), 126.85 ($C_1$-arom.), 124.83 ($C_8$H-arom.), 123.64 ($C_{15}$H-arom.), 122.62 ($C_4$H-arom.), 120.51 ($C_6$H-arom.), 116.95 ($C_{10}$H-arom.), 114.98 ($C_7$-arom.), 111.51 ($C_3$H-arom.), 108.44 ($C_{12}$H-arom.), 66.18 ($C_{17}$H), 48.25 ($C_{18}$), 37.22 ($C_{19}H_2$), 31.96 ($C_{23}H_2$), 26.00 ($C_{21}H_2$), 23.01 ($C_{20}H_2$), 22.75 ($C_{22}H_2$), 21.88 ($C_{24}H_3$).

3-(spiro[cyclohexane-1,3'-indolin]-2'-yl)-7-methyl-1H-indole (Procedure 1)

| | | |
|---|---|---|
| VPC Number<br>13 549 | LabBook Code<br>CA 2-73 F9-15 (yield = 72%) | $IC_{50}$ (eGFP) = 1.7<br>$IC_{50}$ (PSA) = 2.57 |

(Beige Solid)

$t_R$ (HPLC) = 4.58 min    MS (ESI+) m/z = 317.1932 [(M + H)$^+$]
HRMS (ESI+): calculated for $C_{22}H_{25}N_2$, M/Z = 317.2012; found, 317.2022
$^1$H NMR (400 MHz, DMSO-$d_6$): δ (ppm) = 10.88 (s, 1H, $H_9$), 7.25 (d, J = 2.5 Hz, 1H, $H_8$), 7.16 (d, J = 7.0 Hz, 1H, $H_{15}$), 6.98 (t, J = 7.6, 1.2 Hz, 1H, $H_{11}$), 6.85 (d, J = 7.9 Hz, 1H, $H_6$), 6.80 (d, J = 7.0 Hz, 1H, $H_4$), 6.70 (t, J = 7.6 Hz, 1H, $H_5$), 6.60 (td, J =7.4, 1.0 Hz, 1H, $H_{10}$), 6.53 (dd, J = 7.6, 0.4 Hz, 1H, $H_{12}$),5.67 (s, 1H, $H_{16}$), 4.82 (s, 1H, $H_{17}$), 2.43 (s, 3H, $H_{24}$), 1.83-1.17 (m, 10H, $H_{19,20,21,22,23}$).
$^{13}$C NMR (101 MHz, DMSO-$d_6$): δ (ppm) = 151.60 ($C_{13}$-arom.), 137.67 ($C_{14}$-arom.), 136.53 ($C_2$-arom.), 127.56 ($C_{11}$H-arom.), 126.48 ($C_1$-arom.), 124.52 ($C_8$H-arom.), 123.60 ($C_{15}$H-arom.), 121.61 ($C_4$H-arom.), 120.80 ($C_3$-arom.), 118.95 ($C_5$H-arom.), 118.30 ($C_6$H-arom.), 116.98 ($C_{10}$H-arom.), 116.02 ($C_7$-arom.), 108.33 ($C_{12}$H-arom.), 66.00 ($C_{17}$H), 48.28 ($C_{18}$), 37.44 ($C_{19}H_2$), 31.95 ($C_{23}H_2$), 26.00 ($C_{21}H_2$), 22.97 ($C_{20}H_2$), 22.80 ($C_{22}H_2$), 17.25 ($C_{24}H_3$).

3-(spiro[cyclohexane-1,3'-indolin]-2'-yl)-6-(benzyloxy)-1H-indole (Procedure 1)

| | | |
|---|---|---|
| VPC Number<br>13 550 | LabBook Code<br>CA 2-76 F13-24 (yield = 55%) | $IC_{50}$ (eGFP) = 11.8<br>$IC_{50}$ (PSA) = No Data |

(Beige Solid)

$t_R$ (HPLC) = 5.07 min    MS (ESI+) m/z = 409.2254 [(M + H)$^+$]
HRMS (ESI+): calculated for $C_{28}H_{29}N_2O$, m/z = 409.2274; found, 409.2278
$^1$H NMR (400 MHz, DMSO-$d_6$): δ (ppm) = 10.72 (d, J = 1.7 Hz, 1H, $H_{12}$), 7.46-7.42 (m, 2H, $H_{22,26}$), 7.41-7.36 (m, 2H, $H_{23,25}$), 7.34-7.30 (m, 1H, , $H_{24}$), 7.17-7.12 (m, 2H, , $H_{6,11}$), 6.98 (td, J = 7.6, 1.2 Hz, 1H, $H_2$), 6.89 (d, J = 2.2 Hz, 1H, $H_{15}$), 6.82 (br d, J = 8.7 Hz, 1H, $H_{18}$), 6.60 (td, J = 7.4, 1.0Hz, 1H, $H_1$), 6.54-6.50 (m, 2H, , $H_{3-17}$), 5.67 (s, 1H, $H_7$), 5.07 (s, 2H, $H_{20}$), 4.76 (s, 1H, $H_8$), 1.80-1.15 (m, 10H, $H_{19,20,21,22,23}$).
$^{13}$C NMR (101 MHz, DMSO-$d_6$): δ (ppm) = 154.56 ($C_{16}$-arom.), 151.55 ($C_4$-arom.), 138.16 ($C_{21}$-arom.), 137.71 ($C_5$-arom.), 137.65 ($C_{13}$-arom.), 128.82 ($C_{23,25}$H-arom.), 128.04 ($C_{24}$H-arom.), 127.88 ($C_{22,26}$H-arom.), 127.58 ($C_2$H-arom.), 123.67 ($C_6$H-arom.), 123.54 ($C_{11}$H-arom.), 121.34 ($C_{14}$-arom.), 121.31 ($C_{18}$H-arom.), 116.98 ($C_1$H-arom.), 115.58 ($C_{10}$-arom.), 109.47 ($C_{17}$H-arom.), 108.32 ($C_3$H-arom.), 96.43 ($C_{15}$H-arom.), 69.87 ($C_{20}H_2$), 66.04 ($C_8$H), 48.22 ($C_9$), 37.40 ($C_{19}H_2$), 31.91 ($C_{23}H_2$), 25.99 ($C_{21}H_2$), 22.95 ($C_{20}H_2$), 22.83 ($C_{22}H_2$).

3-(spiro[cyclohexane-1,3'-indolin]-2'-yl)-6-hydroxy-1H-indole (Procedure 2)

| | | |
|---|---|---|
| VPC Number<br>13 551 | LabBook Code<br>CA 2-83 F2-7 (yield = 38%) | $IC_{50}$ (eGFP) = 15.5<br>$IC_{50}$ (PSA) = No Data |

(Beige Solid)

$t_R$ (HPLC) = 3.57 min    MS (ESI+) m/z = 319.1824 [(M + H)$^+$]
HRMS (ESI+): calculated for $C_{21}H_{23}N_2O$, m/z = 319.1805; found, 319.1802
$^1$H NMR (400 MHz, DMSO-$d_6$): δ (ppm) = 10.51 (d, J = 1.5 Hz, 1H, $H_{12}$), 8.79 (s, 1H, $H_{24}$), 7.15 (d, J = 7.0 Hz, 1H, $H_6$), 7.04 (d, J = 2.3 Hz, 1H, $H_{11}$), 6.97 (td, J = 7.6, 1.2 Hz, 1H, $H_2$), 6.72 (d, J = 8.5 Hz, 1H, $H_{18}$), 6.67 (d, J =2.0 Hz, 1H, $H_{15}$), 6.59 (td, J = 7.4, 1.0 Hz, 1H, $H_1$), 6.51 (d, J = 7.7 Hz, 1H,$H_3$), 6.30 (dd, J = 8.6, 2.2 Hz, 1H, $H_{17}$), 5.64 (s, 1H, $H_7$), 4.73 (s, 1H, $H_8$), 1.81-1.16 (m, 10H, $H_{19,20,21,22,23}$).
$^{13}$C NMR (101 MHz, DMSO-$d_6$): δ (ppm) = 153.10 ($C_{16}$-arom.), 151.57 ($C_4$-arom.), 138.21 ($C_{13}$-arom.), 137.70 ($C_5$-arom.), 127.52 ($C_2$H-arom.), 123.55 ($C_6$H-arom.), 122.74 ($C_{11}$H-arom.), 121.06 ($C_{18}$H-arom.), 120.26 ($C_{14}$-arom.), 116.91 ($C_1$H-arom.), 115.43 ($C_{10}$-arom.), 109.35 ($C_{17}$H-arom.), 108.29 ($C_3$H-arom.), 96.85 ($C_{15}$H-arom.), 66.16 ($C_8$H), 48.18 ($C_9$), 37.38 ($C_{19}H_2$), 31.91 ($C_{23}H_2$), 26.01 ($C_{21}H_2$), 22.97 ($C_{20}H_2$), 22.83 ($C_{22}H_2$).

3-(spiro[cyclohexane-1,3'-indolin]-2'-yl)-7-hydroxy-1H-indole (Procedure 2)

| VPC Number | LabBook Code | $IC_{50}$ (eGFP) = 1.1 |
|---|---|---|
| 13 552 | CA 2-84 Precipitate | $IC_{50}$ (PSA) = 1.14 |
|  | (yield = 28%) |  |

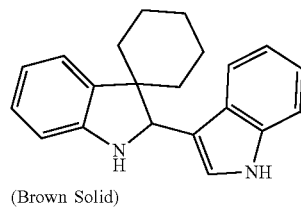

(Brown Solid)

tR (HPLC) = 3.81 min     MS (ESI+) m/z = 319.1728 [(M + H)+]
HRMS (ESI+): calculated for $C_{21}H_{23}N_2O$, m/z = 319.1805; found, 319.1814
$^1$H NMR (400 MHz, DMSO-$d_6$): δ (ppm) = 10.72 (d, J = 1.8 Hz, 1H, $H_{12}$), 9.42 (s, 1H, $H_{24}$), 7.14 (d, J = 7.1 Hz, 1H, $H_6$), 7.12 (d, J = 2.5 Hz, 1H, $H_{11}$), 6.97 (td, J = 7.6, 1.2 Hz, 1H, $H_2$), 6.59 (m, 2H, $H_{1,17}$), 6.52 (m, 2H, $H_{3,18}$), 6.42 (dd, J = 7.4, 0.8 Hz, 1H, $H_{16}$), 5.65 (s, 1H, $H_7$), 4.79 (s, 1H, $H_8$), 1.82-1.16 (m, 10H, $H_{19,20,21,22,23}$).
$^{13}$C NMR (101 MHz, DMSO-$d_6$): δ (ppm) = 151.60 ($C_4$-arom.), 143.87 ($C_{15}$-arom.), 137.66 ($C_5$-arom.), 128.78 ($C_{14}$-arom.), 127.50 ($C_2$H-arom.), 127.06 ($C_{13}$-arom.), 124.10 ($C_{11}$H-arom.), 123.60 ($C_6$H-arom.), 119.38 ($C_{17}$H-arom.), 116.93 ($C_1$H-arom.), 115.94 ($C_{10}$-arom.), 111.78 ($C_{18}$H-arom.), 108.29 ($C_3$H-arom.), 105.41 ($C_{16}$H-arom.), 65.88 ($C_8$H), 48.33 ($C_9$), 37.45 ($C_{19}H_2$), 31.93 ($C_{23}H_2$), 26.00 ($C_{21}H_2$), 22.98 ($C_{20}H_2$), 22.79 ($C_{22}H_2$).

Unexpected Compounds—General Procedure 7

Phenylhydrazine (1.0 eq) aldehyde (isobutyraldehyde or cyclohexanecarboxaldehyde) (1.0 eq) were diluted in AcOH (0.1 M). The mixture was heated at 65° C. for 2 h (until complete conversion). Then, 7-azaindole or 1,5,6,7-Tetrahydro-4H-indol-4-one (1.0 eq) was added and the reaction mixture was stirred additional 24 h at 100° C. (until complete conversion). Acetic acid was removed under vacuo. Then, the residue was poured with $H_2O$ and neutralized at pH 7 with sat. $NaHCO_3$ solution. The aqueous layer was extracted with AcOEt (×3) and organic layers were combined, washed with brine, dried over $Na_2SO_4$ and evaporated under reduced pressure. Then, crude was purified by automated combi-flash to afford the good compound.

3-(3,3-dimethyl-3H-indol-2-yl)-1H-pyrrolo[2,3-b]pyridine (Procedure 7)

| VPC Number | LabBook Code | $IC_{50}$ (eGFP) = 0.7 |
|---|---|---|
| 13 537 | CA 2-39 F9-15 (yield = 25%) | $IC_{50}$ (PSA) = 0.81 |

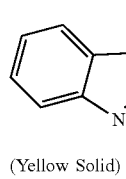

(Yellow Solid)

$t_R$ (HPLC) = 3.17 min     MS (ESI+) m/z = 262.1345 [(M + H)+]
HRMS (ESI+): calculated for $C_{17}H_{16}N_3$, m/z =262.1339; found, 262.1345
$^1$H NMR (400 MHz, DMSO-$d_6$): δ (ppm) = 12.40 (s, 1H, $H_{14}$), 8.94 (dd, J = 7.9, 1.7 Hz, 1H, $H_{18}$), 8.40 (s, 1H, $H_{13}$), 8.35 (dd, J = 4.6, 1.6 Hz, 1H, $H_{20}$), 7.56 (d, J = 7.5 Hz, 1H, $H_3$), 7.49 (d, J = 6.8 Hz, 1H, $H_6$), 7.32 (td, J = 7.6, 1.2 Hz, 1H, $H_2$), 7.28 (dd, J = 7.9, 4.7 Hz, 1H, $H_{19}$), 7.20 (td, J = 7.4, 1.0 Hz, 1H, $H_1$), 1.54 (s, 6H, H10,11).
$^3$C NMR (101 MHz, DMSO-$d_6$): δ (ppm) = 180.97 ($C_8$), 154.77 ($C_4$-arom.), 149.39 ($C_{15}$-arom.), 146.90 ($C_5$-arom.), 144.50 ($C_{20}$H-arom.), 131.69 ($C_{18}$H-arom.), 130.45 ($C_{13}$H-arom.), 127.92 ($C_2$H-arom.), 124.80 ($C_1$H-arom.), 121.61 ($C_6$H-arom.), 119.71 ($C_3$H-arom.), 119.05 ($C_{16}$-arom.), 117.73 ($C_{19}$H-arom.), 108.26 ($C_{12}$-arom.), 53.39 ($C_9$), 25.82 ($C_{10,11}$).

Tetrahydro-3-(3,3-dimethyl-3H-indol-2-yl)-1H-indol-4-one (Procedure 7)

| VPC Number | LabBook Code | IC$_{50}$ (eGFP) = No Data |
|---|---|---|
| 13 539 | CA 2-48 F19-22 (yield = 9%) | IC$_{50}$ (PSA) = No Data |

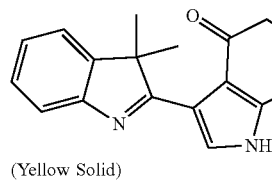

(Yellow Solid)

$t_R$ (HPLC) = 3.54 min  MS (ESI+) m/z = 279.1498 [(M + H)$^+$]
HRMS (ESI+): calculated for C$_{18}$H$_{19}$N$_2$O, m/z = 279.1492; found, 279.1498
$^1$H NMR (400 MHz, DMSO-d$_6$): δ (ppm) = 12.27 (s, 1H, H$_{14}$), 7.54-7.48 (m, 2H, H$_{3,6}$), 7.33 (td, J = 7.6, 1.3 Hz, 1H, H$_2$), 7.22 (td, J = 7.4, 1.0 Hz, 1H, H$_1$), 7.05 (d, J = 1.8 Hz, 1H, H$_{13}$), 2.85 (t, J = 6.1 Hz, 2H, H$_{17}$), 2.39 (t, J = 6.4 Hz, 2H, H$_{17}$), 2.09-2.02 (m, 2H, H$_{18}$), 1.46 (s, 6H, H$_{10,11}$).
$^{13}$C NMR (101 MHz, DMSO-d$_6$): δ (ppm) = 193.35 (C$_{20}$O), 176.21 (C$_8$), 153.76 (C$_4$-arom.), 148.19 (C$_{15}$-arom.), 147.25 (C$_5$-arom.), 128.13 (C$_2$H-arom.), 126.38 (C$_{12}$-arom.), 125.40 (C$_1$H-arom.), 121.96 (C$_6$H-arom.), 121.76 (C$_{16}$-arom.), 119.76 (C$_3$H-arom.), 109.82 (C$_{13}$H-arom.), 52.57 (C$_9$), 38.25 (C$_{19}$H$_2$), 25.49 (C$_{10,11}$H$_3$), 23.71 (C$_{18}$H$_2$), 22.70 (C$_{17}$H$_2$).

3-(spiro[cyclohexane-1,3'-indolin]-2'-yl)-1H-pyrrolo[2,3-b]pyridine (Procedure 7)

| VPC Number | LabBook Code | IC$_{50}$ (eGFP) = 6.6 |
|---|---|---|
| 13 559 | CA 2-110 F18-27 (yield = 23%) | IC$_{50}$ (PSA) = No Data |

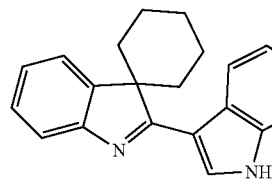

(Brown Solid)

$t_R$ (HPLC) = 3.70 min  MS (ESI+) m/z = 302.1654 [(M + H)$^+$]
HRMS(ESI+): calculated for C$_{20}$H$_{20}$N$_3$, m/z = 302.1652; found, 302.1654
$^1$H NMR (400 MHz, DMSO-d$_6$): δ (ppm) = 12.39 (s, 1H, H$_{17}$), 9.00 (dd, J = 7.9, 1.7 Hz, 1H, H$_{21}$), 8.45 (d, J = 2.0 Hz, 1H, H$_{16}$), 8.35 (dd, J = 4.6, 1.6 Hz, 1H, H$_{23}$), 7.87 (d, J = 7.3 Hz, 1H, H$_6$), 7.62 (dd, J = 7.6, 0.6 Hz, 1H, H$_3$), 7.38 (td, J = 7.6, 1.0 Hz, 1H, H$_2$), 7.27 (dd, J = 7.9, 4.7 Hz, 1H, H$_{22}$), 7.17 (td, J = 7.5, 1.1Hz, 1H, H$_1$), 2.34-2.25 (m, 2H, H$_{10}$), 2.07-1.77 (m, 6H, H$_{11,12,13}$), 1.32-1.26 (m, 2H, H$_{14}$).
$^{13}$C NMR (101 MHz, DMSO-d$_6$): δ (ppm) = 180.61 (C$_8$), 155.41 (C$_4$-arom.), 149.19 (C$_{18}$-arom.), 145.63 (C$_5$-arom.), 144.45 (C$_{23}$H-arom.), 132.08 (C$_{21}$H-arom.), 130.23 (C$_{16}$H-arom.), 127.95 (C$_2$H-arom.), 124.74 (C$_6$H-arom.), 123.93 (C$_1$H-arom.), 120.36 (C$_3$H-arom.), 119.45 (C$_{19}$-arom.), 117.71 (C$_{22}$H-arom.), 107.92(C$_{15}$-arom.), 57.86 (C$_9$), 33.53 (C$_{10,14}$H$_2$), 24.81 (C$_{12}$H$_2$), 21.89 (CH$_{11,13}$H2).

Quinoline Moiety—General Procedure 9

In microwave vessel, quinoline (2.0 eq) and indole (1.0 eq) were mixed together and the system was sealed and placed under nitrogen, after a purge with vacuum/N$_2$ (3 times). Then, HCl solution 4 M in 1,4-dioxane (1.2 eq) was added with the needle immersed in the mixture (exothermic reaction). The reaction mixture was heated with microwave during 2 h at 160° C. The reaction mixture was taken up with a minimum of MeOH and when the residue was dissolved, it was transferred in mixture of AcOEt and saturated NaHCO$_3$ solution. The resulting solution was extracted and the aqueous phase was washed with AcOEt (×2). The organic layers were combined, washed with 0.01 M critic acid solution, saturated NaHCO$_3$ solution, dried over Na$_2$SO$_4$ and concentrated to dryness under reduced pressure. Finally, the crude was purified by automated combi-flash to afford the good compound.

General Procedure 10

Halogenated-compound (1.0 eq), boronic acid (or boronate) (1.1 eq) and Pd(PPh$_3$)$_4$ (10% mol) was added in microwave vessel (10-20 mL). The vial was sealed with a cap and the system was purged with vacuum and placed under N$_2$. Then, the solids were dissolved in mixture of Toluene/EtOH (4.5:2.0, 0.11 M) and purged with vacuum/N$_2$ one more time. Then, a solution of K$_2$CO$_3$ (3.0 eq) in H$_2$O (1.8 M) was added. The reaction mixture was stirred and heated overnight at 95° C. with oil bath. The reaction mixture was filtered on plug of celite. The filtrate was was poured with water and was extracted with AcOEt (×3). The organic layers were combined, washed with brine, dried over Na$_2$SO$_4$ and evaporated under reduced pressure. The residue was taken up in DCM/TFA (5:5) for 2 h at r.t. The solvents were evaporated under reduced pressure. The residue was then neutralized with saturated NaHCO$_3$ solution and extracted with AcOEt (×2). The organic layers were washed, dried and concentrated in vacuo. The residue was precipitate in DCM or purified by automated combi-flash to afford the good compound.

2-(1H-indol-3-yl)-4-methylquinoline

| VPC Number | LabBook Code | IC$_{50}$ (eGFP) = 5.6 |
|---|---|---|
| 13 547 | CA 2-69 F6-11 | IC$_{50}$ (PSA) = No Data |
| | (yield = 62%) | |

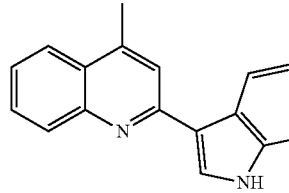

(Beige Solid)

$t_R$ (HPLC) = 3.20 min  MS (ESI+) m/z = 259.1243 [(M + H)$^+$]
Mp = 168-180° C.
HRMS (ESI+): calculated for $C_{18}H_{15}N_2$, m/z = 259.1230; found, 259.1237
$^1$H NMR (400 MHz, DMSO-d$_6$): δ (ppm) = 11.63 (s, 1H, H$_{14}$), 8.90-8.85 (m, 1H, H$_{20}$), 8.32 (d, J = 2.8 Hz, 1H, H$_{13}$), 8.04-7.98 (m, 2H, H$_{3,6}$), 7.94 (d, J = 0.9 Hz, 1H, H$_9$), 7.71 (ddd, J = 8.3, 6.9, 1.4 Hz, 1H, H$_2$), 7.53-7.44 (m, 2H, H$_{1,17}$), 7.24-7.16 (m, 2H, H$_{18,19}$), 2.71 (d, J = 0.8 Hz, 3H, H$_{12}$).
$^{13}$C NMR (101 MHz, DMSO-d6): δ (ppm) = 155.74 (C$_8$-arom.), 148.21 (C$_4$-arom.), 143.61 (C$_{10}$-arom.), 137.64 (C$_{15}$-arom.), 129.51 (C$_2$H-arom.), 129.39 (C$_3$H-arom.), 127.98 (C$_{13}$H-arom.), 126.42 (C$_5$-arom.), 126.13 (C$_{16}$-arom.), 125.18 (C$_1$H-arom.), 124.35 (C$_6$H-arom.), 123.12 (C$_{20}$H-arom.), 122.48 (C$_{18}$H-arom.), 120.68 (C$_{19}$H-arom.), 119.90 (C$_9$H-arom.), 115.97 (C$_{11}$-arom.), 112.16 (C$_{17}$H-arom.), 18.76 (C$_{12}$H$_3$).

2-(7-methoxy-1H-indol-3-yl)-4-methylquinoline

| VPC Number | LabBook Code | IC$_{50}$ (eGFP) = 0.6 |
|---|---|---|
| 13 554 | CA 2-87 F7-10 | IC$_{50}$ (PSA) = 0.67 |
| | (yield = 22%) | |

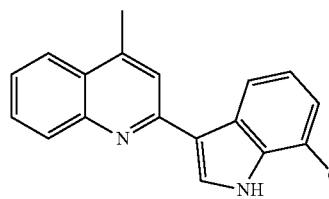

(Yellow Solid)

$t_R$ (HPLC) = 3.37 min  MS (ESI+) m/z = 289.1336 [(M + H)$^+$]
Mp = 146-152° C.
HRMS (ESI+): calculated for $C_{19}H_{17}N_2O$, m/z = 289.1335; found, 289.1335
$^1$H NMR (600 MHz, DMSO-d$_6$): δ (ppm) = 11.73 (s, 1H, H$_{14}$), 8.45 (d, J = 8.0 Hz, 1H, H$_{20}$), 8.21 (d, J = 2.9 Hz, 1H, H$_{13}$), 8.03-7.99 (m, 2H, H$_{3,6}$), 7.95 (d, J = 0.8 Hz, 1H, H$_9$), 7.70 (ddd, J = 8.2, 6.8, 1.3 Hz, 1H, H$_2$), 7.50 (ddd, J = 8.2, 6.9, 1.2 Hz, 1H, H$_1$), 7.11 (t, J = 7.9 Hz, 1H, H$_{19}$), 6.79 (d, J = 7.5 Hz, 1H, H$_{18}$), 3.97 (s, 3H, H$_{22}$), 2.70 (d, J = 0.8 Hz, 3H, H$_{12}$).
$^{13}$C NMR (151 MHz, DMSO-d$_6$): δ (ppm) = 155.23 (C$_8$-arom.), 147.71 (C$_4$-arom.), 146.06 (C$_{17}$-arom.), 143.11 (C$_{10}$-arom.), 129.00 (C$_2$H-arom.), 128.91 (C$_3$H-arom.), 127.23 (C$_{15}$-arom.), 127.14 (C$_{16}$-arom.), 126.97 (C$_{13}$H-arom.), 125.95 (C$_5$-arom.), 124.69 (C$_1$H-arom.), 123.85 (C$_6$H-arom.), 120.76 (C$_{19}$H-arom.), 119.52 (C$_9$H-arom.), 116.09 (C$_{11}$-arom.), 115.37 (C$_{20}$H-arom.), 102.58 (C$_{18}$H-arom.), 55.18 (C$_{22}$H$_3$), 18.24 (C$_{12}$H$_3$).

2-(1H-indol-3-yl)quinoline

| VPC Number | LabBook Code | IC$_{50}$ (eGFP) = 0.06 |
|---|---|---|
| 13 562 | CA 2-128 F8-12 | IC$_{50}$ (PSA) = 0.14 |
| | (yield = 46%) | |

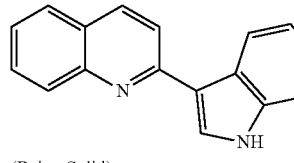

(Beige Solid)

$t_R$ (HPLC) = 2-91 min    MS (ESI+) m/z = 245.1073 [(M + H)$^+$]

Mp = 184-187° C.
HRMS (ESI+): calculated for C$_{17}$H$_{13}$N$_2$, m/z = 245.1073; found, 245.1075
$^1$H NMR (600 MHz, DMSO-d$_6$): δ (ppm) = 11.65 (s, 1H, H$_{13}$), 8.88 (d, J = 8.5 Hz, 1H, H$_{19}$), 8.35 (d, J = 2.7 Hz, 1H, H$_{12}$), 8.26 (d, J = 8.6 Hz, 1H, H$_{10}$), 8.06 (d, J = 8.7 Hz, 1H, H$_9$), 8.04 (d, J = 8.3 Hz, 1H, H$_3$), 7.89 (d, J = 7.9 Hz, 1H, H$_6$), 7.72 (t, J = 7.6 Hz, 1H, H$_2$), 7.51 -7.46 (m, 2H, H1,16), 7.24-7.18 (m, 2H, H$_{17,18}$).
$^{13}$C NMR (101 MHz, DMSO-d$_6$): δ (ppm) = 155.56 (C$_8$-arom.), 147.75 C$_4$-arom.s), 137.21 (C$_{14}$-arom.), 135.59 (C$_{10}$H-arom.), 129.34 (C$_2$H-arom.), 128.34 (C$_3$H-arom.), 27.79 (C$_6$H-arom.), 127.61 (C$_{12}$H-arom.), 125.80 (C$_5$-arom.), 125.58 (C$_{15}$-arom.), 124.88 (C$_1$H-arom.), 122.57 (C$_{19}$H-arom.), 122.08 (C$_{17}$H-arom.), 120.31 (C$_{18}$H-arom.), 119.21 (C$_9$H-arom.), 115.49 (C$_{11}$H-arom.), 111.73 (C$_{16}$H-arom.).

2-(7-fluoro-1H-indol-3-yl)quinoline (Procedure 9)

| VPC Number | LabBook | CodeIC$_{50}$ (eGFP) = 1.6 |
|---|---|---|
| 13 569 | CA 3-45 F13-23 Precipitate | IC$_{50}$ (PSA) = Not Tested |
| | (yield = 34%) | |

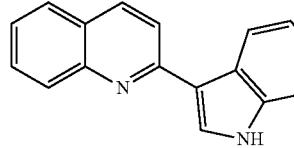

(Red Solid)

$t_R$ (HPLC) = 3.02 min    MS (ESI+) m/z = 263.1009 [(M + H)$^+$]

Mp = 152-154° C.
HRMS (ESI+ ): calculated for C$_{17}$H$_{12}$FN$_2$, m/z = 263.0979; found, 263.0976
$^1$H NMR (500 MHz, DMSO-d$_6$): δ (ppm) = 12.17 (s, 1H, H$_{13}$), 8.71 (d,J = 8.0 Hz, 1H, H$_{19}$), 8.44 (d, J = 2.8 Hz, 1H, H$_{12}$), 8.29 (d, J = 8.7 Hz, 1H, H$_{10}$), 8.10 (d, J = 8.7 Hz, 1H, H$_9$), 8.05 (d, J = 8.3 Hz, 1H, H$_3$), 7.91 (d, J = 7.5 Hz, 1H, H$_6$), 7.73 (t, J = 7.5 Hz, 1H, H$_2$), 7.51 (t, J = 7.5 Hz, 1H, H$_1$), 7.21-7.15 (m, 1H, H$_{18}$), 7.06 (dd, J = 11.4, 7.8 Hz, 1H, H$_{17}$).
$^{13}$C NMR (126 MHz, DMSO-d$_6$): δ (ppm) = 155.50 (C$_8$-arom.), 149.63 (d, J = 243.4 Hz, C$_{16}$-arom.), 148.13 (C$_4$-arom.), 136.29 (C$_{10}$H-arom.), 129.92 (C$_2$H-arom.), 129.85 (d, J = 5.2 Hz, C$_{15}$-arom.), 129.18 (C$_{12}$H-arom.), 128.90 (C$_3$H-arom.), 128.14 (C$_6$H-arom.), 126.41 (C$_5$-arom.), 125.63 (C$_1$H-arom.), 125.52 (d, J = 13.2 Hz, C$_{14}$-arom.), 121.14 (d, J = 6.2 Hz, C$_{18}$H-arom.), 119.76 (C$_9$H-arom.), 119.30 (d, J = 3.0 Hz, C$_{19}$H-arom.), 116.97 (d, J = 1.3 Hz, C$_{11}$H-arom.), 107.43 (d, J = 15.6 Hz, C$_{17}$H-arom.).

2(7-ethyl-1H-indol-3-yl)quinoline

| | | |
|---|---|---|
| VPC Number<br>13 567 | LabBook<br>CA 3-46 P2 F6-13<br>(yield = 45%) | CodeIC$_{50}$ (eGFP) = 0.2<br>IC$_{50}$ (PSA) = 0.23 |

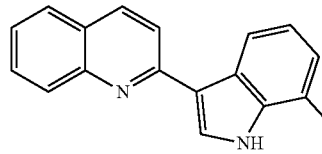

(Yellow Solid)

$t_R$ (HPLC) = 3.16 min  MS (ESI+) m/z = 273.1719 [(M + H)$^+$].
Mp = 159-162° C.
HRMS (ESI+: calculated for C$_{19}$H$_{17}$N$_2$, m/z = 273.1386; found, 273.1389
$^1$H NMR (500 MHz, DMSO-d$_6$): δ (ppm) = 11.63 (s, 1H, H$_{13}$), 8.73 (d, J = 7.9 Hz, 1H, H$_{19}$), 8.34 (d, J = 2.9 Hz, 1H, H$_{12}$), 8.25 (d, J = 8.7 Hz, 1H, H$_{10}$), 8.09 (d, J = 8.7 Hz, 1H, H$_9$), 8.03 (d, J = 8.4 Hz, 1H, H$_3$), 7.88 (d, J = 7.2 Hz, 1H, H$_6$), 7.71 (ddd, J = 8.3, 7.0, 1.4 Hz, 1H, H$_2$), 7.48 (ddd, J = 7.5, 6.5, 1.0 Hz, 1H, H$_1$), 7.15 (t, J = 7.8 Hz, 1H, H$_{18}$), 7.05 (d, J = 6.9 Hz, 1H, H$_{17}$), 2.93 (q, J = 7.5 Hz, 2H, H$_{20}$), 1.32 (t, J = 7.5 Hz, 3H, H$_{21}$).
$^{13}$C NMR (126 MHz, DMSO-d$_6$): δ (ppm) = 156.14 (C$_8$-arom.), 148.27 (C$_4$-arom.), 136.38 (C$_{14}$-arom.), 135.97 (C$_{10}$H-arom.), 129.76 (C$_2$H-arom.), 128.86 (C$_3$H-arom.), 128.07 (C$_6$H-arom.), 127.98 (C$_{12}$H-arom.), 127.62 (C$_{16}$-arom.), 126.28 (C$_5$-arom.), 126.00 (C$_{15}$-arom.), 125.30 (C$_1$H-arom.), 121.28 (C$_{17}$H-arom.), 121.08 (C$_{18}$H-arom.), 120.74 (C$_{19}$H-arom.), 119.80 (C$_9$H-arom.), 116.39 (C$_{11}$-arom.), 24.09 (C$_{20}$H$_2$), 15.01 (C$_{21}$H$_3$).

25

2(2-methyl-1H-indol-3-yl)quinoline

| | | |
|---|---|---|
| VPC Number<br>13 570 | LabBook<br>CA 3-47 F35-40 (yield = 29%) | CodeIC$_{50}$ (eGFP) = 20.0<br>IC$_{50}$ (PSA) = Not Tested |

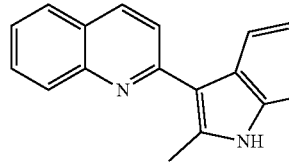

(Brown Solid)

$t_R$ (HPLC) = 2.91 min  MS (ESI+) m/z = 259.1435 [(M + H)$^+$]
Mp = 67-75° C.
HRMS (ESI+): calculated for C$_{18}$H$_{15}$N2, m/z = 259.1230; found, 259.1230
$^1$H NMR (400 MHz, DMSO-d$_6$): δ (ppm) = 11.48 (s, 1H, H$_{13}$), 8.34 (d, J = 8.6 Hz, 1H, H$_{10}$), 8.21 (dd, J = 6.5, 2.4 Hz, 1H, H$_{19}$), 8.01 (d, J = 8.4 Hz, 1H, H$_3$), 7.94 (d, J = 7.6 Hz, 1H, H$_6$), 7.85 (d, J = 8.6 Hz, 1H, H$_9$), 7.73 (ddd, J = 8.4, 6.9, 1.4 Hz, 1H, H$_2$), 7.52 (ddd, J = 8.0, 7.0, 1.1 Hz, 1H, H$_1$), 7.40 (dd, J = 6.4, 2.2 Hz, 1H, H$_{16}$), 7.15-7.11 (m, 2H, H$_{17,18}$), 2.77 (s, 3H, H$_{20}$).
$^{13}$C NMR (126 MHz, DMSO-d$_6$): δ (ppm) = 156.19 (C$_8$-arom.), 148.41 (C$_4$-arom.), 137.38 (C$_{12}$-arom.), 136.27 (C$_{10}$H-arom.), 135.74 (C$_{14}$-arom.), 129.85 (C$_2$H-arom.), 128.87 (C$_3$H-arom.), 128.13 (C$_6$H-arom.), 127.46 (C$_{15}$-arom.), 125.97 (C$_5$-arom.), 125.58 (C$_1$H-arom.), 121.69 (C$_9$H-arom.), 121.53 (C$_{17}$H-arom.), 120.38 (C$_{18}$H-arom.), 120.18 (C$_{19}$H-arom.), 112.46 (C$_{11}$-arom.), 111.34 (C$_{16}$H-arom.), 14.36 (C$_{20}$H$_3$).

2-(δ-bromo-1H-indol-3-yl)quinoline

| | | |
|---|---|---|
| VPC Number<br>13 568 | LabBook Code<br>CA 3-49 F44-63 Precipitate (yield = 46%) | IC$_{50}$ (eGFP) = 1.3<br>IC$_{50}$ (PSA) = 1.56 |

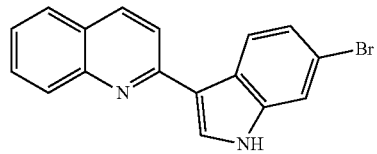 [SMILES: Brc1ccc2c(-c3ccc4ccccc4n3)c[nH]c2c1]

(Yellow Solid)

$t_R$ (HPLC) = 3.29 min  MS (ESI+) m/z = 323.0190, 325.0174 [(M + H)$^+$]
Mp = 189-194° C.
HRMS (ESI+): calculated for C$_{17}$H$_{12}$BrN$_2$, m/z = 323.0178, 325.0159; found, 323.0183, 325.0167
$^1$H NMR (500 MHz, DMSO-d$_6$): δ (ppm) = 11.79 (s, 1H, H$_{13}$), 8.84 (d, J = 8.5 Hz, 1H, H$_{19}$), 8.39 (d, J = 2.8 Hz, 1H, H$_{12}$), 8.28 (d, J = 8.7 Hz, 1H, H$_{10}$), 8.05 (m, 2H, H$_{3, 9}$), 7.90 (d, J = 7.5 Hz, 1H, H$_6$), 7.72 (t, J = 7.5 Hz, 1H, H$_2$), 7.67 (d, J = 1.6 Hz, 1H, H$_{16}$), 7.50 (t, J = 7.5 Hz, 1H, H$_1$), 7.34 (dd, J = 8.5, 1.8 Hz, 1H, H$_{18}$).
$^{13}$C NMR (126 MHz, DMSO-d$_6$): δ (ppm) = 155.52 (C$_8$-arom.), 148.15 (C$_4$-arom.), 138.58 (C$_{14}$-arom.), 136.27 (C$_{10}$H-arom.), 129.91 (C$_2$H-arom.), 129.11 (C$_{12}$H-arom.), 128.88 (C$_3$H-arom.), 128.13 (C$_6$H-arom.), 126.37 (C$_5$-arom.), 125.59 (C$_1$H-arom.), 125.11 (C$_{15}$-arom.), 124.82 (C$_{19}$H-arom.), 123.65 (C$_{18}$H-arom.), 119.57 (C$_9$H-arom.), 116.11 (C$_{11}$-arom.), 115.31 (C$_{17}$-arom.), 114.82 (C$_{16}$H-arom).

2-(1-methyl-1H-indol-3-yl)quinoline

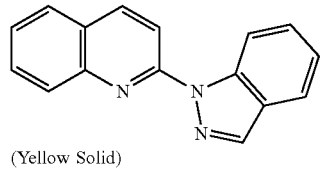

(Yellow Solid)

| | | |
|---|---|---|
| VPC Number<br>13 571 | LabBook Code<br>CA 3-56 Precipitate (yield = 53%) | IC$_{50}$ (eGFP) = 1.1<br>IC$_{50}$ (PSA) = Not Tested |

$t_R$ (HPLC) = 3.05 min    MS (ESI+) m/z = 259.1355 [(M + H)$^+$]

Mp = 175-179° C.
HRMS (ESI+): calculated for C$_{18}$H$_{15}$N$_2$, m/z = 259.1230; found, 259.1232
$^1$H NMR (500 MHz, DMSO-d$_6$): δ (ppm) = 8.88 (d, J = 8.5 Hz, 1H, H$_{19}$), 8.34 (s, 1H, H$_{12}$), 8.27 (d, J = 8.7 Hz, 1H, H$_{10}$), 8.03 (d, J = 8.3 Hz, 1H, H$_3$), 7.98 (d, J = 8.7 Hz, 1H, H$_9$), 7.89 (d, J = 7.2 Hz, 1H, H$_6$), 7.72 (t, J = 7.6 Hz, 1H, H$_2$), 7.54 (d, J = 7.5 Hz, 1H, H$_{16}$), 7.49 (t, J = 7.6 Hz, 1H, H$_2$), 7.29-7.26 (m, 2H, H$_{17, 18}$), 3.91 (s, 3H, H$_{20}$).
$^{13}$C NMR (126 MHz, DMSO-d$_6$): δ (ppm) = 155.64 (C$_8$-arom.), 148.28 (C$_4$-arom.), 138.16 (C$_{14}$-arom.), 136.21 (C$_{10}$H-arom.), 132.24 (C$_{12}$H-arom.), 129.88 (C$_2$H-arom.), 128.84 (C$_3$H-arom.), 128.11 (C$_6$H-arom.), 126.43 (C$_{15}$-arom.), 126.27 (C$_5$-arom.), 125.40 (C$_1$H-arom.), 123.16 (C$_{19}$H-arom.), 122.66 (C$_{17}$H-arom.), 121.07 (C$_{18}$H-arom.), 119.50 (C$_9$H-arom.), 115.00 (C$_{11}$-arom.), 110.58 (C$_{16}$H-arom.), 33.40 (C$_{20}$H$_3$-arom.).

25

2-(1H-indazol-1-yl)quinoline

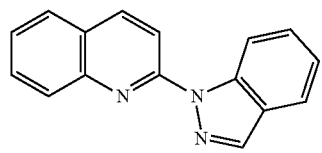 [SMILES: c1ccc2nc(-n3ncc4ccccc43)ccc2c1]

(White Solid)

| | | |
|---|---|---|
| VPC Number<br>13 572 | LabBook Code<br>CA 3-59 F11 (yield = 25%) | IC$_{50}$ (eGFP) = 0.7<br>IC$_{50}$ (PSA) = Not Tested |

$t_R$ (HPLC) = 4.44 min    MS (ESI+) m/z = 246.1019 [(M + H)$^+$]

Mp = 91-96° C.
HRMS (ESI+): calculated for C$_{16}$H$_{12}$N$_3$, m/z = 246.1026; found, 246.1028
$^1$H NMR (500 MHz, CDCl$_3$): δ (ppm) = 9.18 (d, J = 8.5 Hz, 1H, H$_{16}$), 8.28 (d, J = 9.0 Hz, 1H, H$_9$), 8.25-8.21 (m, 2H, H$_{10, 11}$), 8.11 (d, J = 8.4 Hz, 1H, H$_3$), 7.82-7.77 (m, 2H, H$_{6, 19}$), 7.72 (ddd, J = 8.3, 7.0, 1.4 Hz, 1H, H$_2$), 7.59 (ddd, J = 8.3, 7.0, 1.0 Hz, 1H, H$_{17}$), 7.48 (ddd, J = 8.1, 7.0, 1.3 Hz, 1H, H$_1$), 7.32 (ddd, J = 8.0, 7.0, 1.0 Hz, 1H, H$_{18}$).
$^{13}$C NMR (126 MHz, CDCl$_3$): δ (ppm) = 152.95 (C$_8$-arom.), 146.66 (C$_4$-arom.), 139.00 (C$_4$-arom.), 138.46 (C$_{10}$H-arom.), 137.18 (C$_{11}$H-arom.), 130.05 (C$_2$H-arom.), 128.36 (C$_3$H-arom.), 128.22 (C$_{17}$H-arom.), 127.67 (C$_6$H-arom.), 126.28 (C$_5$-arom.), 126.14 (C$_{15}$-arom.), 125.51 (C$_1$H-arom.), 122.95 (C$_{18}$H-arom.), 120.82 (C$_{19}$H-arom.), 116.03 (C$_{16}$H-arom.), 113.48 (C$_9$H-arom.).

2-(7-methyl-1H-indol-3-yl)quinoline (Procedure 9)

(Yellow Solid)

| | | |
|---|---|---|
| VPC Number<br>13 566 | LabBook Code<br>CA 3-67 Precipitate (yield = 48%) | IC$_{50}$ (eGFP) = 0.095<br>IC$_{50}$ (PSA) = 0.056 |

$t_R$ (HPLC) = 3.10 min    MS (ESI+) m/z = 259.1255 [(M + H)$^+$]

Mp = 146-150° C.
HRMS (ESI+): calculated for C$_{18}$H$_{15}$N$_2$, m/z = 259.1230; found, 259.1229
$^1$H NMR (500 MHz, DMSO-d$_6$): δ (ppm) = 11.63 (s, 1H), 8.72 (d, J = 7.9 Hz, 1H), 8.35 (d, J = 2.8 Hz, 1H), 8.25 (d, J = 8.7 Hz, 1H), 8.09 (d, J = 8.7 Hz, 1H), 8.03 (d, J = 8.3 Hz, 1H), 7.88 (d, J = 7.8 Hz, 1H), 7.74-7.68 (m, 1H), 7.48 (t, J = 7.4 Hz, 1H), 7.12 (t, J = 7.5 Hz, 1H), 7.02 (d, J = 7.0 Hz, 1H), 2.54 (s, 3H).

$^{13}$C NMR (126 MHz, DMSO-d$_6$): δ (ppm) = 156.14, 148.27, 137.19, 135.98, 129.77, 128.86, 128.08, 128.02, 126.28, 125.82, 125.31, 123.10, 121.27, 120.98, 120.70, 119.79, 116.41, 17.27.

2-(5-methyl-1H-indol-3-yl)quinoline

| | | |
|---|---|---|
| VPC Number<br>13 577 | LabBook Code<br>CA 3-73 Precipitate (yield = 55%) | $IC_{50}$ (eGFP) = 3.2<br>$IC_{50}$ (PSA) = 1.73 |
| 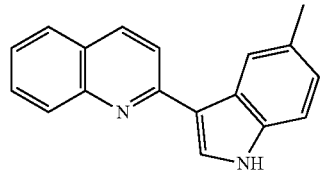 [SMILES: Cc1ccc2[nH]cc(-c3ccc4ccccc4n3)c2c1]<br>(Yellow Solid) | $t_R$ (HPLC) = 3.12 min<br>HRMS (ESI+): calculated for $C_{18}H_{15}N_2$, m/z = 259.1230; found, 259.1218<br>$^1$H NMR (400 MHz, DMSO-$d_6$): δ (ppm) = 12.64 (s, 1H, $H_{13}$), 8.97 (s, 1H, $H_{12}$), 8.89 (d, J = 8.1 Hz, 1H, $H_{10}$), 8.58 (d, J = 8.2 Hz, 1H, $H_3$), 8.42 (d, J = 8.9 Hz, 1H, $H_9$), 8.22 (d, J = 8.0 Hz, 1H, $H_6$), 8.10 (s, 1H, $H_{19}$), 8.02 (t, J = 7.6 Hz, 1H, $H_2$), 7.77 (t, J = 7.5 Hz, 1H, $H_1$), 7.52 (d, J = 8.3 Hz, 1H, $H_{16}$), 7.18 (dd, J = 8.3, 0.9 Hz, 1H, $H_{17}$), 2.51 (s, 3H, $H_{20}$).<br>$^{13}$C NMR = Done but unreadable and it was the same for every compound made with this procedure | MS (ESI+) m/z = 259.1248<br>$[(M + H)^+]$ |

15

2-(δ-fluoro-1H-indol-3-yl)quinoline

| | | |
|---|---|---|
| VPC Number<br>13 576 | LabBook Code<br>CA 3-75 Precipitate2 (yield = 30%) | $IC_{50}$ (eGFP) = 0.144<br>$IC_{50}$ (PSA) = 0.048 |
| 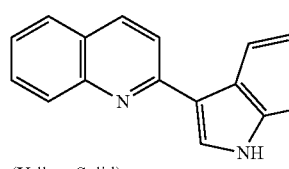<br>(Yellow Solid) | $t_R$ (HPLC) = 3.08 min<br>Mp = 259-266° C.<br>HRMS (ESI+): calculated for $C_{17}H_{11}FN_2Na$, m/z = 285.0798; found, 285.0810<br>$^1$H NMR (600 MHz, DMSO-$d_6$): δ (ppm) = 8.71 (s, 2H, $H_{10,\ 12}$), 8.49 (s, 1H, $H_{19}$), 8.31 (s, 2H, $H_{3,\ 9}$), 8.14 (s, 1H, $H_6$), 7.95 (s, 1H, $H_2$), 7.71 (s, 1H, $H_1$), 7.40 (d, J = 8.3 Hz, 1H, $H_{16}$), 7.18 (t, J = 8.5 Hz, 1H, $H_{18}$).<br>$^{13}$C NMR = Done but unreadable and it was the same for every compound made with this procedure, even proton spectra looked bad. | MS (ESI+) m/z = 263.1223<br>$[(M + H)^+]$ |

2-(δ-(trifluoromethyl)-1H-indol-3-yl)quinoline

| | | |
|---|---|---|
| VPC Number<br>13 580 | LabBook Code<br>CA 3-78 Precipitate (yield = 8%) | $IC_{50}$ (eGFP) = 2.9<br>$IC_{50}$ (PSA) = Not Tested |
| 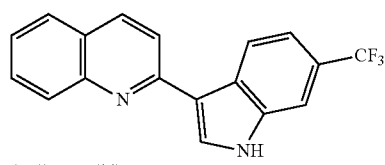<br>(Yellow Solid) | $t_R$ (HPLC) = 3.50 min<br>HRMS (ESI+): calculated for $C_{18}H_{12}F_3N_2$, m/z = 313.0947; found, 313.0947<br>$^1$H NMR (400 MHz, DMSO-$d_6$): δ (ppm) = 8.83 (s, 1H, $H_{12}$), 8.75 (s, 2H, $H_{10,\ 19}$), 8.31 (s, 2H, $H_{3,\ 9}$), 8.11 (s, 1H, $H_6$), 7.93 (s, 2H, $H_{2,\ 16}$), 7.70 (s, 1H, $H_1$), 7.58 (d, J = 7.9 Hz, 1H, $H_{18}$).<br>$^{13}$C NMR Done but unreadable and it was the same for every compound made with this procedure, even proton spectra looked bad. | MS (ESI+) m/z = 313.0949<br>$[(M + H)^+]$ |

2-(7-methyl-1H-indazol-1-yl)quinoline

| | | |
|---|---|---|
| VPC Number<br>13 575 | LabBook Code<br>CA 3-90 F4-12 Precipitate (yield = 21%) | $IC_{50}$ (eGFP) = 3.5<br>$IC_{50}$ (PSA) = 1.36 |
| 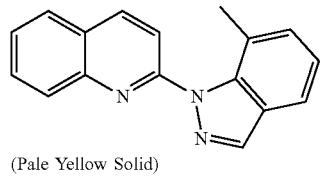<br>(Pale Yellow Solid) | $t_R$ (HPLC) = 4.54 min<br>Mp = 147-152° C.<br>HRMS (ESI+): calculated for $C_{17}H_{14}N_3$, m/z = 260.1182; found, 260.1172<br>$^1$H NMR (500 MHz, DMSO-$d_6$): δ (ppm) = 9.42 (s, 1H, $H_{11}$), 8.69 (d, J = 8.8 Hz, 1H, $H_{10}$), 8.49 (d, J = 8.8 Hz, 1H, $H_9$), 8.12 (d, J = 8.0 Hz, 1H, $H_6$), 8.09 (d, J = 8.5 Hz, 1H, $H_3$), 7.89 (ddd, J = 8.0, 6.5, 1.0 Hz, 1H, $H_2$), 7.71-7.65 (m, 2H, $H_{1,\ 9}$), 7.14 (d, J = 6.6 Hz, 1H, $H_{17}$), 7.05 (dd, J = 8.3, 6.7 Hz, 1H, $H_{18}$), 2.62 (s, 3H, $H_{20}$).<br>$^{13}$C NMR (126 MHz, DMSO-$d_6$): δ (ppm) = 150.74 ($C_{14}$-arom.), 150.56 ($C_8$-arom.), 146.38 ($C_4$-arom.), 140.60 ($C_{10}$H-arom.), 131.47 ($C_2$H-arom.), 128.69 $C_6$H-arom.), 128.66 ($C_3$H-arom.), 127.92 ($C_5$-arom.), 127.89 ($C_{16}$-arom.), 127.33 ($C_1$H-arom.), 126.89 ($C_{17}$H-arom.), 123.64 ($C_{18}$H-arom.), 122.62 ($C_{15}$-arom.), 121.65 ($C_{11}$H-arom.), 119.49 ($C_{19}$H-arom.), 113.50 ($C_9$H-arom.), 17.22 ($C_{20}H_3$). | MS (ESI+) m/z = 260.1176<br>$[(M + H)^+]$ |

2-(δ-(benzyloxy)-1H-indol-3-yl)quinoline

| VPC Number 13 589 | LabBook Code CA 3-94 Precipitate (yield = 20%) | $IC_{50}$ (eGFP) = 5.3 $IC_{50}$ (PSA) = Not Tested |
|---|---|---|
| 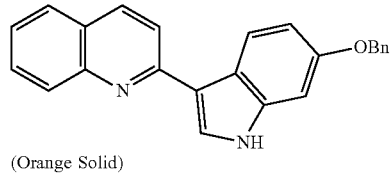 (Orange Solid) | $t_R$ (HPLC) = 3.66 min<br>Mp = 264-269° C.<br>HRMS (ESI+): calculated for $C_{24}H_{19}N_2O$, m/z = 351.1492; found, 351.1494<br>$^1$H NMR (400 MHz, DMSO-$d_6$): δ (ppm) = 12.50 (s, 1H, $H_{13}$), 8.85 (s, 2H, $H_{10}$), 8.52 (d, J = 5.6 Hz, 1H, $H_3$), 8.37 (d, J = 8.7 Hz, 1H, $H_9$), 8.20 (d, J = 7.2 Hz, 2H, $H_{6,\ 19}$), 8.00 (t, J = 7.3 Hz, 1H, $H_2$), 7.75 (t, J = 7.3 Hz, 1H, $H_1$), 7.51 (d, J = 7.2 Hz, 2H, $H_{22,\ 26}$), 7.42 (t, J = 7.4 Hz, 2H, $H_{23,\ 25}$), 7.35 (t, J = 7.3 Hz, 1H, $H_{24}$), 7.19 (d, J = 1.7 Hz, 1H, $H_{16}$), 7.06 (dd, J = 8.8, 2.0 Hz, 1H, $H_{18}$), 5.21 (s, 2H, $H_{27}$).<br>$^{13}$C NMR Done but unreadable and it was the same for every compound made with this procedure, even proton spectra looked bad. | MS (ESI+) m/z = 351.1707 [(M + H)$^+$] |

3-(pyridin-3-yl)-1H-pyrrolo[2,3-c]pyridine    (Procedure 10)

| VPC Number 13 581 | LabBook Code CA 3-105 Purified (yield = 64%) | $IC_{50}$ (eGFP) = 4.9 $IC_{50}$ (PSA) = Not Tested |
|---|---|---|
| 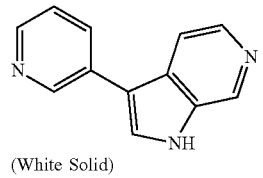 (White Solid) | $t_R$ (HPLC) = 1.45 min<br>Mp = 71-80° C.<br>HRMS (ESI+): calculated for $C_{12}H_{10}N_3$, m/z = 196.0869; found, 196.0862<br>$^1$H NMR (600 MHz, DMSO-$d_6$): δ (ppm) = 12.21 (s, 1H, $H_{13}$), 8.99 (s, 1H, $H_3$), 8.90 (s, 1H, $H_9$), 8.49 (s, 1H, $H_2$), 8.25 (s, 1H, $H_7$), 8.21 (s, 1H, $H_{14}$), 8.16-8.12 (m, 1H, $H_5$), 7.94 (d, J = 4.0 Hz, 1H, $H_{12}$), 7.48 (dd, J = 7.7, 4.8 Hz, 1H, $H_6$).<br>$^{13}$C NMR (151 MHz, DMSO-$d_6$): δ (ppm) = 147.26 ($C_3$H-arom.), 146.80 ($C_2$H-arom.), 137.78 ($C_7$H-arom.), 134.44 ($C_9$H-arom.), 133.82 ($C_{10}$-arom.), 133.41 ($C_5$H-arom.), 130.47 ($C_4$-arom.), 129.35 ($C_{11}$-arom.), 128.95 ($C_{14}$H-arom.), 123.95 ($C_6$H-arom.), 113.91 ($C_{12}$H-arom.), 111.96 ($C_{15}$-arom.). | MS (ESI+) m/z = 196.0861 [(M + H)$^+$] |

3-(pyridin-3-yl)-1H-indazole (Procedure 10)

| VPC Number 13 590 | LabBook Code CA 3-106 Precipitate (yield = 45%) | $IC_{50}$ (eGFP) = No Data $IC_{50}$ (PSA) = No Data |
|---|---|---|
| 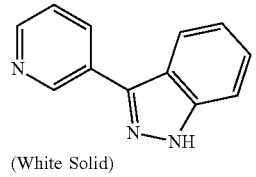 (White Solid) | $t_R$ (HPLC) = 2.53 min<br>Mp = 176-179° C.<br>HRMS (ESI+): calculated for $C_{12}H_{10}N_3$, m/z = 196.0869; found, 196.0871<br>$^1$H NMR (600 MHz, DMSO-$d_6$): δ (ppm) = 9.21 (d, J = 1.5 Hz, 1H, $H_5$), 8.62 (dd, J = 4.7, 1.6 Hz, 1H, $H_2$), 8.38 (td, J = 8.4, 1.8 Hz, 1H, $H_3$), 8.12 (d, J = 8.2 Hz, 1H, $H_{12}$), 7.64 (d, J = 8.4 Hz, 1H, $H_9$), 7.56 (ddd, J = 7.9, 4.8, 0.7 Hz, 1H, $H_1$), 7.45 (ddd, J = 8.4, 7.2, 0.6 Hz, 1H, $H_8$), 7.25 (ddd, J = 7.8, 6.6, 0.6 Hz, 1H, $H_8$).<br>$^{13}$C NMR (151 MHz, DMSO-$d_6$): δ (ppm) = 148.59 ($C_2$H-arom.), 147.42 ($C_5$H-arom.), 141.50 ($C_{10}$-arom.), 140.45 ($C_4$-arom.), 133.90 ($C_3$H-arom.), 129.63 ($C_{15}$-arom.), 126.35 ($C_8$H-arom.), 124.02 ($C_1$H-arom.), 121.41 ($C_7$H-arom.), 120.43 ($C_{12}$H-arom.), 120.06 ($C_{11}$-arom.), 110.72 ($C_9$H-arom.). | MS (ESI+) m/z = 196..0889 [(M + H)$^+$] |

2-(7-bromo-1H-indol-3-yl)quinoline

| VPC Number 13 582 | LabBook Code CA 3-107 F9-17 Precipitate (yield = 20%) | $IC_{50}$ (eGFP) = 0.052 $IC_{50}$ (PSA) = 0.041 |
|---|---|---|
| 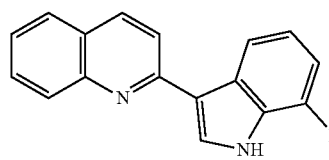 | $t_R$ (HPLC) = 3.25 min<br>Mp = 178-180° C.<br>HRMS (ESI+): calculated for $C_{17}H_{12}BrN_2$, m/z = 323.0178, 325.0159; found, 323.0172, 325.0153<br>$^1$H NMR (600 MHz, DMSO-$d_6$): δ (ppm) = 11.87 (s, 1H, $H_{13}$), 8.94 (d, J = 7.9 Hz, 1H, $H_{19}$), 8.42 (d, J = 2.8 Hz, 1H, $H_{12}$), 8.29 (d, J = 8.6 Hz, 1H, $H_{10}$), | MS (ESI+) m/z = 323.0177, 325.0158 [(M + H)$^+$] |

| (Pale Yellow Solid) | 8.13 (d, J = 8.7 Hz, 1H, $H_9$), 8.06 (d, J = 8.4 Hz, 1H, $H_3$), 7.91 (d, J = 8.0 Hz, 1H, $H_6$), 7.73 (ddd, J = 8.4, 7.2, 1.2 Hz, 1H, $H_2$), 7.51 (ddd, J = 7.8, 6.6, 0.6 Hz, 1H, $H_1$), 7.45 (dd, J = 7.5, 0.5 Hz, 1H, $H_{17}$), 7.17 (t, J = 7.8 Hz, 1H, $H_{18}$). $^{13}$C NMR (151 MHz, DMSO-$d_6$): δ (ppm) = 155.00 ($C_8$-arom.), 147.65 ($C_4$-arom.), 135.81 ($C_{10}$H-arom.), 135.51 ($C_{14}$H-arom.), 129.43 ($C_2$H-arom.), 128.78 ($C_{12}$H-arom.), 128.46 ($C_3$H-arom.), 127.65 ($C_6$H-arom.), 127.36 ($C_{15}$-arom.), 125.96 ($C_5$-arom.), 125.19 ($C_1$H-arom.), 124.73 ($C_{17}$H-arom.), 122.17 ($C_{19}$H-arom.), 121.76 ($C_{18}$H-arom.), 119.31 ($C_9$H-arom.), 116.67 ($C_{11}$-arom.), 104.34 ($C_{16}$-arom.). |

2-(1H-pyrrolo[2,3-c]pyridin-3-yl)quinoline    (Procedure 10)

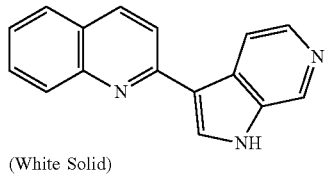

| VPC Number 13 583 | LabBook Code CA 3-109 F22-31 Precipitate (yield = 19%) | $IC_{50}$ (eGFP) = 1.1 $IC_{50}$ (PSA) = 0.93 |
| --- | --- | --- |
| (White Solid) | $t_R$ (HPLC) = 2.52 min<br>Mp = <270° C.<br>HRMS (ESI+): calculated for $C_{16}H_{12}N_3$, m/z = 246.1026; found, 246.1017<br>$^1$H NMR (600 MHz, DMSO-$d_6$): δ (ppm) = 12.12 (s, 1H, $H_{17}$), 8.85 (d, J = 0.8 Hz, 1H, $H_{13}$), 8.72 (dd, J = 5.4, 0.9 Hz, 1H, $H_{16}$), 8.58 (d, J = 2.4 Hz, 1H, $H_{18}$), 8.31 (m, 2H, $H_{10, 11}$), 8.09 (d, J = 8.7 Hz, 1H, $H_9$), 8.07 (d, J = 8.3 Hz, 1H, $H_3$), 7.92 (d, J = 8.0 Hz, 1H, $H_6$), 7.74 (ddd, J = 8.3, 6.9, 1.4 Hz, 1H, $H_2$), 7.52 (ddd, J = 7.8, 7.2, 1.2 Hz, 1H, $H_1$).<br>$^{13}$C NMR (151 MHz, DMSO-$d_6$): δ (ppm) = 154.73 ($C_8$-arom.), 147.73 ($C_4$-arom.), 139.35 ($C_{11}$H-arom.), 136.01 ($C_{10}$-arom.), 134.88 ($C_{13}$H-arom.), 134.37 ($C_{14}$-arom.), 130.89 ($C_{18}$H-arom.), 129.92 ($C_{15}$-arom.), 129.51 ($C_2$H-arom.), 128.46 ($C_3$H-arom.), 127.69 ($C_6$H-arom.), 125.97 ($C_5$-arom.), 125.24 ($C_1$H-arom.), 119.03 ($C_9$H-arom.), 116.77 ($C_{16}$H-arom.), 115.22 ($C_{19}$H-arom.). | MS (ESI+) m/z = 246.1028 [(M + H)$^+$] | tert-butyl    3-iodo-1H-pyrrolo[2,3-b]pyridine-1-carboxylate

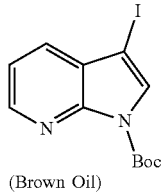

| Intermediate | LabBook Code CA 3-111 F1-14 (yield = 86%) | |
| --- | --- | --- |
| (Brown Oil) | $t_R$ (HPLC) = 4.66 min<br>$^1$H NMR (400 MHz, DMSO-$d_6$): δ (ppm) = 8.44 (dd, J = 4.7, 1.5 Hz, 1H, $H_2$), 8.03 (s, 1H, $H_8$), 7.79 (dd, J = 7.9, 1.6 Hz, 1H, $H_6$), 7.39 (dd, J = 7.9, 4.7 Hz, 1H, $H_1$), 1.62 (s, 9H, $H_{13, 14, 15}$).<br>$^{13}$C NMR (101 MHz, DMSO-$d_6$): δ (ppm) = 147.14 ($C_{16}$ = O), 147.04 ($C_4$-arom.), 146.16 ($C_2$H-arom.), 131.54 ($C_8$H-arom.), 130.04 ($C_6$H-arom.), 125.25 ($C_5$-arom.), 120.04 ($C_1$H-arom.), 84.57 ($C_{12}$-(CH$_3$)$_3$), 63.79 ($C_9$-arom.), 28.08 ($C_{13, 14, 15}H_3$). | MS (ESI+) m/z = 345.0074 [(M + H)$^+$] |

3-(1H-pyrrolo[3,2-c]pyridin-3-yl)quinoline    (Procedure 10)

| VPC Number 13 637 | LabBook Code CA 3-115 Precipitate (yield = 51%) | $IC_{50}$ (eGFP) = Inactive $IC_{50}$ (PSA) = Inactive |
| --- | --- | --- |
| (White Solid) | $t_R$ (HPLC) = 2.22 min<br>Mp = 233-239° C.<br>HRMS (ESI+): calculated for $C_{16}H_{12}N_3$, m/z = 246.1026; found, 246.1016<br>$^1$H NMR (400 MHz, DMSO-$d_6$): δ (ppm) = 12.04 (s, 1H, $H_{13}$), 9.37 (s, 1H, $H_{12}$), 8.76 (d, J = 2.3 Hz, 1H, $H_5$), 8.76 (d, J = 1.9 Hz, 1H, $H_3$), 8.31 (d, J = 5.7 Hz, 1H, $H_8$), 8.19 (d, J = 1.7 Hz, 1H, $H_{14}$), 8.13 (d, J = 7.6 Hz, 1H, $H_{19}$), 8.03 (d, J = 8.3 Hz, 1H, $H_{16}$), 7.72 (ddd, J = 8.4, 6.9, 1.4 Hz, 1H, $H_{17}$), 7.63 (ddd, J = 8.0, 7.2, 1.2 Hz, 1H, $H_{18}$), 7.51 (dd, J = 5.7, 0.7 Hz, 1H, $H_9$).<br>$^{13}$C NMR (101 MHz, DMSO-$d_6$): δ (ppm) = 150.40 ($C_5$-arom.), 146.38 ($C_2$-arom.), 142.88 ($C_{12}$H-arom.), 141.29 ($C_8$H-arom.), 140.94 ($C_{10}$-arom.), 131.31 ($C_3$H-arom.), 129.08 ($C_{17}$H-arom.), 129.04 ($C_{16}$H-arom.), 128.62 ($C_1$-arom.), 128.60 ($C_{19}$H-arom.), 128.35 ($C_4$-arom.), 127.31 ($C_{18}$H-arom.), 126.19 ($C_{14}$H-arom.), 122.63 ($C_{11}$-arom.), 112.66 ($C_{15}$-arom.), 107.80 ($C_9$H-arom.). | MS (ESI+) m/z = 246.1020 [(M + H)$^+$] |

3-(5-bromo-2-methoxyphenyl)-1H-pyrrolo[3,2-c]pyridine (Procedure 10)

| | | |
|---|---|---|
| VPC Number<br>13 638 | LabBook Code<br>CA 3-116 Precipitate (yield = quant.) | IC$_{50}$ (eGFP) = Inactive<br>IC$_{50}$ (PSA) = Inactive |
| (White Solid) | $t_R$ (HPLC) = 2.91 min<br>Mp = <270° C.<br>HRMS (ESI+): calculated for C$_{14}$H$_{12}$BrN$_2$O, m/z = 303.0128, 305.0108; found, 303.0119, 305.0100<br>$^1$H NMR (400 MHz, DMSO-d$_6$): δ (ppm) = 12.03 (s, 1H, H$_{13}$), 8.82 (d, J = 0.6 Hz, 1H, H$_{12}$), 8.20 (d, J = 5.7 Hz, 1H, H$_8$), 7.70 (d, J = 2.0 Hz, 1H, H$_{14}$), 7.65 (d, J = 2.5 Hz, 1H, H$_2$), 7.47 (dd, J = 8.8, 2.6 Hz, 1H, H$_6$), 7.44 (dd, J = 5.7, 1.0 Hz, 1H, H$_9$), 7.12 (d, J = 8.8 Hz, 1H, H$_3$), 3.82 (s, 3H, H$_{18}$).<br>$^{13}$C NMR (101 MHz, DMSO-d$_6$): δ (ppm) = 155.97 (C$_5$-arom.), 143.25 (C$_{12}$H-arom.), 140.41 (C$_8$H-arom.), 140.06 (C$_{10}$-arom.), 132.27 (C$_3$H-arom.), 130.31 (C$_6$H-arom.), 127.00 (C$_{14}$H-arom.), 126.07 (C$_4$-arom.), 123.24 (C$_{11}$-arom.), 114.24 (C$_2$H-arom.), 112.46 (C$_1$-arom.), 110.90 (C$_{15}$-arom.), 107.57 (C$_9$H-arom.), 56.13 (C$_{18}$H$_3$). | MS (ESI+) m/z = 303.0118, 305.0099 [(M + H)$^+$] |

3-(7-bromo-1H-indol-3-yl)quinoline (Procedure 10)

| | | |
|---|---|---|
| VPC Number<br>13 653 | LabBook Code<br>CA 3-123 Precipitate (yield = 39%) | IC$_{50}$ (eGFP) = 1.13<br>IC$_{50}$ (PSA) = 0.29 |
| (Pale Yellow Solid) | $t_R$ (HPLC) = 3.79 min<br>Mp = 217-223° C.<br>HRMS (ESI+): calculated for C$_{17}$H$_{12}$BrN$_2$, m/z = 323.0178, 325.0159; found, 323.0179, 325.0160<br>$^1$H NMR (400 MHz, DMSO-d$_6$): δ (ppm) = 11.86 (s, 1H, H$_{13}$), 9.33 (d, J = 2.2 Hz, 1H, H$_5$), 8.66 (d, J = 1.9 Hz, 1H, H$_3$), 8.12-8.06 (m, 3H, H$_{12,14,19}$), 8.03 (d, J = 8.3 Hz, 1H, H$_{16}$), 7.72 (t, J = 8.2 Hz, 1H, H$_{17}$), 7.63 (t, J = 7.4 Hz, 1H, H$_{18}$), 7.47 (d, J = 7.5 Hz, 1H, H$_8$), 7.14 (t, J = 7.8 Hz, 1H, H$_7$).<br>$^{13}$C NMR (101 MHz, DMSO-d$_6$): δ (ppm) = 150.63 (C$_5$H-arom.), 146.32 (C$_2$-arom.), 135.72 (C$_{10}$-arom.), 131.21 (C$_3$H-arom.), 129.11 (C$_{17}$H-arom.), 128.99 (C$_1$-arom.), 128.86 (C$_{12}$H-arom.), 128.57 (C$_4$-arom.), 128.48 (C$_{19}$H-arom.), 127.28 (C$_{18}$H-arom.), 127.19 (C$_{11}$-arom.), 126.42 (C$_{14}$H-arom.), 125.01 (C$_8$H-arom.), 121.96 (C$_7$H-arom.), 119.28 (C$_{12}$H-arom.), 114.08 (C$_{15}$-arom.), 105.30 (C$_9$-arom.). | MS (ESI+) m/z = 323.0176, 325.0157 [(M + H)$^+$] |

3-(7-methyl-1H-indol-3-yl)quinoline (Procedure 10)

| | | |
|---|---|---|
| VPC Number<br>13 654 | LabBook Code<br>CA 3-125 Precipitate (yield = 56%) | IC$_{50}$ (eGFP) = 0.92<br>IC$_{50}$ (PSA) = 0.16 |
| (White Solid) | $t_R$ (HPLC) = 3.43 min<br>Mp = 215-219° C.<br>HRMS (ESI+): calculated for C$_{18}$H$_{15}$N$_2$, m/z = 259.1230; found, 259.1234<br>$^1$H NMR (400 MHz, DMSO-d$_6$): δ (ppm) = 11.59 (s, 1H, H$_{13}$), 9.34 (d, J = 2.3 Hz, 1H, H$_5$), 8.62 (d, J = 2.1 Hz, 1H, H$_3$), 8.07 (m, 2H, H$_{14,19}$), 8.01 (d, J = 8.4 Hz, 1H, H$_{16}$), 7.92 (d, J = 7.9 Hz, 1H, H$_{12}$), 7.69 (td, J = 8.4, 1.5 Hz, 1H, H$_{17}$), 7.61 (td, J = 8.1, 1.2 Hz, 1H, H$_{18}$), 7.12 (t, J = 7.6 Hz, 1H, H$_7$), 7.03 (d, J = 7.0 Hz, 1H, H$_8$), 2.54 (s, 3H, H$_{20}$).<br>$^{13}$C NMR (101 MHz, DMSO-d$_6$): δ (ppm) = 150.68 (C$_5$H-arom.), 146.10 (C$_2$-arom.), 136.96 (C$_{10}$-arom.), 130.41 (C$_3$H-arom.), 129.74 (C$_{17}$H-arom.), 129.08 (C$_{16}$H-arom.), 128.72 (C$_1$-arom.), 128.64 (C$_4$-arom.), 128.37 (C$_{19}$H-arom.), 127.19 (C$_{18}$H-arom.), 125.16 (C$_{11}$-arom.), 125.01 (C$_{14}$H-arom.), 122.86 (C$_8$H-arom.), 121.80 (C$_9$-arom.), 120.77 (C$_7$H-arom.), 117.24 (C$_{12}$H-arom.), 113.06 (C$_{15}$H-arom.), 17.30 (C$_{20}$H$_3$). | MS (ESI+) m/z = 259.1236 [(M + H)$^+$] |

7-methyl-3-(pyridin-3-yl)-1H-indole (Procedure 10)

| | | |
|---|---|---|
| VPC Number<br>13 655 | LabBook Code<br>CA 3-127 F5 Precipitate (yield = 25%) | $IC_{50}$ (eGFP) = 1.66<br>$IC_{50}$ (PSA) = 0.61 |
| | $t_R$ (HPLC) = 2.69 min | MS (ESI+) m/z = 209.1076<br>$[(M + H)^+]$ |
| | Mp = 164-166° C. | |
| | HRMS (ESI+): calculated for $C_{14}H_{13}N_2$, m/z = 209.1073; found, 209.1075 | |
| | $^1$H NMR (400 MHz, DMSO-$d_6$): δ (ppm) = 11.49 (s, 1H, $H_{13}$), 8.94 (d, J = 1.7 Hz, 1H, $H_5$), 8.43 (dd, J = 4.7, 1.5 Hz, 1H, $H_2$), 8.09 (dt, J = 8.0, 1.9 Hz, 1H, $H_3$), 7.84 (d, J = 2.7 Hz, 1H, $H_{14}$), 7.70 (d, J = 7.8 Hz, 1H, | |
| (White Solid) | $H_{12}$), 7.44 (ddd, J = 7.9, 4.8, 0.6 Hz, 1H), 7.08-6.96 (m, 2H, $H_{7,8}$), 2.51 (s, 3H, $H_{16}$).<br>$^{13}$C NMR (101 MHz, DMSO-$d_6$): δ (ppm) = 147.81 ($C_5$H-arom.), 146.63 ($C_2$H-arom.), 136.86 ($C_{10}$-arom.), 133.75 ($C_3$H-arom.), 132.32 ($C_4$-arom.), 124.99 ($C_{11}$-arom.), 124.40 ($C_{14}$H-arom.), 124.28 ($C_1$H-arom.), 122.66 ($C_8$H-arom.), 121.74 ($C_9$-arom.), 120.62 ($C_7$H-arom.), 116.87 ($C_{12}$H-arom.), 113.02 ($C_{15}$-arom.), 17.28 ($C_{16}H_3$). | | tert-butyl 7-(benzyloxy)-3-iodo-1H-indole-1-carboxylate

| | | |
|---|---|---|
| Intermediate | LabBook Code<br>CA 3-128 F1-4 (yield = 88%) | |
| | $t_R$ (HPLC) = 5.03 min | MS (ESI+) m/z = 450.0575<br>$[(M + H)^+]$ |
| | $^1$H NMR (400 MHz, DMSO-$d_6$): δ (ppm) = 7.84 (s, 1H, $H_8$), 7.57-7.52 (m, 2H, $H_{14,18}$), 7.40-7.27 (m, 4H, $H_{1,15,16,17}$), 7.11 (d, J = 7.6 Hz, 1H, $H_2$), 6.98 (dd, J = 7.8, 0.8 Hz, 1H, $H_6$), 5.25 (s, 2H, $H_{12}$), 1.50 (s, 9H, $H_{21,22,23}$).<br>$^{13}$C NMR (101 MHz, DMSO-$d_6$): δ (ppm) = 148.11 ($C_{24}$O), 147.18 ($C_3$-arom.), 137.44 ($C_{13}$-arom.), 134.78 ($C_5$-arom.), 132.89 ($C_8$-arom.), 128.67 ($C_{15,17}$H-arom.), 128.16 ($C_{16}$H-arom.), 127.88 ($C_{14,18}$H-arom.), 124.89 ($C_1$H-arom.), 124.45 ($C_4$-arom.), 114.11 ($C_6$H-arom.), 109.43 ($C_2$H-arom.), 84.39 ($C_{20}(CH_3)_3$), 70.58 ($C_{12}H_2$), 65.68 ($C_9$-arom.), 27.68 ($C_{21,22,23}H_3$). | |
| (Pale Orange Oil) | | |

5,8-dibromo-2-(7-methyl-1H-indol-3-yl)quinoline (Procedure 9)

| | | |
|---|---|---|
| VPC Number<br>13 679 | LabBook Code<br>CA 3-137 F24-30 Precipitate (yield = 20%) | $IC_{50}$ (eGFP) = Inactive<br>$IC_{50}$ (PSA) = Inactive |
| | $t_R$ (HPLC) = 5.30 min | MS (ESI+) m/z = 414.9448, 416.9430, 418.9416 $[(M + H)^+]$ |
| | Mp = 218-221° C. | |
| | HRMS (ESI+): calculated for $C_{18}H_{13}Br_2N_2$, m/z = 414.9440, 416.942., 418.9402; found, 414.9448, 416.9430, 418.9415 | |
| | $^1$H NMR (400 MHz, DMSO-$d_6$): δ (ppm) = 11.84 (s, 1H, $H_{13}$), 9.01 (d, J = 7.9 Hz, 1H, $H_{19}$), 8.54 (d, J = 2.9 Hz, 1H, $H_{12}$), 8.38 (d, J = 9.0 Hz, 1H, $H_{10}$), 8.33 (d, J = 9.0 Hz, 1H, $H_9$), 8.04 (d, J = 8.1 Hz, 1H, $H_2$), | |
| (Yellow Solid) | 7.73 (d, J = 8.1 Hz, 1H, $H_1$), 7.16 (t, J = 7.6 Hz, 1H, $H_{18}$), 7.05 (d, J = 7.1 Hz, 1H, $H_{17}$), 2.55 (s, 3H, $H_{20}$).<br>$^{13}$C NMR (101 MHz, DMSO-$d_6$): δ (ppm) = 157.55 ($C_8$-arom.), 145.79 ($C_4$-arom.), 137.28 ($C_{14}$-arom.), 135.21 ($C_{10}$H-arom.), 133.70 ($C_2$H-arom.), 129.80 ($C_{12}$H-arom.), 129.33 ($C_1$H-arom.), 126.24 ($C_5$-arom.), 125.67 ($C_{15}$-arom.), 124.03 ($C_3$-arom.), 123.58 ($C_{17}$H-arom.), 122.06 ($C_9$H-arom.), 121.65 ($C_{18}$H-arom.), 121.42 ($C_{16}$-arom.), 121.18 ($C_6$-arom., $C_{19}$H-arom.), 115.73 ($C_{11}$H-arom.), 17.24 ($C_{20}H_3$). | |

5-bromo-2-(7-methyl-1H-indol-3-yl)quinoline (Procedure 9)

| | | |
|---|---|---|
| VPC Number<br>13 678 | LabBook Code<br>CA 3-139 F15-21 Precipitate (yield = 21%) | $IC_{50}$ (eGFP) = Inactive<br>$IC_{50}$ (PSA) = Inactive |
| 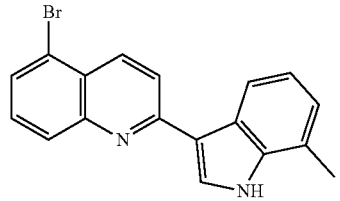 [SMILES: Cc1cccc2c(-c3ccc4c(Br)cccc4n3)c[nH]c12]<br>(Pale Yellow Solid) | $t_R$ (HPLC) = 4.55 min<br>Mp = 200-204° C.<br>HRMS (ESI+): calculated for $C_{18}H_{14}BrN_2$, m/z = 337.0335, 339.0316; found, 337.0345, 339.0331<br>$^1$H NMR (400 MHz, DMSO-$d_6$): δ (ppm) = 11.74 (s, 1H, $H_{13}$), 8.69 (d, J = 8.0 Hz, 1H, $H_{19}$), 8.42 (d, J = 3.0 Hz, 1H, $H_{12}$), 8.36 (dd, J = 9.0, 0.7 Hz, 1H, $H_{10}$), 8.23 (d, J = 9.0 Hz, 1H, $H_9$), 8.06 (dt, J = 8.4, 0.9 Hz, 1H, $H_1$), 7.81 (dd, J = 7.5, 1.0 Hz, 1H, $H_3$), 7.64 (dd, J = 8.4, 7.6 Hz, 1H, $H_2$), 7.13 (t, J = 7.6 Hz, 1H, $H_{18}$), 7.03 (d, J = 7.0 Hz, 1H, $H_{17}$), 2.54 (s, 3H, $H_{20}$).<br>$^{13}$C NMR (101 MHz, DMSO-$d_6$): δ (ppm) = 156.97 ($C_8$-arom.), 149.20 ($C_4$-arom.), 137.24 ($C_{14}$-arom.), 134.47 ($C_{10}$H-arom.), 130.54 ($C_2$H-arom.), 129.10 ($C_1$H-arom.), 129.01 ($C_3$H-arom.), 128.88 ($C_{12}$H-arom.), 125.74 ($C_5$-arom.), 125.10 ($C_{15}$-arom.), 123.32 ($C_{17}$H-arom.), 121.45 ($C_9$H-arom.), 121.43 ($C_{16}$-arom.), 121.37 ($C_6$-arom.), 121.24 ($C_{18}$H-arom.), 120.60 ($C_{19}$H-arom.), 115.71 ($C_{11}$-arom.), 17.25 ($C_{20}H_3$). | | |

MS (ESI+) m/z = 337.0363, 339.0354 [(M + H)$^+$]

3-iodo-7-methyl-1-tosyl-1H-indole

| | | |
|---|---|---|
| Intermediate | LabBook Code<br>CA 3-140 P1-3 (yield = 48%) | |
| 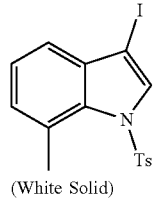<br>(White Solid) | $t_R$ (HPLC) = 5.50 min<br>$^1$H NMR (500 MHz, DMSO-$d_6$): δ (ppm) = 8.07 (s, 1H, $H_8$), 7.68 (d, J = 8.3 Hz, 2H, $H_{13,17}$), 7.41 (d, J = 8.1 Hz, 2H, $H_{14,16}$), 7.29-7.21 (m, 2H, $H_{6,1}$), 7.17 (d, J = 6.7 Hz, 1H, $H_2$), 2.49 (s, 3H, $H_{11}$), 2.35 (s, 3H, $H_{18}$).<br>$^{13}$C NMR (126 MHz, DMSO-$d_6$): δ (ppm) = 145.86 ($C_{15}$-arom.), 135.85 ($C_{12}$-arom.), 134.57 ($C_5$-arom.), 134.23 ($C_4$-arom.), 133.76 ($C_8$H-arom.), 130.85 ($C_{14,16}$H-arom.), 129.76 ($C_2$H-arom.), 126.92 ($C_{13,17}$H-arom.), 125.12 ($C_1$H-arom.), 124.81 ($C_3$-arom.), 120.38 ($C_6$H-arom.), 69.54 ($C_9$-arom.), 21.53 ($C_{18}H_3$), 21.47 ($C_{11}H_3$). | MS (ESI+) m/z = 411.9835 [(M + H)$^+$] |

8-bromo-2-(7-methyl-1H-indol-3-yl)quinoline (Procedure 9)

| | | |
|---|---|---|
| VPC Number<br>13 677 | LabBook Code<br>CA 3-141 F34-54 Precipitate (yield = 20%) | $IC_{50}$ (eGFP) = 0.156<br>$IC_{50}$ (PSA) = 0.11 |
| 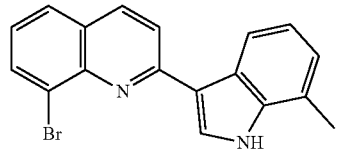 [SMILES: Cc1cccc2c(-c3ccc4cccc(Br)c4n3)c[nH]c12]<br>(Yellow Solid) | $t_R$(HPLC) = 5.03 min<br>Mp = 214-217° C.<br>HRMS (ESI+): calculated for $C_{18}H_{14}BrN_2$, m/z = 337.0335, 339.0316; found, 337.0341, 339.0324<br>$^1$H NMR (400 MHz, DMSO-$d_6$): δ (ppm) = 11.72 (s, 1H, $H_{13}$), 9.04 (d, J = 8.0 Hz, 1H, $H_{19}$), 8.47 (d, J = 3.0 Hz, 1H, $H_{12}$), 8.30 (d, J = 8.8 Hz, 1H, $H_{10}$), 8.20 (d, J = 8.7 Hz, 1H, $H_9$), 8.09 (dd, J = 7.5, 1.3 Hz, 1H, $H_2$), 7.92 (dd, J = 8.1, 1.2 Hz, 1H, $H_6$), 7.39 (t, J = 7.8 Hz, 1H, $H_1$), 7.14 (t, J = 7.4 Hz, 1H, $H_{18}$), 7.03 (d, J = 7.0 Hz, 1H, $H_{17}$), 2.54 (s, 3H, $H_{20}$).<br>$^{13}$C NMR (101 MHz, DMSO-$d_6$): δ (ppm) = 156.88 ($C_8$-arom.), 144.96 ($C_4$-arom.), 137.23 ($C_{14}$-arom.), 136.61 ($C_{10}$H-arom.), 133.25 ($C_2$H-arom.), 128.92 ($C_{12}$H-arom.), 128.20 ($C_6$H-arom.), 127.68 ($C_5$-arom.), 125.91 ($C_1$H-arom.), 125.77 ($C_{15}$-arom.), 123.97 ($C_3$-arom.), 123.36 ($C_{17}$H-arom.), 121.38 ($C_{18}$H-arom.), 121.33 ($C_{19}$H-arom.), 121.23 ($C_{16}$-arom.), 120.45 ($C_9$H-arom.), 116.31 ($C_{11}$-arom.), 17.25 ($C_{20}H_3$). | MS (ESI+) m/z = 337.0361, 339.0345 [(M + H)$^+$] |

3-(naphthalen-2-yl)-1H-pyrrolo[2,3-c]pyridine (Procedure 10)

| | | |
|---|---|---|
| VPC Number 13 675 | LabBook Code CA 3-144 Precipitate (yield = 83%) | IC$_{50}$ (eGFP) = 0.45 IC$_{50}$ (PSA) = 0.468 |

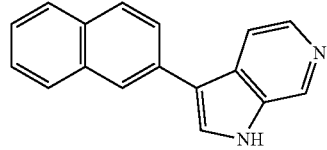 [SMILES: c1ccc2cc(-c3c[nH]c4cnccc34)ccc2c1]

(Pale Yellow Solid)

$t_R$ (HPLC) = 3.26 min

MS (ESI+) m/z = 245.1334 [(M + H)$^+$]

Mp = 243-247° C.

HRMS (ESI+): calculated for C$_{17}$H$_{13}$N$_2$, m/z = 245.1073; found, 245.1079
$^1$H NMR (400 MHz, DMSO-d$_6$): δ (ppm) = 11.99 (s, 1H, H$_{13}$), 8.86 (s, 1H, H$_9$), 8.27 (s, 1H, H$_3$), 8.25 (d, J = 5.2 Hz, 1H, H$_7$), 8.17 (s, 1H, H$_{14}$), 8.05 (dd, J = 5.6, 1.0 Hz, 1H, H$_{12}$), 8.02 (d, J = 8.1 Hz, 1H, H$_{19}$), 8.00-7.90 (m, 3H, H$_{5,6,16}$), 7.53 (ddd, J = 8.1, 6.8, 1.4 Hz, 1H, H$_{18}$), 7.47 (ddd, J = 8.0, 6.9, 1.3 Hz, 1H, H$_{17}$).
$^{13}$C NMR (101 MHz, DMSO-d$_6$): δ (ppm) = 139.14 (C$_7$H-arom.), 135.56 (C$_9$H-arom.), 134.64 (C$_{10}$-arom.), 134.14 (C$_1$-arom.), 132.82 (C$_4$-arom.), 131.87 (C$_2$-arom.), 129.56 (C$_{11}$-arom.), 128.76 (C$_6$H-arom.), 128.43 (C$_{14}$H-arom.), 128.18 (C$_{19}$H-arom.), 127.96 (C$_{16}$H-arom.), 126.72 (C$_{18}$H-arom.), 126.01 (C$_{17}$H-arom.), 125.73 (C$_5$H-arom.), 124.12 (C$_3$H-arom.), 115.47 (C$_{15}$-arom.), 114.55 (C$_{12}$H-arom.).

3-(naphthalen-2-yl)-1H-pyrrolo[2,3-b]pyridine (Procedure 10)

| | | |
|---|---|---|
| VPC Number 13 676 | LabBook Code CA 3-146 Precipitate (yield = 61%) | IC$_{50}$ (eGFP) = 0.053 IC$_{50}$ (PSA) = 0.034 |

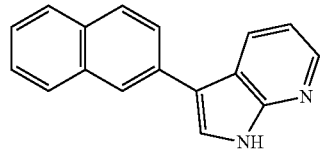 [SMILES: c1ccc2cc(-c3c[nH]c4ncccc34)ccc2c1]

(Yellow Solid)

$t_R$ (HPLC) = 4.50 min

MS (ESI+) m/z = 245.1077 [(M + H)$^+$]

Mp = 207-211° C.

HRMS (ESI+): calculated for C$_{17}$H$_{13}$N$_2$, m/z = 245.1073; found, 245.1077
$^1$H NMR (400 MHz, DMSO-d$_6$): δ (ppm) = 12.01 (s, 1H, H$_{13}$), 8.50 (dd, J = 8.0, 1.1 Hz, 1H, H$_{12}$), 8.32 (dd, J = 4.6, 1.5 Hz, 1H, H$_8$), 8.27 (s, 1H, H$_3$), 8.06 (d, J = 2.7 Hz, 1H, H$_{14}$), 8.00 (d, J = 8.0 Hz, 1H, H$_{19}$), 7.97-7.92 (m, 2H, H$_{5,6}$), 7.91 (d, J = 8.0 Hz, 1H, H$_{16}$), 7.52 (ddd, J = 8.2, 6.9, 1.4 Hz, 1H, H$_{18}$), 7.47 (ddd, J = 8.0, 6.9, 1.3 Hz, 1H, H$_{17}$), 7.22 (dd, J = 8.0, 4.6 Hz, 1H, H$_7$).
$^{13}$C NMR (101 MHz, DMSO-d$_6$): δ (ppm) = 149.69 (C$_{10}$-arom.), 143.50 (C$_8$H-arom.), 134.16 (C$_1$-arom.), 133.12 (C$_4$-arom.), 131.85 (C$_2$-arom.), 128.70 (C$_6$H-arom.), 128.31 (C$_{12}$H-arom.), 128.17 (C$_{19}$H-arom.), 127.94 (C$_{16}$H-arom.), 126.68 (C$_{18}$H-arom.), 125.89 (C$_{17}$H-arom.), 125.66 (C$_5$H-arom.), 124.90 (C$_{14}$H-arom.), 123.88 (C$_3$H-arom.), 117.81 (C$_{11}$-arom.), 116.62 (C$_7$H-arom.), 114.55 (C$_{15}$-arom.).

2-(5-bromo-1H-indol-3-yl)quinoline

| | | |
|---|---|---|
| VPC Number 13 683 | LabBook Code CA 3-147 F36-46 Precipitate (yield = 39%) | IC$_{50}$ (eGFP) = 2.6 IC$_{50}$ (PSA) = 1.906 |

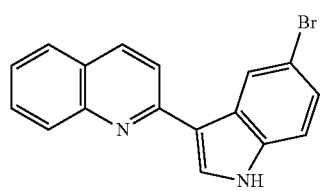 [SMILES: Brc1ccc2[nH]cc(-c3ccc4ccccc4n3)c2c1]

(Yellow Solid)

$t_R$ (HPLC) = 3.60 min

MS (ESI+) m/z = 323.0169, 325.0153 [(M + H)$^+$]

Mp = 200-203° C.

HRMS (ESI+): calculated for C$_{17}$H$_{12}$BrN$_2$, m/z = 323.0178, 325.0159; found, 323.0184, 325.0169
$^1$H NMR (400 MHz, DMSO-d$_6$): δ (ppm) = 11.86 (s, 1H, H$_{13}$), 9.06 (d, J = 2.0 Hz, 1H, H$_{19}$), 8.42 (d, J = 2.8 Hz, 1H, H$_{12}$), 8.27 (d, J = 8.5 Hz, 1H, H$_{10}$), 8.05 (d, J = 8.8 Hz, 1H, H$_9$), 8.02 (d, J = 9.0 Hz, 1H, H$_3$), 7.89 (dd, J = 8.1, 1.2 Hz, 1H, H$_6$), 7.72 (ddd, J = 8.4, 6.9, 1.5 Hz, 1H, H$_6$), 7.50 (ddd, J = 8.0, 6.9, 1.2 Hz, 1H, H$_1$), 7.45 (dd, J = 8.4, 0.4 Hz, 1H, H$_{17}$), 7.34 (dd, J = 8.6, 2.0 Hz, 1H, H$_{17}$).
$^{13}$C NMR (101 MHz, DMSO-d$_6$): δ (ppm) = 155.03 (C$_8$-arom.), 147.62 (C$_4$-arom.), 135.92 (C$_{10}$H-arom.), 135.83 (C$_{14}$-arom.), 129.50 (C$_2$H-arom.), 129.15 (C$_{12}$H-arom.), 128.36 (C$_3$H-arom.), 127.67 (C$_6$H-arom.), 127.30 (C$_{15}$-arom.), 125.88 (C$_5$-arom.), 125.12 (C$_1$H-arom.), 124.71 (C$_{19}$H-arom.), 124.62 (C$_{17}$H-arom.), 119.07 (C$_9$H-arom.), 115.02 (C$_{11}$-arom.), 113.79 (C$_{18}$-arom.), 113.07 (C$_{16}$H-arom.).

3-(1H-indazol-3-yl)quinoline (Procedure 10)

| | | |
|---|---|---|
| VPC Number<br>13 684 | LabBook Code<br>CA 4-13 F3-5 (yield = 46%) | IC$_{50}$ (eGFP) = 1.4<br>IC$_{50}$ (PSA) = 6.609 |
| | t$_R$ (HPLC) = 3.59 min | MS (ESI+) m/z = 246.1322<br>[(M + H)$^+$] |
| (White Solid) | Mp = 212-215° C.<br>HRMS (ESI+): calculated for C$_{16}$H$_{12}$N$_3$, m/z = 246.1026; found, 246.1027<br>$^1$H NMR (400 MHz, DMSO-d$_6$): δ (ppm) = 13.53 (s, 1H, H$_{13}$), 9.60 (d, J = 2.2 Hz, 1H, H$_5$), 8.98 (d, J = 2.0 Hz, 1H, H$_3$), 8.33 (d, J = 8.2 Hz, 1H, H$_{12}$), 8.21 (d, J = 7.9 Hz, 1H, H$_{19}$), 8.09 (d, J = 8.3 Hz, 1H, H$_{16}$), 7.8.79 (ddd, J = 8.4, 7.2, 1.2 Hz, 1H, H$_{17}$), 7.71-7.66 (m, 2H, H$_{9,18}$), 7.48 (t, J = 7.4 Hz, 1H, H$_8$), 7.31 (t, J = 7.5 Hz, 1H, H$_7$).<br>$^{13}$C NMR (101 MHz, DMSO-d$_6$): δ (ppm) = 149.67 (C$_5$H-arom.), 147.27 (C$_2$-arom.), 142.03 (s C$_{10}$-arom.), 141.01 (C$_1$-arom.), 132.67 (C$_3$H-arom.), 129.94 (C$_{17}$H-arom.), 129.20 (C$_{16}$H-arom.), 129.01 (C$_{19}$H-arom.), 128.24 (C$_4$-arom.), 127.52 (C$_{18}$H-arom.), 127.29 (C$_{15}$-arom.), 126.96 (C$_8$H-arom.), 121.96 (C$_7$H-arom.), 121.23 (C$_{12}$H-arom.), 120.81 (C$_{11}$-arom.), 111.26 (C$_9$H-arom.). |

3-(naphthalen-2-yl)-1H-pyrrolo[3,2-c]pyridine (Procedure 10)

| | | |
|---|---|---|
| VPC Number<br>13 685 | LabBook Code<br>CA 4-15 Precipitate2 (yield = 71%) | IC$_{50}$ (eGFP) = Inactive<br>IC$_{50}$ (PSA) = Inactive |
| | t$_R$ (HPLC) = 3.17 min | MS (ESI+) m/z = 245.1082<br>[(M + H)$^+$] |
| (Pale Orange Solid) | Mp = <270° C.<br>HRMS (ESI+): calculated for C$_{17}$H$_{13}$N$_2$, m/z = 245.1073; found, 245.1073<br>$^1$H NMR (400 MHz, DMSO-d$_6$): δ (ppm) = 11.85 (s, 1H, H$_{13}$), 9.39 (s, 1H, H$_{12}$), 8.33 (s, 1H, H$_3$), 8.28 (d, J = 5.6 Hz, 1H, H$_8$), 8.05 (d, J = 8.0 Hz, 1H, H$_{19}$), 8.02-7.94 (m, 3H, H$_{4,6,14}$), 7.92 (d, J = 8.0 Hz, 1H, H$_{16}$), 7.53 (ddd, J = 8.0, 7.2, 1.6 Hz, 1H, H$_{18}$), 7.51-7.45 (m, 2H, H$_{9,17}$).<br>$^{13}$C NMR (101 MHz, DMSO-d$_6$): δ (ppm) = 142.94 (C$_{12}$H-arom.), 141.01 (C$_8$H-arom.), 140.93 (C$_{10}$-arom.), 134.16 (C$_1$-arom.), 132.62 (C$_4$-arom.), 131.97 (C$_2$-arom.), 128.76 (C$_6$H-arom.), 128.30 (C$_{19}$H-arom.), 127.92 (C$_{16}$H-arom.), 126.71 (C$_{18}$H-arom.), 126.21 (C$_{17}$H-arom.), 125.79 (C$_5$H-arom.), 125.55 (C$_{14}$H-arom.), 124.55 (C$_3$H-arom.), 115.92 (C$_{15}$-arom.), 107.71 (C$_9$H-arom.). |

2-phenyl-1H-benzo[d]imidazole

| | | |
|---|---|---|
| VPC Number<br>13 686 | LabBook Code<br>CA 4-16 F3-14 Precipitate (yield = 22%) | IC$_{50}$ (eGFP) = Inactive<br>IC$_{50}$ (PSA) = Inactive |
| | t$_R$ (HPLC) = 2.39 min | MS (ESI+) m/z = 195.1040<br>[(M + H)$^+$] |
| (Pink Solid) | Mp = <270° C.<br>HRMS (ESI+): calculated for C$_{13}$H$_{11}$N$_2$, m/z = 195.0917; found, 195.0919<br>$^1$H NMR (400 MHz, DMOS-d$_6$): δ (ppm) = 12.91 (s, 1H, H$_{13}$), 8.22-8.17 (m, 2H, H$_{3,5}$), 7.67 (br s, 1H, H$_9$), 7.59-7.47 (m, 4H, H$_{1,2,6,12}$), 7.22-7.19 (m, 2H, H$_{7,8}$).<br>$^{13}$C NMR (151 MHz, DMSO-d$_6$): δ (ppm) = 151.19 (C$_{14}$-arom.), 143.79 (C$_{10}$-arom.), 134.98 (C$_{11}$-arom.), 130.15 (C$_4$-arom.), 129.81 (C$_2$H-arom.), 128.92 (C$_{1,6}$H-arom.), 126.40 (C$_{3,5}$H-arom.), 122.50 (C$_7$H-arom.), 121.64 (C$_8$H-arom.), 118.85 (C$_9$H-arom.), 111.30 (C$_{12}$H-arom.). |

2-naphthalen-3-ol-1H-benzo[d]imidazole

| VPC Number | LabBook Code | IC$_{50}$ (eGFP) = Inactive |
|---|---|---|
| 13 687 | CA 4-17 Precipitate2 (yield = 14%) | IC$_{50}$ (PSA) = Inactive |

$t_R$ (HPLC) = 3.32 min  MS (ESI+) m/z = 261.1080 [(M + H)$^+$]

Mp = <270° C.

HRMS (ESI+): calculated for C$_{17}$H$_{13}$N$_2$O, m/z = 261.1022; found, 261.1022

$^1$H NMR (400 MHz, DMSO-d$_6$): δ (ppm) = 13.46 (s, 1H, H$_{20}$), 13.01 (s, 1H, H$_{13}$), 8.72 (s, 1H, H$_3$), 7.90 (d, J = 8.2 Hz, 1H, H$_{19}$), 7.79 (d, J = 8.4 Hz, 1H, H$_{16}$), 7.74 (br s, 2H, , H$_{9,12}$), 7.51 (t, J = 7.5 Hz, 1H, H$_{17}$), 7.43 (s, 1H, H$_6$), 7.39 (t, J = 7.5 Hz, 1H, H$_{18}$), 7.34 (br s, 2H, H$_{7,8}$).

$^{13}$C NMR (101 MHz, DMSO-d$_6$): δ (ppm) = 154.60 (C$_5$-arom.), 151.15 (C$_{14}$-arom.), 141.03 (C$_{10}$-arom.), 135.16 (C$_2$-arom.), 133.41 (C$_{11}$-arom.), 128.13 (C$_{19}$H-arom.), 127.65 (C$_{17}$H-arom.), 126.99 (C$_1$-arom.), 126.80 (C$_3$H-arom.), 126.05 (C$_{16}$H-arom.), 123.77 (C$_{18}$H-arom.), 123.60 (C$_7$H-arom.), 122.57 (C$_8$H-arom.), 118.21 (C$_9$H-arom.), 115.21 (C$_4$-arom.), 111.72 (C$_{12}$H-arom.), 110.80 (C$_6$H-arom.).

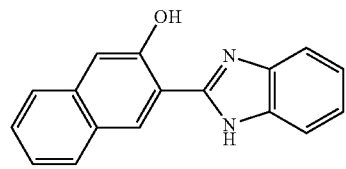

(Dark Green Solid)

tert-butyl 3-iodo-7-nitro-1H-indole-1-carboxylate

| Intermediate | LabBook Code |
|---|---|
| | CA 4-18 F4-18 (yield = 90%) |

$t_R$ (HPLC) = 5.24 min   MS (ESI+) m/z = 410.9828 [(M + Na)$^+$]

$^1$H NMR (400 MHz, DMSO-d$_6$): δ (ppm) = 8.10 (s, 1H, H$_8$), 7.99 (dd, J = 7.9, 0.7 Hz, 1H, H$_2$), 7.78 (dd, J = 7.9, 1.0 Hz, 1H, H$_6$), 7.56 (t, J = 7.9 Hz, 1H, H$_1$), 1.56 (s, 9H, H$_{13,14,15}$).

$^{13}$C NMR (101 MHz, DMSO-d$_6$): δ (ppm) = 147.76 (C$_{16}$O), 138.62 (C$_3$-arom.), 135.66 (C$_5$-arom.), 134.29 (C$_8$H-arom.), 127.30 (C$_6$H-arom.), 124.77 (C$_4$-arom.), 124.25 (C$_1$H-arom.), 121.63 (C$_2$H-arom.), 86.64 (C$_{12}$(CH$_3$)$_3$), 66.56 (C$_9$-arom.), 27.76 (C$_{13,14,15}$H$_3$).

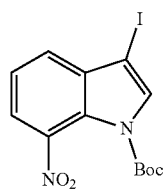

(Yellow Solid)

3-((2H-tetrazol-5-yl)methyl)-1H-indole

| VPC Number | LabBook Code | IC$_{50}$ (eGFP) = Inactive |
|---|---|---|
| 13 700 | CA 4-21 F3-4 (yield = 66%) | IC$_{50}$ (PSA) = Inactive |

$t_R$ (HPLC) = 2.80 min  MS (ESI+) m/z = 200.0936 [(M + H)$^+$]

Mp = 174-181° C.

HRMS (ESI+): calculated for C$_{10}$H$_{10}$N$_5$, m/z = 200.0931; found, 200.0929

$^1$H NMR (400 MHz, DMSO-d$_6$): δ (ppm) = 11.03 (s, 1H, H$_9$), 7.43 (d, J = 8.0 Hz, 1H, H$_6$), 7.38 (d, J = 8.1 Hz, 1H, H$_3$), 7.27 (d, J = 2.4 Hz, 1H, H$_8$), 7.09 (ddd, J = 8.0, 7.2, 1.2 Hz, 1H, H$_5$), 6.98 (ddd, J = 7.9, 7.1, 1.0 Hz, 1H, H$_4$), 4.38 (d, J = 0.6 Hz, 2H, H$_{10}$).

$^{13}$C NMR (101 MHz, DMSO-d$_6$): δ (ppm) = 156.20 (C$_{11}$-arom.), 136.70 (C$_2$-arom.), 126.98 (C$_8$H-arom.), 124.34 (C$_1$-arom.), 121.75 (C$_4$H-arom.), 119.11 (C$_5$H-arom.), 118.57 (C$_6$H-arom.), 112.02 (C$_3$H-arom.), 108.78 (C$_7$-arom.), 19.99 (C$_{10}$H$_2$).

(Pale Yellow Solid)

3-(2H-tetrazol-5-yl)-1H-indole

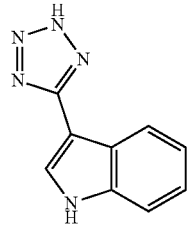

(Brown Solid)

| VPC Number | LabBook Code | IC$_{50}$ (eGFP) = Inactive |
|---|---|---|
| 13 701 | CA 4-22 F9-16 (yield = 33%) | IC$_{50}$ (PSA) = Inactive |

$t_R$ (HPLC) = 2.86 min  MS (ESI+) m/z = 186.2227 [(M + H)$^+$]

Mp = 220-224° C.

HRMS (ESI+): calculated for C$_9$H$_8$N$_5$, m/z = 186.0774; found, 186.0776
$^1$H NMR (400 MHz, DMSO-d$_6$): δ (ppm) = 11.88 (s, 1H, H$_9$), 8.25-8.22 (m, 1H, H$_6$), 8.11 (d, J = 2.9 Hz, 1H, H$_{11}$), 7.57-7.53 (m, 1H, H$_3$), 7.28-7.20 (m, 2H, H$_{4,5}$).
$^{13}$C NMR (101 MHz, DMSO-d$_6$): δ (ppm) = 151.72 (C$_{10}$-arom.), 136.86 (C$_2$H-arom.), 127.53 (C$_8$H-arom.), 124.91 (C$_1$-arom.), 123.08 (C$_4$H-arom.), 121.27 (C$_5$H-arom.), 120.77 (C$_6$H-arom.), 112.73 (C$_3$H-arom.), 99.91 (C$_7$-arom.).

tert-butyl 3-iodo-7-methyl-1H-indole-1-carboxylate

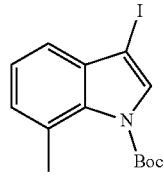

(Brown Solid)

| Intermediate | LabBook Code |
|---|---|
|  | CA 4-23 P1-3 (yield = 81%) |

$t_R$ (HPLC) = 5.78 min  MS (ESI+) m/z =
$^1$H NMR (400 MHz, DMSO-d$_6$): δ (ppm) = 7.88 (s, 1H, H$_8$), 7.30-7.19 (m, 3H, H$_{1,2,6}$), 2.54 (s, 3H, H$_{11}$), 1.61 (s, 9H, H$_{14,15,16}$).
$^{13}$C NMR (101 MHz, DMSO-d$_6$): δ (ppm) = 148.55 (C$_{17}$O), 134.13 (C$_4$-arom.), 133.33 (C$_5$-arom.), 132.74 (C$_8$H-arom.), 128.83 (C$_2$H-arom.), 125.22 (C$_3$-arom.), 124.29 (C$_1$H-arom.), 119.45 (C$_6$H-arom.), 84.70 (C$_{13}$(CH$_3$)$_3$), 66.84 (C$_9$-arom.), 27.90 (C$_{14,15,16}$H$_3$), 21.68 (C$_{11}$H$_3$).

tert-butyl 3-iodo-1H-pyrrolo[3,2-b]pyridine-1-carboxylate

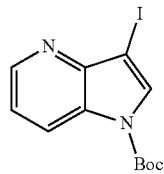

(White Solid)

| Intermediate | LabBook Code |
|---|---|
|  | CA 4-24 F1-6 (yield = 77%) |

$t_R$ (HPLC) = 4.59 min  MS (ESI+) m/z = 345.0111 [(M + H)$^+$]
$^1$H NMR (400 MHz, DMSO-d$_6$): δ (ppm) = 8.56 (dd, J = 4.7, 1.4 Hz, 1H, H$_1$), 8.32 (dd, J = 8.3, 1.3 Hz, 1H, H$_3$), 8.19 (s, 1H, H$_8$), 7.43 (dd, J = 8.3, 4.7 Hz, 1H, H$_2$), 1.64 (s, 9H, H$_{13,14,15}$).
$^{13}$C NMR (101 MHz, DMSO-d$_6$): δ (ppm) = 148.26 (C$_{16}$O), 147.90 (C$_4$-arom.), 146.39 (C$_1$H-arom.), 133.51 (C$_8$H-arom.), 128.04 (C$_5$-arom.), 122.61 (C$_3$H-arom.), 120.60 (C$_2$H-arom.), 85.59 (C$_{12}$(CH$_3$)$_3$), 69.42 (C$_9$-arom.), 28.05 (C$_{13,14,15}$H$_3$).

3-(naphthalen-2-yl)-7-nitro-1H-indole (Procedure 10)

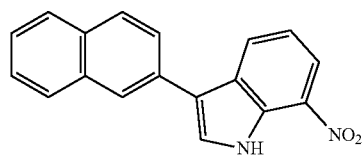

(Red Solid)

| VPC Number | LabBook Code | IC$_{50}$ (eGFP) = 0.2 |
|---|---|---|
| 13 702 | CA 4-27 F20-51 Precipitate3 (yield = 56%) | IC$_{50}$ (PSA) = 0.14 |

$t_R$ (HPLC) = 4.40 min  MS (ESI+) m/z = 289.0915 [(M + H)$^+$]

Mp = 166-171° C.

HRMS (ESI+): calculated for C$_{18}$H$_{13}$N$_2$O$_2$, m/z = 289.0972; found, 289.0975
$^1$H NMR (400 MHz, CDCl$_3$): δ (ppm) = 10.13 (s, 1H, H$_{13}$), 8.38 (d, J = 7.8 Hz, 1H, H$_{12}$), 8.28 (d, J = 8.1 Hz, 1H, H$_8$), 8.11 (s, 1H, H$_3$), 7.99 (d, J = 8.4 Hz, 1H, H$_6$), 7.95-7.90 (m, 2H, H$_{16,19}$), 7.78 (dd, J = 8.5, 1.8 Hz, 1H, H$_5$), 7.67 (d, J = 2.4 Hz, 1H, H$_{14}$), 7.59-7.50 (m, 2H, H$_{17,18}$), 7.35 (t, J = 8.0 Hz, 1H, H$_7$).

$^{13}$C NMR (101 MHz, CDCl$_3$): δ (ppm) = 133.82 (C$_4$-arom.), 133.21 (C$_9$-arom.), 132.41 (C$_2$-arom.), 131.32 (C$_1$-arom.), 130.08 (C$_{10}$-arom.), 129.92 (C$_{11}$-arom.), 128.67 (C$_6$H-arom.), 128.16 (C$_{12}$H-arom.), 127.83 (C$_{19}$H-arom.), 127.78 (C$_{19}$H-arom.), 126.48 (C$_5$H-arom.), 126.42 (C$_{18}$H-arom.), 126.14 (C$_3$H-arom.), 125.86 (C$_{17}$H-arom.), 124.23 (C$_{14}$H-arom.), 119.88 (C$_{15}$-arom.), 119.81 (C$_7$H-arom.), 119.77 (C$_8$H-arom.).

3-(naphthalen-2-yl)-1H-pyrrolo[3,2-b]pyridine (Procedure 10)

| VPC Number | LabBook Code | IC$_{50}$ (eGFP) = 0.1 |
|---|---|---|
| 13 703 | CA 4-28 Precipitate (yield = 84%) | IC$_{50}$ (PSA) = 0.097 | t$_R$ (HPLC) = 4.28 min  
MS (ESI+) m/z = 245.1068 [(M + H)$^+$]

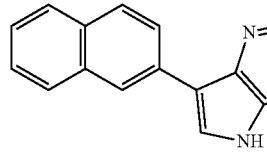

(Beige Solid)

Mp = 221-224° C.
HRMS (ESI+): calculated for C$_{17}$H$_{13}$N$_2$, m/z = 245.1073; found, 245.1068
$^1$H NMR (400 MHz, DMSO-d$_6$): δ (ppm) = 11.66 (s, 1H, H$_{14}$), 8.97 (d, J = 0.8 Hz, 1H, H$_3$), 8.53 (dd, J = 4.6, 1.5 Hz, 1H, H$_7$), 8.35 (dd, J = 8.6, 1.7 Hz, 1H, H$_5$), 8.33 (d, J = 2.9 Hz, 1H, H$_{14}$), 7.95-7.90 (m, 2H, H$_{6,19}$), 7.89-7.84 (m, 2H, H$_{9,16}$), 7.50 (ddd, J = 8.2, 6.9, 1.4 Hz, 1H, H$_{18}$), 7.44 (ddd, J = 8.0, 6.9, 1.3 Hz, 1H, H$_{17}$), 7.22 (dd, J = 8.2, 4.6 Hz, 1H, H$_8$).

$^{13}$C NMR (101 MHz, DMSO-d$_6$): δ (ppm) = 144.11 (C$_{11}$-arom.), 143.30 (C$_7$H-arom.), 134.01 (C$_1$-arom.), 132.82 (C$_4$-arom.), 131.77 (C$_2$-arom.), 130.16 (C$_{10}$-arom.), 128.07 (C$_{6,16}$H-arom.), 128.06 (C$_{19}$H-arom.), 127.67 (C$_{14}$H-arom.), 126.53 (C$_{18}$H-arom.), 125.51 (C$_5$H-arom.), 125.34 (C$_{17}$H-arom.), 123.77 (C$_3$H-arom.), 119.47 (C$_9$H-arom.), 117.21 (C$_8$H-arom.), 114.52 (C$_{15}$-arom.).

7-bromo-3-(naphthalen-2-yl)-1H-indole (Procedure 10)

LabBook Code
CA 4-29 P2 F3-7 (yield = 12%)

t$_R$ (HPLC) = 5.13 min  
MS (ESI+) m/z = 323.0095, 325.0076 [(M + H)$^+$]

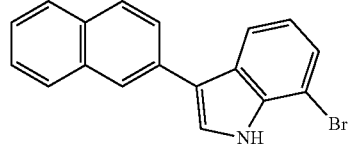

(White Solid)

$^1$H NMR (400 MHz, DMSO-d$_6$): δ (ppm) = 11.70 (s, 1H, H$_{13}$), 8.24 (s, 1H, H$_3$), 8.07 (d, J = 8.0 Hz, 1H, H$_{12}$), 8.00 (d, J = 8.3 Hz, 1H, H$_{19}$), 7.98 (d, J = 8.6 Hz, 1H, H$_6$), 7.94-7.89 (m, 3H, H$_{5,14,16}$), 7.53 (ddd, J = 8.1, 6.7, 1.4 Hz, 1H, H$_{18}$), 7.48 (ddd, J = 8.1, 6.8, 1.3 Hz, 1H, H$_{17}$), 7.44 (d, J = 7.4 Hz, 1H, H$_8$), 7.12 (t, J = 7.8 Hz, 1H, H$_7$).
$^{13}$C NMR → n.d.

3-(naphthalen-2-yl)-1H-indol-7-amine

LabBook Code
CA 4-34 F6-10 (yield = 28%)

t$_R$ (HPLC) = 4.04 min  
MS (ESI+) m/z = 259.1295 [(M + H)$^+$]

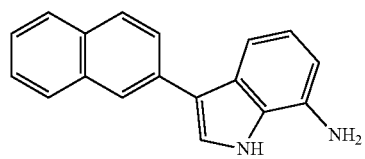

(Dark Oil)

$^1$H NMR (400 MHz, CDCl$_3$) δ (ppm) = 8.22 (s, 1H, H$_{13}$), 8.18 (s, 1H, H$_7$), 7.96-7.88 (m, 3H, H$_{3,6,10}$), 7.85 (dd, J = 8.5, 1.7 Hz, 1H, H$_9$), 7.62 (d, J = 7.9 Hz, 1H, H$_{19}$), 7.57-7.49 (m, 2H, H$_{1,2}$), 7.36 (s, 1H, H$_{12}$), 7.21 (t, J = 7.8 Hz, 1H, H$_{18}$), 6.69 (d, J = 7.5 Hz, 1H, H$_{17}$).
$^{13}$C NMR → n.d.

tert-butyl 7-methyl-3-((trimethylsilyl)ethynyl)-1H-indole-1-carboxylate

| Intermediate | LabBook Code | |
|---|---|---|
| 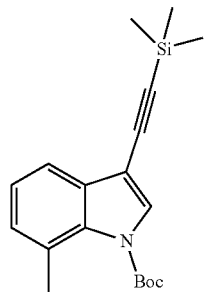<br>(Yellow Solid) | CA 4-35 F5-7 (yield = Quant %)<br><br>$t_R$ (HPLC) = 5.48 min    MS (ESI+) m/z =<br>$^1$H NMR (400 MHz, CDCl$_3$): δ (ppm) = 7.77 (s, 1H, H$_8$), 7.54 (d, J = 7.6 Hz, 1H, H$_6$), 7.25 (t, J = 7.5 Hz, 1H, H$_1$), 7.18 (d, J = 7.3 Hz, 1H, H$_2$), 2.67 (s, 3H), 1.66 (s, 9H), 0.33 (s, 9H).<br>$^{13}$C NMR (101 MHz, CDCl$_3$): δ (ppm) = 148.78 (C$_{22}$O), 134.06 (C$_4$-arom.), 131.84 (C$_5$-arom.), 131.67 (C$_8$H-arom.), 128.58 (C$_2$H-arom.), 125.44 (C$_3$-arom.), 123.61 (C$_1$H-arom.), 117.80 (C$_6$H-arom.), 103.32 (C$_9$-arom.), 97.93 (C$_{12}$≡), 96.91 (C$_{10}$≡), 83.94 (C$_{18}$(CH$_3$)$_3$), 28.01 (C$_{19,20,21}$H$_3$), 22.09 (C$_{11}$H$_3$), 0.14 (C$_{14,15,16}$H$_3$). | |

3-([1,1'-biphenyl]-4-yl)-7-methyl-1H-indole (Procedure 10)

| VPC Number | LabBook Code | IC$_{50}$ (eGFP) = 3.815 |
|---|---|---|
| 13 733 | CA 4-38 Precipitate (yield = 25 %) | IC$_{50}$ (PSA) = 0.919 |
| 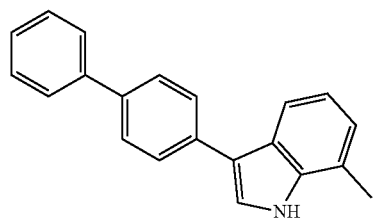<br>(White Solid) | $t_R$ (HPLC) = 4.50 min<br>Mp = 199-202° C.<br>HRMS (ESI-): calculated for C$_{21}$H$_{16}$N, m/z = 282.1288; found, 282.1286<br>$^1$H NMR (400 MHz, DMSO-d$_6$): δ (ppm) = 11.38 (s, 1H, H$_{13}$), 7.84-7.79 (m, 2H, H$_{3,5}$), 7.78-7.70 (m, 6H, H$_{1,6,12,14,18,22}$), 7.52-7.46 (m, 2H, H$_{19,21}$), 7.40-7.34 (m, 1H, H$_{20}$), 7.04 (t, J = 7.2 Hz, 1H, H$_7$), 6.98 (d, J = 7.0 Hz, 1H, H$_8$), 2.52 (s, 3H, H$_{17}$).<br>$^{13}$C NMR (101 MHz, DMSO-d$_6$): δ (ppm) = 140.51 (C$_{16}$-arom.), 137.29 (C$_2$-arom.), 136.90 (C$_{10}$-arom.), 135.75 (C$_4$-arom.), 129.40 (C$_{19,21}$H-arom.), 127.57 (C$_{20}$H-arom.), 127.43 (C$_{1,6}$H-arom.), 127.33 (C$_{3,5}$H-arom.), 126.79 (C$_{18,22}$H-arom.), 125.14 (C$_{11}$-arom.), 123.85 (C$_{14}$H-arom.), 122.44 (C$_8$H- | MS (ESI-) m/z = 282.1207 [(M + H)$^-$] | arom.), 121.62 (C$_9$-arom.), 120.37 (C$_7$H-arom.), 117.16 (C$_{12}$H-arom.), 116.06 (C$_{15}$-arom.), 17.31 (C$_{17}$H$_3$).

3-([1,1'-biphenyl]-4-yl)-1H-pyrrolo[2,3-b]pyridine (Procedure 10)

| VPC Number | LabBook Code | IC$_{50}$ (eGFP) = 4.08 |
|---|---|---|
| 13 715 | CA 4-39 Precipitate3 (yield = 51%) | IC$_{50}$ (PSA) = 0.35 |
| 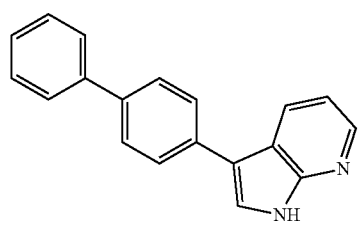 [SMILES: c1ccc(-c2ccc(-c3c[nH]c4cccnc34)cc2)cc1]<br>(Beige Solid) | $t_R$ (HPLC) = 4.23 min<br>Mp = <270° C.<br>HRMS (ESI+): calculated for C$_{19}$H$_{15}$N$_2$, m/z = 271.1230; found, 271.1232<br>$^1$H NMR (500 MHz, DMSO-d$_6$): δ (ppm) = 11.97 (s, 1H, H$_{13}$), 8.35 (d, J = 7.9 Hz, 1H, H$_{12}$), 8.30 (dd, J = 4.6, 1.4 Hz, 1H, H$_8$), 7.96 (d, J = 2.6 Hz, 1H, H$_{14}$), 7.84 (d, J = 8.3 Hz, 2H, H$_{3,5}$), 7.79-7.71 (m, 4H, H$_{1,6,17,21}$), 7.49 (t, J = 7.7 Hz, 2H, H$_{20,18}$), 7.38 (t, J = 7.4 Hz, 1H, H$_{19}$), 7.19 (dd, J = 7.9, 4.6 Hz, 1H, H$_7$).<br>$^{13}$C NMR (126 MHz, DMSO-d$_6$): δ (ppm) = 149.60 (C$_{10}$-arom.), 143.42 (C$_8$-arom.), 140.39 (C$_{16}$-arom.), 137.73 (C$_2$-arom.), 134.78 (C$_4$-arom.), 129.43 (C$_{18,20}$H-arom.), 128.02 (C$_{12}$H-arom.), 127.68 (C$_{19}$H-arom.), 127.55 (C$_{1,6}$H- | MS (ESI-) m/z = 271.1232 [(M + H)$^+$] | arom.), 127.11 (C$_{3,5}$H-arom.), 126.84 (C$_{17,21}$H-arom.), 124.41 (C$_{14}$H-arom.), 117.74 (C$_{11}$H-arom.), 116.57 (C$_7$H-arom.), 114.24 (C$_{15}$-arom.).

3-(4-bromophenyl)-1H-pyrrolo[2,3-b]pyridine (Procedure 10)

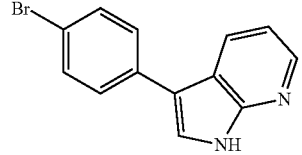

(Beige Solid)

| VPC Number | LabBook Code | IC$_{50}$ (eGFP) = 0.067 |
|---|---|---|
| 13 716 | CA 4-40 Precipitate (yield = 37%) | IC$_{50}$ (PSA) = 0.058 |

$t_R$ (HPLC) = 3.96 min  
MS (ESI−) m/z = 273.0029, 275.0010 [(M + H)$^+$]  
Mp = 262-266° C.  
HRMS (ESI+): calculated for $C_{13}H_{10}BrN_2$, m/z = 273.0022, 275.0002; found, 273.0024, 275.0005  
$^1$H NMR (400 MHz, DMSO-d$_6$): δ (ppm) = 12.00 (s, 1H, H$_{13}$), 8.30-8.27 (m, 2H, H$_{8,12}$), 7.95 (d, J = 2.7 Hz, 1H, H$_{14}$), 7.72-7.68 (m, 2H, H$_{1,6}$), 7.63-7.59 (m, 2H, H$_{3,5}$), 7.20-7.15 (m, 1H, H$_7$).  
$^{13}$C NMR (101 MHz, DMSO-d$_6$): δ (ppm) = 149.54 (C$_{10}$-arom.), 143.52 (C$_8$H-arom.), 134.83 (C$_4$-arom.), 132.14 (C$_{3,5}$H-arom.), 128.60 (C$_{1,6}$H-arom.), 127.89 (C$_{12}$H-arom.), 124.70 (C$_{14}$H-arom.), 118.79 (C$_2$-arom.), 117.47 (C$_{11}$-arom.), 116.64 (C$_7$H-arom.), 113.46 (C$_{15}$-arom.).

3-([1,1'-biphenyl]-3-yl)-1H-pyrrolo[2,3-b]pyridine (Procedure 10)

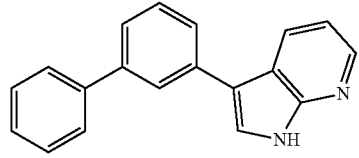

(White Solid)

| VPC Number | LabBook Code | IC$_{50}$ (eGFP) = 11.01 |
|---|---|---|
| 13 734 | CA 4-48 Precipitate (yield = 39%) | IC$_{50}$ (PSA) = 4.129 |

$t_R$ (HPLC) = 4.34 min  
MS (ESI−) m/z = 271.1226 [(M + H)$^+$]  
Mp = 182-185° C.  
HRMS (ESI+): calculated for $C_{19}H_{15}N_2$, m/z = 271.1230; found, 271.1227  
$^1$H NMR (400 MHz, DMSO-d$_6$): δ (ppm) = 11.97 (s, 1H, H$_{13}$), 8.34 (dd, J = 8.0, 1.5 Hz, 1H, H$_{12}$), 8.30 (dd, J = 4.6, 1.5 Hz, 1H, H$_8$), 8.01 (s, 1H, H$_{14}$), 7.95 (d, J = 0.7 Hz, 1H, H$_3$), 7.80-7.75 (m, 2H, H$_{17,21}$), 7.74-7.71 (m, 1H, H$_5$), 7.57-7.47 (m, 4H, H$_{2,6,18,20}$), 7.43-7.39 (m, 1H, H$_{19}$), 7.18 (dd, J = 7.9, 4.7 Hz, 1H, H$_7$).  
$^{13}$C NMR (101 MHz, DMSO-d$_6$): δ (ppm) = 149.56 (C$_{10}$-arom.), 143.39 (C$_8$H-arom.), 141.37 (C$_1$-arom.), 140.88 (C$_{16}$-arom.), 136.18 (C$_4$-arom.), 129.97 (C$_6$H-arom.), 129.38 (C$_{18,20}$H-arom.), 127.94 (C$_{12,19}$H-arom.), 127.37 (C$_{17,21}$H-arom.), 125.87 (C$_5$H-arom.), 125.07 (C$_3$H-arom.), 124.62 (C$_{2,14}$H-arom.), 117.79 (C$_{11}$-arom.), 116.59 (C$_7$H-arom.), 114.66 (C$_{15}$-arom.).

4-(4-bromothiazol-2-yl)morpholine

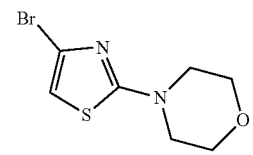

Intermediate (Beige Solid)

| | LabBook Code | |
|---|---|---|
| | CA 4-50 Ap Tmt (yield = Quant %) | |

$t_R$ (HPLC) = 3.44 min  
MS (ESI+) m/z = 248.9720; 250.9700 [(M + H)$^+$]

$^1$H NMR (400 MHz, DMSO-d$_6$): δ (ppm) = 6.92 (s, 1H, H$_2$), 3.72-3.67 (m, 4H, H$_{8,10}$), 3.38-3.34 (m, 4H, H$_{7,11}$).  
$^{13}$C NMR (101 MHz, DMSO-d$_6$): δ (ppm) = 171.17 (C$_4$-arom.), 121.03 (C$_1$-arom.), 105.37 (C$_2$H-arom.), 65.72 (C$_{8,10}$H$_2$), 48.08 (C$_{7,11}$H$_2$).

3-([1,1'-biphenyl]-4-yl)-1H-pyrrolo[3,2-b]pyridine (Procedure 10)

| VPC Number | LabBook Code | |
|---|---|---|
| 13 735 | CA 4-55 Precipitate (yield = 79%) | $IC_{50}$ (eGFP) = 3.86 |
| | | $IC_{50}$ (PSA) = 1.433 |
| | $t_R$ (HPLC) = 3.55 min | MS (ESI−) m/z = 271.1169 [(M + H)$^+$] |

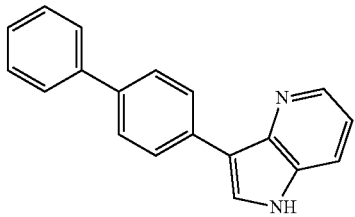

(White Solid)

Mp = 254-259 °C.
HRMS (ESI+): calculated for $C_{19}H_{15}N_2$, m/z = 271.1230; found, 271.1225
$^1$H NMR (400 MHz, DMSO-d$_6$): δ (ppm) = 11.62 (s, 1H, H$_{13}$), 8.48 (dd, J = 4.6, 1.5 Hz, 1H, H$_7$), 8.43-8.39 (m, 2H, H$_{3,5}$), 8.24 (s, 1H, H$_{14}$), 7.85 (dd, J = 8.2, 1.5 Hz, 1H, H$_9$), 7.72 (m, 4H, H$_{1,6,17,21}$), 7.49 (m, 2H, H$_{18,20}$), 7.39-7.35 (m, 1H, H$_{19}$), 7.20 (dd, J = 8.2, 4.6 Hz, 1H, H$_8$).
$^{13}$C NMR (101 MHz, DMSO-d$_6$): δ (ppm) = 144.02 (C$_{11}$-arom.), 143.19 (C$_7$H-arom.), 140.64 (C$_{16}$-arom.), 137.19 (C$_2$-arom.), 134.48 (C$_4$-arom.), 130.04 (C$_{10}$-arom.), 129.36 (C$_{18,20}$H-arom.), 127.50 (C$_{19}$H-arom.), 127.16 (C$_{14}$H-arom.), 126.99 (C$_{1,6}$H-arom.), 126.77 (C$_{17,21}$H-arom.), 126.69 (C$_{3,5}$H-arom.), 119.42 (C$_9$H-arom.), 117.09 (C$_8$H-arom.), 114.21 (C$_{15}$-arom.).

3-(4-bromophenyl)-1H-pyrrolo[3,2-b]pyridine (Procedure 10)

| VPC Number | LabBook Code | |
|---|---|---|
| 13 737 | CA 4-64 Precipitate (yield = 25 %) | $IC_{50}$ (eGFP) = 0.08 |
| | | $IC_{50}$ (PSA) = 0.037 |
| | $t_R$ (HPLC) = 2.84 min | MS (ESI−) m/z = 273.0043, 275.0023 [(M + H)$^+$] |

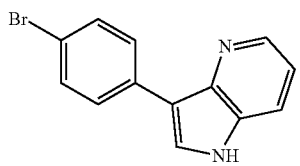 [SMILES: Brc1ccc(-c2c[nH]c3cccnc23)cc1]

(Pale Yellow Solid)

Mp = 213-221° C.

HRMS (ESI+): calculated for $C_{13}H_{10}BrN_2$, m/z = 273.0022, 275.0002; found, 273.0015, 274.9995

$^1$H NMR (400 mHz, DMSO-d$_6$): δ (ppm) = 11.66 (s, 1H, H$_{13}$), 8.46 (dd, J = 4.6, 1.5 Hz, 1H, H$_7$), 8.32-8.27 (m, 2H, H$_{1,6}$), 8.24 (s, 1H, H$_{14}$), 7.84 (dd, J = 8.2, 1.5 Hz, 1H, H$_9$), 7.61-7.55 (m, 2H, H$_{3,5}$), 7.19 (dd, J = 8.2, 4.6 Hz, 1H, H$_8$).

$^{13}$C NMR (101 MHz, DMSO-d$_6$): δ (ppm) = 143.76 (C$_{11}$-arom.), 143.27 (C$_7$H-arom.), 134.53 (C$_4$-arom.), 131.61 (C$_{3,5}$H-arom.), 130.02 (C$_{10}$-arom.), 128.10 (C$_{1,6}$H-arom.), 127.44 (C$_{14}$H-arom.), 119.53 (C$_9$H-arom.), 118.24 (C$_2$-arom.), 117.19 (C$_8$H-arom.), 113.32 (C$_{15}$-arom.).

3-(4-bromophenyl)-7-nitro-1H-indole (Procedure 10)

| VPC Number | LabBook Code | IC$_{50}$ (eGFP) = 0.083 |
|---|---|---|
| 13 738 | CA 4-65 Precipitate (yield = 12%) | IC$_{50}$ (PSA) = 0.062 |
| | t$_R$ (HPLC) = 4.29 min | MS (ESI−) m/z = 314.9732, 316.9703 [(M + H)$^-$] |

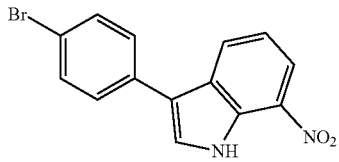

(Orage Solid)

Mp = 192-196° C.
HRMS (ESI−): calculated for C$_{14}$H$_8$BrN$_2$O$_2$, m/z = 314.9775, 316.9755; found, 314.9769, 316.9748
$^1$H NMR (600 MHz, DMSO-d$_6$): δ (ppm) = 12.21 (s, 1H, H$_{13}$), 8.34 (dd, J = 7.9, 0.8 Hz, 1H, H$_{12}$), 8.20 (dd, J = 8.0, 0.5 Hz, 1H, H$_8$), 7.89 (s, 1H, H$_{14}$), 7.71-7.63 (m, 4H, H$_{1,3,5,6}$), 7.36 (t, J = 8.0 Hz, 1H, H$_7$).
$^{13}$C NMR (151 MHz, DMSO-d$_6$): δ (ppm) = 133.24 (C$_4$-arom.), 132.90 (C$_9$-arom.), 131.78 (C$_{1,6}$H-arom.), 129.25 (C$_{3,5}$H-arom.), 129.11 (C$_{11}$-arom.), 128.95 (C$_{10}$-arom.), 127.65 (C$_{12}$H-arom.), 126.89 (C$_{14}$H-arom.), 119.58 (C$_7$H-arom.), 119.26 (C$_2$-arom.), 119.13 (C$_8$H-arom.), 116.42 (C$_{15}$-arom.).

methyl 3-(4-bromophenyl)-1H-indole-7-carboxylate (Procedure 10)

| VPC Number | LabBook Code | IC$_{50}$ (eGFP) = 0.62 |
|---|---|---|
| 13 736 | CA 4-74 Precipitate (yield = 36 %) | IC$_{50}$ (PSA) = 0.68 |
| | t$_g$ (HPLC) = 4.37 min | MS (ESI−) m/z = 327.9978 [(M + H)$^-$] |

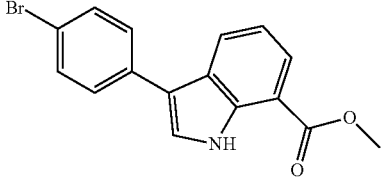 [SMILES: COC(=O)c1cccc2c(-c3ccc(Br)cc3)c[nH]c12]

(Grey Solid)

Mp = 149-155° C.
HRMS (ESI−): calculated for C$_{16}$H$_{11}$BrNO$_2$, m/z = 327.9979; found, 327.9978
$^1$H NMR (600 MHz, DMSO-d$_6$): δ (ppm) = 11.49 (s, 1H, H$_{13}$), 8.16 (d, J = 7.9 Hz, 1H, H$_{12}$), 7.87 (d, J = 6.8 Hz, 1H, H$_8$), 7.78 (d, J = 2.6 Hz, 1H, H$_{14}$), 7.70-7.67 (m, 2H, H$_{3,5}$), 7.65-7.61 (m, 2H, H$_{1,6}$), 7.26 (t, J = 7.7 Hz, 1H, H$_7$), 3.97 (s, 3H, H$_7$).
$^{13}$C NMR (151 MHz, DMSO-d$_6$): δ (ppm) = 166.39 (C$_{17}$O), 135.02 (C$_{10}$-arom.), 134.18 (C$_4$-arom.), 131.67 (C$_{1,6}$H-arom.), 128.88 (C$_{3,5}$H-arom.), 126.54 (C$_{11}$-arom.), 125.42 (C$_{14}$H-arom.), 124.83 (C$_{12}$H-arom.), 124.30 (C$_8$H-arom.), 119.49 (C$_7$H-arom.), 118.57 (C$_2$-arom.), 115.07 (C$_{15}$-arom.), 113.07 (C$_9$-arom.), 51.94 (C$_{20}$H$_3$).

3-phenyl-1H-pyrrolo[2,3-b]pyridine (Procedure 10)

| VPC Number | LabBook Code | | |
|---|---|---|---|
| 13 739 | CA 4-75 Precipitate (yield = 54%) | $IC_{50}$ (eGFP) = 0.66 | $IC_{50}$ (PSA) = 0.67 |

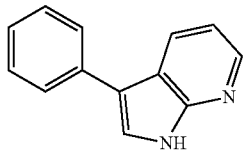 [SMILES: c1ccc(-c2c[nH]c3ncccc23)cc1]

$t_R$ (HPLC) = 3.40 min

MS (ESI+) m/z = 195.0920 [(M + H)$^+$]

(Beige Solid)

Mp = 92-94° C.
HRMS (ESI+): calculated for $C_{13}H_{11}N_2$, m/z = 195.0917; found, 195.0919
$^1$H NMR (600 MHz, DMSO-$d_6$): δ (ppm) = 11.90 (s, 1H, $H_{13}$), 8.30-8.26 (m, 2H, $H_{8,12}$), 7.87 (d, J = 2.6 Hz, 1H, $H_{14}$), 7.73 (dd, J = 8.2, 1.1 Hz, 2H, $H_{3,5}$), 7.45 (dd, J = 8.0, 7.5 Hz, 2H, $H_{1,6}$), 7.26 (tdd, J = 7.2, 6.0, 1.2 Hz, 1H, $H_2$), 7.16 (dd, J = 7.9, 4.7 Hz, 1H, $H_7$).
$^{13}$C NMR (151 MHz, DMSO-$d_6$): δ (ppm) = 149.06 ($C_{10}$-arom.), 142.87 ($C_8$H-arom.), 135.05 ($C_4$-arom.), 128.84 ($C_{1,6}$H-arom.), 127.43 ($C_{12}$H-arom.), 126.23 ($C_{3,5}$H-arom.), 125.63 ($C_2$H-arom.), 123.67 ($C_{14}$H-arom.), 117.25 ($C_{11}$-arom.), 116.00 ($C_7$H-arom.), 114.25 ($C_{15}$-arom.).

tert-butyl 3-(4,4,5,5-tetramethyl-1,3,2-dioxaborolan-2-yl)-1H-indole-1-carboxylate

| Intermediate | LabBook Code | | |
|---|---|---|---|
| | CA 4-76 F2-6 (yield = 68%) | | |

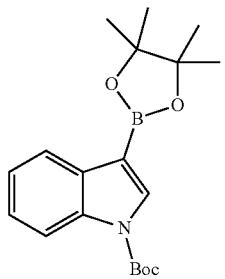 [SMILES: CC(C)(C)OC(=O)n1cc(B2OC(C)(C)C(C)(C)O2)c2ccccc21]

$t_R$ (HPLC) = 4.99 min

MS (ESI+) m/z = n.d.

(White Solid)

$^1$H NMR (400 MHz, DMSO-$d_6$): δ (ppm) = 8.11-8.06 (m, 1H, $H_3$), 7.88 (s, 1H, $H_8$), 7.87-7.82 (m, 1H, $H_6$), 7.37-7.32 (m, 1H, $H_2$), 7.31-7.26 (m, 1H, $H_1$), 1.64 (s, 9H, $H_{21,22,23}$), 1.33 (s, 12H, $H_{15,16,17,18}$).
$^{13}$C NMR (101 MHz, DMSO-$d_6$): δ (ppm) = 149.11 ($C_{24}$O), 135.87 ($C_4$-arom.), 135.33 ($C_8$H-arom.), 133.22 ($C_5$-arom.), 124.86 ($C_2$H-arom.), 123.48 ($C_1$H-arom.), 122.66 ($C_6$H-arom.), 115.06 ($C_3$H-arom.), 107.92 ($C_9$-arom.), 84.79 ($C_{20}$(CH$_3$)$_3$), 83.74 ($C_{12,13}$(CH$_3$)$_2$), 28.07 ($C_{21,22,23}H_3$), 25.14 ($C_{15,16,17,18}H_3$).

3-(4-fluorophenyl)-1H-pyrrolo[2,3-b]pyridine (Procedure 10)

| VPC Number | LabBook Code | | |
|---|---|---|---|
| 13 740 | CA 4-85 Precipitate (yield = 50%) | $IC_{50}$ (eGFP) = 0.12 | $IC_{50}$ (PSA) = 0.12 |

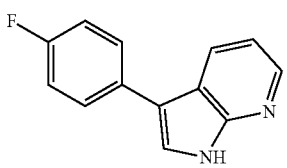 [SMILES: Fc1ccc(-c2c[nH]c3ncccc23)cc1]

$t_R$ (HPLC) = 3.59 min

MS (ESI+) m/z = 213.0830 [(M + H)$^+$]

(Beige Solid)

| VPC Number | LabBook Code | $IC_{50}$ (eGFP) = 0.12 |
|---|---|---|
| 13 740 | CA 4-85 Precipitate (yield = 50%) | $IC_{50}$ (PSA) = 0.12 |

Mp = 188-192° C.
HRMS (ESI+): calculated for $C_{13}H_{10}FN_2$, m/z = 213.0823; found, 213.0823
$^1$H NMR (600 MHz, DMSO-$d_6$): δ (ppm) = 11.91 (s, 1H, $H_{13}$), 8.28 (dd, J = 4.6, 1.3 Hz, 1H, $H_{12}$), 8.26 (dd, J = 8.0, 1.1 Hz, 1H, $H_8$), 7.86 (d, J = 2.6 Hz, 1H, $H_{14}$), 7.77-7.73 (m, 2H, $H_{3,5}$), 7.29-7.24 (m, 2H, $H_{1,6}$), 7.16 (dd, J = 7.9, 4.6 Hz, 1H, $H_7$).
$^{13}$C NMR (151 MHz, DMSO-$d_6$): δ (ppm) = 160.52 (d, J = 242.3 Hz, $C_2$F-arom.), 148.96 ($C_{10}$-arom.), 142.92 ($C_8$H-arom.), 131.49 (d, J = 3.0 Hz, $C_4$-arom.), 127.99 (d, J = 7.8 Hz, $C_{3,5}$H-arom.), 127.27 ($C_{12}$H-arom.), 123.66 ($C_{14}$H-arom.), 117.15 ($C_{11}$-arom.), 116.02 ($C_7$H-arom.), 115.61 (d, J = 21.2 Hz, $C_{1,6}$H-arom.), 113.28 ($C_{15}$-arom.).

3-(5-(trifluoromethyl)pyridin-2-yl)-1H-indole (Procedure 10)

| VPC Number | LabBook Code | $IC_{50}$ (eGFP) = 0.29 |
|---|---|---|
| 13 741 | CA 4-88 Crystals (yield = 22%) | $IC_{50}$ (PSA) = 0.29 |

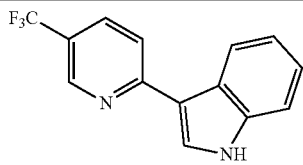 [SMILES: FC(F)(F)c1ccc(-c2c[nH]c3ccccc23)nc1]

$t_R$ (HPLC) = 4.03 min    MS (ESI+) m/z = 263.0793 [(M + H)$^+$]

(Colorless Solid)

Mp = 154-157° C.
HRMS (ESI+) : calculated for $C_{14}H_2{}_1OF_3N_2$, m/z = 263.0791; found, 263.0789
$^1$H NMR (600 MHz, DMSO-$d_6$): δ (ppm) = 11.77 (s, 1H, $H_{13}$), 8.94-8.92 (m, 1H, $H_1$), 8.50 (d, J = 7.7 Hz, 1H, $H_{12}$), 8.32 (d, J = 2.9 Hz, 1H, $H_{14}$), 8.02-8.04 (m, 2H, $H_{5,6}$), 7.49 (d, J = 7.8 Hz, 1H, $H_9$), 7.23-7.16 (m, 2H, $H_{7,8}$).
$^{13}$C NMR (151 MHz, DMSO-$d_6$): δ (ppm) = 159.25 (d, J = 1.2 Hz, $C_4$-arom.), 145.86 (q, J = 4.2 Hz, $C_1$H-arom.), 137.12 ($C_{10}$-arom.), 133.25 (q, J = 3.1 Hz, $C_6$H-arom.), 128.17 ($C_{14}$H-arom.), 125.13 ($C_{11}$-arom.), 124.31 (q, J = 271.5 Hz, $C_{16}F_3$), 122.14 ($C_8$H-arom.), 121.63 ($C_{12}$H-arom.), 120.55 ($C_7$H-arom.), 120.30 (q, J = 32.1 Hz, $C_2$-arom.), 119.02 ($C_5$-arom.), 114.24 ($C_{15}$-arom.), 111.99 ($C_9$H-arom.).

tert-butyl 7-methyl-3-(4,4,5,5-tetramethyl-1,3,2-dioxaborolan-2-yl)-1H-indole-1-carboxylate

| | LabBook Code |
|---|---|
| Intermediate | CA 4-89 F10-24 (yield = 68%) |

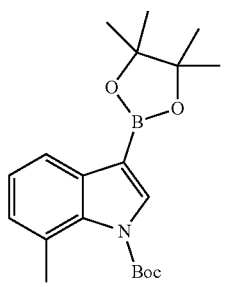 [SMILES: Cc1cccc2c(B3OC(C)(C)C(C)(C)O3)cn(C(=O)OC(C)(C)C)c12]

$t_R$ (HPLC) = 5.20 min    MS (ESI+) m/z = n.d.

(White Solid)

$^1$H NMR (400 MHz, DMSO-$d_6$): δ (ppm) = 7.85 (s, 1H, $H_8$), 7.71 (d, J = 7.1 Hz, 1H, $H_6$), 7.19 (t, J = 7.5 Hz, 1H, $H_1$), 7.11 (d, J = 7.1 Hz, 1H, $H_2$), 2.53 (s, 3H, $H_{19}$), 1.62 (s, 9H, $H_{22,23,24}$), 1.33 (s, 12H, $H_{15,16,17,18}$).

| Intermediate | LabBook Code<br>CA 4-89 F10-24 (yield = 68%) |
|---|---|

$^{13}$C NMR (151 MHz, DMSO-d$_6$): δ (ppm) = 148.60 (C$_{25}$O), 137.15 (C$_8$H-arom.), 134.66 (C$_4$-arom.), 133.93 (C$_5$-arom.), 127.27 (C$_2$H-arom.), 124.23 (C$_3$-arom.), 123.28 (C$_1$H-arom.), 119.88 (C$_6$H-arom.), 107.29 (C$_9$-arom.), 84.18 (C$_{20}$(CH$_3$)$_3$), 83.18 (C$_{12,13}$(CH$_3$)$_2$), 27.42 (C$_{22,23,24}$H$_3$), 24.67 (C$_{15,16,17,18}$H$_3$, 21.39 (C$_{19}$H$_3$).

3-(2-(trifluoromethyl)phenyl)-1H-indole (Procedure 10)

| VPC Number<br>13 745 | LabBook Code<br>CA 4-95 F4-8 (yield = 50%) | IC$_{50}$ (eGFP) = 1.01<br>IC$_{50}$ (PSA) = 0.95 |
|---|---|---|
| | t$_R$ (HPLC) = 4.15 min | MS (ESI+) m/z = 260.0687<br>[(M + H)$^+$] |

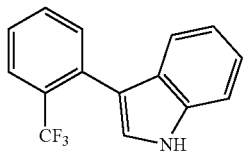

(Beige Solid)

Mp = 62-67° C.
HRMS (ESI−): calculated for C$_{15}$H$_9$F$_3$N, m/z = 260.0693; found, 260.0687
$^1$H NMR (600 MHz, DMSO-d$_6$): δ (ppm) = 11.39 (s, 1H, H$_{13}$), 7.85 (d, J = 7.9 Hz, 1H, H$_1$), 7.72 (t, J = 7.4 Hz, 1H, H$_6$), 7.59 (d, J = 7.5 Hz, 1H, H$_5$), 7.55 (t, J = 7.5 Hz, 1H, H$_2$), 7.49 (d, J = 8.1 Hz, 1H, H$_9$), 7.40 (s, 1H, H$_{14}$), 7.36 (d, J = 7.9 Hz, 1H, H$_{12}$), 7.16 (t, J = 7.5 Hz, 1H, H$_8$), 7.04 (t, J = 7.4 Hz, 1H, H$_7$).
$^{13}$C NMR (151 MHz, DMSO-d$_6$): δ (ppm) = 135.73 (C$_{10}$-arom.), 134.23 (d, J = 1.3 Hz, C$_4$-arom.), 133.18 (C$_5$H-arom.), 132.04 (C$_6$H-arom.), 127.71 (q, J = 28.6 Hz, C$_3$-arom.), 127.01 (C$_{11}$-arom.), 126.89 (C$_2$H-arom.), 126.26 (q, J = 5.4 Hz, C$_1$H-arom.), 124.40 (d, J = 2.9 Hz, C$_{14}$H-arom.), 124.39 (q, J = 273.6 Hz, C$_{16}$F$_3$), 121.46 (C$_8$H-arom.), 119.42 (C$_7$H-arom.), 118.32 (C$_{12}$H-arom.), 112.44 (C$_{15}$-arom.), 111.70 (C$_9$H-arom.).

2,3,4-trifluoro-6-iodoaniline

| Intermediate | LabBook Code<br>CA 4-100 F6-11 (yield = 36%) |
|---|---|
| | t$_R$ (HPLC) = 3.78 min     MS (ESI+) m/z = 273.9338<br>[(M + H)$^+$] |

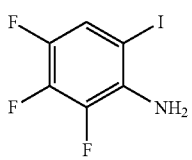 [SMILES: Nc1c(I)cc(F)c(F)c1F]

(Dark Solid)

$^1$H NMR( 600 MHz, CDCl$_3$): δ (ppm) = 7.33 (ddd, J = 9.3, 7.6, 2.5 Hz, 1H, H$_6$), 4.07 (s, 2H, H$_7$).
$^{13}$C NMR (151 MHz, CDCl$_3$): δ (ppm) = 143.20 (ddd, J = 244.0, 10.8, 2.8 Hz, C$_3$-arom.), 139.98 (ddd, J = 250.5, 161.1, 13.7 Hz, C$_2$-arom.), 138.48 (ddd, J = 247.1, 12.6, 3.3 Hz, C$_1$-arom.), 133-43 (dd, J = 11.2 2.4 Hz, C$_4$-arom.), 119.96 (dd, J = 20.1, 3.9 Hz, C$_6$H-arom.), 73.21 (ddd, J = 8.2, 4.5, 2.1 Hz, C$_5$-arom.).

2-(5,6,7-trifluoro-1H-indol-3-yl)quinoline

| | LabBook Code | |
| --- | --- | --- |
| | CA 4-101 F4-6 (yield = 13%) | |
| | $t_R$ (HPLC) = 4.32 min | MS (ESI+) m/z = 299.0820 [(M + H)$^+$] |

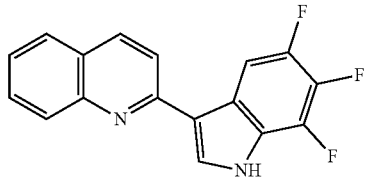 [SMILES: Fc1cc2c(-c3ccc4ccccc4n3)c[nH]c2c(F)c1F]

(White Solid)

HRMS (ESI+): calculated for $C_{17}H_{10}F_3N_2$, m/z = 299.0791; found, 299.0791
$^1$H NMR (600 MHz, CDCl$_3$): δ (ppm) = 9.99 (s, 1H, H$_{15}$), 8.21 (d, J = 8.4 Hz, 1H, H$_{10}$), 8.12 (d, J = 8.1 Hz, 1H, H$_3$), 7.87 (d, J = 8.4 Hz, 1H, H$_9$), 7.84 (d, J = 8.4 Hz, 1H, H$_6$), 7.77 (t, J = 7.5 Hz, 1H, H$_2$), 7.57 (t, J = 7.3 Hz, 1H, H$_1$), 7.23 (ddd, J = 9.7, 6.5, 1.6 Hz, 1H, H$_{19}$), 7.12 (s, 1H, H$_{14}$).
$^{13}$C NMR (151 MHz, CDCl$_3$): δ (ppm) = 148.30 (C$_8$-arom.), 147.32 (C$_4$-arom.), 146.70 (dd, J = 240.3, 12.2 Hz, C$_{16}$-arom.), 138.72 (C$_{13}$-arom.), 137.53 (ddd, J = 249.3, 13.6, 4.5 Hz, C$_{17}$-arom.), 136.93 (ddd, J = 244.8, 17.1, 11.3 Hz, C$_{16}$-arom.), 136.35 (C$_{10}$-arom.), 129.70 (C$_2$H-arom.), 128.58 (C$_3$H-arom.), 127.22 (C$_6$H-arom.), 127.06 (C$_5$-arom.), 126.14 (C$_1$H-arom.), 124.01 (dd, J = 6.9, 5.5 Hz, C$_{12}$-arom.), 121.44 (dd, J = 7.7, 2.9 Hz, C$_{11}$-arom.), 117.52 (C$_9$H-arom.), 101.92 (m, C$_{14,19}$H-arom.).

7-(7-methyl-1H-indol-3-yl)quinoline (Procedure 10)

| VPC Number 13 744 | LabBook Code CA 4-102 Precipitate (yield = 32 %) | IC$_{50}$ (eGFP) = 0.76 IC$_{50}$ (PSA) = 0.75 |
| --- | --- | --- |
| | $t_R$ (HPLC) = 2.94 min | MS (ESI+) m/z = 259.1272 [(M + H)$^+$] |

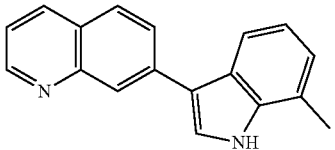 [SMILES: Cc1cccc2c(-c3ccc4cccnc4c3)c[nH]c12]

(Green Solid)

Mp = 199-201° C.
HRMS (ESI+): calculated for $C_{18}H_{15}N_2$, m/z = 259.1230; found, 259.1228
$^1$H NMR (600 MHz, DMSO-d$_6$): δ (ppm) = 11.54 (s, 1H, H$_{13}$), 8.89 (dd, J = 4.2, 1.7 Hz, 1H, H$_{19}$), 8.34 (dd, J = 8.2, 0.9 Hz, 1H, H$_{17}$), 8.30 (s, 1H, H$_3$), 8.04-8.00 (m, 2H, H$_{5,6}$), 7.98 (d, J = 2.4 Hz, 1H, H$_{14}$), 7.87 (d, J = 8.0 Hz, 1H, H$_{12}$), 7.47 (dd, J = 8.2, 4.2 Hz, 1H, H$_{18}$), 7.10 (t, J = 7.5 Hz, 1H, H$_8$), 7.02 (d, J = 7.0 Hz, 1H, H$_8$), 2.54 (s, 3H, H$_{16}$).
$^{13}$C NMR (101 MHz, DMSO-d$_6$): δ (ppm) = 150.65 (C$_{19}$H-arom.), 148.56 (C$_1$-arom.), 137.35 (C$_4$-arom.), 136.61 (C$_{10}$-arom.), 135.55 (C$_{17}$H-arom.), 128.24 (C$_6$H-arom.), 126.41 (C$_5$H-arom.), 125.92 (C$_2$-arom.), 124.71 (C$_{14}$H-arom.), 124.62 (C$_{11}$-arom.), 124.05 (C$_3$H-arom.), 122.23 (C$_8$H-arom.), 121.36 (C$_9$-arom.), 120.40 (C$_7$H-arom.), 120.28 (C$_{18}$H-arom.), 116.64 (C$_{12}$H-arom.), 115.27 (C$_{15}$-arom.), 16.83 (C$_{16}$H$_3$).

tert-butyl 3-iodo-1H-pyrrolo[3,2-b]pyridine-1-carboxylate

| Intermediate | LabBook Code<br>CA 4-104 F1-21 (yield = 83%) | |
|---|---|---|
| 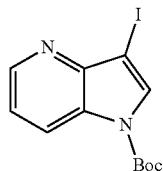<br>(White Solid) | $t_R$ (HPLC) = 4.07 min | MS (ESI+) m/z = 345.0106<br>$[(M + H)^+]$ |
| | $^1$H NMR (400 MHz, DMSO-$d_6$): δ (ppm) = 8.56 (dd, J = 4.7, 1.4 Hz, 1H, H$_1$), 8.32 (dd, J = 8.3, 1.3 Hz, 1H, H$_3$), 8.19 (s, 1H, H$_8$), 7.43 (dd, J = 8.3, 4.7 Hz, 1, H$_2$), 1.64 (s, 9H, H$_{13,14,15}$).<br>$^{13}$C NMR = n.d. | |

3-(4-(trifluoromethyl)phenyl)-1H-indole (Procedure 10)

| VPC Number<br>13 743 | LabBook Code<br>CA 4-105 F8-16 (yield = 51%) | IC$_{50}$ (eGFP) = 0.38<br>IC$_{50}$ (PSA) = 0.39 |
|---|---|---|
| 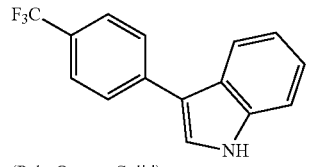<br>(Pale Orange Solid) | $t_R$ (HPLC) = 4.34 min | MS (ESI+) m/z = 262.0850<br>$[(M + H)^+]$ |
| | Mp = 126-129° C.<br>HRMS (ESI+): calculated for $C_{15}H_{11}F_3N$, m/z = 262.0838; found, 262.0850<br>$^1$H NMR (600 MHz, DMSO-$d_6$): δ (ppm) = 11.59 (s, 1H, H$_{13}$), 7.94 (d, J = 8.2 Hz, 3H, H$_{3,5,12}$), 7.90 (d, J = 2.6 Hz, 1H, H$_{14}$), 7.76 (d, J = 8.2 Hz, 2H, H$_{1,6}$), 7.50 (d, J = 8.0 Hz, 1H, H$_9$), 7.22-7.18 (m, 1H, H$_8$), 7.17-7.13 (m, 1H, H$_7$). | |
| | $^{13}$C NMR (151 MHz, DMSO-$d_6$): δ (ppm) = 140.18 (d, J= 0.8 Hz, C$_4$-arom.), 137.04 (C$_{10}$-arom.), 126.48 (C$_{3,5}$H-arom.), 125.58 (q, J= 3.7 Hz, C$_{1,6}$H-arom.), 125.25 (d, J= 31.7 Hz, C$_2$-arom.), 125.00 (C$_{14}$H-arom.), 124.66 (C$_{11}$H-arom.), 124.62 (q, J = 271.5 Hz, C$_{16}$F$_3$), 121.76 (C$_8$H-arom.), 120.11 (C$_7$H-arom.), 118.92 (C$_{12}$H-arom.), 114.12 (C$_{15}$-arom.), 112.19 (C$_9$H-arom.). | |

1-methyl-5-(naphthalen-2-yl)-1H-indole (Procedure 10)

| VPC Number<br>13 756 | LabBook Code<br>CA 4-108 Precipitate (yield = 45%) | IC$_{50}$ (eGFP) = 2.0<br>IC$_{50}$ (PSA) = 1.49 |
|---|---|---|
| (Pale Yellow Solid) | $t_R$ (HPLC) = 4.56 min | MS (ESI+) m/z = 258.1260<br>$[(M + H)^+]$ |
| | Mp = 200-204° C.<br>HRMS (ESI+): calculated for $C_{19}H_{16}N$, m/z = 258.1277; found, 258.1276<br>$^1$H NMR (600 MHz, DMSO-$d_6$): δ (ppm) = 8.21 (d, J = 0.7 Hz, 1H, H$_7$), 8.00-7.97 (m, 3H, H$_{6,10,16}$), 7.93 (d, J = 8.0 Hz, 1H, H$_3$), 7.91 (dd, J= 8.5, 1.7 Hz, 1H, H$_9$), 7.64 (dd, J = 8.5, 1.6 Hz, 1H, H$_{14}$), 7.57 (d, J = 8.5 Hz, 1H, H$_{13}$), 7.54 (t, J = 7.3 Hz, 1H, H$_1$), 7.49 (t, J = 7.3 Hz, 1H, H$_2$), 7.39 (d, J = 3.0 Hz, 1H, H$_{18}$), 6.53 (d, J = 3.0 Hz, 1H, H$_{19}$), 3.85 (s, 3H, H$_{20}$). | |
| | $^{13}$C NMR (151 MHz, DMSO-$d_6$): δ (ppm) = 139.02 (C$_8$-arom.), 136.09 (C$_{11}$-arom.), 133.52 (C$_5$-arom.), 131.70 (C$_4$-arom.), 131.12 (C$_{15}$-arom.), 130.43 (C$_{18}$H-arom.), 128.68 (C$_{12}$-arom.), 128.20 (C$_{10}$H-arom.), 127.95 (C$_6$H-arom.), 127.41 (C$_3$H-arom.), 126.19 (C$_1$H-arom.), 125.62 (C$_2$H-arom.), 125.50 (C$_9$H-arom.), 124.60 (C$_7$H-arom.), 120.61 (C$_{14}$H-arom.), 118.75 (C$_{16}$H-arom.), 110.20 (C$_{13}$H-arom.), 100.86 (C$_{19}$H-arom.), 32.58 (C$_{20}$H$_3$). | |

3-(4-(trifluoromethyl)phenyl)-1H-pyrrolo[3,2-b]pyridine (Procedure 10)

| VPC Number | LabBook Code | $IC_{50}$ (eGFP) = |
|---|---|---|
| 13 | CA 4-109 Precipitate (yield = 69%) | $IC_{50}$ (PSA) = |

$t_R$ (HPLC) = 2.89 min

MS (ESI+) m/z = 263.0792 [(M + H)$^+$]

Mp = 223-226° C.

HRMS (ESI+): calculated for $C_{14}H_{10}F_3N_2$, m/z = 263.0791; found, 263.0790

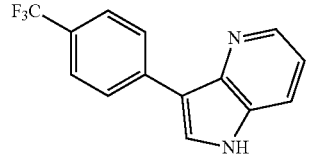

(Pale Yellow Solid)

$^1$H NMR (600 MHz, DMSO-d$_6$): δ (ppm) = 11.78 (s, 1H, H$_{11}$), 8.55 (d, J = 8.2 Hz, 2H, H$_{3,5}$), 8.49 (dd, J = 4.5, 1.3 Hz, 1H, H$_{13}$), 8.36 (s, 1H, H$_7$), 7.87 (dd, J = 8.2, 1.4 Hz, 1H, H$_{15}$), 7.75 (d, J = 8.3 Hz, 2H, H$_{2,6}$), 7.22 (dd, J = 8.2, 4.5 Hz, 1H, H$_{14}$).

$^{13}$C NMR (101 MHz, DMSO-d$_6$): δ (ppm) = 143.41 (C$_9$-arom.), 143.07 (C$_{13}$H-arom.), 139.02 (d, J = 0.9 Hz, C$_4$-arom.), 129.64 (C$_{10}$-arom.), 128.07 (C$_7$H-arom.), 125.77 (C$_{3,5}$H-arom.), 125.16 (q, J = 3.7 Hz, C$_{2,6}$H-arom.), 125.14 (q, J = 31.6 Hz, C$_1$-arom.), 124.67 (q, J = 271.4 Hz, C$_{16}$F$_3$), 119.23 (C$_{15}$H-arom.), 116.93 (C$_{14}$H-arom.), 112.60 (C$_8$-arom.).

3-(2-bromophenyl)-1H-pyrrolo[3,2-b]pyridine (Procedure 10)

LabBook Code
CA 4-110 Precipitate2 (yield = 37%)

$t_R$ (HPLC) = 2.61 min

MS (ESI+) m/z = 273.0018, 274.9998 [(M + H)$^+$]

HRMS (ESI+): calculated for $C_{13}H_{10}BrN_2$, m/z = 2273.0022, 275.0002; found, 273.0018, 274.9998

$^1$H NMR (600 MHz, DMSO-d$_6$): δ (ppm) = 11.61 (s, 1H, H$_{11}$), 8.37 (d, J = 4.4 HZ, 1H, H$_{13}$), 7.99 (s, 1H, H$_7$), 7.90 (d, J = 7.7 Hz, 1H, H$_5$), 7.85 (d, J = 8.1 Hz, 1H, H$_{15}$), 7.74 (d, J = 7.9 Hz, 1H, H$_2$), 7.45 (t, J = 7.5 Hz, 1H, H$_6$), 7.24 (t, J =

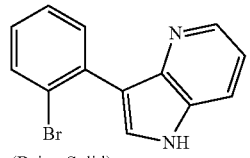

(Beige Solid)

7.6 Hz, 1H, H$_1$), 7.18 (dd, J = 8.1, 4.5 Hz, 1H, H$_{14}$).

$^{13}$C NMR (101 MHz, DMSO-d$_6$): δ (ppm) = 143.75 (C$_9$-arom.), 142.71 (C$_{13}$H-arom.), 134.57 (C$_4$-arom.), 132.93 (C$_2$H-arom.), 132.70 (C$_5$H-arom.), 128.75 (C$_7$H-arom.), 128.29 (C$_{10}$-arom.), 127.86 (C$_1$H-arom.), 127.21 (C$_6$H-arom.), 122.57 (C$_3$-arom.), 118.89 (C$_{15}$H-arom.), 116.70 (C$_{14}$H-arom.), 113.74 (C$_8$-arom.).

6(7-methyl-1H-indol-3-yl)benzo[d]thiazole (Procedure 10)

| VPC Number | LabBook Code | $IC_{50}$ (eGFP) = Inactive |
|---|---|---|
| 13 757 | CA 4-114 F9-15 Precipitate (yield = 27%) | $IC_{50}$ (PSA) = Inactive |

$t_R$ (HPLC) = 4.02 min

MS (ESI+) m/z = 265.0787 [(M + H)$^+$]

Mp = 183-185° C.

HRMS (ESI+): calculated for $C_{16}H_{13}N_2S$, m/z = 265.0794; found, 265.0793

$^1$H NMR (600 MHz, DMSO-d$_6$): δ (ppm) = 11.42 (s, 1H, H$_{14}$), 9.32 (s, 1H, H$_8$), 8.48 (d, J = 0.8 Hz, 1H, H$_6$), 8.12 (d, J = 8.5 Hz, 1H, H$_3$), 7.90 (dd, J = 8.5, 1.6 Hz, 1H, H$_4$), 7.84-7.80 (m, 2H, H$_{13,18}$), 7.05 (t, J = 7.5 Hz, 1H, H$_{17}$), 6.99 (d, J = 7.0 Hz, 1H, H$_{16}$), 2.52 (s, 3H, H$_{19}$).

(Beige Solid)

$^{13}$C NMR (151 MHz, DMSO-d$_6$): δ (ppm) = 154.81 (C$_8$H-arom.), 150.95 (C$_1$-arom.), 136.43 (C$_{10}$-arom.), 134.50 (C$_2$-arom.), 133.67 (C$_5$-arom.), 125.37 (C$_4$H-arom.), 124.63 (C$_{11}$-arom.), 123.87 (C$_{13}$H-arom.), 123.01 (C$_3$H-arom.), 122.07 (C$_{16}$H-arom.), 121.15 (C$_{15}$-arom.), 119.98 (C$_{17}$H-arom.), 119.15 (C$_6$H-arom.), 116.70 (C$_{18}$H-arom.), 115.44 (C$_{12}$-arom.), 16.81 (C$_{19}$H$_3$).

2-(quinolin-5-yl)thiazole

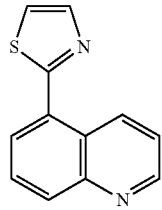 [SMILES: c1cc(-c2nccs2)c2cccnc2c1]

(Pale Yellow Solid)

LabBook Code
CA 4-116 F14-17 (yield = 36%)

$t_R$ (HPLC) = 2.95 min   MS (ESI+) m/z = 213.0468
                          [(M + H)$^+$]

$^1$H NMR (600 MHz, DMSO-d$_6$): δ (ppm) = 9.31 (d, J = 8.7 Hz, 1H, H$_6$), 9.00 (dd, J = 4.0, 1.6 Hz, 1H, H$_4$), 8.18 (d, J = 8.4 Hz, 1H, H$_{10}$), 8.13 (d, J = 3.3 Hz, 1H, H$_{12}$), 8.05 (d, J = 7.2 Hz, 1H, H$_8$), 7.98 (d, J = 3.3 Hz, 1H, H$_{11}$), 7.89 (dd, J = 8.3, 7.4 Hz, 1H, H$_9$), 7.67 (dd, J = 8.7, 4.1 Hz, 1H, H$_5$).

$^{13}$C NMR (101 MHz, DMSO-d$_6$): δ (ppm) = 165.68 (C$_{14}$-arom.), 150.97 (C$_4$H-arom.), 148.04 (C$_2$-arom.), 143.95 (C$_{12}$H-arom.), 134.04 (C$_6$H-arom.), 131.25 (C$_{10}$H-arom.), 130.17 (C$_7$-arom.), 129.09 (C$_9$H-arom.), 128.68 (C$_8$H-arom.), 124.92 (C$_1$-arom.), 122.51 (C$_5$H-arom.), 121.55 (C$_{11}$H-arom.).

5-(7-methyl-1H-indol-3-yl)benzo[d]thiazole   (Procedure 10)

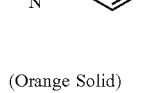

(Orange Solid)

| VPC Number | LabBook Code | IC$_{50}$ (eGFP) = Inactive |
|---|---|---|
| 13 758 | CA 4-118 F18-25 (yield = 68%) | IC$_{50}$ (PSA) = Inactive |

$t_R$ (HPLC) = 3.93 min      MS (ESI+) m/z = 265.0790
                             [(M + H)$^+$]

Mp = 133-136° C.
HRMS (ESI+): calculated for C$_{16}$H$_{13}$N$_2$S, m/z = 265.0794; found, 265.0790

$^1$H NMR (600 MHz, DMSO-d$_6$): δ (ppm) = 11.43 (s, 1H, H$_{15}$), 9.41 (s, 1H, H$_8$), 8.39 (d, J = 1.1 Hz, 1H, H$_6$), 8.20 (d, J = 8.3 Hz, 1H, H$_3$), 7.87 (dd, J = 8.4, 1.5 Hz, 1H, H$_4$), 7.86 (d, J = 2.6 Hz, 1H, H$_{13}$), 7.79 (d, J = 8.0 Hz, 1H, H$_{18}$), 7.06 (t, J = 7.5 Hz, 1H, H$_{17}$), 6.99 (d, J = 7.0 Hz, 1H, H$_{16}$), 2.54 (s, 3H, H$_{19}$).

$^{13}$C NMR (151 MHz, DMSO-d$_6$): δ (ppm) = 156.22 (C$_8$H-arom.), 153.99 (C$_2$-arom.), 136.44 (C$_{10}$-arom.), 134.47 (C$_5$-arom.), 130.24 (C$_1$-arom.), 124.84 (C$_4$H-arom.), 124.70 (C$_{11}$-arom.), 123.76 (C$_{13}$H-arom.), 122.52 (C$_3$H-arom.), 122.05 (C$_{16}$H-arom.), 121.21 (C$_{15}$-arom.), 120.04 (C$_6$H-arom.), 120.01 (C$_{17}$H-arom.), 116.45 (C$_{18}$H-arom.), 115.56 (C$_{12}$-arom.), 16.83 (C$_{19}$H$_3$).

5-(7-methyl-1H-indol-3-yl)benzo[d]oxazole   (Procedure 10)

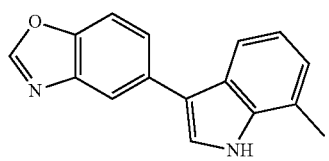 [SMILES: Cc1cccc2c(-c3ccc4ocnc4c3)c[nH]c12]

(Mauve Solid)

| VPC Number | LabBook Code | IC$_{50}$ (eGFP) = 0.3 |
|---|---|---|
| 13 759 | CA 4-119 Precipitate (yield = 26%) | IC$_{50}$ (PSA) = 0.27 |

$t_R$ (HPLC) = 3.87 min      MS (ESI+) m/z = 249.1041
                             [(M + H)$^+$]

Mp = 171-172° C.
HRMS (ESI+): calculated for C$_{16}$H$_{13}$N$_2$O, m/z = 249.1022; found, 249.1016

$^1$H NMR (600 MHz, DMSO-d$_6$): δ (ppm) = 11.35 (s, 1H, H$_{14}$), 8.75 (s, 1H, H$_8$), 8.03 (d, J = 1.3 Hz, 1H, H$_6$), 7.82 (d, J = 8.4 Hz, 1H, H$_3$), 7.77 (dd, J = 8.4, 1.6 Hz, 1H, H$_4$), 7.75 (d, J = 2.6 Hz, 1H, H$_{13}$), 7.72 (d, J = 8.0 Hz, 1H, H$_{18}$), 7.03 (t, J = 7.5 Hz, 1H, H$_{17}$), 6.98 (d, J = 7.0 Hz, 1H, H$_{16}$), 2.52 (s, 3H, H$_{19}$).

$^{13}$C NMR (151 MHz, DMSO-d$_6$): δ (ppm) = 154.42 (C$_8$H-arom.), 147.60 (C$_1$-arom.), 140.40 (C$_2$-arom.), 136.31 (C$_{10}$-arom.), 132.98 (C$_5$-arom.), 124.75 (C$_4$H-arom.), 124.70 (C$_{11}$-arom.), 123.40 (C$_{13}$H-arom.), 121.95 (C$_{16}$H-arom.), 121.11 (C$_{15}$-arom.), 119.88 (C$_{17}$H-arom.), 117.38 (C$_6$H-arom.), 116.32 (C$_{18}$H-arom.), 115.79 (C$_{12}$-arom.), 111.18 (C$_3$H-arom.), 16.81 (C$_{19}$H$_3$).

2-(7-methyl-1H-indol-3-yl)benzo[d]thiazole (Procedure 10)

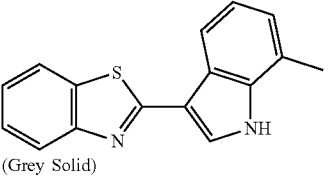

| VPC Number | LabBook Code | IC$_{50}$ (eGFP) = 0.1 |
|---|---|---|
| 13 760 | CA 4-120 F12-18 Precipitate (yield = 30%) | IC$_{50}$ (PSA) = 0.52 | t$_R$ (HPLC) = 4.02 min  MS (ESI+) m/z = 265.0788 [(M + H)$^+$]

Mp = 179-182° C.
HRMS (ESI+): calculated for C$_{16}$H$_{13}$N$_2$S, m/z = 265.0794; found, 265.0790
$^1$H NMR (600 MHz, DMSO-d$_6$): δ (ppm) = 11.95 (s, 1H, H$_5$), 8.25 (d, J = 2.9 Hz, 1H, H$_4$), 8.22 (d, J = 7.9 Hz, 1H, H$_9$), 8.06 (d, J = 7.9 Hz, 1H, H$_{13}$), 7.97 (d, J = 8.1 Hz, 1H, H$_{16}$), 7.49 (t, J = 7.6 Hz, 1H, H$_{15}$), 7.37 (t, J = 7.6 Hz, 1H, H$_{14}$), 7.17 (t, J = 7.5 Hz, 1H, H$_8$), 7.07 (d, J = 7.1 Hz, 1H, H$_7$), 2.54 (s, 3H, H$_{10}$).
$^{13}$C NMR (151 MHz, DMSO-d$_6$): δ (ppm) = 162.90 (C$_{18}$-arom.), 153.68 (C$_{12}$-arom.), 136.26 (C$_1$-arom.), 133.03 (C$_{11}$-arom.), 128.52 (C$_4$H-arom.), 126.09 (C$_{15}$H-arom.), 124.32 (C$_2$-arom.), 124.17 (C$_{14}$H-arom.), 123.25 (C$_7$H-arom.), 121.71 (C$_{13}$H-arom.), 121.63 (C$_6$-arom.), 121.53 (C$_{16}$H-arom.), 121.30 (C$_8$H-arom.), 118.22 (C$_9$H-arom.), 110.81 (C$_3$-arom.), 16.74 (C$_{10}$H$_3$).

(Grey Solid)

3-(3-bromophenyl)-1H-pyrrolo[3,2-b]pyridine (Procedure 10)

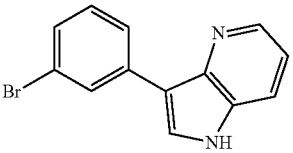 [SMILES: Brc1cccc(-c2c[nH]c3cccnc23)c1]

| VPC Number | LabBook Code |
|---|---|
| 13 760 | CA 4-124 Precipitate (yield = 30%) | t$_R$ (HPLC) = 2.71 min  MS (ESI+) m/z = 273.0006, 274.9986 [(M + H)+]
HRMS (ESI+): calculated for C$_{13}$H$_{10}$BrN$_2$, m/z = 273.0022, 275.0002; found, 273.0023, 275.0003
$^1$H NMR (600 MHz, DMSO-d$_6$): δ (ppm) = 11.69 (s, 1H), 8.65 (s, 1H), 8.49 (d, J = 3.5 Hz, 1H), 8.29 (d, J = 2.8 Hz, 1H), 8.28-8.25 (m, 1H), 7.85 (dd, J = 8.2, 1.0 Hz, 1H), 7.38-7.34 (m, 2H), 7.20 (dd, J = 8.1, 4.6 Hz, 1H).
$^{13}$C NMR = n.d.

(White Solid)

4-bromo-2-(7-methyl-1H-indol-3-yl)thiazole (Procedure 10)

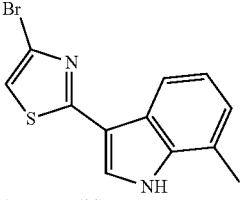 [SMILES: Cc1cccc2c(-c3nc(Br)cs3)c[nH]c12]

| VPC Number | LabBook Code | IC$_{50}$ (eGFP) = 0.045 |
|---|---|---|
| 13766 | CA 4-125 F7-11 (yield = 43%) | IC$_{50}$ (PSA) = 0.02 | t$_R$ (HPLC) = 4.00 min  MS (ESI+) m/z = 292.9743, 294.9724 [(M + H)$^+$]

Mp = 127-130° C.
HRMS (ESI+): calculated for C$_{12}$H$_{10}$BrN$_2$S, m/z = 292.9743, 294.9722; found, 292.9743, 294.9723
$^1$H NMR (600 MHz, DMSO-d$_6$): δ (ppm) = 11.86 (s, 1H, H$_5$), 8.16 (s, 1H, H$_4$), 7.93 (d, J = 7.7 Hz, 1H, H$_9$), 7.62 (s, 1H, H$_{14}$), 7.13 (t, J = 7.3 Hz, 1H, H$_8$), 7.04 (d, J = 6.6 Hz, 1H, H$_7$), 2.52 (s, 3H, H$_{10}$).
$^{13}$C NMR (151 MHz, DMSO-d$_6$): δ (ppm) = 164.43 (C$_{11}$-arom.), 136.06 (C$_1$-arom.), 126.82 (C$_4$H-arom.), 123.71 (C$_{13}$-arom.), 123.69 (C$_2$-arom.), 123.09 (C$_7$H-arom.), 121.67 (C$_6$H-arom.), 121.19 (C$_8$H-arom.), 117.45 (C$_9$H-arom.), 113.69 (C$_{14}$H-arom.), 110.13 (C$_3$-arom.), 16.71 (C$_{10}$H$_3$).

(Green Solid)

tert-butyl 6-fluoro-3-iodo-1H-indole-1-carboxylate

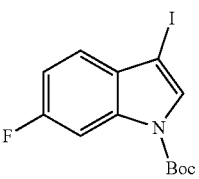

| Intermediate | LabBook Code |
|---|---|
| | CA 4-126 F1-6 (yield = 95%) | t$_R$ (HPLC) = 4.80 min  MS (ESI+) m/z = n.d.
$^1$H NMR (600 MHz, DMSO-d$_6$): δ (ppm) = 7.90 (s, 1H, H$_8$), 7.82 (dd, J = 10.2, 2.0 Hz, 1H, H$_3$), 7.40 (dd, J = 8.7, 5.3 Hz, 1H, H$_6$), 7.24 (td, J = 9.1, 2.4 Hz, 1H, H$_1$), 1.64 (s, 9H, H$_{14,15,16}$).
$^{13}$C NMR (151 MHz, DMSO-d$_6$): δ (ppm) = 160.69 (d, J = 239.6 Hz, C$_2$-arom.), 147.88 (C$_{17}$O), 134.17 (d, J = 13.2 Hz, C$_4$-arom.), 130.75 (d, J = 3.8 Hz, C$_8$H-arom.), 128.47 (C$_5$-arom.), 122.61 (d, J = 10.3 Hz, C$_6$H-arom.), 111.66 (d, J = 24.4 Hz, C$_1$H-arom.), 101.61 (d, J = 28.9 Hz, C$_3$H-arom.), 84.90 (C$_{13}$), 66.05 (C$_9$-arom.), 27.55 (s C$_{14,15,16}$H$_3$).

(Pale Brown Solid)

3-(4-methoxyphenyl)-1H-pyrrolo[3,2-b]pyridine (Procedure 10)

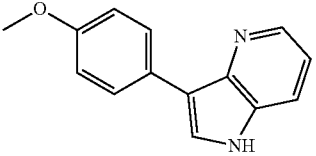 [SMILES: COc1ccc(-c2c[nH]c3cccnc23)cc1]

| VPC Number | LabBook Code | $IC_{50}$ (eGFP) = |
| --- | --- | --- |
| 13 | CA 4-127 Precipitate (yield = 89%) | $IC_{50}$ (PSA) = |
| | $t_R$ (HPLC) = 2.54 min | MS (ESI+) m/z = 225.1037 [(M + H)$^+$] |
| | Mp = 202-206° C. | |
| | HRMS (ESI+): calculated for $C_{14}H_{13}N_2O$, m/z = 225.1022; found, 2251027 | |
| | $^1$H NMR (600 MHz, DMSO-$d_6$): δ (ppm) = 11.42 (s, 1H, $H_{11}$), 8.43 (dd, J = 4.5, 1.5 Hz, 1H, $H_{13}$), 8.22-8.18 (m, 2H, $H_{2,6}$), 8.04 (d, J = 2.8 Hz, 1H, $H_7$), 7.80 (dd, J = 8.2, 1.5 Hz, 1H, $H_{15}$), 7.16 (dd, J = 8.1, 4.5 Hz, 1H, $H_{14}$), 7.01- | |
| (Pale Brown Solid) | 6.96 (m, 2H, $H_{3,5}$), 3.79 (s, 3H, $H_{17}$). | |
| | $^{13}$C NMR (151 MHz, DMSO-$d_6$): δ (ppm) = 157.12 ($C_1$-arom.), 143.36 ($C_9$-arom.), 142.39 ($C_{13}$H-arom.), 129.37 ($C_{10}$-arom.), 127.28 ($C_4$-arom.), 127.01 ($C_{2,6}$H-arom.), 125.43 ($C_7$H-arom.), 118.69 ($C_{15}$H-arom.), 116.38 ($C_{14}$H-arom.), 114.10 ($C_8$-arom.), 113.76 ($C_{3,5}$H-arom.), 55.01 ($C_{17}H_3$). | |

6-(7-methyl-1H-indol-3-yl)isoquinoline (Procedure 10)

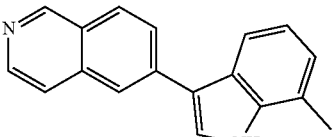

| VPC Number | LabBook Code | $IC_{50}$ (eGFP) = inactive |
| --- | --- | --- |
| 13765 | CA 4-128 Precipitate (yield = 34%) | $IC_{50}$ (PSA) = inactive |
| | $t_R$ (HPLC) = 3.01 min | MS (ESI+) m/z = 259.1230 [(M + H)$^+$] |
| | Mp = 222-225° C. | |
| | HRMS (ESI+): calculated for $C_{18}H_{15}N_2$, m/z = 259.1230; found, 259.1231 | |
| | $^1$H NMR (600 MHz, DMSO-$d_6$): δ (ppm) = 11.59 (s, 1H, H5), 9.25 (s, 1H, $H_{16}$), 8.47 (d, J= 5.7 Hz, 1H, $H_{12}$), 8.27 (s, 1H, $H_{17}$), 8.15-8.09 (m, 2H, $H_{19,20}$), 8.01 (d, J = 2.7 Hz, 1H, $H_4$), 7.95 (d, J = 8.0 Hz, 1H, $H_9$), 7.88 (d, J = | |
| (Yellowish Solid) | 5.8 Hz, 1H, $H_{13}$), 7.11 (t, J = 7.5 Hz, 1H, $H_9$), 7.03 (d, J = 7.0 Hz, 1H, $H_7$), 2.54 (s, 3H, $H_{10}$). | |
| | $^{13}$C NMR (151 MHz, DMSO-$d_6$): δ (ppm) = 151.69 ($C_{16}$H-arom.), 143.10 ($C_{12}$H-arom.), 138.20 ($C_{18}$-arom.), 136.65 ($C_1$-arom.), 136.13 ($C_{14}$-arom.), 127.81 ($C_{20}$H-arom.), 127.20 ($C_{19}$H-arom.), 126.42 ($C_{15}$-arom.), 125.23 ($C_4$H-arom.), 124.55 ($C_2$-arom.), 122.35 ($C_7$H-arom.), 121.35 ($C_6$-arom.), 121.17 ($C_{17}$H-arom.), 120.35 ($C_8$-arom.), 120.20 ($C_{13}$H-arom.), 116.98 ($C_9$H-arom.), 115.17 ($C_3$-arom.), 16.81 ($C_{10}H_3$). | |

2-(δ-fluoro-1H-indol-3-yl)quinoline

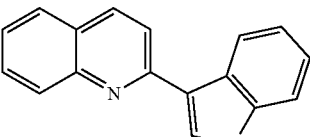

| VPC Number | LabBook Code | $IC_{50}$ (eGFP) = 0.1 |
| --- | --- | --- |
| 13764 | CA 4-131 F25-28 Precipitate (yield = 5%) | $IC_{50}$ (PSA) = 0.082 |
| | $t_R$ (HPLC) = 3.07 min | MS (ESI+) m/z = 263.0968 [(M + H)$^+$] |
| | Mp = 195-198° C. | |
| | HRMS (ESI+): calculated for $C_{17}H_{12}FN_2$, m/z = 263.0979; found, 263.0981 | |
| | $^1$H NMR (600 MHz, DMSO-$d_6$): δ (ppm) = 11.71 (s, 1H, $H_{17}$), 8.90 (dd, J = 8.7, 5.9 Hz, 1H, $H_{16}$), 8.36 (d, J = 2.6 Hz, 1H, $H_{18}$), 8.27 (d, J = 8.7 Hz, 1H, $H_{10}$), 8.06-8.02 (m, 2H, $H_{3,9}$), 7.90 (d, J = 7.7 Hz, 1H, $H_2$), 7.72 (ddd, J = | |
| (Pale Yellow Solid) | 8.3, 7.2, 1.3 Hz, 1H, $H_6$), 7.49 (ddd, J = 7.8, 6.6, 0.6 Hz, 1H, $H_1$), 7.26 (dd, J = 9.8, 2.4 Hz, 1H, $H_{13}$), 7.07 (td, J = 9.6, 2.4 Hz, 1H, $H_{11}$). | |
| | $^{13}$C NMR (151 MHz, DMSO-$d_6$): δ (ppm) = 159.13 (d, J = 235.8 Hz, $C_{12}$-arom.), 155.18 ($C_8$-arom.), 147.68 ($C_4$-arom.), 137.16 (d, J = 12.5 Hz, $C_{14}$-arom.), 135.69 ($C_{10}$H-arom.), 129.38 ($C_2$H-arom.), 128.39 ($C_3$H-arom.), 128.32 (d, J = 2.8 Hz, $C_{18}$H-arom.), 127.63 ($C_6$H-arom.), 125.87 ($C_5$-arom.), 125.02 ($C_1$H-arom.), 123.78 (d, J = 9.8 Hz, $C_{16}$H-arom.), 122.40 ($C_{15}$-arom.), 119.08 ($C_9$H-arom.), 115.58 ($C_{19}$-arom.), 108.64 (d, J = 23.6 Hz, $C_{11}$H-arom.), 97.73 (d, J = 25.4 Hz, $C_{13}$H-arom.). | |

A person of skill in the art based on the general knowledge in the art and the information provided herein would be able to synthesize the compounds described herein or modify the compounds described herein.

eGFP Cellular Transcription Assay

AR transcriptional activity was assayed as previously described (Tavassoli, P. et al. Rapid, non-destructive, cell-based screening assays for agents that modulate growth, death, and androgen receptor activation in prostate cancer cells. Prostate 2007, 67, 416-426). Briefly, stably transfected eGFP-expressing LNCaP human prostate cancer cells (LN-ARR2PB-eGFP) containing an androgen responsive probasin-derived promoter (ARR2PB) were grown in phenol red free RPMI 1640 supplemented with 5% CSS. After 5 days, the cells were plated into a 96-well plate (35,000 cells/well) with 0.1 nM of the synthetic androgen R1881 and increasing concentrations (0-100 μM) of compound. The cells were incubated for three days and the fluorescence was then measured (excitation 485 nm, emission 535 nm). The viability of these cells was assayed by MTS cell proliferation assay (CellTiter 961™ Aqueous One Solution Reagent, Promega™).

Structure Solution and Refinement

The ternary complex structure was solved by molecular replacement using the Phaser program (McCoy, A. J. et al. Phaser crystallographic software. J Appl Crystallogr 2007, 40, 658-674) and the coordinate of an apo-protein structure of AR-testosterone complex (Protein Data Bank entry 2AM9) as the search model. The structures were refined with iterative cycles of manual density fitting with COOT and refinement with Refmac (Murshudov, G. N. et al. Refinement of macromolecular structures by the maximum-likelihood method. Acta Crystallogr D Biol Crystallogr. 1997, 53, 240-255). The extra density of testosterone was clearly observed at the initial refinement step. A characteristic electron density of the compound was observed at the BF3 binding site.

Heterologous Expression of Androgen Receptor

The AR ligand binding domain was expressed and purified as previously described (Estebanez-Perpina, E. et al. Proc. Nat. Acad. Sci. USA (2007) 104:16074-16079).

eGFP Cellular AR Transcription Assay:

AR transcriptional activity was assayed as previously described.[21] Briefly, stably transfected eGFP-expressing LNCaP human prostate cancer cells (LN-ARR2PBeGFP) containing an androgen-responsive probasin-derived promoter (ARR2PB) were grown in phenol-red-free RPMI 1640 supplemented with 5% CSS. After 5 days, the cells were plated into a 96-well plate (35,000 cells/well) with 0.1 nM R1881 and increasing concentrations (0-100 µM) of compound. The cells were incubated for 3 days, and the fluorescence was then measured (excitation, 485 nm; emission, 535 nm). The viability of these cells has been assayed by the MTS cell proliferation assay (CellTiter 961 Aqueous One Solution Reagent, Promega) according to the instructions of the manufacturer.

Prostate Surface Antigen assay:

The evaluation of PSA excreted into the media was performed in parallel to the eGFP assay using the same plates (see above description). After the cells were incubated for 3 days 150 µl of the media was taken from each well, and added to 150 µl of PBS. PSA levels were then evaluated using Cobas e 411 analyzer instrument (Roche Diagnostics) according to the manufacturer's instructions.

EXAMPLES

Example 1—Virtual Screen for Potential BF3 Binders

Using a previously described (Axerio-Cilies, P. et al. Inhibitors of Androgen Receptor Activation Function-2 (AF2) Site Indentified Through Virtual Screening. J Med Chem 2011 54(18):6197-205), consensus-based in silico methodology we conducted a virtual screen of ~10 million purchasable chemical substances from the ZINC database to identify BF3-specific binders (also one NCI compound). The screening method used a combination of large-scale docking, ligand-based QSAR modeling, pharmacophore search, molecular field analysis, molecular-mechanic and molecular dynamic simulations (Cherkasov, A. et al. Progressive docking: a hybrid QSAR/docking approach for accelerating in silico high throughput screening. J Med Chem. 2006, 49, 7466-7478; Cherkasov, A. et al. 'Inductive' charges on atoms in proteins: comparative docking with the extended steroid benchmark set and discovery of a novel SHBG ligand. J Chem Inf Model 2005, 45, 1842-1853; and Santos-Filho, O. A. and Cherkasov, A. Using molecular docking, 3D-QSAR, and cluster analysis for screening structurally diverse data sets of pharmacological interest. J Chem Inf Model 2008, 48, 2054-2065). The results from each stage of this multi-parametric approach were compiled and the compounds were ranked using a consensus scoring procedure. The highest ranked compounds were visualized and initial candidates, predicted to have a high potential for binding to the BF3 pocket, were selected for empirical testing.

Example 2—Cell-Based Testing

All compounds were screened for their ability to inhibit AR transcriptional activity using a non-destructive, cell-based eGFP screening assay (Tavassoli, P. et al. Rapid, non-destructive, cell-based screening assays for agents that modulate growth, death, and androgen receptor activation in prostate cancer cells. Prostate 2007, 67, 416-426). In this assay, the expression of eGFP is under the control of an androgen responsive probasin-derived promoter and can quantify AR transcriptional activity. From the compounds tested, 7 showed sub-µM IC50 values in the eGFP assay. Compounds that exhibited non-specific cellular toxicity were removed from further analysis. The most potent molecules had $IC_{50}$'s ranging in from 0.11 to 50 µM range (TABLE 3). Some compounds were also tested in the PSA assay (TABLE 3).

TABLE 3

Structural and experimental data for the AR $BF_3$ interactors.

| Internal Number | ZINC Number | STRUCTURE | eGFP $IC_{50}$ (µM) | PSA $IC_{50}$ (µM) |
|---|---|---|---|---|
| 13555 | Synthetic derivative | 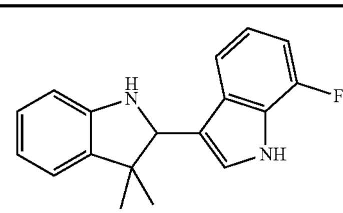 | Inactive | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13557 | Synthetic derivative | 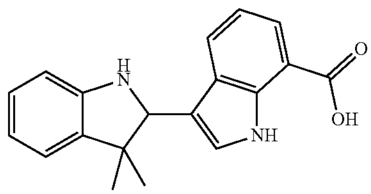 [SMILES: CC1(C)c2ccccc2NC1c1c[nH]c2c(C(=O)O)cccc12] | Inactive | Not tested |
| 9039 | Synthetic derivative | 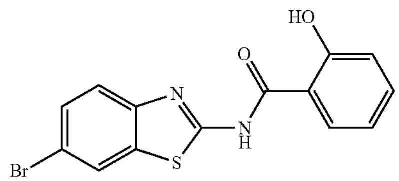 [SMILES: O=C(Nc1nc2ccc(Br)cc2s1)c1ccccc1O] | >200 | Not tested |
| 13312 | ZINC00298052 | 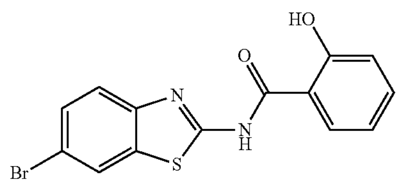 [SMILES: O=C(Nc1nc2ccc(Br)cc2s1)c1ccccc1O] | 200.0 | Not tested |
| 9040 | Synthetic derivative | 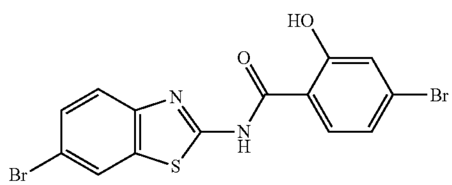 [SMILES: O=C(Nc1nc2ccc(Br)cc2s1)c1ccc(Br)cc1O] | 39.13 | Not tested |
| 13309 | ZINC01234071 | 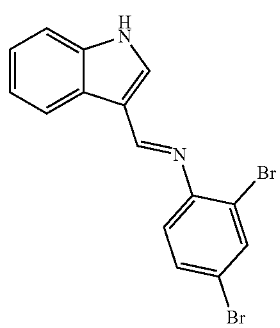 [SMILES: Brc1ccc(/N=C/c2c[nH]c3ccccc23)c(Br)c1] | 27.2 | Not tested |
| 9034 | Synthetic derivative | 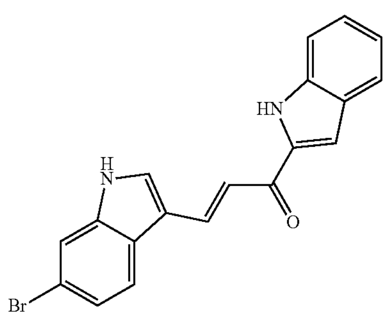 [SMILES: O=C(/C=C/c1c[nH]c2cc(Br)ccc12)c1cc2ccccc2[nH]1] | 20 | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13551 | Synthetic derivative | 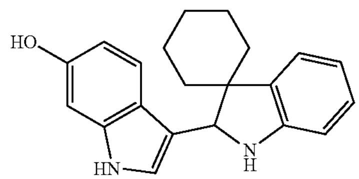 [SMILES: Oc1ccc2c(C3Nc4ccccc4C34CCCCC4)c[nH]c2c1] | 15.5 | Not tested |
| 13550 | Synthetic derivative | 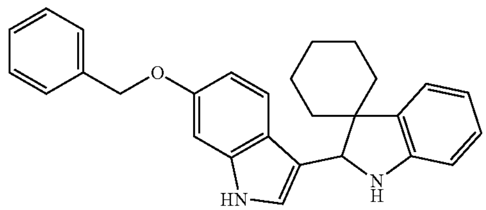 [SMILES: c1ccc(COc2ccc3c(C4Nc5ccccc5C45CCCCC5)c[nH]c3c2)cc1] | 11.75 | Not tested |
| 9026 | Synthetic derivative | 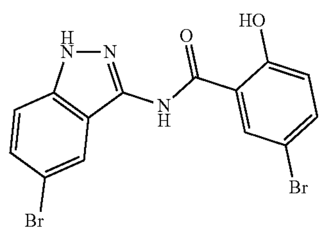 [SMILES: O=C(Nc1n[nH]c2ccc(Br)cc12)c1cc(Br)ccc1O] | 11.67 | Not tested |
| 13544 | Synthetic derivative | 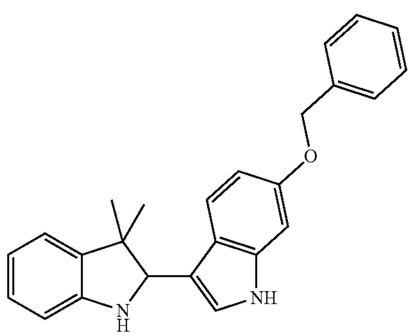 [SMILES: CC1(C)c2ccccc2NC1c1c[nH]c2cc(OCc3ccccc3)ccc12] | 11.4 | |
| 13561 | Synthetic derivative | 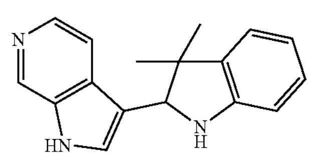 [SMILES: CC1(C)c2ccccc2NC1c1c[nH]c2cnccc12] | 10.7 | Not tested |
| 13310 | ZINC00297221 | 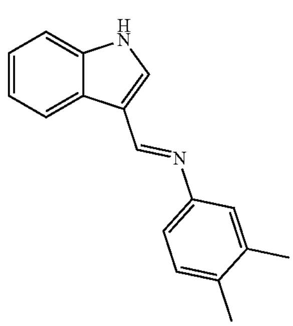 [SMILES: Cc1ccc(/N=C/c2c[nH]c3ccccc23)cc1C] | 10.3 | Not tested |

219
220
TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13232 | ZINC02992016 | 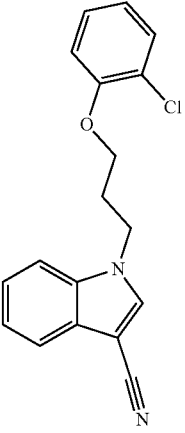 [SMILES: N#Cc1cn(CCCOc2ccccc2Cl)c2ccccc12] | 10 | Not tested |
| 9028 | Synthetic derivative | 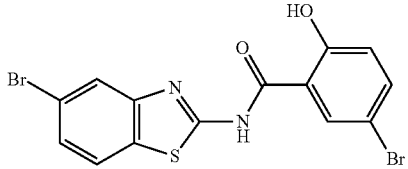 | 10 | Not tested |
| 13050 | ZINC03365783 | 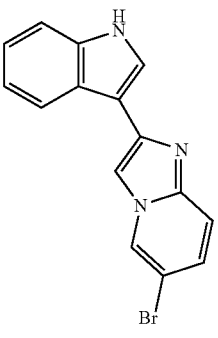 [SMILES: Brc1ccc2nc(-c3c[nH]c4ccccc34)cn2c1] | 9.725 | Not Determined |
| 13300 | ZINC00270867 | 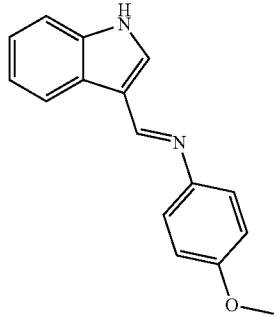 [SMILES: COc1ccc(/N=C/c2c[nH]c3ccccc23)cc1] | 9.3 | 6.76 |

TABLE 3-continued

Structural and experimental data for the AR $BF_3$ interactors.

| Internal Number | ZINC Number | STRUCTURE | eGFP $IC_{50}$ (μM) | PSA $IC_{50}$ (μM) |
|---|---|---|---|---|
| 13299 | ZINC00499454 | (structure) | 8.2 | Not tested |
| 9027 | Synthetic derivative | (structure) | 7.721 | Not tested |
| 13538 | Synthetic derivative | (structure) | 7.7 | |
| 13304 | ZINC00270887 | (structure) | 7.3 | 4.54 |
| 13258 | ZINC18191564 | (structure) | 6.8 | Not tested |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13559 | Synthetic derivative | 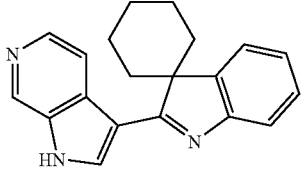 [SMILES: c1ccc2c(c1)N=C(c1c[nH]c3cnccc13)C21CCCCC1] | 6.6 | Not tested |
| 13512 | Synthetic derivative | 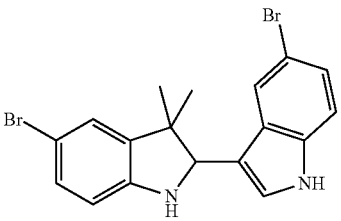 [SMILES: CC1(C)c2cc(Br)ccc2NC1c1c[nH]c2ccc(Br)cc12] | 6.0 | |
| 13542 | Synthetic derivative | 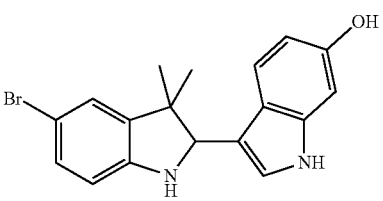 [SMILES: CC1(C)c2cc(Br)ccc2NC1c1c[nH]c2cc(O)ccc12] | 5.7 | |
| 9125 | ZINC30469682 | 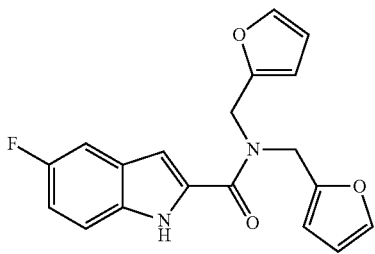 [SMILES: O=C(c1cc2cc(F)ccc2[nH]1)N(Cc1ccco1)Cc1ccco1] | 5.2 | 2.4 |
| 13186 | ZINC00513042 | 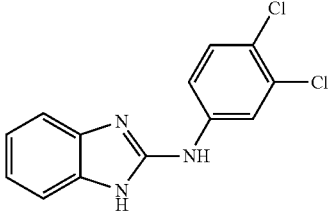 [SMILES: Clc1ccc(Nc2nc3ccccc3[nH]2)cc1Cl] | 5 | Not determined |
| 13224 | ZINC04106386 | 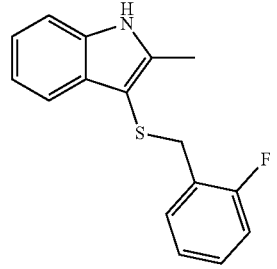 [SMILES: Cc1[nH]c2ccccc2c1SCc1ccccc1F] | 5 | Not determined |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13524 | Synthetic derivative | 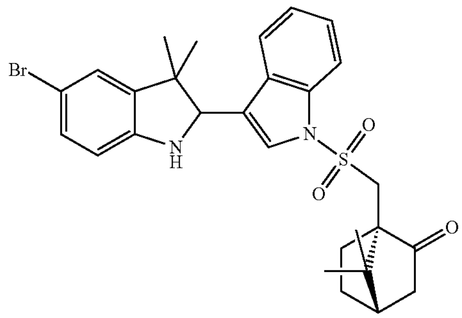 [SMILES: CC1(C)c2cc(Br)ccc2NC1c1cn(S(=O)(=O)C[C@]23CC[C@@H](CC2=O)C3(C)C)c2ccccc12] | 4.9 | 6.65 |
| 13508 | Synthetic derivative | 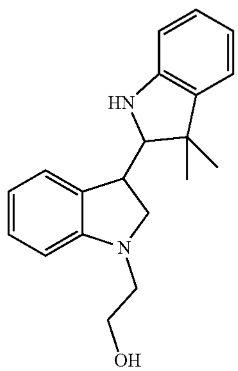 [SMILES: CC1(C)c2ccccc2NC1C1CN(CCO)c2ccccc21] | 4.8 | 2.7 |
| 13250 | ZINC03149578 | 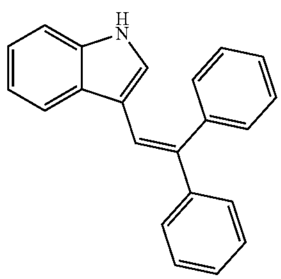 [SMILES: C(=C(c1ccccc1)c1ccccc1)c1c[nH]c2ccccc12] | 4.7 | Not tested |
| 13530 | Synthetic derivative | 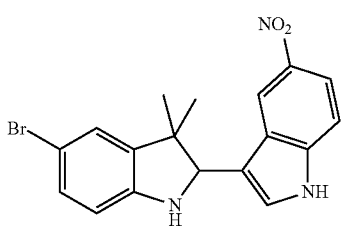 [SMILES: CC1(C)c2cc(Br)ccc2NC1c1c[nH]c2ccc([N+](=O)[O-])cc12] | 4.7 | 1.60 |
| 13303 | ZINC00270884 | 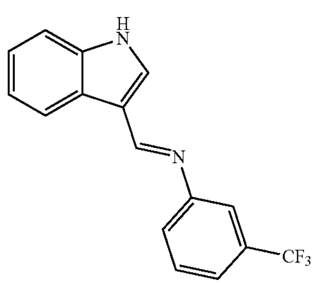 [SMILES: FC(F)(F)c1cccc(/N=C/c2c[nH]c3ccccc23)c1] | 4.5 | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13503 | Synthetic derivative | 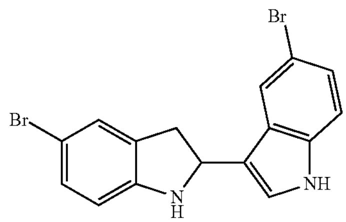 [SMILES: Brc1ccc2c(c1)CC(c1c[nH]c3ccc(Br)cc13)N2] | 4.5 | Not tested |
| 13257 | ZINC12345945 | 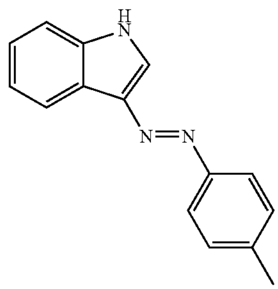 [SMILES: Cc1ccc(/N=N/c2c[nH]c3ccccc23)cc1] | 4.2 | Not tested |
| 13502 | Synthetic derivative | 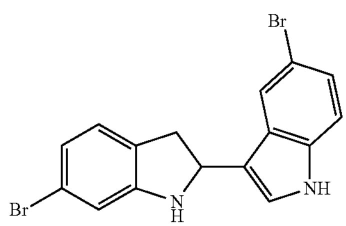 [SMILES: Brc1ccc2c(c1)NC(c1c[nH]c3ccc(Br)cc13)C2] | 4.1 | Not tested |
| 9037 | Synthetic derivative | 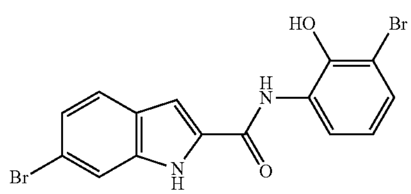 [SMILES: O=C(Nc1cccc(Br)c1O)c1cc2ccc(Br)cc2[nH]1] | 4.093 | Not tested |
| 13243 | ZINC00253227 | 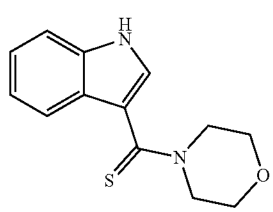 [SMILES: S=C(c1c[nH]c2ccccc12)N1CCOCC1] | 3.9 | Not tested |
| 13543 | Synthetic derivative | 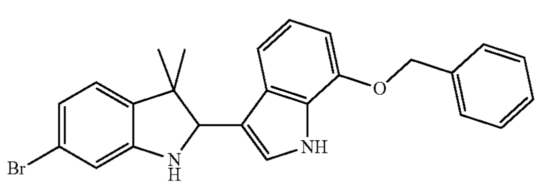 [SMILES: CC1(C)c2ccc(Br)cc2NC1c1c[nH]c2c(OCc3ccccc3)cccc12] | 3.7 | 3.19 |

TABLE 3-continued
Structural and experimental data for the AR BF3 interactors.
| Internal Number | ZINC Number | STRUCTURE | eGFP IC$_{50}$ (μM) | PSA IC$_{50}$ (μM) |
|---|---|---|---|---|
| 13424 | ZINC12346351 | 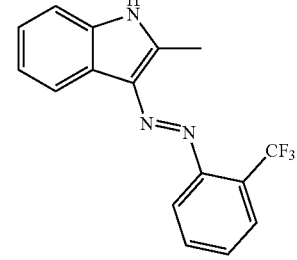 | 3.7 | 3.58 |
| 13516 | Synthetic derivative | 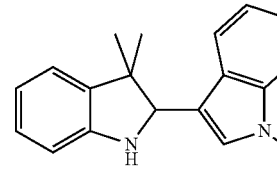 | 3.6 | Not tested |
| 6054 | ZINC08718421 | 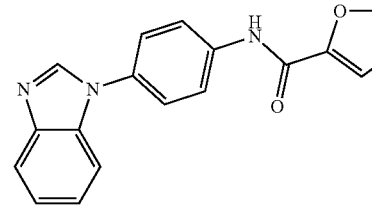 | 3.4 | Not Determined |
| 13505 | Synthetic derivative | 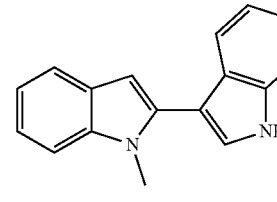 | 3.4 | Not tested |
| 13522 | Synthetic derivative | 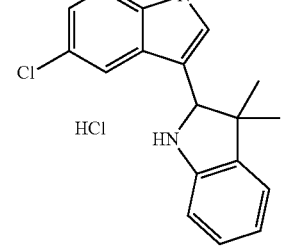 | 3.4 | 2.19 |
| 13029 | ZINC00210926 | 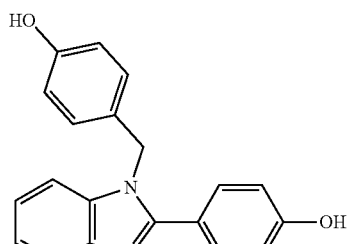 | 3.221 | Not Determined |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13548 | Synthetic derivative | 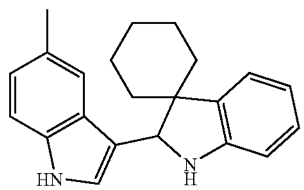 [SMILES: Cc1ccc2[nH]cc(C3Nc4ccccc4C34CCCCC4)c2c1] | 3.21 | 4.24 |
| 9128 | ZINC47424036 | 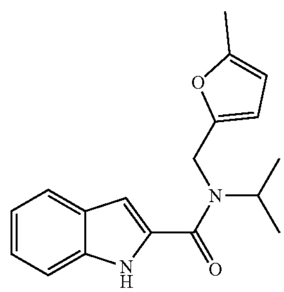 [SMILES: Cc1ccc(CN(C(=O)c2cc3ccccc3[nH]2)C(C)C)o1] | 3.2 | 3.5 |
| 13525 | Synthetic derivative | 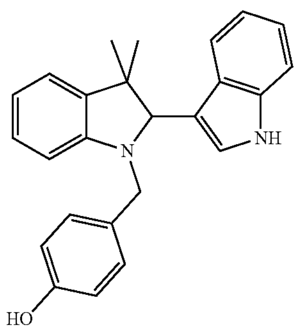 [SMILES: CC1(C)c2ccccc2N(Cc2ccc(O)cc2)C1c1c[nH]c2ccccc12] | 3.1 | 7.09 |
| 13511 | Synthetic derivative | 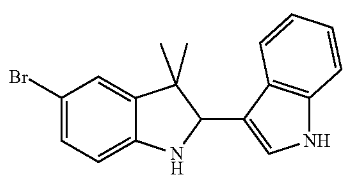 [SMILES: CC1(C)c2cc(Br)ccc2NC1c1c[nH]c2ccccc12] | 3.0 | 1.9 |
| 13216 | ZINC06025409 | 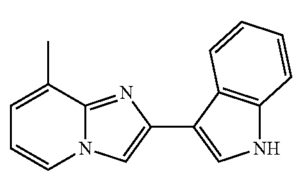 [SMILES: Cc1cccn2cc(-c3c[nH]c4ccccc34)nc12] | 2.8 | Not Determined |
| 13532 | Synthetic derivative | 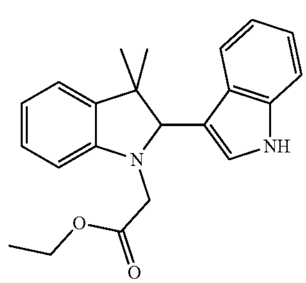 [SMILES: CCOC(=O)CN1c2ccccc2C(C)(C)C1c1c[nH]c2ccccc12] | 2.8 | 3.10 |

TABLE 3-continued
Structural and experimental data for the AR BF₃ interactors.
| Internal Number | ZINC Number | STRUCTURE | eGFP IC$_{50}$ (μM) | PSA IC$_{50}$ (μM) |
|---|---|---|---|---|
| 13260 | ZINC4941101 | 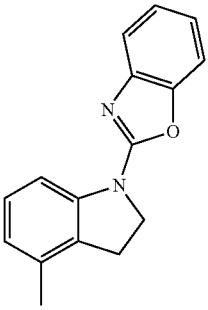 [SMILES: Cc1cccc2c1CCN2c1nc2ccccc2o1] | 2.7 | Not tested |
| 13416 | ZINC01869964 | 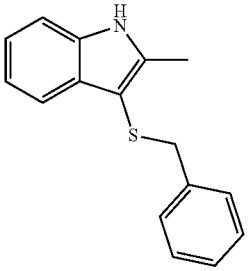 [SMILES: Cc1[nH]c2ccccc2c1SCc1ccccc1] | 2.7 | 2.32 |
| 13509 | Synthetic derivative | 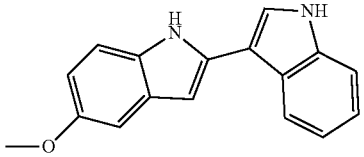 [SMILES: COc1ccc2[nH]c(-c3c[nH]c4ccccc34)cc2c1] | 2.6 | 3.1 |
| 9043 | Synthetic derivative | 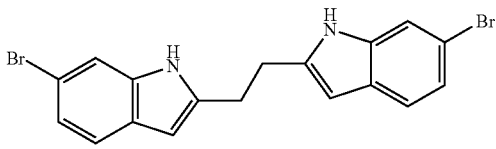 [SMILES: Brc1ccc2cc(CCc3cc4ccc(Br)cc4[nH]3)[nH]c2c1] | 2.503 | Not tested |
| 13202 | ZINC01768344 | 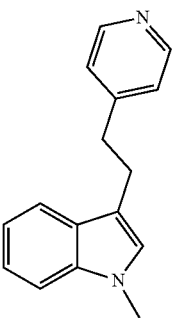 [SMILES: Cn1cc(CCc2ccncc2)c2ccccc21] | 2.5 | Not Determined |
| 13510 | Synthetic derivative | 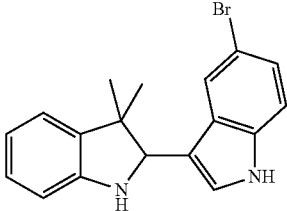 [SMILES: CC1(C)c2ccccc2NC1c1c[nH]c2ccc(Br)cc12] | 2.5 | 1.54 |

TABLE 3-continued
Structural and experimental data for the AR BF₃ interactors.
| Internal Number | ZINC Number | STRUCTURE | eGFP IC$_{50}$ (μM) | PSA IC$_{50}$ (μM) |
|---|---|---|---|---|
| 13540 | Synthetic derivative | 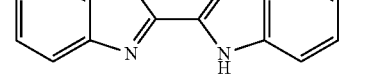 | 2.5 | Not tested |
| 13411 | ZINC04106386 | 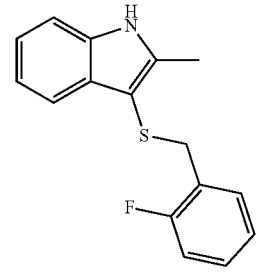 [SMILES: Cc1[nH]c2ccccc2c1SCc1ccccc1F] | 2.4 | 2.4 |
| 13560 | Synthetic derivative | 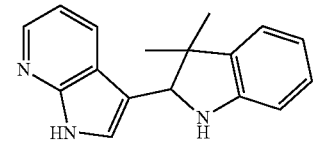 [SMILES: CC1(C)c2ccccc2NC1c1c[nH]c2ncccc12] | 2.3 | 7.5 |
| 13214 | ZINC26472877 | 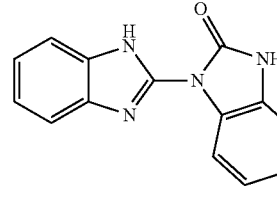 | 2.2 | Not Determined |
| 13235 | ZINC01037115 | 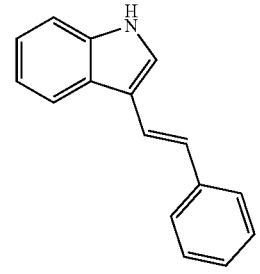 [SMILES: C(=C\c1c[nH]c2ccccc12)/c1ccccc1] | 2.2 | 1.01 |
| 13536 | Synthetic derivative | 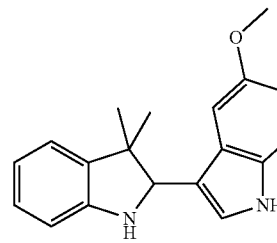 | 2.2 | 2.521 |
| 13556 | Synthetic derivative | 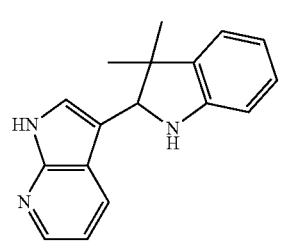 [SMILES: CC1(C)c2ccccc2NC1c1c[nH]c2ncccc12] | 2.112 | 2.18 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13127 | ZINC00392643 | 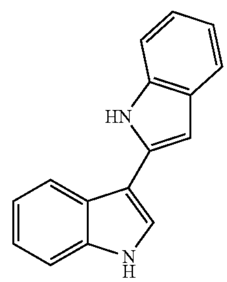 [SMILES: c1ccc2[nH]c(-c3c[nH]c4ccccc34)cc2c1] | 2.1 | 0.11 |
| 13261 | ZINC48546225 | 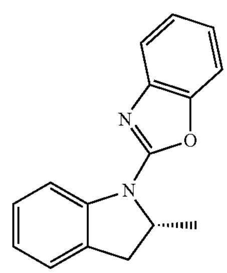 [SMILES: C[C@@H]1Cc2ccccc2N1c1nc2ccccc2o1] | 2.1 | Not tested |
| 13215 | ZINC05504717 | 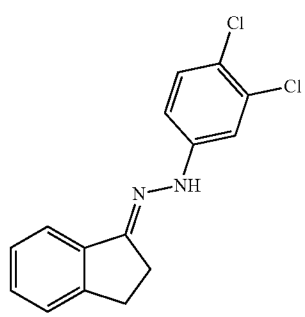 [SMILES: Clc1ccc(N/N=C2\CCc3ccccc32)cc1Cl] | 2 | Not Determined |
| 13504 | Synthetic derivative | 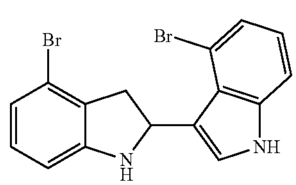 [SMILES: Brc1cccc2c1CC(c1c[nH]c3cccc(Br)c13)N2] | 2.0 | 1.69 |
| 13167 | NSC105329 | 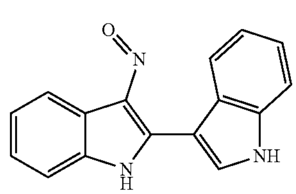 [SMILES: O=Nc1c(-c2c[nH]c3ccccc23)[nH]c2ccccc12] | 1.9 | 1.25 |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13206 | ZINC04962047 | 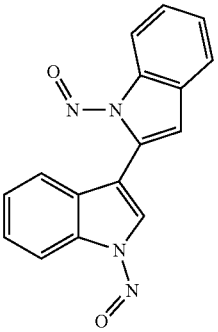 [SMILES: O=Nn1cc(-c2cc3ccccc3n2N=O)c2ccccc21] | 1.8 | Not Determined |
| 13145 | ZINC34603778 | 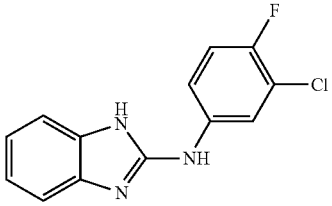 [SMILES: Fc1ccc(Nc2nc3ccccc3[nH]2)cc1Cl] | 1.7 | 2.46 |
| 13549 | Synthetic derivative | 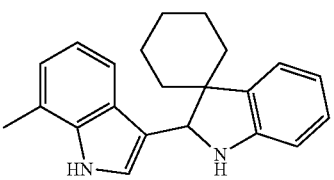 [SMILES: Cc1cccc2c(C3Nc4ccccc4C34CCCCC4)c[nH]c12] | 1.7 | 2.57 |
| 13245 | ZINC00555700 | 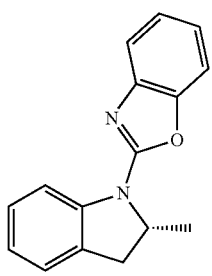 | 1.7 | 1.69 |
| 13036 | ZINC14961821 | 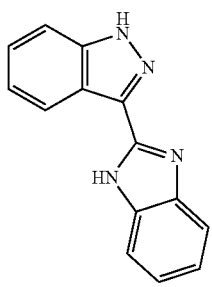 [SMILES: c1ccc2[nH]c(-c3n[nH]c4ccccc34)nc2c1] | 1.602 | Not Determined |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13166 | ZINC01723993 | 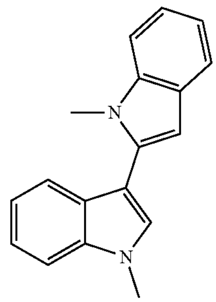 [SMILES: Cn1cc(-c2cc3ccccc3n2C)c2ccccc21] | 1.6 | 2.12 |
| 13558 | Synthetic derivative | 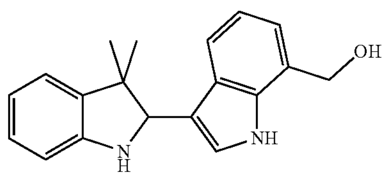 [SMILES: CC1(C)c2ccccc2NC1c1c[nH]c2c(CO)cccc12] | 1.6 | 2.1 |
| 13535 | Synthetic derivative | 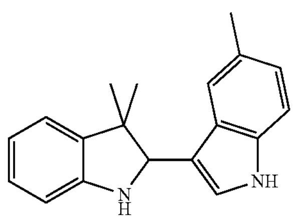 [SMILES: Cc1ccc2[nH]cc(C3Nc4ccccc4C3(C)C)c2c1] | 1.5 | 1.873 |
| 13164-B | ZINC02046058 | 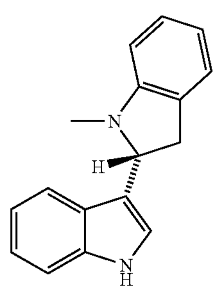 | 1.3 | 1.59 |
| 13500 | Synthetic derivative | 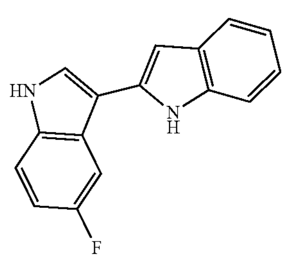 [SMILES: Fc1ccc2[nH]cc(-c3cc4ccccc4[nH]3)c2c1] | 1.23 | 0.41 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13254 | ZINC18191551 | 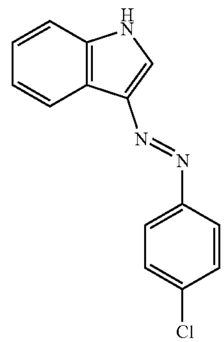 [SMILES: Clc1ccc(/N=N/c2c[nH]c3ccccc23)cc1] | 1.2 | Not tested |
| 13410 | ZINC04106383 | 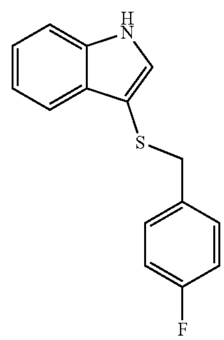 [SMILES: Fc1ccc(CSc2c[nH]c3ccccc23)cc1] | 1.2 | 2.03 |
| 13552 | Synthetic derivative | 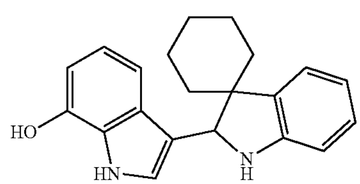 [SMILES: Oc1cccc2c(C3Nc4ccccc4C34CCCCC4)c[nH]c12] | 1.125 | 1.14 |
| 13423 | ZINC18191568 | 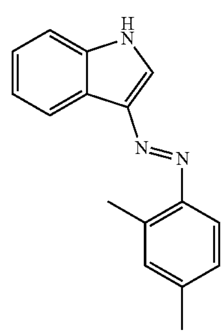 [SMILES: Cc1ccc(/N=N/c2c[nH]c3ccccc23)c(C)c1] | 1.1 | 1.2 |
| 13222 | ZINC02718340 | 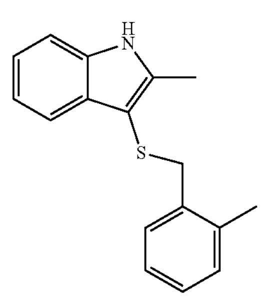 [SMILES: Cc1ccccc1CSc1c(C)[nH]c2ccccc12] | 0.95 | 0.74 |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13247 | ZINC48090221 | 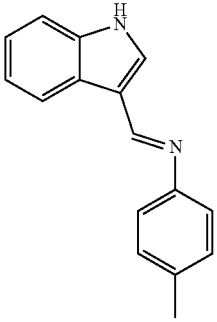 [SMILES: Cc1ccc(/N=C/c2c[nH]c3ccccc23)cc1] | 0.9 | 0.43 |
| 13412 | ZINC02718340 | 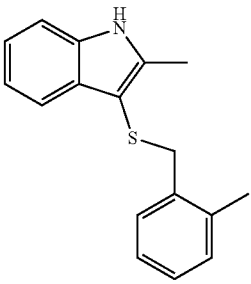 [SMILES: Cc1ccccc1CSc1c(C)[nH]c2ccccc12] | 0.9 | 1.23 |
| 13534 | Synthetic derivative | 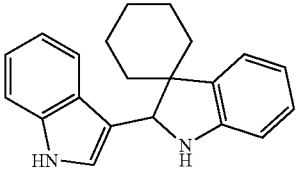 [SMILES: c1ccc2c(c1)NC(c1c[nH]c3ccccc13)C21CCCCC1] | 0.8 | 1.251 |
| 13434 | ZINC00069102 | 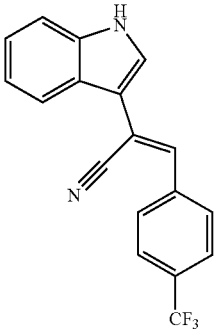 [SMILES: N#C/C(=C\c1ccc(C(F)(F)F)cc1)c1c[nH]c2ccccc12] | 0.8 | 0.73 |
| 13164-A | ZINC02046058 | 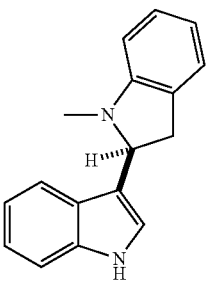 | 0.77 | 0.67 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13220 | ZINC48544111 | 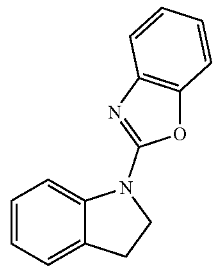 [SMILES: c1ccc2c(c1)CCN2c1nc2ccccc2o1] | 0.7 | Not Determined |
| 13225 | ZINC18191568 | 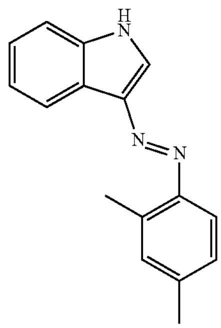 [SMILES: Cc1ccc(/N=N/c2c[nH]c3ccccc23)c(C)c1] | 0.7 | 0.9 |
| 13537 | Synthetic derivative | 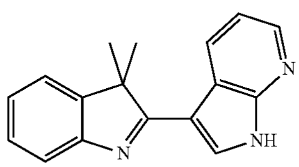 [SMILES: CC1(C)C(c2c[nH]c3ncccc23)=Nc2ccccc21] | 0.7 | 0.8057 |
| 13436 | ZINC00068959 | 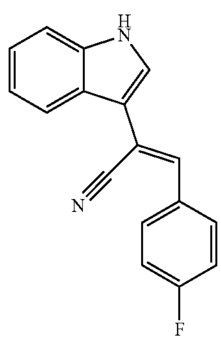 [SMILES: N#C/C(=C\c1ccc(F)cc1)c1c[nH]c2ccccc12] | 0.6 | 0.4 |
| 13554 | Synthetic derivative | 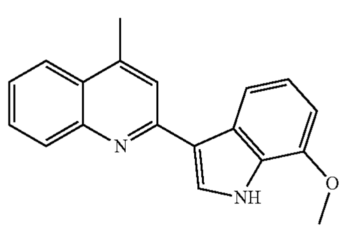 [SMILES: COc1cccc2c(-c3cc(C)c4ccccc4n3)c[nH]c12] | 0.59 | 0.67 |
| 13541 | Synthetic derivative | 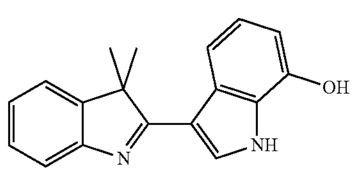 [SMILES: CC1(C)C(c2c[nH]c3c(O)cccc23)=Nc2ccccc21] | 0.5 | 0.94 |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13255 | ZINC18191553 | 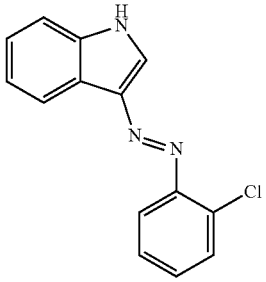 [SMILES: Clc1ccccc1/N=N/c1c[nH]c2ccccc12] | 0.5 | 0.46 |
| 13163-A | ZINC02043019 | 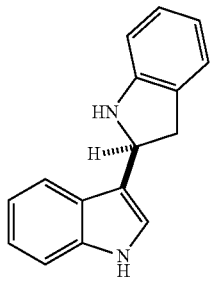 | 0.48 | 0.16 |
| 13163-B | ZINC02043019 | 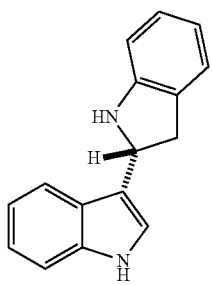 | 0.48 | 0.24 |
| 13256 | ZINC05848672 | 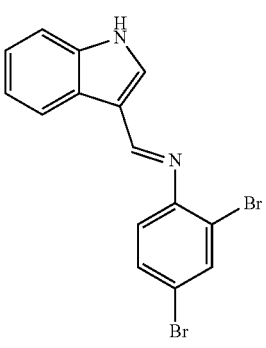 [SMILES: Brc1ccc(/N=C/c2c[nH]c3ccccc23)c(Br)c1] | 0.4 | 0.13 |
| 13521 | Synthetic derivative | 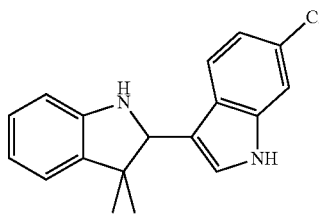 | 0.4 | 0.26 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13427 | ZINC00588219 | (indole-CH=N-phenyl-C(O)NH₂ structure) | 0.4 | 0.31 |
| 13259 | ZINC18191559 | (indole-N=N-phenyl-CF₃ structure) | 0.3 | 0.25 |
| 13506 | Synthetic derivative | (bis-indole with gem-dimethyl indoline structure) | 0.18 | 0.6 |
| 13226 | ZINC18191571 | (indole-N=N-phenyl-Cl structure) 23 | 0.11 | 0.076 |
| 13562 | Known see U.S. Pat. No. 6,207,679 | (2-(indol-3-yl)quinoline structure) | 0.06 | 0.14 |
| 13566 | Known see U.S. Pat. No. 6,207,679 | (2-(7-methyl-indol-3-yl)quinoline structure) | 0.004 | 0.011 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13567 | Synthetic derivative | 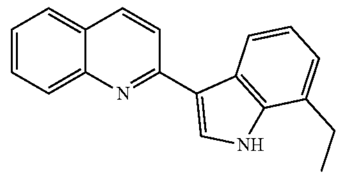 [SMILES: CCc1cccc2c(-c3ccc4ccccc4n3)c[nH]c12] | 0.200 | 0.230 |
| 13568 | Synthetic derivative | 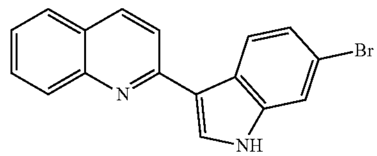 [SMILES: Brc1ccc2c(-c3ccc4ccccc4n3)c[nH]c2c1] | 1.300 | 1.560 |
| 13569 | Synthetic derivative | 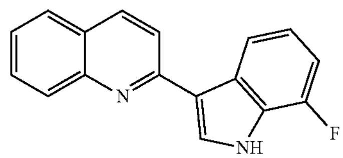 | 1.600 | Not tested |
| 13570 | Synthetic derivative | 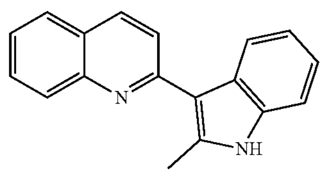 [SMILES: Cc1[nH]c2ccccc2c1-c1ccc2ccccc2n1] | 20.000 | Not tested |
| 13571 | Synthetic derivative | 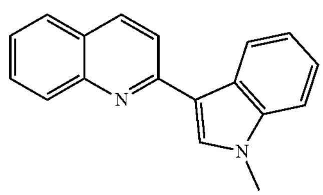 [SMILES: Cn1cc(-c2ccc3ccccc3n2)c2ccccc21] | 1.100 | Not tested |
| 13573 | Synthetic derivative | 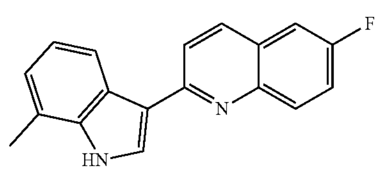 [SMILES: Cc1cccc2c(-c3ccc4cc(F)ccc4n3)c[nH]c12] | 0.560 | Not tested |
| 13574 | Synthetic derivative | 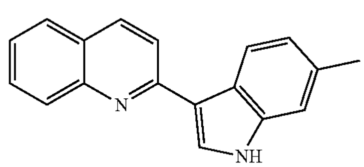 [SMILES: Cc1ccc2c(-c3ccc4ccccc4n3)c[nH]c2c1] | 2.570 | Not tested |
| 13576 | Synthetic derivative | 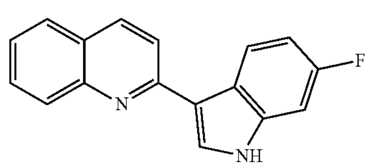 [SMILES: Fc1ccc2c(-c3ccc4ccccc4n3)c[nH]c2c1] | 0.144 | 0.048 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13577 | Synthetic derivative | 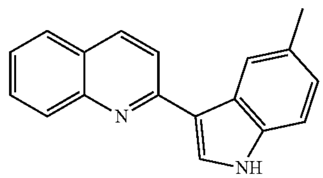 [SMILES: Cc1ccc2[nH]cc(-c3ccc4ccccc4n3)c2c1] | 3.200 | 1.730 |
| 13579 | Synthetic derivative | 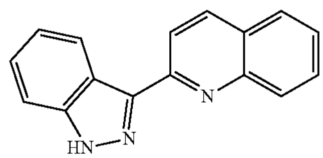 | 0.101 | 0.043 |
| 13580 | Synthetic derivative | 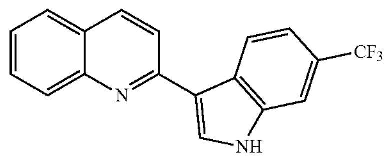 [SMILES: FC(F)(F)c1ccc2c(-c3ccc4ccccc4n3)c[nH]c2c1] | 2.900 | Not tested |
| 13582 | Synthetic derivative | 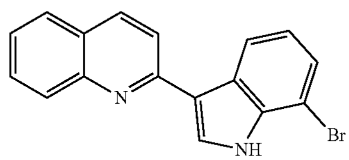 [SMILES: Brc1cccc2c(-c3ccc4ccccc4n3)c[nH]c12] | 0.052 | 0.041 |
| 13585 | Synthetic derivative | 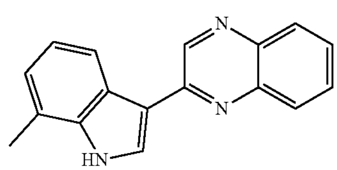 [SMILES: Cc1cccc2c(-c3cnc4ccccc4n3)c[nH]c12] | 0.110 | 0.039 |
| 13587 | Synthetic derivative | 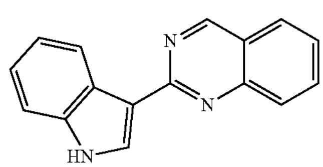 [SMILES: c1ccc2nc(-c3c[nH]c4ccccc34)ncc2c1] | 0.760 | 0.530 |
| 13589 | Synthetic derivative | 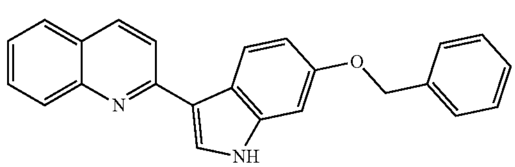 [SMILES: c1ccc(COc2ccc3c(-c4ccc5ccccc5n4)c[nH]c3c2)cc1] | 5.300 | Not tested |
| 13591 | Synthetic derivative | 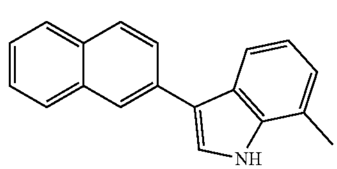 [SMILES: Cc1cccc2c(-c3ccc4ccccc4c3)c[nH]c12] | 0.042 | 0.085 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13592 | Synthetic derivative | 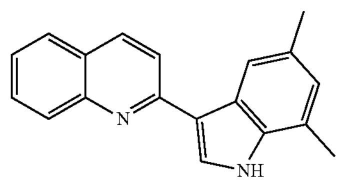 [SMILES: Cc1cc(C)c2[nH]cc(-c3ccc4ccccc4n3)c2c1] | 1.590 | 1.220 |
| 13593 | Synthetic derivative | 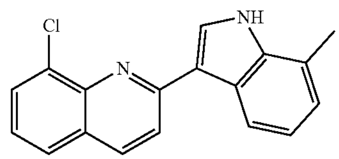 | 0.198 | 0.130 |
| 13594 | Synthetic derivative | 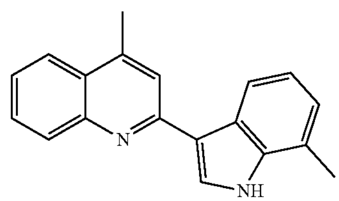 [SMILES: Cc1cc(-c2c[nH]c3c(C)cccc23)nc2ccccc12] | 0.166 | 0.099 |
| 13595 | Synthetic derivative | 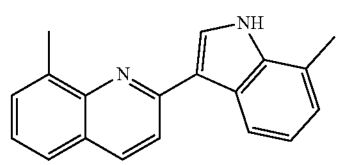 | 0.177 | Not tested |
| 13596 | Synthetic derivative | 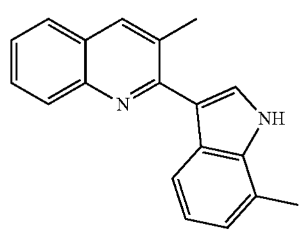 [SMILES: Cc1cc2ccccc2nc1-c1c[nH]c2c(C)cccc12] | Inactive | Inactive |
| 13597 | Synthetic derivative | 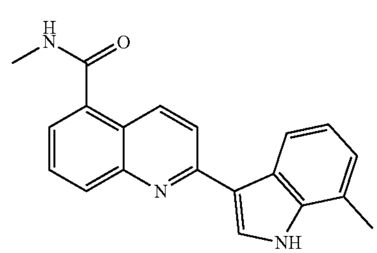 | 0.236 | 0.132 |
| 13598 | Synthetic derivative | 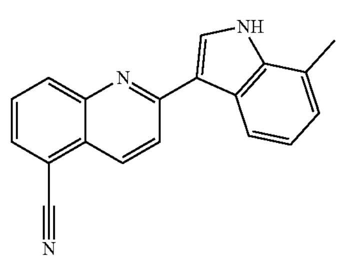 [SMILES: Cc1cccc2c(-c3ccc4c(C#N)cccc4n3)c[nH]c12] | Inactive | Inactive |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13599 | Synthetic derivative | 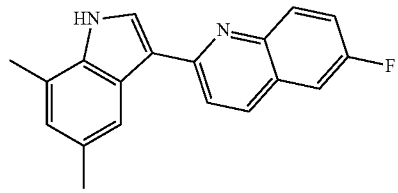 [SMILES: Cc1cc(C)c2[nH]cc(-c3ccc4cc(F)ccc4n3)c2c1] | Inactive | Inactive |
| 13600 | Synthetic derivative | 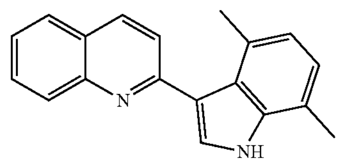 [SMILES: Cc1ccc(C)c2c(-c3ccc4ccccc4n3)c[nH]c12] | 1.249 | 0.929 |
| 13601 | Synthetic derivative | 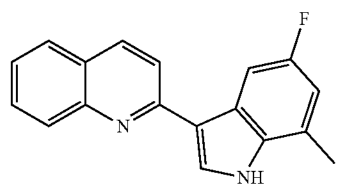 [SMILES: Cc1cc(F)cc2c(-c3ccc4ccccc4n3)c[nH]c12] | 0.233 | 0.165 |
| 13602 | Synthetic derivative | 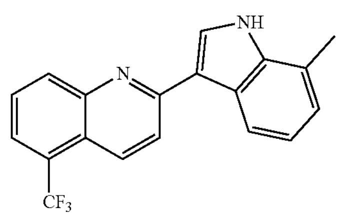 | 0.240 | 0.182 |
| 13603 | Synthetic derivative | 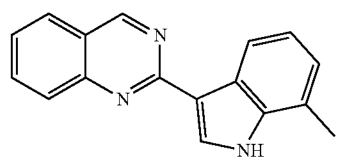 [SMILES: Cc1cccc2c(-c3ncc4ccccc4n3)c[nH]c12] | 0.633 | 0.339 |
| 13604 | Synthetic derivative | 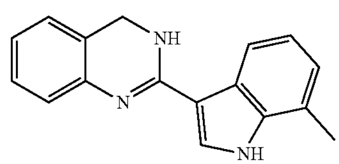 [SMILES: Cc1cccc2c(C3=Nc4ccccc4CN3)c[nH]c12] | Inactive | Inactive |
| 13605 | Synthetic derivative | 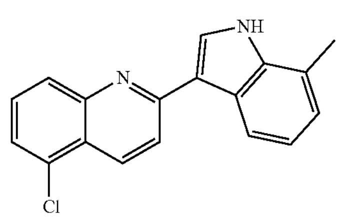 [SMILES: Cc1cccc2c(-c3ccc4c(Cl)cccc4n3)c[nH]c12] | Inactive | Inactive |
| 13606 | Synthetic derivative | 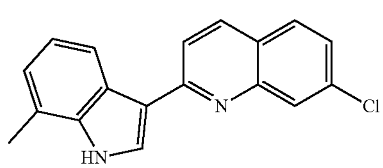 [SMILES: Cc1cccc2c(-c3ccc4ccc(Cl)cc4n3)c[nH]c12] | 1.649 | 1.427 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13607 | Synthetic derivative | 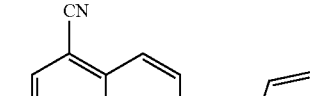 | 0.168 | 0.087 |
| 13608 | Synthetic derivative | 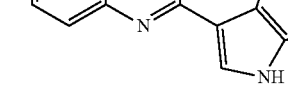 | Inactive | Inactive |
| 13609 | Synthetic derivative | 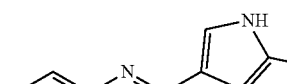 | Inactive | Inactive |
| 13610 | Synthetic derivative | 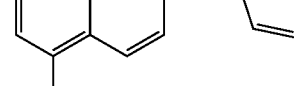 | 0.032 | 0.013 |
| 13611 | Synthetic derivative | 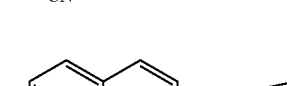 | 0.297 | 0.121 |
| 13612 | Synthetic derivative | 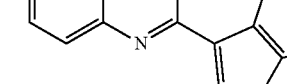 | 1.44 | 0.813 |
| 13613 | Synthetic derivative | 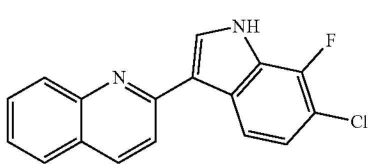 [SMILES: Fc1c(Cl)ccc2c(-c3ccc4ccccc4n3)c[nH]c12] | 11.540 | 1.738 |
| 13614 | Synthetic derivative | 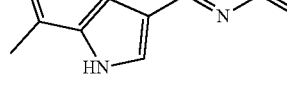 | 1.117 | 0.597 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13615 | Synthetic derivative | 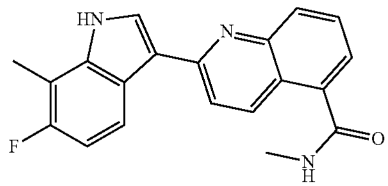 [SMILES: CNC(=O)c1cccc2nc(-c3c[nH]c4c(C)c(F)ccc34)ccc12] | Inactive | Inactive |
| 13616 | Synthetic derivative | 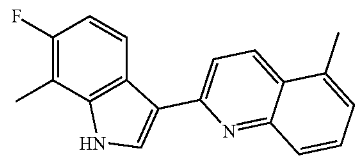 [SMILES: Cc1cccc2nc(-c3c[nH]c4c(C)c(F)ccc34)ccc12] | Inactive | Inactive |
| 13617 | Synthetic derivative | 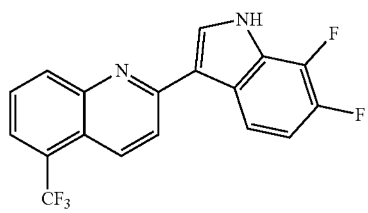 [SMILES: Fc1ccc2c(-c3ccc4c(C(F)(F)F)cccc4n3)c[nH]c2c1F] | Inactive | Inactive |
| 13618 | Synthetic derivative | 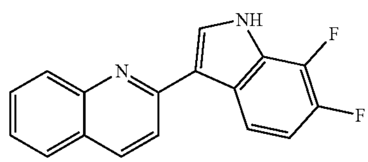 [SMILES: Fc1ccc2c(-c3ccc4ccccc4n3)c[nH]c2c1F] | 0.194 | 0.13 |
| 13619 | Synthetic derivative | 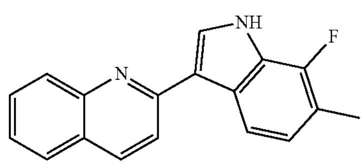 [SMILES: Cc1ccc2c(-c3ccc4ccccc4n3)c[nH]c2c1F] | 2.170 | Not tested |
| 13620 | Synthetic derivative | 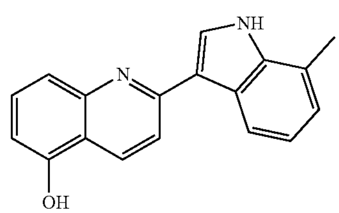 [SMILES: Cc1cccc2c(-c3ccc4c(O)cccc4n3)c[nH]c12] | Inactive | Inactive |
| 13621 | Synthetic derivative | 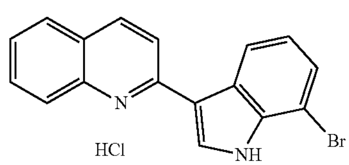 [SMILES: Brc1cccc2c(-c3ccc4ccccc4n3)c[nH]c12 ; Cl] | 0.02 | 0.008 |
| 13622 | Synthetic derivative | 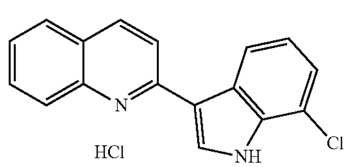 [SMILES: Clc1cccc2c(-c3ccc4ccccc4n3)c[nH]c12 ; Cl] | 0.1 | 0.075 |

TABLE 3-continued
Structural and experimental data for the AR BF3 interactors.
| Internal Number | ZINC Number | STRUCTURE | eGFP IC$_{50}$ (μM) | PSA IC$_{50}$ (μM) |
|---|---|---|---|---|
| 13623 | Synthetic derivative | 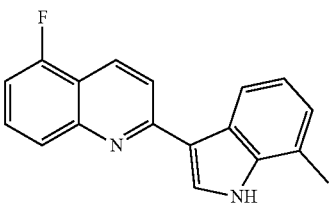 [SMILES: Cc1cccc2c(-c3ccc4c(F)cccc4n3)c[nH]c12] | Inactive | Inactive |
| 13624 | Synthetic derivative | 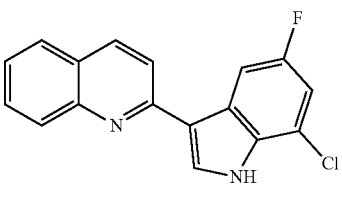 | 0.100 | 0.042 |
| 13625 | Synthetic derivative | 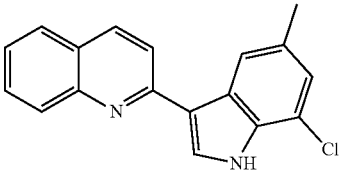 [SMILES: Cc1cc(Cl)c2[nH]cc(-c3ccc4ccccc4n3)c2c1] | 1.900 | 1.230 |
| 13626 | Synthetic derivative | 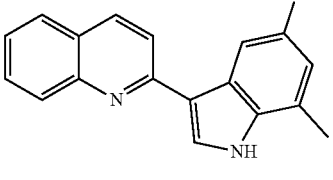 | 2.700 | 1.650 |
| 13627 | Synthetic derivative | 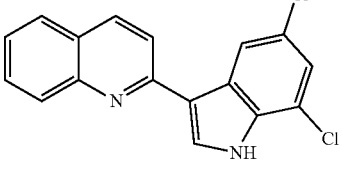 | 1.500 | 1.160 |
| 13628 | Synthetic derivative | 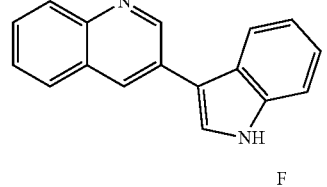 | 0.800 | 0.610 |
| 13629 | Synthetic derivative | 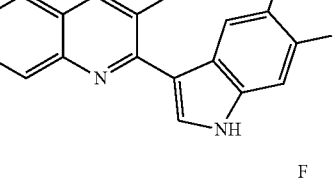 | 4.900 | 1.780 |
| 13630 | Synthetic derivative | 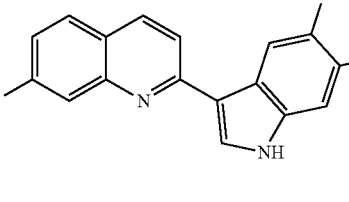 | 0.600 | 0.430 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13631 | Synthetic derivative | 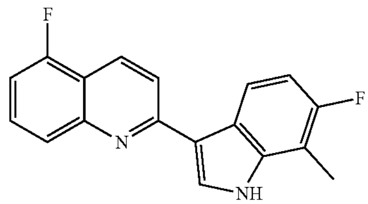 [SMILES: Cc1c(F)ccc2c(-c3ccc4c(F)cccc4n3)c[nH]c12] | Inactive | Inactive |
| 13632 | Synthetic derivative | 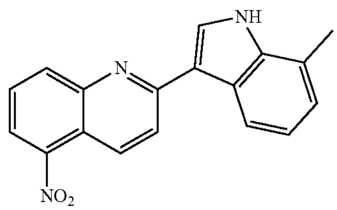 [SMILES: Cc1cccc2c(-c3ccc4c([N+](=O)[O-])cccc4n3)c[nH]c12] | Inactive | Inactive |
| 13633 | Synthetic derivative | 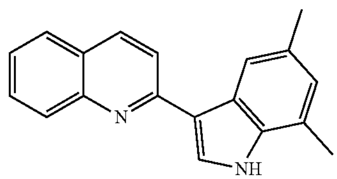 [SMILES: Cc1cc(C)c2[nH]cc(-c3ccc4ccccc4n3)c2c1] | 6.000 | Not tested |
| 13634 | Synthetic derivative | 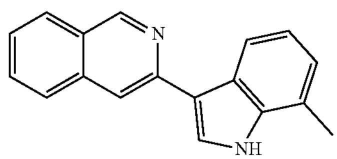 | 5.000 | Not tested |
| 13635 | Synthetic derivative | 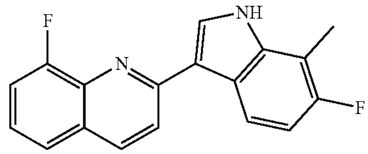 [SMILES: Cc1c(F)ccc2c(-c3ccc4cccc(F)c4n3)c[nH]c12] | Inactive | Inactive |
| 13636 | Synthetic derivative | 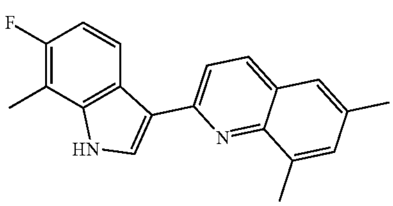 [SMILES: Cc1cc(C)c2nc(-c3c[nH]c4c(C)c(F)ccc34)ccc2c1] | Inactive | Inactive |
| 13637 | Synthetic derivative | 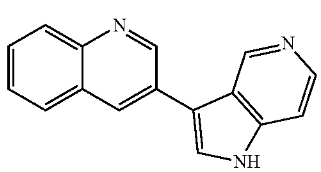 [SMILES: c1ccc2ncc(-c3c[nH]c4ccncc34)cc2c1] | Inactive | Inactive |
| 13638 | Synthetic derivative | 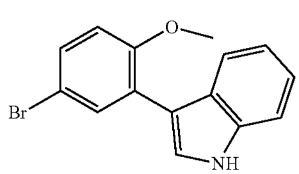 [SMILES: COc1ccc(Br)cc1-c1c[nH]c2ccccc12] | Inactive | Inactive |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13639 | Synthetic derivative | 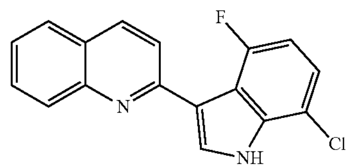 [SMILES: Fc1ccc(Cl)c2[nH]cc(-c3ccc4ccccc4n3)c12] | 0.549 | 0.544 |
| 13640 | Synthetic derivative | 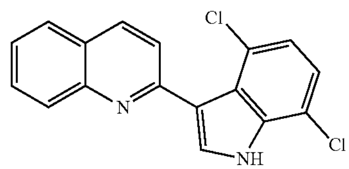 [SMILES: Clc1ccc(Cl)c2c(-c3ccc4ccccc4n3)c[nH]c12] | 12.670 | Not tested |
| 13641 | Synthetic derivative | 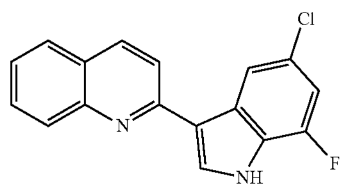 [SMILES: Fc1cc(Cl)cc2c(-c3ccc4ccccc4n3)c[nH]c12] | 0.132 | 0.403 |
| 13642 | Synthetic derivative | 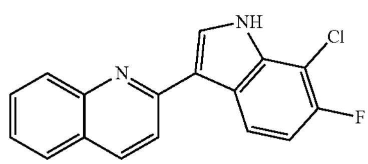 [SMILES: Fc1ccc2c(-c3ccc4ccccc4n3)c[nH]c2c1Cl] | 0.033 | 0.025 |
| 13643 | Synthetic derivative | 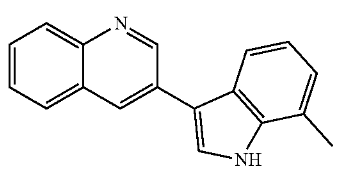 [SMILES: Cc1cccc2c(-c3cnc4ccccc4c3)c[nH]c12] | 0.1638 | 0.156 |
| 13644 | Synthetic derivative | 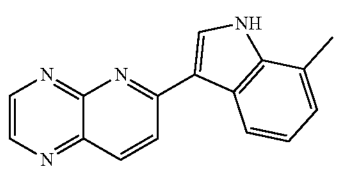 [SMILES: Cc1cccc2c(-c3ccc4nccnc4n3)c[nH]c12] | 3.000 | Not tested |
| 13645 | Synthetic derivative | 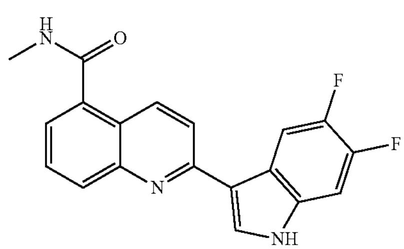 [SMILES: CNC(=O)c1cccc2nc(-c3c[nH]c4cc(F)c(F)cc34)ccc12] | 0.261 | 0.247 |
| 13646 | Synthetic derivative | 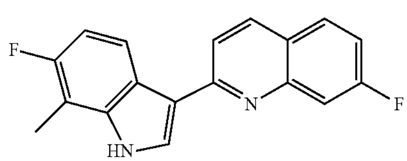 [SMILES: Cc1c(F)ccc2c(-c3ccc4ccc(F)cc4n3)c[nH]c12] | 0.179 | 0.224 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13647 | Synthetic derivative | 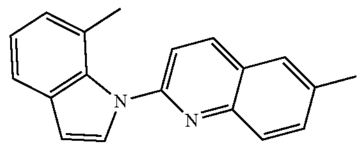 [SMILES: Cc1ccc2nc(-n3ccc4cccc(C)c43)ccc2c1] | Inactive | Inactive |
| 13648 | Synthetic derivative | 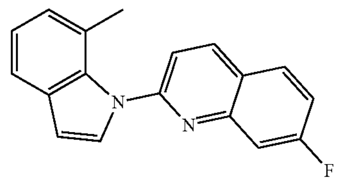 [SMILES: Cc1cccc2ccn(-c3ccc4ccc(F)cc4n3)c12] | Inactive | Inactive |
| 13649 | Synthetic derivative | 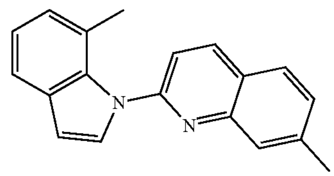 [SMILES: Cc1ccc2ccc(-n3ccc4cccc(C)c43)nc2c1] | Inactive | Inactive |
| 13650 | Synthetic derivative | 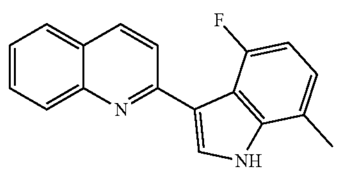 [SMILES: Cc1ccc(F)c2c(-c3ccc4ccccc4n3)c[nH]c12] | 1.631 | Not tested |
| 13651 | Synthetic derivative | 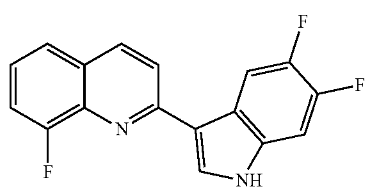 [SMILES: Fc1cc2[nH]cc(-c3ccc4cccc(F)c4n3)c2cc1F] | 0.404 | Not tested |
| 13652 | Synthetic derivative | 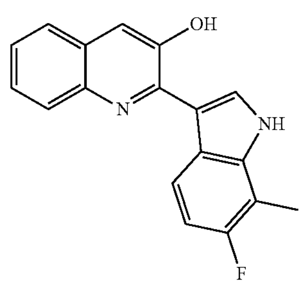 [SMILES: Cc1c(F)ccc2c(-c3nc4ccccc4cc3O)c[nH]c12] | 3.54 | 1.76 |
| 13653 | Synthetic derivative | 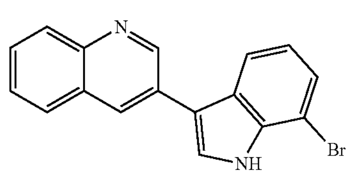 [SMILES: Brc1cccc2c(-c3cnc4ccccc4c3)c[nH]c12] | 1.13 | 0.29 |
| 13654 | Synthetic derivative | 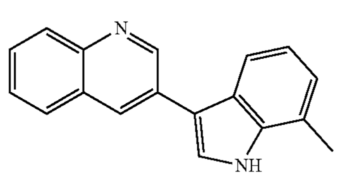 [SMILES: Cc1cccc2c(-c3cnc4ccccc4c3)c[nH]c12] | 0.92 | 0.16 |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13655 | Synthetic derivative | 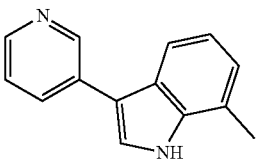 [SMILES: Cc1cccc2c(-c3cccnc3)c[nH]c12] | 1.66 | 0.61 |
| 13656 | Synthetic derivative | 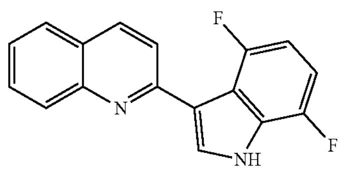 [SMILES: Fc1ccc(F)c2c(-c3ccc4ccccc4n3)c[nH]c12] | 0.99 | 0.46 |
| 13657 | Synthetic derivative | 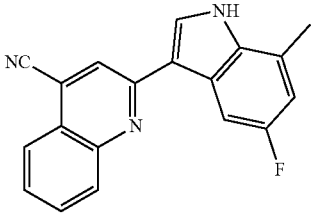 [SMILES: Cc1cc(F)cc2c(-c3cc(C#N)c4ccccc4n3)c[nH]c12] | Inactive | Inactive |
| 13658 | Synthetic derivative | 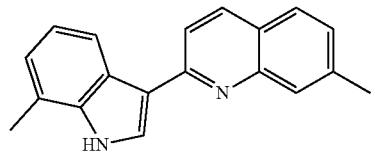 | 2.85 | 2.21 |
| 13659 | Synthetic derivative | 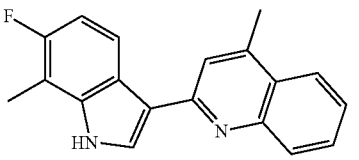 [SMILES: Cc1cc(-c2c[nH]c3c(C)c(F)ccc23)nc2ccccc12] | Inactive | Inactive |
| 13660 | Synthetic derivative | 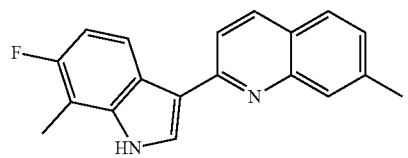 [SMILES: Cc1ccc2ccc(-c3c[nH]c4c(C)c(F)ccc34)nc2c1] | 2.5 | 1.89 |
| 13661 | Synthetic derivative | 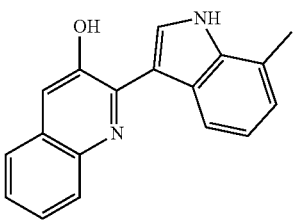 [SMILES: Cc1cccc2c(-c3nc4ccccc4cc3O)c[nH]c12] | Inactive | Inactive |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
| --- | --- | --- | --- | --- |
| 13662 | Synthetic derivative | 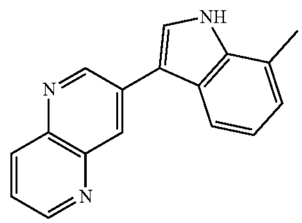 [SMILES: Cc1cccc2c(-c3cnc4cccnc4c3)c[nH]c12] | Inactive | Inactive |
| 13663 | Synthetic derivative | 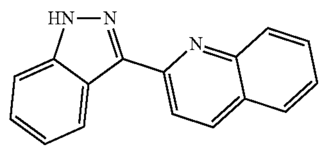 [SMILES: c1ccc2nc(-c3n[nH]c4ccccc34)ccc2c1] | Inactive | Inactive |
| 13664 | Synthetic derivative | 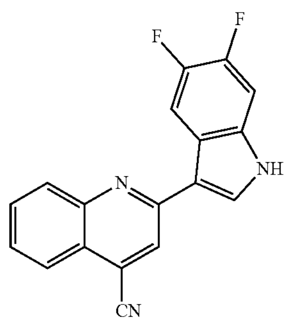 [SMILES: N#Cc1cc(-c2c[nH]c3cc(F)c(F)cc23)nc2ccccc12] | Inactive | Inactive |
| 13665 | Synthetic derivative | 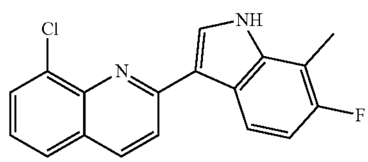 | 0.27 | 0.21 |
| 13666 | Synthetic derivative | 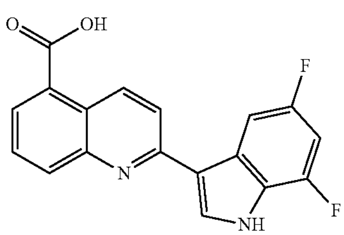 [SMILES: O=C(O)c1cccc2nc(-c3c[nH]c4c(F)cc(F)cc34)ccc12] | Inactive | Inactive |
| 13667 | Synthetic derivative | 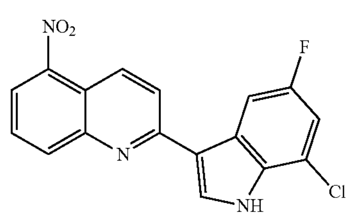 [SMILES: O=[N+]([O-])c1cccc2nc(-c3c[nH]c4c(Cl)cc(F)cc34)ccc12] | Inactive | Inactive |
| 13668 | Synthetic derivative | 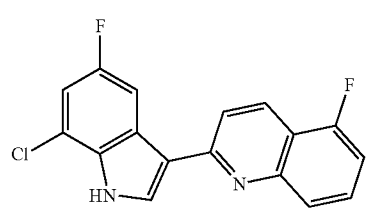 [SMILES: Fc1cc(Cl)c2[nH]cc(-c3ccc4c(F)cccc4n3)c2c1] | Inactive | Inactive |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13669 | Synthetic derivative | 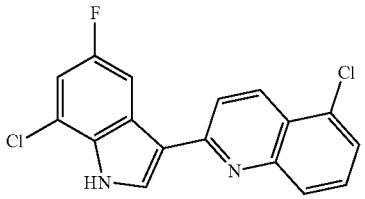 | Inactive | Inactive |
| 13670 | Synthetic derivative | 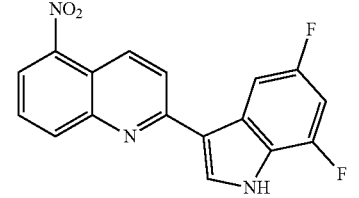 [SMILES: O=[N+]([O-])c1cccc2nc(-c3c[nH]c4c(F)cc(F)cc34)ccc12] | Inactive | Inactive |
| 13671 | Synthetic derivative | 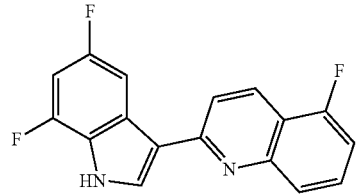 | Inactive | Inactive |
| 13672 | Synthetic derivative | 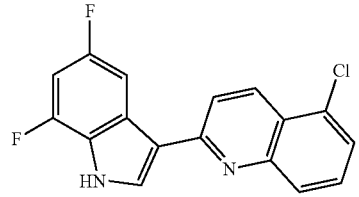 [SMILES: Fc1cc(F)c2[nH]cc(-c3ccc4c(Cl)cccc4n3)c2c1] | Inactive | Inactive |
| 13673 | Synthetic derivative | 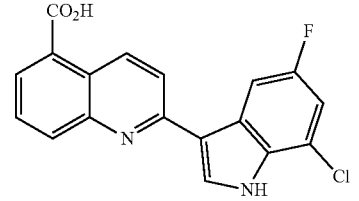 [SMILES: O=C(O)c1cccc2nc(-c3c[nH]c4c(Cl)cc(F)cc34)ccc12] | Inactive | Inactive |
| 13674 | Synthetic derivative | 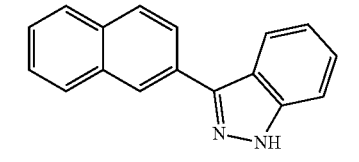 | 0.075 | 0.051 |
| 13677 | Synthetic derivative | 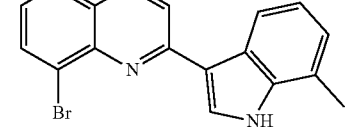 | 0.156 | 0.11 |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13678 | Synthetic derivative | 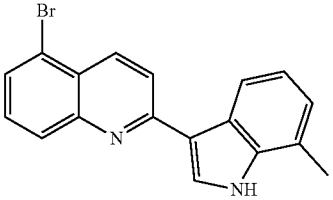 [SMILES: Cc1cccc2c(-c3ccc4c(Br)cccc4n3)c[nH]c12] | Inactive | Inactive |
| 13679 | Synthetic derivative | 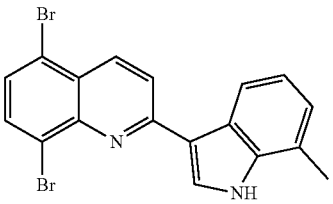 [SMILES: Cc1cccc2c(-c3ccc4c(Br)ccc(Br)c4n3)c[nH]c12] | Inactive | Inactive |
| 13680 | Synthetic derivative | 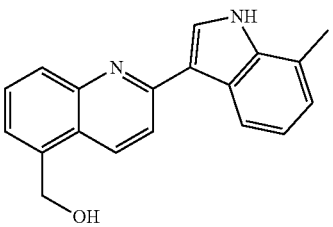 [SMILES: Cc1cccc2c(-c3ccc4c(CO)cccc4n3)c[nH]c12] | 0.8 | Not tested |
| 13681 | Synthetic derivative | 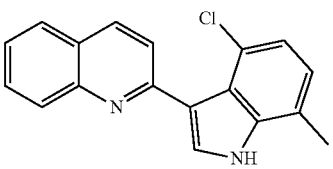 [SMILES: Cc1ccc(Cl)c2c(-c3ccc4ccccc4n3)c[nH]c12] | 2.5 | 1.7 |
| 13682 | Synthetic derivative | 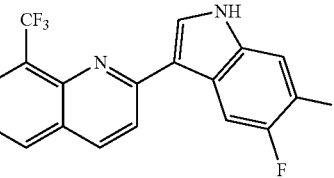 | 0.89 | 0.99 |
| 13683 | Synthetic derivative | 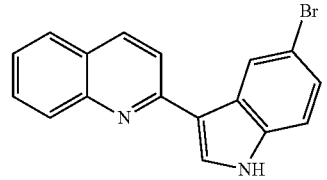 [SMILES: Brc1ccc2[nH]cc(-c3ccc4ccccc4n3)c2c1] | 2.6 | 1.906 |
| 13684 | Synthetic derivative | 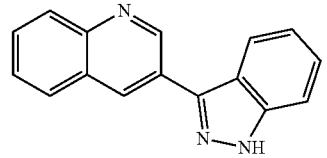 | 1.4 | 6.609 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13685 | Synthetic derivative | 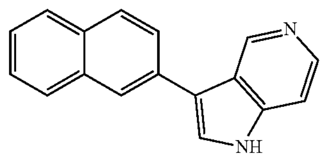 [SMILES: c1ccc2cc(-c3c[nH]c4ccncc34)ccc2c1] | Inactive | Inactive |
| 13686 | Synthetic derivative | 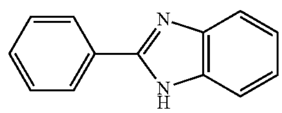 [SMILES: c1ccc(-c2nc3ccccc3[nH]2)cc1] | Inactive | Inactive |
| 13687 | Synthetic derivative | 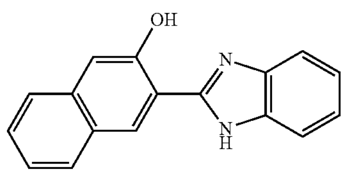 [SMILES: Oc1cc2ccccc2cc1-c1nc2ccccc2[nH]1] | Inactive | Inactive |
| 13688 | Synthetic derivative | 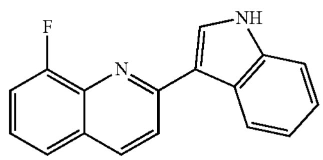 [SMILES: Fc1cccc2ccc(-c3c[nH]c4ccccc34)nc12] | 0.069 | 0.068 |
| 13689 | Synthetic derivative | 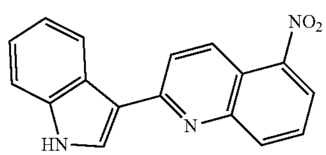 [SMILES: O=[N+]([O-])c1cccc2nc(-c3c[nH]c4ccccc34)ccc12] | Inactive | Inactive |
| 13690 | Synthetic derivative | 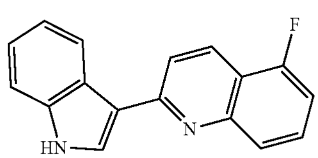 [SMILES: Fc1cccc2nc(-c3c[nH]c4ccccc34)ccc12] | Inactive | Inactive |
| 13691 | Synthetic derivative | 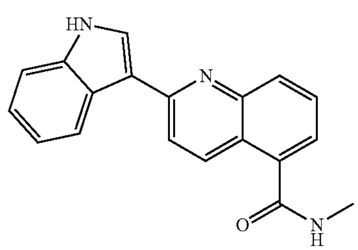 [SMILES: CNC(=O)c1cccc2nc(-c3c[nH]c4ccccc34)ccc12] | 0.4 | 0.48 |
| 13692 | Synthetic derivative | 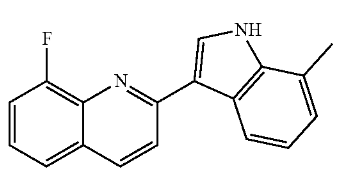 | 0.1 | 0.082 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13693 | Synthetic derivative | 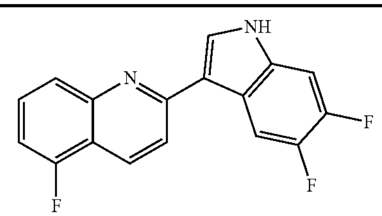 | 0.11 | 0.12 |
| 13694 | Synthetic derivative | 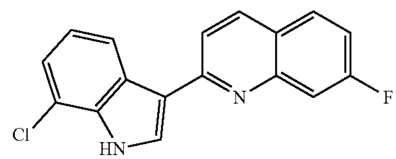 [SMILES: Fc1ccc2ccc(-c3c[nH]c4c(Cl)cccc34)nc2c1] | 0.07 | 0.067 |
| 13695 | Synthetic derivative | 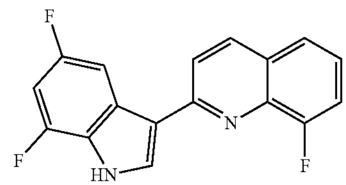 [SMILES: Fc1cc(F)c2[nH]cc(-c3ccc4cccc(F)c4n3)c2c1] | 0.069 | 0.087 |
| 13696 | Synthetic derivative | 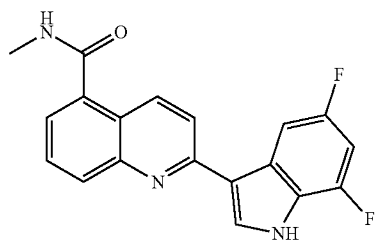 | 0.042 | 0.042 |
| 13697 | Synthetic derivative | 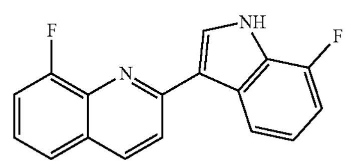 [SMILES: Fc1cccc2ccc(-c3c[nH]c4c(F)cccc34)nc12] | 0.029 | 0.029 |
| 13698 | Synthetic derivative | 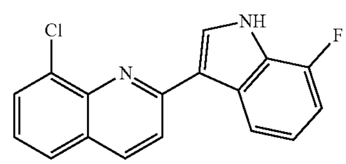 | 0.041 | 0.041 |
| 13699 | Synthetic derivative | 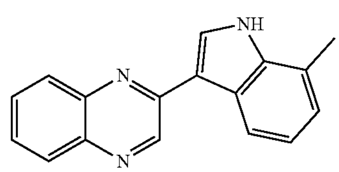 [SMILES: Cc1cccc2c(-c3cnc4ccccc4n3)c[nH]c12] | 0.073 | 0.073 |
| 13700 | Synthetic derivative | 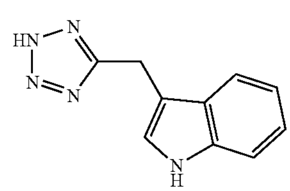 [SMILES: c1ccc2c(Cc3nn[nH]n3)c[nH]c2c1] | Inactive | Inactive |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13701 | Synthetic derivative | 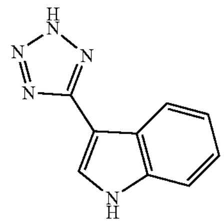 [SMILES: c1ccc2c(-c3nn[nH]n3)c[nH]c2c1] | Inactive | Inactive |
| 13702 | Synthetic derivative | 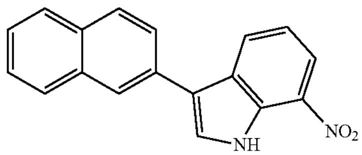 [SMILES: O=[N+]([O-])c1cccc2c(-c3ccc4ccccc4c3)c[nH]c12] | 0.21 | 0.14 |
| 13704 | Synthetic derivative | 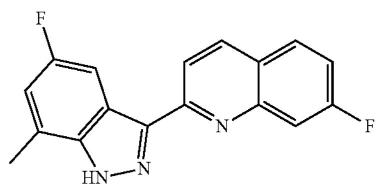 [SMILES: Cc1cc(F)cc2c(-c3ccc4ccc(F)cc4n3)n[nH]c12] | 0.35 | 0.169 |
| 13705 | Synthetic derivative | 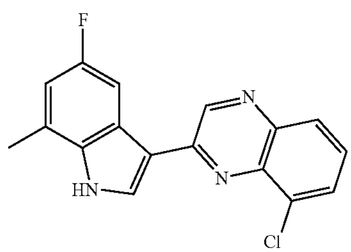 [SMILES: Cc1cc(F)cc2c(-c3cnc4cccc(Cl)c4n3)c[nH]c12] | Inactive | Inactive |
| 13706 | Synthetic derivative | 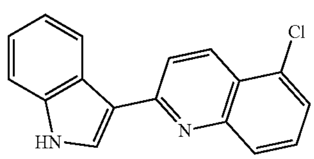 [SMILES: Clc1cccc2nc(-c3c[nH]c4ccccc34)ccc12] | Inactive | Inactive |
| 13707 | Synthetic derivative | 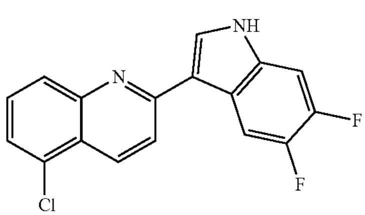 [SMILES: Fc1cc2[nH]cc(-c3ccc4c(Cl)cccc4n3)c2cc1F] | Inactive | Inactive |
| 13708 | Synthetic derivative | 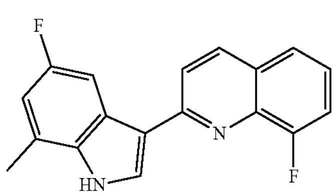 [SMILES: Cc1cc(F)cc2c(-c3ccc4cccc(F)c4n3)c[nH]c12] | 0.29 | 0.29 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
| --- | --- | --- | --- | --- |
| 13709 | Synthetic derivative | 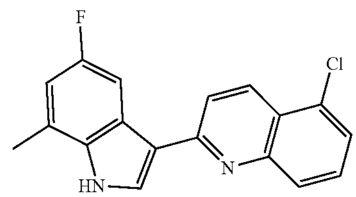 [SMILES: Cc1cc(F)cc2c(-c3ccc4c(Cl)cccc4n3)c[nH]c12] | Inactive | Inactive |
| 13710 | Synthetic derivative | 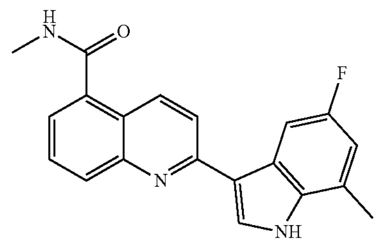 | 0.23 | 0.25 |
| 13711 | Synthetic derivative | 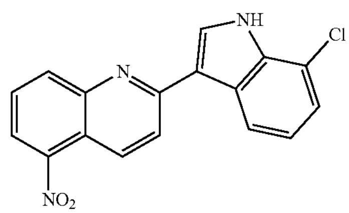 [SMILES: O=[N+]([O-])c1cccc2nc(-c3c[nH]c4c(Cl)cccc34)ccc12] | Inactive | Inactive |
| 13712 | Synthetic derivative | 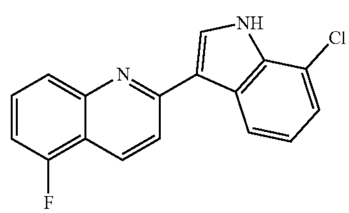 [SMILES: Fc1cccc2nc(-c3c[nH]c4c(Cl)cccc34)ccc12] | Inactive | Inactive |
| 13713 | Synthetic derivative | 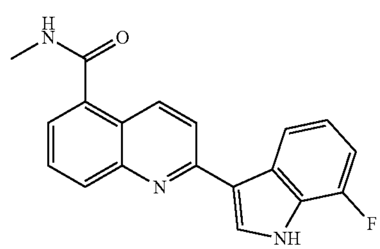 [SMILES: CNC(=O)c1cccc2nc(-c3c[nH]c4c(F)cccc34)ccc12] | 0.037 | |
| 13714 | Synthetic derivative | 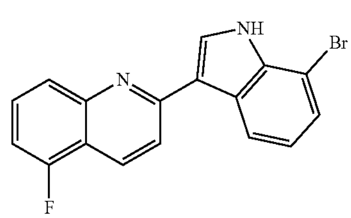 [SMILES: Fc1cccc2nc(-c3c[nH]c4c(Br)cccc34)ccc12] | Inactive | Inactive |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13717 | Synthetic derivative | 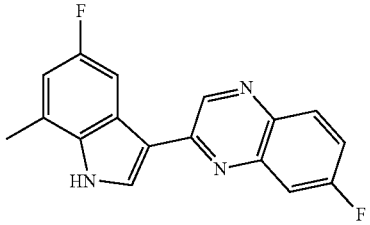 [SMILES: Cc1cc(F)cc2c(-c3cnc4ccc(F)cc4n3)c[nH]c12] | 0.49 | 0.33 |
| 13718 | Synthetic derivative | 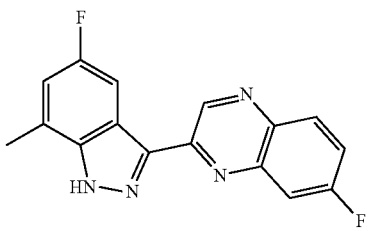 [SMILES: Cc1cc(F)cc2c(-c3cnc4ccc(F)cc4n3)n[nH]c12] | 0.37 | 0.11 |
| 13719 | Synthetic derivative | 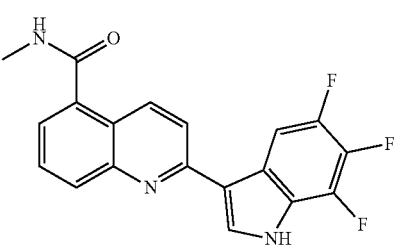 [SMILES: CNC(=O)c1cccc2nc(-c3c[nH]c4c(F)c(F)c(F)cc34)ccc12] | 0.11 | 0.13 |
| 13720 | Synthetic derivative | 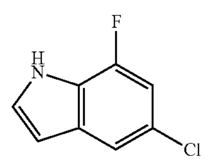 [SMILES: Fc1cc(Cl)cc2cc[nH]c12] | Inactive | Inactive |
| 13721 | Synthetic derivative | 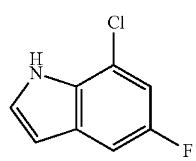 [SMILES: Fc1cc(Cl)c2[nH]ccc2c1] | Inactive | Inactive |
| 13722 | Synthetic derivative | 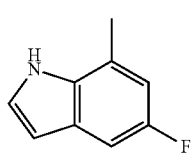 | Inactive | Inactive |
| 13723 | Synthetic derivative | 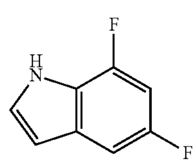 [SMILES: Fc1cc(F)c2[nH]ccc2c1] | Inactive | Inactive |
| 13724 | Synthetic derivative | 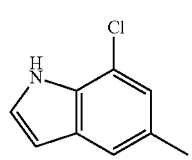 | Inactive | Inactive |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13725 | Synthetic derivative | 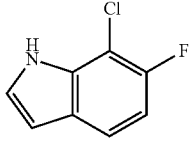 | Inactive | Inactive |
| 13726 | Synthetic derivative | 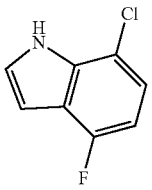 [SMILES: Fc1ccc(Cl)c2[nH]ccc12] | Inactive | Inactive |
| 13727 | Synthetic derivative | 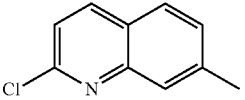 | Inactive | Inactive |
| 13728 | Synthetic derivative | 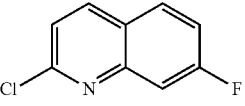 [SMILES: Fc1ccc2ccc(Cl)nc2c1] | Inactive | Inactive |
| 13729 | Synthetic derivative | 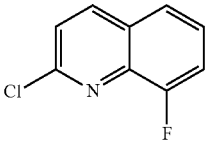 [SMILES: Fc1cccc2ccc(Cl)nc12] | Inactive | Inactive |
| 13730 | Synthetic derivative | 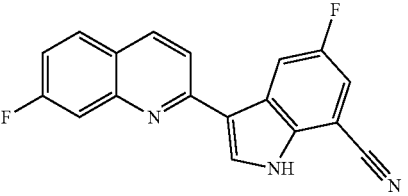 [SMILES: N#Cc1cc(F)cc2c(-c3ccc4ccc(F)cc4n3)c[nH]c12] | 0.149 | 0.198 |
| 13731 | Synthetic derivative | 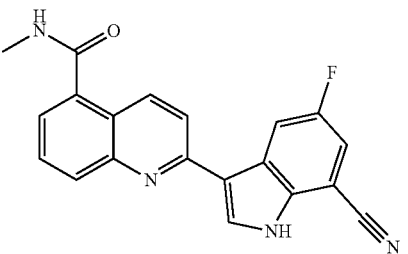 [SMILES: CNC(=O)c1cccc2nc(-c3c[nH]c4c(C#N)cc(F)cc34)ccc12] | 0.304 | 0.255 |
| 13732 | Synthetic derivative | 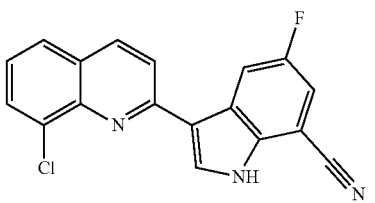 [SMILES: N#Cc1cc(F)cc2c(-c3ccc4cccc(Cl)c4n3)c[nH]c12] | 0.42 | Not tested |

TABLE 3-continued
Structural and experimental data for the AR BF$_3$ interactors.
| Internal Number | ZINC Number | STRUCTURE | eGFP IC$_{50}$ (μM) | PSA IC$_{50}$ (μM) |
|---|---|---|---|---|
| 13733 | Synthetic derivative | 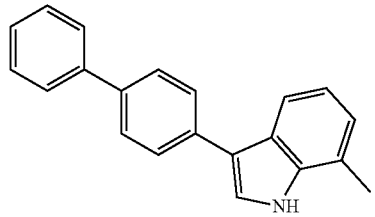 [SMILES: Cc1cccc2c(-c3ccc(-c4ccccc4)cc3)c[nH]c12] | 3.815 | 0.9194 |
| 13736 | Synthetic derivative | 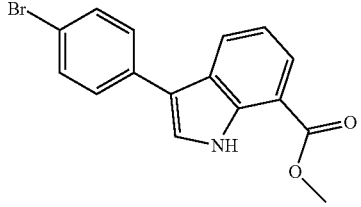 [SMILES: COC(=O)c1cccc2c(-c3ccc(Br)cc3)c[nH]c12] | 0.62 | 0.68 |
| 13738 | Synthetic derivative | 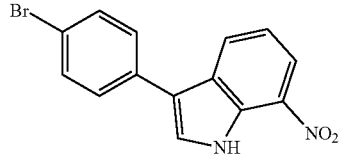 [SMILES: O=[N+]([O-])c1cccc2c(-c3ccc(Br)cc3)c[nH]c12] | 0.083 | 0.062 |
| 13741 | Synthetic derivative | 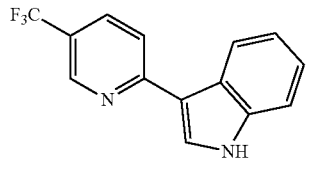 | 0.29 | 0.29 |
| 13742 | Synthetic derivative | 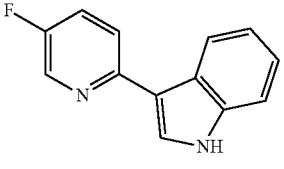 | 0.22 | 0.2 |
| 13743 | Synthetic derivative | 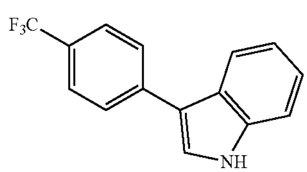 [SMILES: FC(F)(F)c1ccc(-c2c[nH]c3ccccc23)cc1] | 0.38 | 0.39 |
| 13744 | Synthetic derivative | 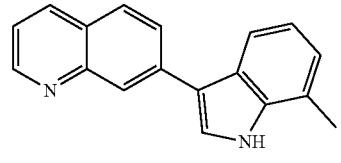 | 0.76 | 0.75 |
| 13745 | Synthetic derivative | 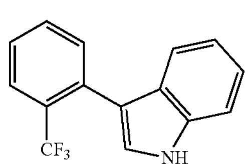 [SMILES: FC(F)(F)c1ccccc1-c1c[nH]c2ccccc12] | 1.01 | 0.95 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13746 | Synthetic derivative | 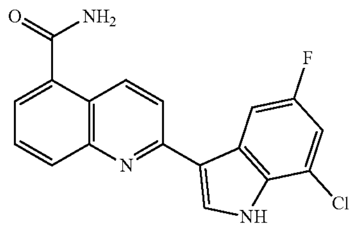 [SMILES: NC(=O)c1cccc2nc(-c3c[nH]c4c(Cl)cc(F)cc34)ccc12] | Inactive | Inactive |
| 13747 | Synthetic derivative | 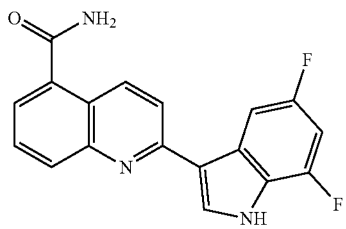 [SMILES: NC(=O)c1cccc2nc(-c3c[nH]c4c(F)cc(F)cc34)ccc12] | Inactive | Inactive |
| 13748 | Synthetic derivative | 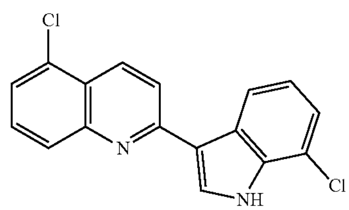 [SMILES: Clc1cccc2nc(-c3c[nH]c4c(Cl)cccc34)ccc12] | Inactive | Inactive |
| 13749 | Synthetic derivative | 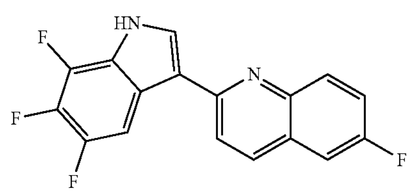 [SMILES: Fc1ccc2nc(-c3c[nH]c4c(F)c(F)c(F)cc34)ccc2c1] | 0.29 | 0.22 |
| 13750 | Synthetic derivative | 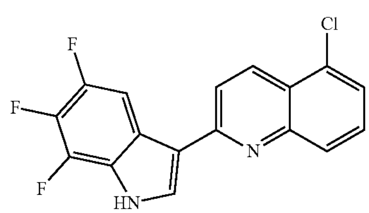 | Inactive | Inactive |
| 13751 | Synthetic derivative | 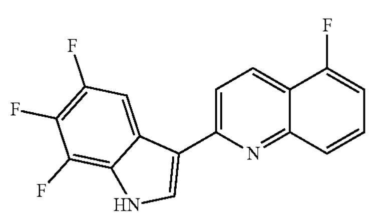 [SMILES: Fc1cc2c(-c3ccc4c(Cl)cccc4n3)c[nH]c2c(F)c1F] | Inactive | Inactive |
| 13752 | Synthetic derivative | 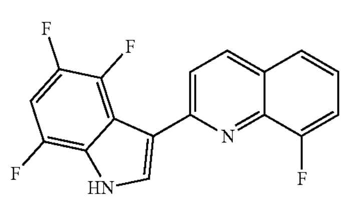 [SMILES: Fc1cc(F)c2[nH]cc(-c3ccc4cccc(F)c4n3)c2c1F] | 0.37 | 0.26 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13753 | Synthetic derivative | 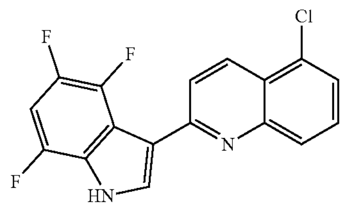 [SMILES: Fc1cc(F)c2[nH]cc(-c3ccc4c(Cl)cccc4n3)c2c1F] | 0.16 | 0.098 |
| 13754 | Synthetic derivative | 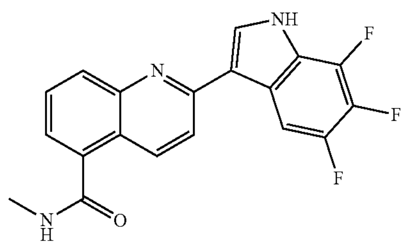 [SMILES: CNC(=O)c1cccc2nc(-c3c[nH]c4c(F)c(F)c(F)cc34)ccc12] | 0.09 | 0.051 |
| 13755 | Synthetic derivative | 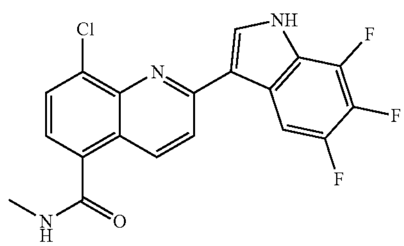 [SMILES: CNC(=O)c1ccc(Cl)c2nc(-c3c[nH]c4c(F)c(F)c(F)cc34)ccc12] | 0.47 | 0.47 |
| 13757 | Synthetic derivative | 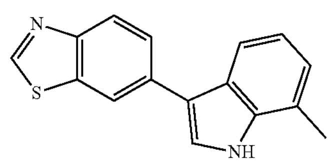 [SMILES: Cc1cccc2c(-c3ccc4ncsc4c3)c[nH]c12] | Inactive | Inactive |
| 13758 | Synthetic derivative | 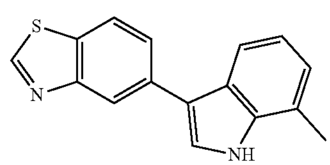 | Inactive | Inactive |
| 13759 | Synthetic derivative | 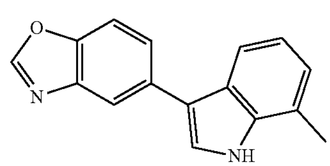 [SMILES: Cc1cccc2c(-c3ccc4ocnc4c3)c[nH]c12] | 0.3 | 0.27 |
| 13760 | Synthetic derivative | 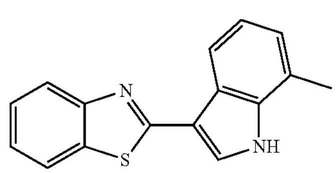 [SMILES: Cc1cccc2c(-c3nc4ccccc4s3)c[nH]c12] | 0.1 | 0.052 |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13761 | Synthetic derivative | 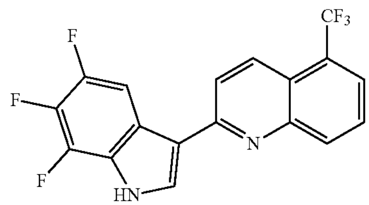 [SMILES: Fc1cc2c(-c3ccc4c(C(F)(F)F)cccc4n3)c[nH]c2c(F)c1F] | 0.5481 | 0.3829 |
| 13762 | Synthetic derivative | 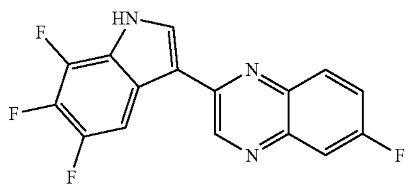 [SMILES: Fc1ccc2nc(-c3c[nH]c4c(F)c(F)c(F)cc34)cnc2c1] | 0.4792 | 0.429 |
| 13764 | Synthetic derivative | 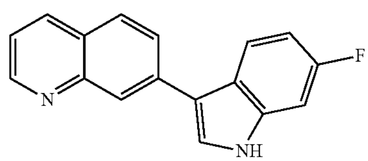 [SMILES: Fc1ccc2c(-c3ccc4cccnc4c3)c[nH]c2c1] | 0.1 | 0.082 |
| 13765 | Synthetic derivative | 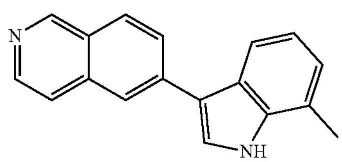 [SMILES: Cc1cccc2c(-c3ccc4cnccc4c3)c[nH]c12] | Inactive | Inactive |
| 13766 | Synthetic derivative | 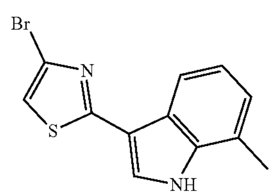 [SMILES: Cc1cccc2c(-c3nc(Br)cs3)c[nH]c12] | 0.045 | 0.020 |
| 13769 | Synthetic derivative | 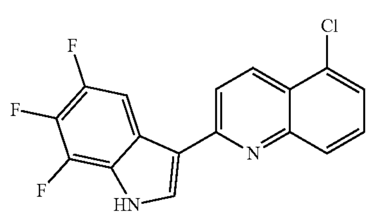 [SMILES: Fc1cc2c(-c3ccc4c(Cl)cccc4n3)c[nH]c2c(F)c1F] | Inactive | Inactive |
| 13770 | Synthetic derivative | 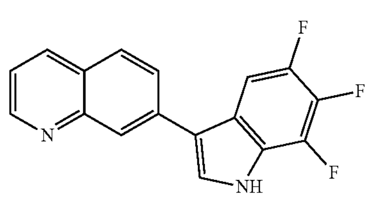 [SMILES: Fc1cc2c(-c3ccc4cccnc4c3)c[nH]c2c(F)c1F] | 0.1 | 0.017 |

TABLE 3-continued

Structural and experimental data for the AR BF₃ interactors.

| Internal Number | ZINC Number | STRUCTURE | eGFP IC$_{50}$ (μM) | PSA IC$_{50}$ (μM) |
|---|---|---|---|---|
| 13771 | Synthetic derivative | 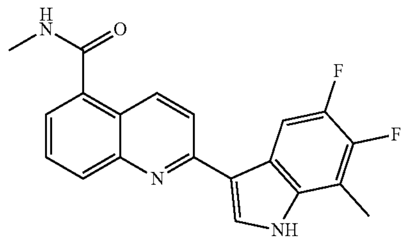 | 0.2 | 0.090 |
| 13772 | Synthetic derivative | 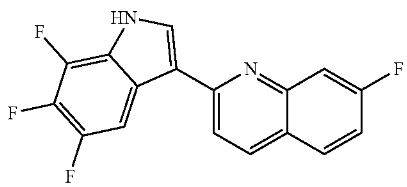 [SMILES: Fc1ccc2ccc(-c3c[nH]c4c(F)c(F)c(F)cc34)nc2c1] | 0.2 | 0.172 |
| 13773 | Synthetic derivative | 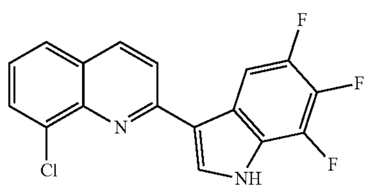 [SMILES: Fc1cc2c(-c3ccc4cccc(Cl)c4n3)c[nH]c2c(F)c1F] | 0.3 | 0.303 |
| 13774 | Synthetic derivative | 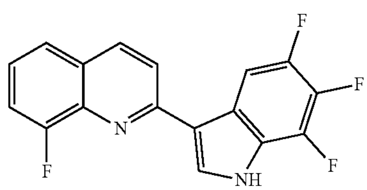 | 0.7 | 0.773 |
| 13775 | Synthetic derivative | 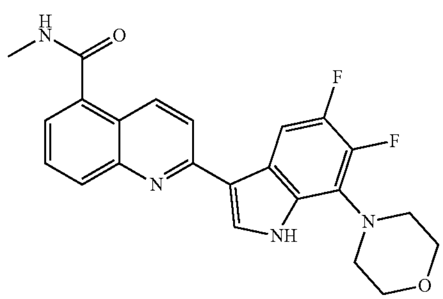 [SMILES: CNC(=O)c1cccc2nc(-c3c[nH]c4c(N5CCOCC5)c(F)c(F)cc34)ccc12] | 3.7 | Not tested |
| 13776 | Synthetic derivative | 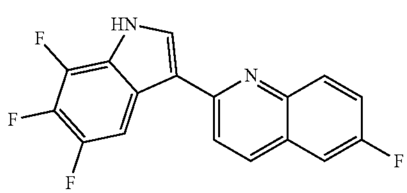 [SMILES: Fc1ccc2nc(-c3c[nH]c4c(F)c(F)c(F)cc34)ccc2c1] | 0.21 | 0.19 |
| 13777 | Synthetic derivative | 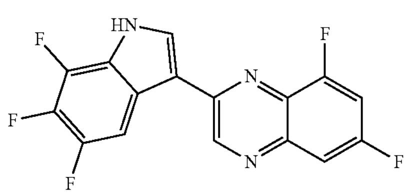 [SMILES: Fc1cc(F)c2nc(-c3c[nH]c4c(F)c(F)c(F)cc34)cnc2c1] | Not tested | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13778 | Synthetic derivative | 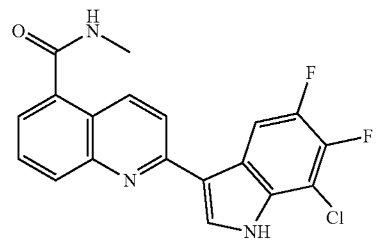 [SMILES: CNC(=O)c1cccc2nc(-c3c[nH]c4c(Cl)c(F)c(F)cc34)ccc12] | Not tested | Not tested |
| 13779 | Synthetic derivative | 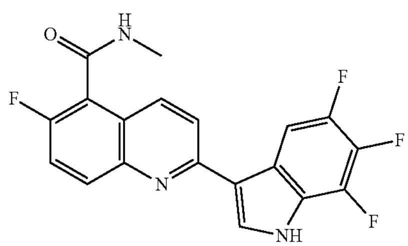 [SMILES: CNC(=O)c1c(F)ccc2nc(-c3c[nH]c4c(F)c(F)c(F)cc34)ccc12] | Not tested | Not tested |
| 13780 | Synthetic derivative | 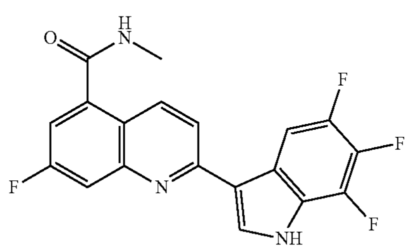 [SMILES: CNC(=O)c1cc(F)cc2nc(-c3c[nH]c4c(F)c(F)c(F)cc34)ccc12] | Not tested | Not tested |
| 13781 | Synthetic derivative | 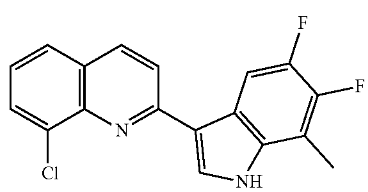 [SMILES: Cc1c(F)c(F)cc2c(-c3ccc4cccc(Cl)c4n3)c[nH]c12] | Not tested | Not tested |
| 13782 | Synthetic derivative | 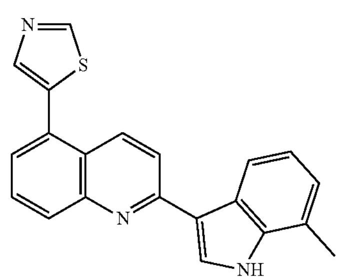 [SMILES: Cc1cccc2c(-c3ccc4c(-c5cncs5)cccc4n3)c[nH]c12] | 0.11 | Not tested |
| 13783 | Synthetic derivative | 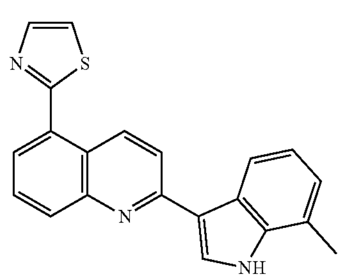 [SMILES: Cc1cccc2c(-c3ccc4c(-c5nccs5)cccc4n3)c[nH]c12] | Not tested | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13784 | Synthetic derivative | 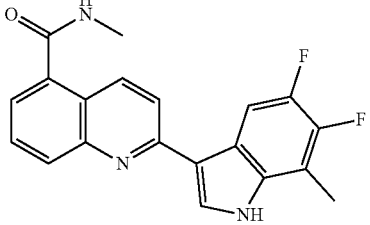 | Not tested | Not tested |
| 13785 | Synthetic derivative | 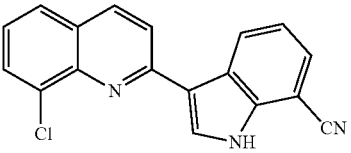 [SMILES: N#Cc1cccc2c(-c3ccc4cccc(Cl)c4n3)c[nH]c12] | 0.036 | Not tested |
| 13786 | Synthetic derivative | 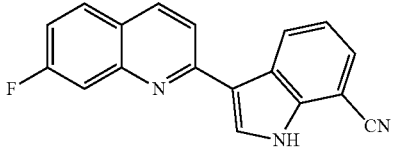 [SMILES: N#Cc1cccc2c(-c3ccc4ccc(F)cc4n3)c[nH]c12] | 0.013 | Not tested |
| 13787 | Synthetic derivative | 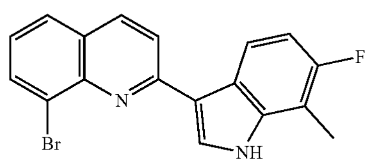 [SMILES: Cc1c(F)ccc2c(-c3ccc4cccc(Br)c4n3)c[nH]c12] | 0.19 | Not tested |
| 13788 | Synthetic derivative | 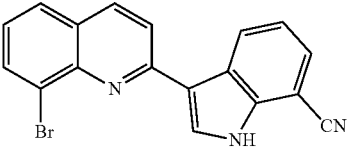 | Not tested | Not tested |
| 13507 | Synthetic derivative | 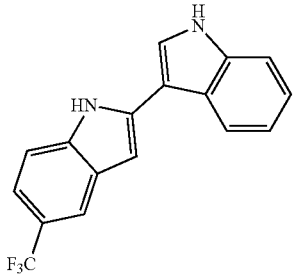 [SMILES: FC(F)(F)c1ccc2[nH]c(-c3c[nH]c4ccccc34)cc2c1] | Not tested | Not tested |
| 13513 | Synthetic derivative | 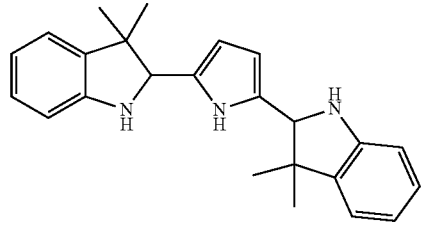 [SMILES: CC1(C)c2ccccc2NC1c1ccc(C2Nc3ccccc3C2(C)C)[nH]1] | Not tested | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13514 | Synthetic derivative | 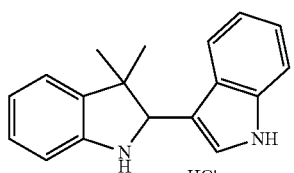 | Not tested | Not tested |
| 13515 | Synthetic derivative | 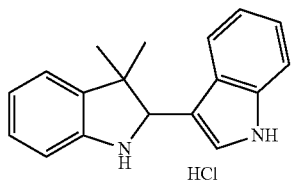 [SMILES: CC1(C)c2ccccc2NC1c1c[nH]c2ccccc12 ; Cl] | Not tested | Not tested |
| 13517 | Synthetic derivative | 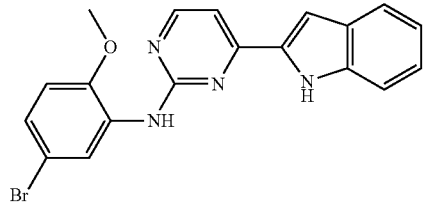 [SMILES: COc1ccc(Br)cc1Nc1nccc(-c2cc3ccccc3[nH]2)n1] | Not tested | Not tested |
| 13518 | Synthetic derivative | 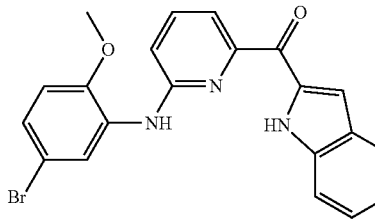 | Not tested | Not tested |
| 13519 | Synthetic derivative | 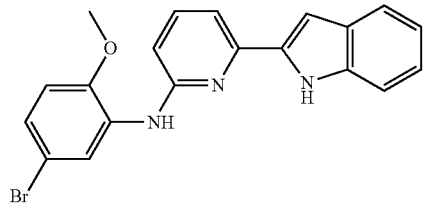 [SMILES: COc1ccc(Br)cc1Nc1cccc(-c2cc3ccccc3[nH]2)n1] | Not tested | Not tested |
| 13520 | Synthetic derivative | 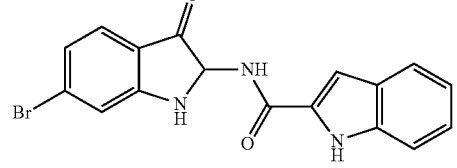 | Not tested | Not tested |
| 13523 | Synthetic derivative | 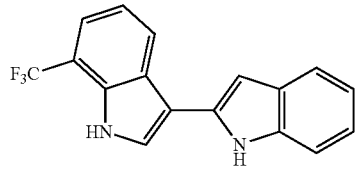 [SMILES: FC(F)(F)c1cccc2c(-c3cc4ccccc4[nH]3)c[nH]c12] | Not tested | Not tested |

TABLE 3-continued

Structural and experimental data for the AR BF$_3$ interactors.

| Internal Number | ZINC Number | STRUCTURE | eGFP IC$_{50}$ (μM) | PSA IC$_{50}$ (μM) |
|---|---|---|---|---|
| 13526 | Synthetic derivative | 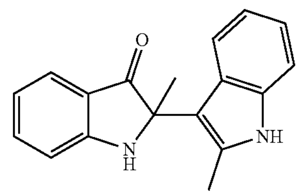 [SMILES: Cc1[nH]c2ccccc2c1C1(C)Nc2ccccc2C1=O] | Not tested | Not tested |
| 13527 | Synthetic derivative | 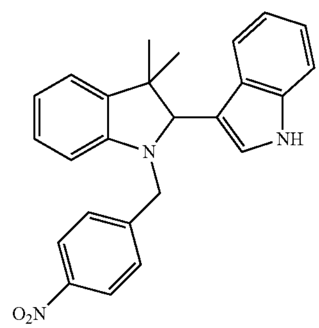 [SMILES: CC1(C)c2ccccc2N(Cc2ccc([N+](=O)[O-])cc2)C1c1c[nH]c2ccccc12] | Not tested | Not tested |
| 13531 | Synthetic derivative | 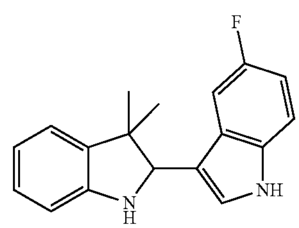 [SMILES: CC1(C)c2ccccc2NC1c1c[nH]c2ccc(F)cc12] | Not tested | Not tested |
| 13539 | Synthetic derivative | 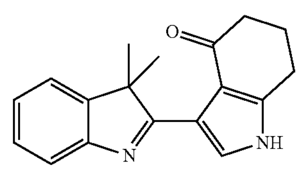 [SMILES: CC1(C)C(c2c[nH]c3c2C(=O)CCC3)=Nc2ccccc21] | Not tested | Not tested |
| 13545 | Synthetic derivative | 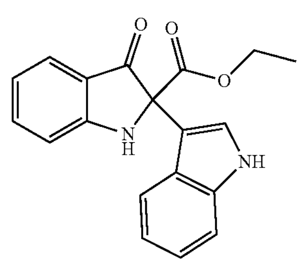 [SMILES: CCOC(=O)C1(c2c[nH]c3ccccc23)Nc2ccccc2C1=O] | Not tested | Not tested |
| 13546 | Synthetic derivative | 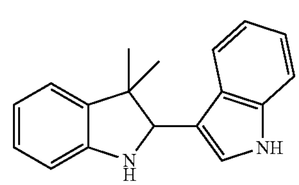 [SMILES: CC1(C)c2ccccc2NC1c1c[nH]c2ccccc12] | Not tested | Not tested |

TABLE 3-continued

Structural and experimental data for the AR BF₃ interactors.

| Internal Number | ZINC Number | STRUCTURE | eGFP IC$_{50}$ (µM) | PSA IC$_{50}$ (µM) |
|---|---|---|---|---|
| 13547 | Synthetic derivative | 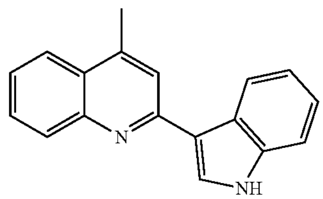 [SMILES: Cc1cc(-c2c[nH]c3ccccc23)nc2ccccc12] | Not tested | Not tested |

Where a compound is described as "inactive", no activity was detected for the compound in the assays on which it was tested.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

What is claimed is:

1. A compound having the structure of Formula II:

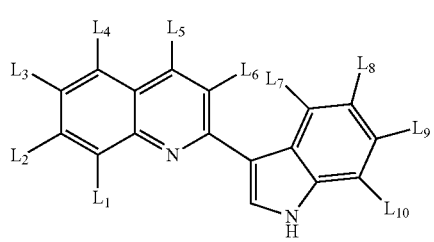

II wherein,
$L_1$ is H;
$L_2$ is H, Cl, F or Br;
$L_3$ is H, Cl, F or Br;
$L_4$ is C(O)NHCH$_3$, CF$_3$,

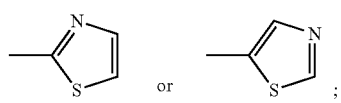

$L_5$ is H;
$L_6$ is H;
$L_7$ is H;
$L_8$ is Cl, F or Br;
$L_9$ is Cl, F or Br; and
$L_{10}$ is Cl, F or Br.

2. The compound of claim 1, wherein
$L_2$ is H, Cl or F; and
$L_3$ is H, Cl or F.

3. The compound of claim 1, wherein
$L_2$ is H, Cl or F;
$L_3$ is H, Cl or F;
$L_8$ is Cl or F;
$L_9$ is Cl or F; and
$L_{10}$ is Cl or F.

4. The compound of claim 1, wherein
$L_2$ is H, Cl or F;
$L_3$ is H, Cl or F;
$L_8$ is F;
$L_9$ is F; and
$L_{10}$ is F.

5. The compound of claim 1, wherein
$L_4$ is C(O)NHCH$_3$.

6. The compound of claim 1, wherein
$L_4$ is CF$_3$,

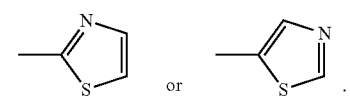

7. The compound of claim 1, wherein
$L_2$ is H, Cl or F;
$L_3$ is H, Cl or F;
$L_4$ is C(O)NHCH$_3$, CF$_3$,

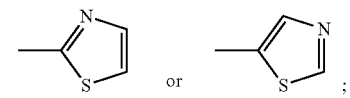

$L_8$ is Cl or F;
$L_9$ is Cl or F; and
$L_{10}$ is Cl or F.

8. The compound of claim 1, wherein
$L_2$ is H, Cl or F;
$L_3$ is H, Cl or F;
$L_4$ is C(O)NHCH$_3$;
$L_8$ is Cl or F;

$L_9$ is Cl or F, and
$L_{10}$ is Cl or F.

9. The compound of claim 1, wherein
$L_2$ is H, Cl or F;
$L_3$ is H, Cl or F;
$L_4$ is C(O)NHCH$_3$ or CF$_3$;
$L_8$ is Cl or F;
$L_9$ is Cl or F; and
$L_{10}$ is Cl or F.

10. The compound of claim 1, wherein
$L_2$ is H, Cl or F;
$L_3$ is H, Cl or F;
$L_4$ is C(O)NHCH$_3$,

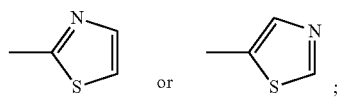 or ;

$L_8$ is Cl or F;
$L_9$ is Cl or F, and
$L_{10}$ is Cl or F.

11. The compound of claim 1, wherein
$L_2$ is H, Cl or F;
$L_3$ is H, Cl or F;
$L_4$ is C(O)NHCH$_3$, CF$_3$ or

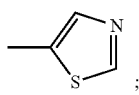 ;

$L_8$ is Cl or F;
$L_9$ is Cl or F; and
$L_{10}$ is Cl or F.

12. The compound of claim 1, wherein the compound is:

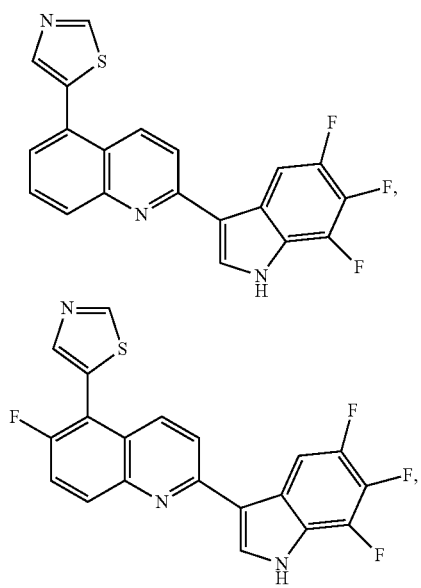

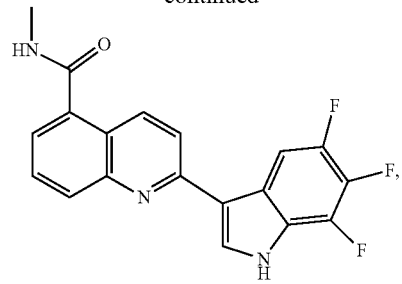

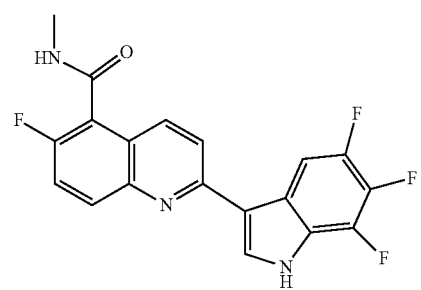

and

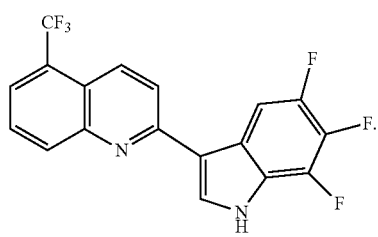

13. A pharmaceutical composition comprising a compound or pharmaceutically acceptable salt thereof according to claim 1 and a pharmaceutically acceptable excipient.

14. The pharmaceutical composition of claim 13, wherein the compound is selected from:

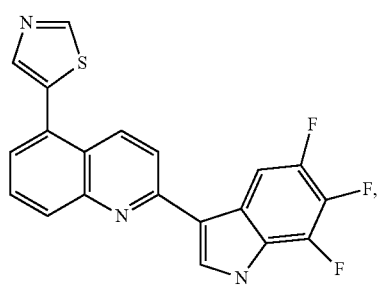

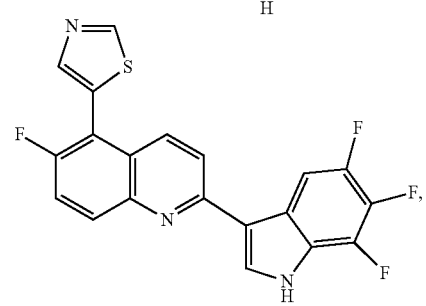

-continued
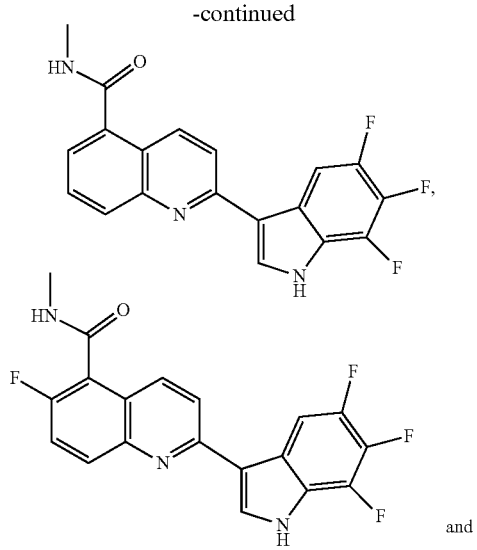
and
-continued
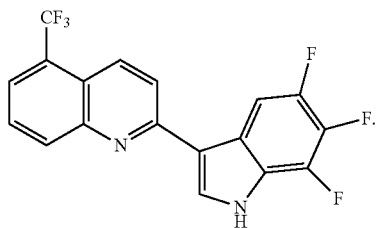
15. A method of modulating AR activity, the method comprising (a) administering a compound of claim 1 to a subject in need thereof.
16. The method of claim 15, wherein the modulating AR activity is for the treatment of prostate cancer.
* * * * *